(12) United States Patent
Reeves et al.

(10) Patent No.: US 7,148,005 B2
(45) Date of Patent: Dec. 12, 2006

(54) NUCLEIC ACID-BASED METHODS OF DETECTING BACTERIAL O-ANTIGENS

(75) Inventors: Peter Richard Reeves, Glebe (AU); Lei Wang, North Ryde (AU)

(73) Assignee: The University of Sydney, Sydney (AU)

( * ) Notice: Subject to any disclaimer, the term of this patent is extended or adjusted under 35 U.S.C. 154(b) by 0 days.

(21) Appl. No.: 09/423,093

(22) PCT Filed: May 1, 1998

(86) PCT No.: PCT/AU98/00315

§ 371 (c)(1),
(2), (4) Date: Nov. 1, 1999

(87) PCT Pub. No.: WO98/50531

PCT Pub. Date: Nov. 12, 1998

(65) Prior Publication Data

US 2003/0018349 A1      Jan. 23, 2003

(30) Foreign Application Priority Data

May 1, 1997   (AU) ..................... PO6545
Jul. 22, 1997  (AU) ..................... PO8162

(51) Int. Cl.
  *C12Q 1/68*   (2006.01)
  *C12P 19/34*  (2006.01)
  *C07H 21/02*  (2006.01)
(52) U.S. Cl. .................. 435/6; 435/91.1; 435/91.2; 435/183; 536/23.1; 536/24.31

(58) Field of Classification Search .................... 435/6, 435/183, 270, 243, 252.1, 252.8, 822, 849, 435/879, 91.1, 91.2, 287.2; 436/94; 536/23.1, 536/24.31, 24.33
See application file for complete search history.

(56) References Cited

U.S. PATENT DOCUMENTS 5,474,796 A * 12/1995  Brennan ................. 427/2.13
5,652,102 A *  7/1997  Fratamico et al. ............. 435/6
6,165,724 A * 12/2000  Fukushima et al. ............ 435/6

OTHER PUBLICATIONS

Liu et al., Journal of Bacteriology, vol. 178, No. 7, Apr. 1996, pp. 2102-2107.*
Bastin et al., "Sequence and analysis of the O antigen gene (rfb) cluster of *Escherichia coli* O111," Gene, 164 (1995) 17-23.*
Liu et al., "An O-Antigen Processing Function for Wzx (RfbX): a Promising Candidate for O-Unit Flippase," Journal of Bacteriology, 178(7), Apr. 1996, 2102-107.*
Salazar et al., "Nucleic acid scanning-by-hybridization of enterohemorrhagic *Escherichia coli* isolates using oligonucleotie arrays," Nucleic Acis Research, 24(24), 1996, 5056-5057.*
Wang et al, *Infection and Immunity*, 66(8):3545-3551 (1998).
Brown et al, *Molecular Microbiology*, 6(10):1385-1394 (1992).
Wang et al, *J. of Bacteriology*, 178(9):2598-2604 (1996).
Jiang et al, *Molecular Microbiology*, 5(3):695-713 (1991).

* cited by examiner

*Primary Examiner*—Bradley L. Sisson
(74) *Attorney, Agent, or Firm*—Sughrue Mion, PLLC

(57) ABSTRACT

The present invention relates to method of testing a sample for the presence of nucleic acids encoding *E. coli* polysaccharide O-antigen serotype O111, *S. enterica* polysaccharide O-antigen serotype C2 and *S. enterica* polysaccharide O-antigen serotype B.

22 Claims, 58 Drawing Sheets

| | |
|---|---:|
| GATCTGATGGCCGTAGGGCGCTACGTGCTTTCTGCTGATATCTGGGCTGAGTTGGAAAAA | 60 |
| ACTGCTCCAGGTGCCTGGGGACGTATTCAACTGACTGATGCTATTGCAGAGTTGGCTAAA | 120 |
| AAACAGTCTGTTGATGCCATGCTGATGACCGGCGACAGCTACGACTGCGGTAAGAAGATG | 180 |
| GGCTATATGCAGGCATTCGTTAAGTATGGGCTGCGCAACCTTAAAGAAGGGGCGAAGTTC | 240 |
| CGTAAGAGCATCAAGAAGCTACTGAGTGAGTAGAGATTTACACGTCTTTGTGACGATAAG | 300 |
| CCAGAAAAAATAGCGGCAGTTAACATCCAGGCTTCTATGCTTTAAGCAATGGAATGTTAC | 360 |
| TGCCGTTTTTTATGAAAAATGACCAATAATAACAAGTTAACCTACCAAGTTTAATCTGCT | 420 |
| TTTTGTTGGATTTTTTCTTGTTTCTGGTCGCATTTGGTAAGACAATTAGCGTGAGTTTTA | 480 |
| GAGAGTTTTGCGGGATCTCGCGGAACTGCTCACATCTTTGGCATTTAGTTAGTGCACTGG | 540 |
| TAGCTGTTAAGCCAGGGGCGGTAGCTTGCCTAATTAATTTTTAACGTATACATTTATTCT | 600 |
| TGCCGCTTATAGCAAATAAAGTCAATCGGATTAAACTTCTTTTCCATTAGGTAAAAGAGT | 660 |
| GTTTGTAGTCGCTCAGGGAAATTGGTTTTGGTAGTAGTACTTTTCAAATTATCCATTTTC | 720 |

```
                     Start of orf1
                 M  L  L  C  C  I  H  I  N  V  Y  Y  L  L
CGATTTAGATGGCAGTTGATGTTACTATGCTGCATACATATCAATGTATATTATTTACTT    780
 L  E  C  D  M  K  K  I  V  I  I  G  N  V  A  S  M  M  L  R
TTAGAATGTGATATGAAAAAAATAGTGATCATAGGCAATGTAGCGTCAATGATGTTAAGG    840
 F  R  K  E  L  I  M  N  L  V  R  Q  G  D  N  V  Y  C  L  A
TTCAGGAAAGAATTAATCATGAATTTAGTGAGGCAAGGTGATAATGTATATTGTCTAGCA    900
 N  D  F  S  T  E  D  L  K  V  L  S  S  W  G  V  K  G  V  K
AATGATTTTTCCACTGAAGATCTTAAAGTACTTTCGTCATGGGGCGTTAAGGGGGTTAAA    960
 F  S  L  N  S  K  G  I  N  P  F  K  D  I  I  A  V  Y  E  L
TTCTCTCTTAACTCAAAGGGTATTAATCCTTTTAAGGATATAATTGCTGTTTATGAACTA   1020
 K  K  I  L  K  D  I  S  P  D  I  V  F  S  Y  F  V  K  P  V
AAAAAAATTCTTAAGGATATTTCCCCAGATATTGTATTTTCATATTTTGTAAAGCCAGTA   1080
 I  F  G  T  I  A  S  K  L  S  K  V  P  R  I  V  G  M  I  E
ATATTTGGAACTATTGCTTCAAAGTTGTCAAAAGTGCCAAGGATTGTTGGAATGATTGAA   1140
 G  L  G  N  A  F  T  Y  Y  K  G  K  Q  T  T  K  T  K  M  I
GGTCTAGGTAATGCCTTCACTTATTATAAGGGAAAGCAGACCACAAAAACTAAAATGATA   1200
 K  W  I  Q  I  L  L  Y  K  L  A  L  P  M  L  D  D  L  I  L
AAGTGGATACAAATTCTTTTATATAAGTTAGCATTACCGATGCTTGATGATTTGATTCTA   1260
 L  N  H  D  D  K  K  D  L  I  D  Q  Y  N  I  K  A  K  V  T
TTAAATCATGATGATAAAAAAGATTTAATCGATCAGTATAATATTAAAGCTAAGGTAACA   1320
 V  L  G  G  I  G  L  D  L  N  E  F  S  Y  K  E  P  P  K  E
GTGTTAGGTGGGATTGGATTGGATCTTAATGAGTTTTCATATAAAGAGCCACCGAAAGAG   1380
 K  I  T  F  I  F  I  A  R  L  L  R  E  K  G  I  F  E  F  I
AAAATTACCTTTATTTTTATAGCAAGGTTATTAAGAGAGAAAGGGATATTTGAGTTTATT   1440
 E  A  A  K  F  V  K  T  T  Y  P  S  S  E  F  V  I  L  G  G
GAAGCCGCAAAAGTTCGTTAAGACAACTTATCCAAGTTCTGAATTTGTAATTTTAGGAGGT   1500
```

```
       F  E  S  N  N  P  F  S  L  Q  K  N  E  I  E  S  L  R  K  E
    TTTGAGAGTAATAATCCTTTCTCATTACAAAAAAATGAAATTGAATCGCTAAGAAAAGAA       1560

H  D  L  I  Y  P  G  H  V  E  N  V  Q  D  W  L  E  K  S  S
    CATGATCTTATTTATCCTGGTCATGTGGAAAATGTTCAAGATTGGTTAGAGAAAAGTTCT       1620

V  F  V  L  P  T  S  Y  R  E  G  V  P  R  V  I  Q  E  A  M
    GTTTTTGTTTTACCTACATCATATCGAGAAGGCGTACCAAGGGTGATCCAAGAAGCTATG      1680

A  I  G  R  P  V  I  T  T  N  V  P  G  C  R  D  I  I  N  D
    GCTATTGGTAGACCTGTAATAACAACTAATGTACCTGGGTGTAGGGATATAATAAATGAT      1740

G  V  N  G  F  L  I  P  P  F  E  I  N  L  L  A  E  K  M  K
    GGGGTCAATGGCTTTTTGATACCTCCATTTGAAATTAATTTACTGGCAGAAAAAATGAAA      1800

Y  F  I  E  N  K  D  K  V  L  E  M  G  L  A  G  R  K  F  A
    TATTTTATTGAGAATAAAGATAAAGTACTCGAAATGGGGCTTGCTGGAAGGAAGTTTGCA      1860

E  K  N  F  D  A  F  E  K  N  N  R  L  A  S  I  I  K  S  N
    GAAAAAAACTTTGATGCTTTTGAAAAAAATAATAGACTAGCATCAATAATAAAATCAAAT     1920

End of orf1
       N  D  F  *
    AATGATTTT TGACTTGAGCAGAAATTATTTATATTTCAATCTGAAAAATAAAGGCTGTTA      1980

Start of orf2
              M  N  K  V  A  L  I  T  G  I  T  G  Q  D  G  S  Y  L  A
    TTATGAATAAAGTGGCATTAATTACTGGTATCACTGGGCAAGATGGCTCCTATTTGGCAG      2040

E  L  L  L  E  K  G  Y  E  V  H  G  I  K  R  R  A  S  S  F
    AATTATTGTTAGAAAAAGGTTATGAAGTTCATGGTATTAAACGCCGTGCATCTTCATTTA      2100

N  T  E  R  V  D  H  I  Y  Q  D  S  H  L  A  N  P  K  L  F
    ATACTGAGCGAGTGGATCACATCTATCAGGATTCACATTTAGCTAATCCTAAACTTTTTC      2160

L  H  Y  G  D  L  T  D  T  S  N  L  T  R  I  L  K  E  V  Q
    TACACTATGGCGATTTGACAGATACTTCCAATCTGACCCGTATTTTAAAAGAAGTTCAAC      2220

P  D  E  V  Y  N  L  G  A  M  S  H  V  A  V  S  F  E  S  P
    CAGATGAAGTTTACAATTTGGGGGCGATGAGCCATGTAGCGGTATCATTTGAGTCACCAG      2280

E  Y  T  A  D  V  D  A  I  G  T  L  R  L  L  E  A  I  R  I
    AATACACTGCTGATGTTGATGCGATAGGAACATTGCGTCTTCTTGAAGCTATCAGGATAT      2340

L  G  L  E  K  K  T  K  F  Y  Q  A  S  T  S  E  L  Y  G  L
    TGGGGCTGGAAAAAAAGACAAAATTTTATCAGGCTTCAACTTCAGAGCTTTATGGTTTGG      2400

V  Q  E  I  P  Q  K  E  T  T  P  F  Y  P  R  S  P  Y  A  V
    TTCAAGAAATTCCACAAAAAGAGACTACGCCATTTTATCCACGTTCGCCTTATGCTGTTG      2460

A  K  L  Y  A  Y  W  I  T  V  N  Y  R  E  S  Y  G  M  F  A
    CAAAATTATATGCCTATTGGATCACTGTTAATTATCGTGAGTCTTATGGTATGTTTGCCT      2520

C  N  G  I  L  F  N  H  E  S  P  R  R  G  E  T  F  V  T  R
    GCAATGGTATTCTCTTTAACCACGAATCACCTCGCCGTGGCGAGACCTTTGTTACTCGTA     2580

K  I  T  R  G  I  A  N  I  A  Q  G  L  D  K  C  L  Y  L  G
    AAATAACACGCGGGATAGCAAATATTGCTCAAGGTCTTGATAAATGCTTATACTTGGGAA     2640

N  M  D  S  L  R  D  W  G  H  A  K  D  Y  V  K  M  Q  W  M
    ATATGGATTCTCTGCGTGATTGGGGACATGCTAAGGATTATGTCAAAATGCAATGGATGA     2700
```

Figure 7/2

```
         M   L   Q   Q   E   T   P   E   D   F   V   I   A   T   G   I   Q   Y   S   V
         TGCTGCAGCAAGAAACTCCAGAAGATTTTGTAATTGCTACAGGAATTCAATATTCTGTCC              2760

R   E   F   V   T   M   A   A   E   Q   V   G   I   E   L   A   F   E   G   E
         GTGAGTTTGTCACAATGGCGGCAGAGCAAGTAGGCATAGAGTTAGCATTTGAAGGTGAGG              2820

G   V   N   E   K   G   V   V   V   S   V   N   G   T   D   A   K   A   V   N
         GAGTAAATGAAAAAGGTGTTGTTGTTTCGGTCAATGGCACTGATGCTAAAGCTGTAAACC              2880

P   G   D   V   I   I   S   V   D   P   R   Y   F   R   P   A   E   V   E   T
         CGGGCGATGTAATTATATCTGTAGATCCAAGGTATTTTAGGCCTGCAGAAGTTGAAACCT              2940

L   L   G   D   P   T   N   A   H   K   K   L   G   W   S   P   E   I   T   L
         TGCTTGGCGATCCTACTAATGCGCATAAAAAATTAGGATGGAGCCCTGAAATTACATTGC              3000

R   E   M   V   K   E   M   V   S   S   D   L   A   I   A   K   K   N   V   L
         GTGAAATGGTAAAAGAAATGGTTTCCAGCGATTTAGCAATAGCGAAAAAGAACGTCTTGC              3060

End of orf2
         L   K   A   N   N   I   A   T   N   I   P   Q   E   *
         TGAAAGCTAATAACATTGCCACTAATATTCCGCAAGAATAAAAAGATAATACATTAAAT              3120

Start of orf3
                                                          M   F
         AATTAAAAATGGTGCTAGATTTATTAGTACCATTATTTTTTTTGGGTGACTAATGTTTA              3180

I   T   S   D   K   F   R   E   I   I   K   L   V   P   L   V   S   I   D   L
         TTACATCAGATAAATTTAGAGAAATTATCAAGTTAGTTCCATTAGTATCAATTGATCTGC              3240

L   I   E   N   E   N   G   E   Y   L   F   G   L   R   N   N   R   P   A   K
         TAATTGAAAACGAGAATGGTGAATATTTATTTGGTCTTAGGAATAATCGACCGGCCAAAA              3300

N   Y   F   F   V   P   G   G   R   I   R   K   N   E   S   I   K   N   A   F
         ATTATTTTTTTGTTCCAGGTGGTAGGATTCGCAAAAATGAATCTATTAAAAATGCTTTTA              3360

K   R   I   S   S   M   E   L   G   K   E   Y   G   I   S   G   S   V   F   N
         AAAGAATATCATCTATGGAATTAGGTAAAGAGTATGGTATTTCAGGAAGTGTTTTTAATG              3420

G   V   W   E   H   F   Y   D   D   G   F   F   S   E   G   E   A   T   H   Y
         GTGTATGGGAACATTTCTATGATGATGGTTTTTTTTCTGAAGGCGAGGCAACACATTATA              3480

I   V   L   C   Y   T   L   K   V   L   K   S   E   L   N   L   P   D   D   Q
         TAGTGCTTTGTTACACACTGAAAGTTCTTAAAAGTGAATTGAATCTCCCAGATGATCAAC              3540

H   R   E   Y   L   W   L   T   K   H   Q   I   N   A   K   Q   D   V   H   N
         ATCGTGAATACCTTTGGCTAACTAAACACCAAATAAATGCTAAACAAGATGTTCATAACT              3600

End of orf3                      Start of orf4
         Y   S   K   N   Y   F   L   *                               M
         ATTCAAAAAATTATTTTTTGTAATTTTTATTAAAAATTAATATGCGAGAGAATTGTATGT              3660

S   Q   C   L   Y   P   V   I   I   A   G   G   T   G   S   R   L   W   P   L
         CTCAATGTCTTTACCCTGTAATTATTGCCGGAGGAACCGGAAGCCGTCTATGGCCGTTGT              3720

S   R   V   L   Y   P   K   Q   F   L   N   L   V   G   D   S   T   M   L   Q
         CTCGAGTATTATACCCTAAACAATTTTTAAATTTAGTTGGGGATTCTACAATGTTGCAAA              3780

T   T   I   T   R   L   D   G   I   E   C   E   N   P   I   V   I   C   N   E
         CAACAATTACGCGTTTGGATGGCATCGAATGCGAAAATCCAATTGTTATCTGCAATGAAG              3840

D   H   R   F   I   V   A   E   Q   L   R   Q   I   G   K   L   T   K   N   I
         ATCACCGATTTATTGTAGCAGAGCAATTACGACAGATTGGTAAGCTAACCAAGAATATTA              3900

I   L   E   P   K   G   R   N   T   A   P   A   I   A   L   A   A   F   I   A
         TACTTGAGCCGAAAGGCCGTAATACTGCACCTGCCATAGCTTTAGCTGCTTTTATCGCTC              3960
```

Figure 7/3

```
Q  K  N  N  P  N  D  D  P  L  L  L  V  L  A  A  D  H  S  I
AGAAGAATAATCCTAATGACGACCCTTTATTATTAGTACTTGCGGCAGACCACTCTATAA              4020

N  N  E  K  A  F  R  E  S  I  I  K  A  M  P  Y  A  T  S  G
ATAATGAAAAAGCATTTCGAGAGTCAATAATAAAAGCTATGCCGTATGCAACTTCTGGGA              4080

K  L  V  T  F  G  I  I  P  D  T  A  N  T  G  Y  G  Y  I  K
AGTTAGTAACATTTGGAATTATTCCGGACACGGCAAATACTGGTTATGGATATATTAAGA              4140

R  S  S  S  A  D  P  N  K  E  F  P  A  Y  N  V  A  E  F  V
GAAGTTCTTCAGCTGATCCTAATAAAGAATTCCCAGCATATAATGTTGCGGAGTTTGTAG              4200

E  K  P  D  V  K  T  A  Q  E  Y  I  S  S  G  N  Y  Y  W  N
AAAAACCAGATGTTAAAACAGCACAGGAATATATTTCGAGTGGGAATTATTACTGGAATA              4260

S  G  M  F  L  F  R  A  S  K  Y  L  D  E  L  R  K  F  R  P
GCGGAATGTTTTATTTCGCGCCAGTAAATATCTTGATGAACTACGGAAATTTAGACCAG              4320

D  I  Y  H  S  C  E  C  A  T  A  N  I  D  M  D  F  V
ATATTTATCATAGCTGTGAATGTGCAACCGCTACAGCAAATATAGATATGGACTTTGTCC              4380

R  I  N  E  A  E  F  I  N  C  P  E  E  S  I  D  Y  A  V  M
GAATTAACGAGGCTGAGTTTATTAATTGTCCTGAAGAGTCTATCGATTATGCTGTGATGG              4440

E  K  T  K  D  A  V  V  L  P  I  D  I  G  W  N  D  V  G  S
AAAAAACAAAAGACGCTGTAGTTCTTCCGATAGATATTGGCTGGAATGACGTGGGTTCTT              4500

W  S  S  L  W  D  I  S  Q  K  D  C  H  G  N  V  C  H  G  D
GGTCATCACTTTGGGATATAAGCCAAAAGGATTGCCATGGTAATGTGTGCCATGGGGATG              4560

V  L  N  H  D  G  E  N  S  F  I  Y  S  E  S  S  L  V  A  T
TGCTCAATCATGATGGAGAAAATAGTTTTATTTACTCTGAGTCAAGTCTGGTTGCGACAG              4620

V  G  V  S  N  L  V  I  V  Q  T  K  D  A  V  L  V  A  D  R
TCGGAGTAAGTAATTTAGTAATTGTCCAAACCAAGGATGCTGTACTGGTTGCGGACCGTG              4680

D  K  V  Q  N  V  K  N  I  V  D  D  L  K  K  R  K  R  A  E
ATAAAGTCCAAAATGTTAAAAACATAGTTGACGATCTAAAAAAGAGAAAACGTGCTGAAT              4740

Y  Y  M  H  R  A  V  F  R  P  W  G  K  F  D  A  I  D  Q  G
ACTACATGCATCGTGCAGTTTTTCGCCCTTGGGGTAAATTCGATGCAATAGACCAAGGCG              4800

D  R  Y  R  V  K  K  I  I  V  K  P  G  E  G  L  D  L  R  M
ATAGATATAGAGTAAAAAAAATAATAGTTAAACCAGGAGAAGGGTTAGATTTAAGGATGC              4860

H  H  H  R  A  E  H  W  I  V  V  S  G  T  A  K  V  S  L  G
ATCATCATAGGGCAGAGCATTGGATTGTTGTATCCGGTACTGCTAAAGTTTCACTAGGTA              4920

S  E  V  K  L  L  V  S  N  E  S  I  Y  I  P  Q  G  A  K  Y
GTGAAGTTAAACTATTAGTTTCTAATGAGTCTATATATATCCCTCAGGGAGCAAAATATA              4980

S  L  E  N  P  G  V  I  P  L  H  L  I  E  V  S  S  G  D  Y
GTCTTGAGAATCCAGGCGTAATACCTTTGCATCTAATTGAAGTAAGTTCTGGTGATTACC              5040

L  E  S  D  D  I  V  R  F  T  D  R  Y  N  S  K  Q  F  L  K
TTGAATCAGATGATATAGTGCGTTTTACTGACAGATATAACAGTAAACAATTCCTAAAGC              5100
```

End of orf4 Start of orf5
```
                      M  N  K  I  T  C  F  K  A  Y  D  I  R  G  R  L
R  D  *
GAGATTGATAAATATGAATAAAATAACTTGCTTCAAAGCATATGATATACGTGGGCGTCT              5160
```

Figure 7/4

```
     G   A   E   L   N   D   E   I   A   Y   R   I   G   R   A   Y   G   E   F   F
TGGTGCTGAATTGAATGATGAAATAGCATATAGAATTGGTCGCGCTTATGGTGAGTTTTT              5220

K   P   Q   T   V   V   V   G   G   D   A   R   L   T   S   E   S   L   K   K
TAAACCTCAAACTGTAGTTGTGGGAGGAGATGCTCGCTTAACAAGTGAGAGTTTAAAGAA              5280

S   L   S   N   G   L   C   D   A   G   V   N   V   L   D   L   G   M   C   G
ATCACTCTCAAATGGGCTATGTGATGCAGGCGTAAATGTCTTAGATCTTGGAATGTGTGG              5340

T   E   E   I   Y   F   S   T   W   Y   L   G   I   D   G   G   I   E   V   T
TACTGAAGAGATATATTTTTCCACTTGGTATTTAGGAATTGATGGTGGAATCGAGGTAAC              5400

A   S   H   N   P   I   D   Y   N   G   M   K   L   V   T   K   G   A   R   P
TGCAAGCCATAATCCAATTGATTATAATGGAATGAAATTAGTAACCAAAGGTGCTCGACC              5460

I   S   S   D   T   G   L   K   D   I   Q   Q   L   V   E   S   N   N   F   E
AATCAGCAGTGACACAGGTCTCAAAGATATACAACAATTAGTAGAGAGTAATAATTTTGA              5520

E   L   N   L   E   K   K   G   N   I   T   K   Y   S   T   R   D   A   Y   I
AGAGCTCAACCTAGAAAAAAAGGGAATATTACCAAATATTCCACCCGAGATGCCTACAT              5580

N   H   L   M   G   Y   A   N   L   Q   K   I   K   K   I   K   I   V   V   N
AAATCATTTGATGGGCTATGCTAATCTGCAAAAAATAAAAAAAATCAAAATAGTTGTGAA              5640

S   G   N   G   A   A   G   P   V   I   D   A   I   E   E   C   F   L   R   N
TTCTGGGAATGGTGCAGCTGGTCCTGTTATTGATGCTATTGAGGAATGCTTTTTACGGAA              5700

N   I   P   I   Q   F   V   K   I   N   N   T   P   D   G   N   F   P   H   G
CAATATTCCGATTCAGTTTGTAAAAATAAATAATACACCCGATGGTAATTTTCCACATGG              5760

I   P   N   P   L   L   P   E   C   R   E   D   T   S   S   A   V   I   R   H
TATCCCTAATCCATTACTACCTGAGTGCAGAGAAGATACCAGCAGTGCGGTTATAAGACA              5820

S   A   D   F   G   I   A   F   D   G   D   F   D   R   C   F   F   F   D   E
TAGTGCTGATTTTGGTATTGCATTTGATGGTGATTTTGATAGGTGTTTTTTCTTTGATGA              5880

N   G   Q   F   I   E   G   Y   Y   I   V   G   L   L   A   E   V   F   L   G
AAATGGACAATTTATTGAAGGATACTACATTGTTGGTTTATTAGCGGAAGTTTTTTTAGG              5940

K   Y   P   N   A   K   I   I   H   D   P   R   L   I   W   N   T   I   D   I
GAAATATCCAAACGCAAAAATCATTCATGATCCTCGCCTTATATGGAATACTATTGATAT              6000

V   E   S   H   G   G   I   P   I   M   T   K   T   G   H   A   Y   I   K   Q
CGTAGAAAGTCATGGTGGTATACCTATAATGACTAAAACCGGTCATGCTTACATTAAGCA              6060

R   M   R   E   E   D   A   V   Y   G   G   E   M   S   A   H   H   Y   F   K
AAGAATGCGTGAAGAGGATGCCGTATATGGCGGCGAAATGAGTGCGCATCATTATTTTAA              6120

D   F   A   Y   C   D   S   G   M   I   P   W   I   L   I   C   E   L   L   S
AGATTTTGCATACTGCGATAGTGGAATGATTCCTTGGATTTTAATTTGTGAACTTTTGAG              6180

L   T   N   K   K   L   G   E   L   V   C   G   C   I   N   D   W   P   A   S
TCTGACAAATAAAAAATTAGGTGAACTGGTTTGTGGTTGTATAAACGACTGGCCGGCAAG              6240

G   E   I   N   C   T   L   D   N   P   Q   N   E   I   D   K   L   F   N   R
TGGAGAAATAAACTGTACACTAGACAATCCGCAAAATGAAATAGATAAATTATTTAATCG              6300

Y   K   D   S   A   L   A   V   D   Y   T   D   G   L   T   M   E   F   S   D
TTACAAAGATAGTGCCTTAGCTGTTGATTACACTGATGGATTAACTATGGAGTTCTCTGA              6360

W   R   F   N   V   R   C   S   N   T   E   P   V   V   R   L   N   V   E   S
TTGGCGTTTTAATGTTAGATGCTCAAATACAGAACCTGTAGTACGATTGAATGTAGAATC              6420

R   N   N   A   I   L   M   Q   E   K   T   E   E   I   L   N   F   I   S   K
TAGGAATAATGCTATTCTTATGCAGGAAAAAACAGAAGAAATTCTGAATTTTATATCAAA              6480
```

Figure 7/5

End of orf5                     Start of orf6

```
                                         M  K  V  L  L  T  G
ATAAATTTGCACCTGAGTTCATAATGGCAACAAGAAATATATGAAAGTACTTCTGACTGG      6540

S  T  G  M  V  G  K  N  I  L  E  H  D  S  A  S  K  Y  N  I
CTCAACTGGCATGGTTGGTAAGAATATATTAGAGCATGATAGTGCAAGTAAATATAATAT      6600

L  T  P  T  S  S  D  L  N  L  L  D  K  N  E  I  E  K  F  M
ACTTACTCCAACCAGCTCTGATTTGAATTTATTAGATAAAAATGAAATAGAAAAATTCAT      6660

L  I  N  M  P  D  C  I  I  H  A  A  G  L  V  G  G  I  H  A
GCTTATCAACATGCCAGACTGTATTATACATGCAGCGGGATTAGTTGGAGGCATTCATGC      6720

N  I  S  R  P  F  D  F  L  E  K  N  L  Q  M  G  L  N  L  V
AAATATAAGCAGGCCGTTTGATTTTCTGGAAAAAAATTTGCAGATGGGTTTAAATTTAGT      6780

S  V  A  K  K  L  G  I  K  K  V  L  N  L  G  S  S  C  M  Y
TTCCGTCGCAAAAAAACTAGGTATCAAGAAAGTGCTTAACTTGGGTAGTTCATGCATGTA      6840

P  K  N  F  E  E  A  I  P  E  K  A  L  L  T  G  E  L  E  E
CCCCAAAAACTTTGAAGAGGCTATTCCTGAGAAAGCTCTGTTAACTGGTGAGCTAGAAGA      6900

T  N  E  G  Y  A  I  A  K  I  A  V  A  K  A  C  E  Y  I  S
AACTAATGAGGGATATGCTATTGCGAAAATTGCTGTAGCAAAAGCATGCGAATATATATC      6960

R  E  N  S  N  Y  F  Y  K  T  I  I  P  C  N  L  Y  G  K  Y
AAGAGAAAACTCTAATTATTTTTATAAAACAATTATCCCATGTAATTTATATGGGAAATA      7020

D  K  F  D  D  N  S  S  H  M  I  P  A  V  I  K  K  I  H  H
TGATAAATTTGATGATAACTCGTCACATATGATTCCGGCAGTTATAAAAAAAATCCATCA      7080

A  K  I  N  N  V  P  E  I  E  I  W  G  D  N  S  R  R  E
TGCGAAAATTAATAATGTCCCAGAGATCGAAATTTGGGGGGATGGTAATTCGCGCCGTGA      7140

F  M  Y  A  E  D  L  A  D  L  I  F  Y  V  I  P  K  I  E  F
GTTTATGTATGCAGAAGATTTAGCTGATCTTATTTTTTATGTTATTCCTAAAATAGAATT      7200

M  P  N  M  V  N  A  G  L  G  Y  D  Y  S  I  N  D  Y  Y  K
CATGCCTAATATGGTAAATGCTGGTTTAGGTTACGATTATTCAATTAATGACTATTATAA      7260

I  I  A  E  E  I  G  Y  T  G  S  F  S  H  D  L  T  K  P  T
GATAATTGCAGAAGAAATTGGTTATACTGGGAGTTTTTCTCATGATTTAACAAAACCAAC      7320

G  M  K  R  K  L  V  D  I  S  L  L  N  K  I  G  W  S  S  H
AGGAATGAAACGGAAGCTAGTAGATATTTCATTGCTTAATAAAATTGGTTGGTCAAGTCA      7380

F  E  L  R  D  G  I  R  K  T  Y  N  Y  Y  L  E  N  Q  N  K
CTTTGAACTCAGAGATGGCATCAGAAAGACCTATAATTATTACTTGGAGAATCAAAATAA      7440
```

Start of orf7, End of orf6

```
  M  I  T  Y  P  L  A  S  N  T  W  D  E  Y  E  Y  A  A  I  Q
  *
  ATGATTACATACCCACTTGCTAGTAATACTTGGGATGAATATGAGTATGCAGCAATACAG    7500

S  V  I  D  S  K  M  F  T  M  G  K  K  V  E  L  Y  E  K  N
TCAGTAATTGACTCAAAAAATGTTTACCATGGGTAAAAAGGTTGAGTTATATGAGAAAAAT      7560

F  A  D  L  F  G  S  K  Y  A  V  M  V  S  S  G  S  T  A  N
TTTGCTGATTTGTTTGGTAGCAAATATGCCGTAATGGTTAGCTCTGGTTCTACAGCTAAT      7620
```

Figure 7/6

```
L  L  M  I  -  A  A  L  F  F  T  -  N  K  P  K  L  K  R  G  D  E
CTGTTAATGATTGCTGCCCTTTTCTTCACTAATAAACCAAAACTTAAAAGAGGTGATGAA           7680

I  I  V  P  A  V  S  W  S  T  T  Y  Y  P  L  Q  Q  Y  G  L
ATAATAGTACCTGCAGTGTCATGGTCTACGACATATTACCCTCTGCAACAGTATGGCTTA           7740

K  V  K  F  V  D  I  N  K  E  T  L  N  I  D  I  D  S  L  K
AAGGTGAAGTTTGTCGATATCAATAAAGAAACTTTAAATATTGATATCGATAGTTTGAAA          7800

N  A  I  S  D  K  T  K  A  I  L  T  V  N  L  L  G  N  P  N
AATGCTATTTCAGATAAAACAAAAGCAATATTGACAGTAAATTTATTAGGTAATCCTAAT          7860

D  F  A  K  I  N  E  I  I  N  N  R  D  I  I  L  L  E  D  N
GATTTTGCAAAAATAAATGAGATAATAAATAATAGGGATATTATCTTACTAGAAGATAAC          7920

C  E  S  M  G  A  V  F  Q  N  K  Q  A  G  T  F  G  V  M  G
TGTGAGTCGATGGGCGCGGTCTTTCAAAATAAGCAGGCAGGCACATTCGGAGTTATGGGT          7980

T  F  S  S  F  Y  S  H  H  I  A  T  M  E  G  G  C  V  V  T
ACCTTTAGTTCTTTTTACTCTCATCATATAGCTACAATGGAAGGGGGCTGCGTAGTTACT          8040

D  D  E  E  L  Y  H  V  L  L  C  R  A  H  G  W  T  R  N
GATGATGAAGAGCTGTATCATGTATTGTTGTGCCTTCGAGCTCATGGTTGGACAAGAAAT          8100

L  P  K  E  N  M  V  T  G  T  K  S  D  D  I  F  E  E  S  F
TTACCAAAAGAGAATATGGTTACAGGCACTAAGAGTGATGATATTTTCGAAGAGTCGTTT          8160

K  F  V  L  P  G  Y  N  V  R  P  L  E  M  S  G  A  I  G  I
AAGTTTGTTTTACCAGGATACAATGTTCGCCCACTTGAAATGAGTGGTGCTATTGGGATA          8220

E  Q  L  K  K  L  P  G  F  I  S  T  R  R  S  N  A  Q  Y  F
GAGCAACTTAAAAAGTTACCAGGTTTTATATCCACCAGACGTTCCAATGCACAATATTTT          8280

V  D  K  F  K  D  H  P  F  L  D  I  Q  K  E  V  G  E  S  S
GTAGATAAATTTAAAGATCATCCATTCCTTGATATACAAAAAGAAGTTGGTGAAAGTAGC          8340

W  F  G  F  S  F  V  I  K  E  G  A  A  I  E  R  K  S  L  V
TGGTTTGGTTTTTCCTTCGTTATAAAGGAGGGAGCTGCTATTGAGAGGAAGAGTTTAGTA          8400

N  N  L  I  S  A  G  I  E  C  R  P  I  V  T  G  N  F  L  K
AATAATCTGATCTCAGCAGGCATTGAATGCCGACCAATTGTTACTGGGAATTTTCTCAAA          8460

N  E  R  V  L  S  Y  F  D  Y  S  V  H  D  T  V  A  N  A  E
AATGAACGTGTTTTGAGTTATTTTGATTACTCTGTACATGATACGGTAGCAAATGCCGAA          8520

Y  I  D  K  N  G  F  F  V  G  N  H  Q  I  P  L  F  N  E  I
TATATAGATAAGAATGGTTTTTTTGTCGGAAACCACCAGATACCTTTGTTTAATGAAATA          8580

End of orf7
 D  Y  L  R  K  V  L  K  *
GATTATCTACGAAAAGTATTAAAATAACTAACGAGGCACTCTATTTCGAATAGAGTGCCT          8640

Start of orf8
        M  V  L  T  V  K  K  I  L  A  F  G  Y  S  K  V  L  P
TTAAGATGGTATTAACAGTGAAAAAAATTTTAGCGTTTGGCTATTCTAAAGTACTACCAC          8700

P  V  I  E  Q  F  V  N  P  I  C  I  F  I  I  T  P  L  I  L
CCGTTATTGAACAGTTTGTCAATCCAATTTGCATCTTCATTATCACACCACTAATACTCA          8760

N  H  L  G  K  Q  S  Y  G  N  W  I  L  L  I  T  I  V  S  F
ACCACCTGGGTAAGCAAAGCTATGGTAATTGGATTTTATTAATTACTATTGTATCTTTTT          8820
```

Figure 7/7

```
S  Q  L  I  -C  G  G  C  S  A -W  I  A  K  I  I  A  E  Q  R
CTCAGTTAATATGTGGAGGATGTTCCGCATGGATTGCAAAAATCATTGCAGAACAGAGAA        8880

I  L  S  D  L  S  K  K  N  A  L  R  Q  I  S  Y  N  F  S  I
TTCTTAGTGATTTATCAAAAAAAAATGCTTTACGTCAAATTTCCTATAATTTTCAATTG        8940

V  I  I  A  F  A  V  L  I  S  F  L  I  L  S  I  C  F  F  D-
TTATTATCGCATTTGCGGTATTGATTTCTTTTCTTATATTAAGTATTTGTTCTTCGATG        9000

V  A  R  N  N  S  S  F  L  F  A  I  I  I  C  G  F  F  Q  E
TTGCGAGGAATAATTCTTCATTCTTATTCGCGATTATTATTTGTGGTTTTTTTCAGGAAG      9060

V  D  N  L  F  S  G  A  L  K  G  F  E  K  F  N  V  S  C  F
TTGATAATTTATTTAGTGGTGCGCTAAAAGGTTTTGAAAAATTTAATGTATCATGTTTTT       9120

F  E  V  I  T  R  V  L  W  A  S  I  V  I  Y  G  I  Y  G  N
TTGAAGTAATTACAAGAGTGCTCTGGGCTTCTATAGTAATATATGGCATTTACGGAAATG      9180

A  L  L  Y  F  T  C  L  A  F  T  I  K  G  M  L  K  Y  I  L
CACTCTTATATTTTACATGTTTAGCCTTTACCATTAAAGGTATGCTAAAATATATTCTTG      9240

V  C  L  N  I  T  G  C  F  I  N  P  N  F  N  R  V  G  I  V
TATGTCTGAATATTACCGGTTGTTTCATCAATCCTAATTTTAATAGAGTTGGGATTGTTA      9300

N  L  L  N  E  S  K  W  M  F  L  Q  L  T  G  G  V  S  L  S
ATTTGTTAAATGAGTCAAAAATGGATGTTTCTTCAATTAACTGGTGGCGTCTCACTTAGTT    9360

L  F  D  R  L  V  I  P  L  I  L  S  V  S  K  L  A  S  Y  V
TGTTTGATAGGCTCGTAATACCATTGATTTTATCTGTCAGTAAACTGGCTTCTTATGTCC     9420

P  C  L  Q  L  A  Q  L  M  F  T  L  S  A  S  A  N  Q  I  L
CTTGCCTTCAACTAGCTCAATTGATGTTCACTCTTTCTGCGTCTGCAAATCAAATATTAC     9480

L  P  M  F  A  R  M  K  A  S  N  T  F  P  S  N  C  F  F  K
TACCAATGTTTGCTAGAATGAAAGCATCTAACACATTTCCCTCTAATTGTTTTTTTAAAA   9540

I  L  L  V  S  L  I  S  V  L  P  C  L  A  L  F  F  F  G  R
TTCTGCTTGTATCACTAATTTCTGTTTTGCCTTGTCTTGCGTTATTCTTTTTTGGTCGTG    9600

D  I  L  S  I  W  I  N  P  T  F  A  T  E  N  Y  K  L  M  Q
ATATATTATCAATATGGATAAACCCTACATTTGCAACTGAAAATTATAAATTAATGCAAA   9660

I  L  A  I  S  Y  I  L  L  S  M  M  T  S  F  H  F  L  L  L
TTTTAGCTATAAGTTACATTTTATTGTCAATGATGACATCTTTTCATTTCTTGTTATTAG     9720

G  I  G  K  S  K  L  V  A  N  L  N  L  V  A  G  L  A  L  A
GAATTGGTAAATCTAAGCTTGTTGCAAATTTAAATCTGGTTGCAGGGCTCGCACTTGCTG     9780

A  S  T  L  I  A  A  H  Y  G  L  Y  A  I  S  M  V  K  I  I
CTTCAACGTTAATCGCAGCTCATTATGGCCTTTATGCAATATCTATGGTAAAAATAATAT     9840

Y  P  A  F  Q  F  Y  Y  L  Y  V  A  F  V  Y  F  N  R  A  K
ATCCGGCTTTTCAATTTTATTACCTTTATGTAGCTTTTGTCTATTTTAATAGAGCGAAAA    9900
```

Start of orf9, End of orf8

```
     M  S  I  D  L  L  F  S  I  T  E  I  A  I  V  F  S  C  T  I
N  V  Y  *
ATGTCTATTGATTTACTTTTTTCAATTACTGAAATCGCAATTGTTTTTTCTTGCACTATT        9960

Y  I  F  T  Q  C  L  L  M  R  R  I  Y  L  D  K  S  I  L  I
TACATATTTACTCAATGTTTGTTAATGCGGAGGATCTATTTAGATAAAAGTATTTTAATT      10020

L  L  C  L  L  F  F  L  V  I  I  Q  L  P  E  L  N  V  N  G
CTTTTATGCTTGCTCTTTTTTTTAGTAATCATTCAACTTCCTGAGCTTAATGTAAACGGT      10080
```

Figure 7/8

```
         L  V  D  S  L  K  L  S  L  P  L  L  M  V  F  I  A  F  Q  K
         TTGGTCGATTCTTTAAAGTTATCACTGCCTTTATTGATGGTCTTTATCGCTTTTCAAAAA     10140

P  K  L  C  L  W  V  I  I  A  L  L  F  L  N  S  A  F  N  F
         CCGAAATTATGCTTGTGGGTTATTATTGCATTGTTGTTTTTGAACTCTGCATTTAATTTT     10200

L  Y  L  K  T  F  D  K  F  S  S  F  P  F  T  F  F  I  L  L
         TTATATTTAAAGACATTCGATAAGTTTAGCTCATTTCCTTTTACTTTTTTTATATTGCTG     10260

F  Y  L  F  R  L  G  I  G  N  L  P  V  Y  K  N  K  K  F  Y
         TTTTACTTGTTTAGATTGGGAATTGGTAATTTACCGGTTTATAAAAATAAAAAATTTTAC     10320

A  L  I  F  L  F  I  L  I  D  I  M  Q  S  L  L  I  N  Y  R
         GCGTTGATTTTTCTCTTTATATTAATAGACATAATGCAGTCATTGTTAATAAATTATAGG     10380

G  Q  I  L  Y  S  V  I  C  I  L  I  L  V  F  K  V  N  L  R
         GGGCAGATTTTATATTCCGTAATTTGCATCCTGATACTTGTGTTTAAAGTTAATTTAAGA     10440

K  K  I  P  Y  F  F  L  M  L  P  V  L  Y  V  I  I  M  A  Y
         AAAAAGATTCCATACTTTTTTTTAATGCTGCCAGTTTTATATGTAATTATTATGGCTTAT     10500

I  G  F  N  Y  F  N  K  G  V  T  F  F  E  P  T  A  S  N  I
         ATTGGTTTTAATTATTTCAATAAAGGCGTAACTTTTTTTGAACCTACAGCAAGTAATATT     10560

E  R  T  G  M  I  Y  Y  L  V  S  Q  L  G  D  Y  I  F  H  G
         GAACGTACGGGGATGATATATTATTTGGTTTCACAGCTTGGTGATTATATATTCCATGGT     10620

M  G  T  L  N  F  L  N  N  G  G  Q  Y  K  T  L  Y  G  L  P
         ATGGGGACATTAAATTTCTTAAATAACGGCGGACAATATAAGACGTTATATGGACTTCCA     10680

S  L  I  P  N  D  P  H  D  F  L  L  R  F  F  I  S  I  G  V
         TCATTAATTCCTAATGACCCTCATGATTTTTTATTACGGTTCTTTATAAGTATTGGTGTG     10740

I  G  A  L  V  Y  H  S  I  F  F  V  F  F  R  R  I  S  F  L
         ATAGGAGCATTGGTTTATCATTCTATATTTTTTGTTTTTTTTAGGAGAATATCTTTCTTA     10800

L  Y  E  R  N  A  P  F  I  V  V  S  C  L  L  L  L  Q  V  V
         TTATATGAGAGAAATGCTCCTTTCATTGTTGTAAGTTGTTTGTTACTGTTACAAGTTGTG     10860

L  I  Y  T  L  N  P  F  D  A  F  N  R  L  I  C  G  L  T  V
         TTAATTTATACATTAAACCCTTTTGATGCTTTTAATCGATTGATTTGCGGGCTTACAGTT     10920

Start of orf10                   End of orf9
         G  V  V  Y  G  F  A  K  I  R  *
                      M  D  L  Q  K  L  D  K  Y  T  C  N  G  N  L  D  A
         GGAGTTGTTTATGGATTTGCAAAAATTAGATAAGTATACCTGTAATGGAAATTTAGACGC     10980

P  L  V  S  I  I  I  A  T  Y  N  S  E  L  D  I  A  K  C  L
         TCCACTTGTTTCAATAATCATTGCAACTTATAATTCTGAACTTGATATAGCTAAGTGTTT     11040

Q  S  V  T  N  Q  S  Y  K  N  I  E  I  I  I  M  D  G  G  S
         GCAATCGGTAACTAATCAATCTTATAAGAATATTGAAATCATAATAATGGATGGAGGATC     11100

S  D  K  T  L  D  I  A  K  S  F  K  D  D  R  I  K  I  V  S
         TTCTGATAAAACGCTTGATATTGCAAAATCGTTTAAAGACGACCGAATAAAAATAGTTTC     11160

E  K  D  R  G  I  Y  D  A  W  N  K  A  V  D  L  S  I  G  D
         AGAGAAAGATCGTGGAATTTATGATGCCTGGAATAAAGCAGTTGATTTATCCATTGGTGA     11220

W  V  A  F  I  G  S  D  D  V  Y  Y  H  T  D  A  I  A  S  L
         TTGGGTAGCATTTATTGGTTCAGATGATGTTTACTATCATACAGATGCAATTGCTTCATT     11280

M  K  G  V  M  V  S  N  G  A  P  V  V  Y  G  R  T  A  H  E
         GATGAAGGGGGTTATGGTATCTAATGGCGCCCCTGTGGTTTATGGGAGGACAGCGCACGA     11340
```

Figure 7/9

```
             G  P  D  R  N  I  S  G  F  S  G  S  E  W  Y  N  L  T  G  F
         AGGTCCCGATAGGAACATATCTGGATTTTCAGGCAGTGAATGGTACAACCTAACAGGATT        11400

K  F  N  Y  Y  K  C  N  L  P  L  P  I  M  S  A  I  Y  S  R
         TAAGTTTAATTATTACAAATGTAATTTACCATTGCCCATTATGAGCGCAATATATTCTCG        11460

D  F  F  R  N  E  R  F  D  I  K  L  K  I  V  A  D  A  D  W
         TGATTTCTTCAGAAACGAACGTTTTGATATTAAATTAAAAATTGTTGCTGACGCTGATTG        11520

F  L  R  C  F  I  K  W  S  K  E  K  S  P  Y  F  I  N  D  T
         GTTTCTGAGATGTTTCATCAAATGGAGTAAAGAGAAGTCACCTTATTTATTAATGACAC        11580

T  P  I  V  R  M  G  Y  G  G  V  S  T  D  I  S  S  Q  V  K
         GACCCCTATTGTTAGAATGGGATATGGTGGGGTTTCGACTGATATTTCTTCTCAAGTTAA        11640

T  T  L  E  S  F  I  V  R  K  K  N  N  I  S  C  L  N  I  Q
         AACTACGCTAGAAAGTTTCATTGTACGCAAAAAGAATAATATATCCTGTTTAAACATACA        11700

L  I  L  R  Y  A  K  I  L  V  M  V  A  I  K  N  I  F  G  N
         GCTGATTCTTAGATATGCTAAAATTCTGGTGATGGTAGCGATCAAAAATATTTTTGGCAA        11760

N  V  Y  K  L  M  H  N  G  Y  H  S  L  K  K  I  K  N  K  I
         TAATGTTTATAAATTAATGCATAACGGGTATCATTCCCTAAAGAAAATCAAGAATAAAAT        11820

Start of orf11, End of orf10
             M  K  I  V  Y  I  I  T  G  L  T  C  G  G  A  E  H  L  M  T
             *
         ATGAAGATTGTTTATATAATAACCGGGCTTACTTGTGGTGGAGCCGAACACCTTATGACG        11880

Q  L  A  D  Q  M  F  I  R  G  H  D  V  N  I  I  C  L  T  G
         CAGTTAGCAGACCAAATGTTTATACGCGGGCATGATGTTAATATTATTTGTCTAACTGGT        11940

I  S  E  V  K  P  T  Q  N  I  N  I  H  Y  V  N  M  D  K  N
         ATATCTGAGGTAAAGCCAACACAAAATATTAATATTCATTATGTTAATATGGATAAAAAT        12000

F  R  S  F  F  R  A  L  F  Q  V  K  K  I  I  V  A  L  K  P
         TTTAGAAGCTTTTTTAGAGCTTTATTTCAAGTAAAAAAAATAATTGTCGCCTTAAAGCCA        12060

D  I  I  H  S  M  F  H  A  N  I  F  S  R  F  I  R  M  L
         GATATAATACATAGTCATATGTTTCATGCTAATATTTTTAGTCGTTTTATTAGGATGCTG        12120

I  P  A  V  P  L  I  C  T  A  H  N  K  N  E  G  G  N  A  R
         ATTCCAGCGGTGCCCCTGATATGTACCGCACACAACAAAAATGAAGGTGGCAATGCAAGG        12180

M  F  C  Y  R  L  S  D  F  L  A  S  I  T  T  N  V  S  K  E
         ATGTTTTGTTATCGACTGAGTGATTTTTTAGCTTCTATTACTACAAATGTAAGTAAAGAG        12240

A  V  Q  E  F  I  A  R  K  A  T  P  K  N  K  I  V  E  I  P
         GCTGTTCAAGAGTTTATAGCAAGAAAGGCTACACCTAAAAATAAAATAGTAGAGATTCCG        12300

N  F  I  N  T  N  K  F  D  F  D  I  N  V  R  K  K  T  R  D
         AATTTTATTAATACAAATAAATTTGATTTTGATATTAATGTCAGAAAGAAAACGCGAGAT        12360

A  F  N  L  K  D  S  T  A  V  L  L  A  V  G  R  L  V  E  A
         GCTTTTAATTTGAAAGACAGTACAGCAGTACTGCTCGCAGTAGGAAGACTTGTTGAAGCA        12420

K  D  Y  P  N  L  L  N  A  I  N  H  L  I  L  S  K  T  S  N
         AAAGACTATCCGAACTTATTAAATGCAATAAATCATTTGATTCTTTCAAAAACATCAAAT        12480

C  N  D  F  I  L  L  I  A  G  D  G  A  L  R  N  K  L  L  D
         TGTAATGATTTTATTTTGCTTATTGCTGGCGATGGCGCATTAAGAAATAAATTATTGGAT        12540

L  V  C  Q  L  N  L  V  D  K  V  F  F  L  G  Q  R  S  D  I
         TTGGTTTGTCAATTGAATCTTGTGGATAAAGTTTTCTTCTTGGGGCAAAGAAGTGATATT        12600
```

Figure 7/10

```
        K  E  L  M  C  A  A  D  L  F  V  L  S  S  E  W  E  G  F  G
     AAAGAATTAATGTGTGCTGCAGATCTTTTTGTTTTGAGTTCTGAGTGGGAAGGTTTTGGT      12660

L  V  V  A  E  A  M  A  C  E  R  P  V  V  A  T  D  S  G  G
     CTCGTTGTTGCAGAAGCTATGGCGTGTGAACGTCCCGTTGTTGCTACCGATTCTGGTGGA      12720

V  K  E  V  V  G  P  H  N  D  V  I  P  V  S  N  H  I  L  L
     GTTAAAGAAGTCGTTGGACCTCATAATGATGTTATCCCTGTCAGTAATCATATTCTGTTG      12780

A  E  K  I  A  E  T  L  K  I  D  D  N  A  R  K  I  I  G  M
     GCAGAGAAAATCGCTGAGACACTTAAAATAGATGATAACGCAAGAAAAATAATAGGTATG      12840

K  N  R  E  Y  I  V  S  N  F  S  I  K  T  I  V  S  E  W  E
     AAAAATAGAGAATATATTGTTTCCAATTTTTCAATTAAAACGATAGTGAGTGAGTGGGAG      12900

End of orf11
        R  L  Y  F  K  Y  S  K  R  N  N  I  I  D  *
     CGCTTATATTTTAAATATTCCAAGCGTAATAATATAATTGATTGAAAATATAAGTTTGTA      12960

CTCTGGATGCAATAGTTTCTCTATGCTGTTTTTTTACTGGCTCCGTATTTTTACTTATAG      13020

CTGGATTTTGTTATATATCAGTATTAATCTGTCTCAACTTCATCTAGACTACATTCAAGC      13080

Start of gnd
                                                M  S  K  Q  Q  I
     CGCGCATGCGTCGCGCGGTGACTACACCTGACAGGAGTATGTAATGTCCAAGCAACAGAT      13140

G  V  V  G  M  A  V  M  G  R  N  L  A  L  N  I  E  S  R  G
     CGGCGTCGTCGGTATGGCAGTGATGGGGCGCAACCTGGCGCTCAACATCGAAAGCCGCGG      13200

Y  T  V  S  I  F  N  R  S  R  E  K  T  E  E  V  V  A  E  N
     TTATACCGTCTCCATCTTCAACCGCTCCCGCGAGAAAACTGAAGAAGTTGTTGCCGAGAA      13260

P  D  K  K  L  V  P  Y  Y  T  V  K  E  F  V  E  S  L  E  T
     CCCGGATAAGAAACTGGTTCCTTATTACACGGTGAAAGAGTTCGTCGAGTCTCTTGAAAC      13320

P  R  R  I  L  L  M  V  K  A  G  A  G  T  D  A  A  I  D  S
     CCCACGTCGTATCCTGTTAATGGTAAAAGCAGGGGCGGGAACTGATGCTGCTATCGATTC      13380

L  K  P  Y  L  D  K  G  D  I  I  I  D  G  G  N  T  F  F  Q
     CCTGAAGCCGTATCTGGATAAAGGCGACATCATTATTGATGGTGGCAACACCTTCTTCCA      13440

D  T  I  R  R  N  R  E  L  S  A  E  G  F  N  F  I  G  T  G
     GGACACTATCCGTCGTAACCGTGAACTGTCCGCGGAAGGCTTTAACTTCATCGGTACCGG      13500

V  S  G  G  E  E  G  A  L  K  G  P  S  I  M  P  G  G  Q  K
     CGTGTCCGGCGGTGAAGAGGGCGCCCTGAAAGGCCCATCTATCATGCCAGGTGGCCAGAA      13560

E  A  Y  E  L  V  A  P  I  L  T  K  I  A  A  V  A  E  D  G
     AGAAGCGTATGAGCTGGTTGCGCCTATCCTGACCAAGATTGCTGCGGTTGCTGAAGATGG      13620

E  P  C  I  T  Y  I  G  A  D  G  A  G  H  Y  V  K  M  V  H
     CGAACCATGTATAACTTACATCGGTGCTGACGGTGCGGGTCACTACGTGAAGATGGTGCA      13680

N  G  I  E  Y  G  D  M  Q  L  I  A  E  A  Y  S  L  L  K  G
     CAACGGTATCGAATATGGCGATATGCAGCTGATTGCTGAAGCCTATTCTCTGCTTAAAGG      13740

G  L  N  L  S  N  E  E  L  A  T  T  F  T  E  W  N  E  G  E
     CGGCCTTAATCTGTCTAACGAAGAGCTGGCAACCACTTTTACCGAGTGGAATGAAGGCGA      13800

L  S  S  Y  L  I  D  I  T  K  D  I  F  T  K  K  D  E  E  G
     GCTAAGTAGCTACCTGATTGACATCACCAAAGACATCTTCACCAAAAAAGATGAAGAGGG      13860
```

Figure 7/11

```
     K  Y  L  V  D  V  I  L  D  E  A  A  N  K  G  T  G  K  W  T
TAAATACCTGGTTGATGTGATCCTGGACGAAGCTGCGAACAAAGGCACCGGTAAATGGAC        13920

S  Q  S  S  L  D  L  G  E  P  L  S  L  I  T  E  S  V  F  A
CAGCCAGAGCTCTCTGGATCTGGGTGAACCGCTGTCGCTGATCACCGAATCCGTATTCGC        13980

R  Y  I  S  S  L  K  D  Q  R  I  A  A  S  K  V  L  S  G  P
TCGCTACATCTCTTCTCTGAAAGACCAGCGCATTGCGGCATCTAAAGTGCTGTCTGGTCC        14040

Q  A  K  L  A  G  D  K  A  E  F  V  E  K  V  R  R  A  L  Y
GCAGGCTAAACTGGCTGGTGATAAAGCAGAGTTCGTTGAGAAAGTCCGTCGCGCGCTGTA        14100

L  G  K  I  V  S  Y  A  Q  G  F  S  Q  L  R  A  A  S  D  E
CCTGGGTAAAATCGTCTCTTATGCCCAAGGCTTCTCTCAACTGCGTGCCGCGTCTGACGA        14160

Y  N  W  D  L  N  Y  G  E  I  A  K  I  F  R  A  G  C  I  I
ATACAACTGGGATCTGAACTACGGCGAAATCGCGAAGATCTTCCGCGCGGGCTGCATCAT        14220

R  A  Q  F  L  Q  K  I  T  D  A  Y  A  E  N  K  G  I  A  N
TCGTGCGCAGTTCCTGCAGAAAATTACTGACGCGTATGCTGAAAACAAAGGCATTGCTAA        14280

L  L  L  A  P  Y  F  K  N  I  A  D  E  Y  Q  Q  A  L  R  D
CCTGTTGCTGGCTCCGTACTTCAAAAATATCGCTGATGAATATCAGCAAGCGCTGCGTGA        14340

V  V  A  Y  A  V  Q  N  G  I  P  V  P  T  F  S  A  A  V  A
TGTAGTGGCTTATGCTGTGCAGAACGGTATTCCGGTACCGACCTTCTCTGCAGCGGTAGC        14400

Y  Y  D  S  Y  R  S  A  V  L  P  A  N  L  I  Q  A  Q  R  D
CTACTACGACAGCTACCGTTCTGCGGTACTGCCGGCTAATCTGATTCAGGCACAGCGTGA        14460

Y  F  G  A  H  T  Y  K  R  T  D  K  E  G  V  F  H  T  G
TTACTTCGGTGCGCACACGTATAAACGCACTGATAAAGAAGGTGTGTTCCACACCG           14516
```

Figure 7/12

```
                GTAACCAAGGGCGGTACGTGCATAAATTTTAATGCTTATCAAAACTATTAGCATTAAAAA            60

Start of orf1
                        M  N  K  E  T  V  S  I  I  M  P  V  Y  N
                TATATAAGAAATTCTCAAATGAACAAAGAAACCGTTTCAATAATTATGCCCGTTTACAAT            120

G  A  K  T  I  I  S  S  V  E  S  I  I  H  Q  S  Y  Q  D  F
 GGGGCCAAAACTATAATCTCATCAGTAGAATCAATTATACATCAATCTTATCAAGATTTT                           180

V  L  Y  I  I  D  D  C  S  T  D  D  T  F  S  L  I  N  S  R
 GTTTTGTATATCATTGACGATTGTAGCACCGATGATACATTTTCATTAATCAACAGTCGA                           240

Y  K  N  N  Q  K  I  R  I  L  R  N  K  T  N  L  G  V  A  E
 TACAAAAACAATCAGAAAATAAGAATATTGCGTAACAAGACAAATTTAGGTGTTGCAGAA                           300

S  R  N  Y  G  I  E  M  A  T  G  K  Y  I  S  F  C  D  A  D
 AGTCGAAATTATGGAATAGAAATGGCCACGGGGAAATATATTTCTTTTTGTGATGCGGAT                           360

D  L  W  H  E  K  K  L  E  R  Q  I  E  V  L  N  N  E  C  V
 GATTTGTGGCACGAGAAAAAATTAGAGCGTCAAATCGAAGTGTTAAATAATGAATGTGTA                           420

D  V  V  C  S  N  Y  Y  V  I  D  N  N  R  N  I  V  G  E  V
 GATGTGGTATGTTCTAATTATTATGTTATAGATAACAATAGAAATATTGTTGGCGAAGTT                           480

N  A  P  H  V  I  N  Y  R  K  M  L  M  K  N  Y  I  G  N  L
 AATGCTCCTCATGTGATAAATTATAGAAAAATGCTCATGAAAAACTACATAGGGAATTTG                           540

T  G  I  Y  N  A  N  K  L  G  K  F  Y  Q  K  K  I  G  H  E
 ACAGGAATCTATAATGCCAACAAATTGGGTAAGTTTTATCAAAAAAAGATTGGTCACGAG                           600

D  Y  L  M  W  L  E  I  I  N  K  T  N  G  A  I  C  I  Q  D
 GATTATTTGATGTGGCTGGAAATAATTAATAAAACAAATGGTGCTATTTGTATTCAAGAT                           660

N  L  A  Y  Y  M  R  S  N  N  S  L  S  G  N  K  I  K  A  A
 AATCTGGCGTATTACATGCGTTCAAATAATTCACTATCGGGTAATAAAATTAAAGCTGCA                           720

K  W  T  W  S  I  Y  R  E  H  L  H  L  S  F  P  K  T  L  Y
 AAATGGACATGGAGTATATATAGAGAACATTTACATTTGTCCTTTCCAAAAACATTATAT                           780

Y  F  L  L  Y  A  S  N  G  V  M  K  K  I  T  H  S  L  L  R
 TATTTTTTATTATATGCTTCAAATGGAGTCATGAAAAAAATAACACATTCACTATTAAGG                           840

Start of orf2, End of orf1
 R  K  E  T  K  K  *
                        V  K  S  A  A  K  L  I  F  L  F  L  F  T
 AGAAAGGAGACTAAAAAGTGAAGTCAGCGGCTAAGTTGATTTTTTTATTCCTATTTACAC                           900

L  Y  S  L  Q  L  Y  G  V  I  I  D  D  R  I  T  N  F  D  T
 TTTATAGTCTCCAGTTGTATGGGGTTATCATAGATGATCGTATAACAAATTTTGATACAA                           960

K  V  L  T  S  I  I  I  I  F  Q  I  F  F  V  L  L  F  Y  L
 AGGTATTAACTAGTATTATAATTATATTTCAGATTTTTTTTGTTTTATTATTTTATCTAA                           1020

T  I  I  N  E  R  K  Q  Q  K  K  F  I  V  N  W  E  L  K  L
 CGATTATAAATGAAAGAAAACAGCAGAAAAAATTTATCGTGAACTGGGAGCTAAAGTTAA                           1080

I  L  V  F  L  F  V  T  I  E  I  A  A  V  V  L  F  L  K  E
 TACTCGTTTTCCTTTTTGTGACTATAGAAATTGCTGCTGTAGTTTTATTTCTTAAAGAAG                           1140

G  I  P  I  F  D  D  D  P  G  G  A  K  L  R  I  A  E  G  N
 GTATTCCTATATTTGATGATGATCCAGGGGGGGCTAAACTTAGAATAGCTGAAGGTAATG                           1200
```

Figure 8/1

```
         G  L  Y  I  R  Y  I  K  Y  F  G  N  I  V  V  F  A  L  I  I
         GACTTTACATTAGATATATTAAGTATTTTGGTAATATAGTTGTGTTTGCATTAATTATTC        1260

L  Y  D  E  H  K  F  K  Q  R  T  I  I  F  V  Y  F  T  T  I
         TTTATGATGAGCATAAATTCAAACAGAGGACCATCATATTTGTATATTTTACAACGATTG        1320

A  L  F  G  Y  R  S  E  L  V  L  L  I  L  Q  Y  I  L  I  T
         CTTTATTTGGTTATCGTTCTGAATTGGTGTTGCTCATTCTTCAATATATATTGATTACCA        1380

N  I  L  S  K  D  N  R  N  P  K  I  K  R  I  I  G  Y  F  L
         ATATCCTGTCAAAGGATAACCGTAATCCTAAAATAAAAAGAATAATAGGGTATTTTTTAT        1440

L  V  G  V  V  C  S  L  F  Y  L  S  L  G  Q  D  G  E  Q  N
         TGGTAGGGGTTGTATGCTCGTTGTTTTATCTAAGTTTAGGACAAGACGGAGAACAAAATG        1500

D  S  Y  N  N  M  L  R  I  I  N  R  L  T  I  E  Q  V  E  G
         ACTCATATAATAATATGTTAAGGATAATTAATAGGTTAACAATAGAGCAAGTTGAAGGTG        1560

V  P  Y  V  V  S  E  S  I  K  N  D  F  F  P  T  P  E  L  E
         TTCCATATGTTGTTTCTGAATCTATTAAGAACGATTTCTTTCCGACACCAGAGTTAGAAA        1620

K  E  L  K  A  I  I  N  R  I  Q  G  I  K  H  Q  D  L  F  Y
         AGGAATTAAAAGCAATAATAAATAGAATACAGGGAATAAAGCATCAAGACTTATTTTATG        1680

G  E  R  L  H  K  Q  V  F  G  D  M  G  A  N  F  L  S  V  T
         GAGAACGGTTACATAAACAAGTATTTGGAGACATGGGAGCAAATTTTTTATCAGTTACTA        1740

T  Y  G  A  E  L  L  V  F  F  G  F  L  C  V  F  I  I  P  L
         CGTATGGAGCAGAACTGTTAGTTTTTTTTGGTTTTCTCTGTGTATTCATTATCCCTTTAG        1800

G  I  Y  I  P  F  Y  L  L  K  R  M  K  K  T  H  S  S  I  N
         GGATATATATACCTTTTTATCTTTTAAAGAGAATGAAAAAAACCCATAGCTCGATAAATT        1860

C  A  F  Y  S  Y  I  I  M  I  L  L  Q  Y  L  V  A  G  N  A
         GCGCATTCTATTCATATATCATTATGATTTTATTGCAATACTTAGTGGCTGGGAATGCAT        1920

S  A  F  F  F  G  P  F  L  S  V  L  I  M  C  T  P  L  I  L
         CGGCCTTCTTTTTTGGTCCTTTTCTCTCCGTATTGATAATGTGTACTCCTCTGATCTTAT        1980

Start of orf3
                                       M  K  I  S  V  I  T  V  T  Y
         L  H  D  T  L  K  R  L  S  R  N  E  N  I  S  Y  N  C  D  L
         TGCATGATACGTTAAAGAGATTATCACGAAATGAAAATATCAGTTATAACTGTGACTTAT        2040

End of orf2
         N  N  A  E  G  L  E  K  T  L  S  S  L  S  I  L  K  I  K  P
         *
         AATAATGCTGAAGGGTTAGAAAAAACTTTAAGTAGTTTATCAATTTTAAAAATAAAACCT        2100

F  E  I  I  V  D  G  G  S  T  D  G  T  N  R  V  I  S  R
         TTTGAGATTATTATAGTTGATGGCGGCTCTACAGATGGAACGAATCGTGTCATTAGTAGA        2160

F  T  S  M  N  I  T  H  V  Y  E  K  D  E  G  I  Y  D  A  M
         TTTACTAGTATGAATATTACACATGTTTATGAAAAAGATGAAGGGATATATGATGCGATG        2220

N  K  G  R  M  L  A  K  G  D  L  I  H  Y  L  N  A  G  D  S
         AATAAGGGCCGAATGTTGGCCAAAGGCGACTTAATACATTATTTAAACGCCGGCGATAGC        2280

V  I  G  D  I  Y  K  N  I  K  E  P  C  L  I  K  V  G  L  F
         GTAATTGGAGATATATATAAAAATATCAAAGAGCCATGTTTGATTAAAGTTGGCCTTTTC        2340

E  N  D  K  L  L  G  F  S  S  I  T  H  S  N  T  G  Y  C  H
         GAAAATGATAAACTTCTGGGATTTTCTTCTATAACCCATTCAAATACAGGGTATTGTCAT        2400
```

Figure 8/2

```
        Q   G   V   I   F   P   K   N   H   S   E   Y   D   L   R   Y   K   I   C   A
        CAAGGGGTGATTTTCCCAAAGAATCATTCAGAATATGATCTAAGGTATAAAATATGTGCT         2460

D   Y   K   L   I   Q   E   V   F   P   E   G   L   R   S   L   S   L   I   T
        GATTATAAGCTTATTCAAGAGGTGTTTCCTGAAGGGTTAAGATCTCTATCTTTGATTACT         2520

S   G   Y   V   K   Y   D   M   G   G   V   S   S   K   K   R   I   L   R   D
        TCGGGTTATGTAAAATATGATATGGGGGGAGTATCTTCAAAAAAAGAATTTTAAGAGAT          2580

K   E   L   A   K   I   M   F   E   K   N   K   K   N   L   I   K   F   I   P
        AAAGAGCTTGCCAAAATTATGTTTGAAAAAAATAAAAAAAACCTTATTAAGTTTATTCCA         2640

I   S   I   I   K   I   L   F   P   E   R   L   R   R   V   L   R   K   M   Q
        ATTTCAATAATCAAAATTTTATTCCCTGAACGTTTAAGAAGAGTATTGCGGAAAATGCAA         2700

Start of orf4    End of orf3
        Y   I   C   L   T   L   F   F   M   K   N   S   S   P   Y   D   N   E   *
                                                        M   I   M   N   K   I
        TATATTTGTCTAACTTTATTCTTCATGAAGAATAGTTCACCATATGATAATGAATAAAAT        2760

K   K   I   L   K   F   C   T   L   K   K   Y   D   T   S   S   A   L   G   R
        CAAAAAAATACTTAAATTTTGCACTTTAAAAAAATATGATACATCAAGTGCTTTAGGTAG        2820

E   Q   E   R   Y   R   I   I   S   L   S   V   I   S   S   L   I   S   K   I
        AGAACAGGAAAGGTACAGGATTATATCCTTGTCTGTTATTTCAAGTTTGATTAGTAAAAT        2880

L   S   L   L   S   L   I   L   T   V   S   L   T   L   P   Y   L   G   Q   E
        ACTCTCACTACTTTCTCTTATATTAACTGTAAGTTTAACTTTACCTTATTTAGGACAAGA        2940

R   F   G   V   W   M   T   I   T   S   L   G   A   A   L   T   F   L   D   L
        GAGATTTGGTGTATGGATGACTATTACCAGTCTTGGTGCTGCTCTGACATTTTTGGACTT        3000

G   I   G   N   A   L   T   N   R   I   A   H   S   F   A   C   G   K   N   L
        AGGTATAGGAAATGCATTAACAAACAGGATCGCACATTCATTTGCGTGTGGCAAAAATTT        3060

K   M   S   R   Q   I   S   G   G   L   T   L   L   A   G   L   S   F   V   I
        AAAGATGAGTCGGCAAATTAGTGGTGGGCTCACTTTGCTGGCTGGATTATCGTTTGTCAT        3120

T   A   I   C   Y   I   T   S   G   M   I   D   W   Q   L   V   I   K   G   I
        AACTGCAATATGCTATATTACTTCTGGCATGATTGATTGGCAACTAGTAATAAAAGGTAT        3180

N   E   N   V   Y   A   E   L   Q   H   S   I   K   V   F   V   I   I   F   G
        AAACGAGAATGTGTATGCAGAGTTACAACACTCAATTAAAGTCTTTGTAATCATATTTGG        3240

L   G   I   Y   S   N   G   V   Q   K   V   Y   M   G   I   Q   K   A   Y   I
        ACTTGGAATTTATTCAAATGGTGTGCAAAAAGTTTATATGGGAATACAAAAAGCCTATAT        3300

S   N   I   V   N   A   I   F   I   L   L   S   I   I   T   L   V   I   S   S
        AAGTAATATTGTTAATGCCATATTTATATTGTTATCTATTATTACTCTAGTAATATCGTC        3360

K   L   H   A   G   L   P   V   L   I   V   S   T   L   G   I   Q   Y   I   S
        GAAACTACATGCGGGACTACCAGTTTTAATTGTCAGCACTCTTGGTATTCAATACATATC        3420

G   I   Y   L   T   I   N   L   I   I   K   R   L   I   K   F   T   K   V   N
        GGGAATCTATTTAACAATTAATCTTATTATAAAGCGATTAATAAAGTTTACAAAAGTTAA        3480

I   H   A   K   R   E   A   P   Y   L   I   L   N   G   F   F   F   F   I   L
        CATACATGCTAAAAGAGAAGCTCCATATTTGATATTAAACGGTTTTTTCTTTTTTATTTT        3540

Q   L   G   T   L   A   T   W   S   G   D   N   F   I   I   S   I   T   L   G
        ACAGTTAGGCACTCTGGCAACATGGAGTGGTGATAACTTTATAATATCTATAACATTGGG        3600
```

Figure 8/3

```
           V  T  Y  V  A  V  F  S  I  T  Q  R  L  F  Q  I  S  T  V  P
         TGTTACTTATGTTGCTGTTTTTAGCATTACACAGAGATTATTTCAAATATCTACGGTCCC     3660

L  T  I  Y  N  I  P  L  W  A  A  Y  A  D  A  H  A  R  N  D
         TCTTACGATTTATAACATCCCGTTATGGGCTGCTTATGCAGATGCTCATGCACGCAATGA     3720

T  Q  F  I  K  K  T  L  R  T  S  L  K  I  V  G  I  S  S  F
         TACTCAATTTATAAAAAAGACGCTCAGAACATCATTGAAAATAGTGGGTATTTCATCATT     3780

L  L  A  F  I  L  V  V  F  G  S  E  V  V  N  I  W  T  E  G
         CTTATTGGCCTTCATATTAGTAGTGTTCGGTAGTGAAGTCGTTAATATTTGGACAGAAGG     3840

K  I  Q  V  P  R  T  F  I  I  A  Y  A  L  W  S  V  I  D  A
         AAAGATTCAGGTACCTCGAACATTCATAATAGCTTATGCTTTATGGTCTGTTATTGATGC     3900

F  S  N  T  F  A  S  F  L  N  G  L  N  I  V  K  Q  Q  M  L
         TTTTTCGAATACATTTGCAAGCTTTTTAAATGGTTTGAACATAGTTAAACAACAAATGCT     3960

A  V  V  T  L  I  L  I  A  I  P  A  K  Y  I  I  V  S  H  F
         TGCTGTTGTAACATTGATATTGATCGCAATTCCAGCAAAATACATCATAGTTAGCCATTT     4020

G  L  T  V  M  L  Y  C  F  I  F  I  Y  I  V  N  Y  F  I  W
         TGGGTTAACTGTTATGTTGTACTGCTTCATTTTTATATATATTGTAAATTACTTTATATG     4080

Start of orf5, End of orf4
                                                              M  K  M
           Y  K  C  S  F  K  K  H  I  D  R  Q  L  N  I  R  G  *
         GTATAAATGTAGTTTTAAAAAACATATCGATAGACAGTTAAATATAAGAGGATGAAAATG     4140

K  Y  I  P  V  Y  Q  P  S  L  T  G  K  E  K  E  Y  V  N  E
         AAATATATACCAGTTTACCAACCGTCATTGACAGGAAAAGAAAAGAATATGTAAATGAA     4200

C  L  D  S  T  W  I  S  S  K  G  N  Y  I  Q  K  F  E  N  K
         TGTCTGGACTCAACGTGGATTTCATCAAAAGGAAACTATATTCAGAAGTTTGAAAATAAA     4260

F  A  E  Q  N  H  V  Q  Y  A  T  T  V  S  N  G  T  V  A  L
         TTTGCGGAACAAAACCATGTGCAATATGCAACTACTGTAAGTAATGGAACGGTTGCTCTT     4320

H  L  A  L  L  A  L  G  I  S  E  G  D  E  V  I  V  P  T  L
         CATTTAGCTTTGTTAGCGTTAGGTATATCGGAAGGAGATGAAGTTATTGTTCCAACACTG     4380

T  Y  I  A  S  V  N  A  I  K  Y  T  G  A  T  P  I  F  V  D
         ACATATATAGCATCAGTTAATGCTATAAAATACACAGGAGCCACCCCCATTTTCGTTGAT     4440

S  D  N  E  T  W  Q  M  S  V  S  D  I  E  Q  K  I  T  N  K
         TCAGATAATGAAACTTGGCAAATGTCTGTTAGTGACATAGAACAAAAAATCACTAATAAA     4500

T  K  A  I  M  C  V  H  L  Y  G  H  P  C  D  M  E  Q  I  V
         ACTAAAGCTATTATGTGTGTCCATTTATACGGACATCCATGTGATATGGAACAAATTGTA     4560

E  L  A  K  S  R  N  L  F  V  I  E  D  C  A  E  A  F  G  S
         GAACTGGCCAAAAGTAGAAATTTGTTTGTAATTGAAGATTGCGCTGAAGCCTTTGGTTCT     4620

K  Y  K  G  K  Y  V  G  T  F  G  D  I  S  T  F  S  F  F  G
         AAATATAAAGGTAAATATGTGGGAACATTTGGAGATATTTCTACTTTTAGCTTTTTTGGA     4680

N  K  T  I  T  T  G  E  G  G  M  V  V  T  N  D  K  T  L  Y
         AATAAAACTATTACTACAGGTGAAGGTGGAATGGTTGTCACGAATGACAAAACACTTTAT     4740

D  R  C  L  H  F  K  G  Q  G  L  A  V  H  R  Q  Y  W  H  D
         GACCGTTGTTTACATTTTAAAGGCCAAGGATTAGCTGTACATAGGCAATATTGGCATGAC     4800

V  I  G  Y  N  Y  R  M  T  N  I  C  A  A  I  G  L  A  Q  L
         GTTATAGGCTACAATTATAGGATGACAAATATCTGCGCTGCTATAGGATTAGCCCAGTTA     4860
```

Figure 8/4

```
          E  Q  A  D  D  F  I  S  R  K  R  E  I  A  D  I  Y  K  K  N
          GAACAAGCTGATGATTTTATATCACGAAAACGTGAAATTGCTGATATTTATAAAAAAAT          4920

I  N  S  L  V  Q  V  H  K  E  S  K  D  V  F  H  T  Y  W  M
          ATCAACAGTCTTGTACAAGTCCACAAGGAAAGTAAAGATGTTTTTCACACTTATTGGATG          4980

V  S  I  L  T  R  T  A  E  E  R  E  E  L  R  N  H  L  A  D
          GTCTCAATTCTAACTAGGACCGCAGAGGAAAGAGAGGAATTAAGGAATCACCTTGCAGAT          5040

K  L  I  E  T  R  P  V  F  Y  P  V  H  T  M  P  M  Y  S  E
          AAACTCATCGAAACAAGGCCAGTTTTTTACCCTGTCCACACGATGCCAATGTACTCGGAA          5100

K  Y  Q  K  H  P  I  A  E  D  L  G  W  R  G  I  N  L  P  S
          AAATATCAAAAGCACCCTATAGCTGAGGATCTTGGTTGGCGTGGAATTAATTTACCTAGT          5160

F  P  S  L  S  N  E  Q  V  I  Y  I  C  E  S  I  N  E  F  Y
          TTCCCCAGCCTATCGAATGAGCAAGTTATTTATATTTGTGAATCTATTAACGAATTTTAT          5220

End of orf5                  Start of orf6
          S  D  K  *                         M  K  I  A  L  N  S  D
          AGTGATAAATAGCCTAAAATATTGTAAAGGTCATTCATGAAAATTGCGTTGAATTCAGAT          5280

G  F  Y  E  W  G  G  G  I  D  F  I  K  Y  I  L  S  I  L  E
          GGATTTTACGAGTGGGGCGGTGGAATTGATTTTATTAAATATATTCTGTCAATATTAGAA          5340

T  K  P  E  I  C  I  D  I  L  L  P  R  N  D  I  H  S  L  I
          ACGAAACCAGAAATATGTATCGATATTCTTTTACCGAGAAATGATATACATTCTCTTATA          5400

R  E  K  A  F  P  F  K  S  I  L  K  A  I  L  K  R  E  R  P
          AGAGAAAAAGCATTTCCTTTTAAAAGTATATTAAAAGCAATTTTAAAGAGGGAAAGGCCT          5460

R  W  I  S  L  N  R  F  N  E  Q  Y  Y  R  D  A  F  T  Q  N
          CGATGGATTTCATTAAATAGATTTAATGAGCAATACTATAGAGATGCCTTTACACAAAAT          5520

N  I  E  T  N  L  T  F  I  K  S  K  S  S  A  F  Y  S  Y  F
          AATATAGAGACGAATCTTACCTTTATTAAAAGTAAGAGCTCTGCCTTTTATTCATATTTT          5580

D  S  S  D  C  D  V  I  L  P  C  M  R  V  P  S  G  N  L  N
          GATAGTAGCGATTGTGATGTTATTCTTCCTTGCATGCGTGTTCCTTCGGGAAATTTGAAT          5640

K  K  A  W  I  G  Y  I  Y  D  F  Q  H  C  Y  Y  P  S  F  F
          AAAAAAGCATGGATTGGTTATATTTATGACTTTCAACACTGTTACTATCCTTCATTTTTT          5700

S  K  R  E  I  D  Q  R  N  V  F  F  K  L  M  L  N  C  A  N
          AGTAAGCGAGAAATAGATCAAAGGAATGTGTTTTTTAAATTGATGCTCAATTGCGCTAAC          5760

N  I  I  V  N  A  H  S  V  I  T  D  A  N  K  Y  V  G  N  Y
          AATATTATTGTTAATGCACATTCAGTTATTACCGATGCAAATAAATATGTTGGGAATTAT          5820

S  A  K  L  H  S  L  P  F  S  P  C  P  Q  L  K  W  F  A  D
          TCTGCAAAACTACATTCTCTTCCATTTAGTCCATGCCCTCAATTAAAATGGTTCGCTGAT          5880

Y  S  G  N  I  A  K  Y  N  I  D  K  D  Y  F  I  I  C  N  Q
          TACTCTGGTAATATTGCCAAATATAATATTGACAAGGATTATTTTATAATTTGCAATCAA          5940

F  W  K  H  K  D  H  A  T  A  F  R  A  F  K  I  Y  T  E  Y
          TTTTGGAAACATAAAGATCATGCAACTGCTTTTAGGGCATTTAAAATTTATACTGAATAT          6000

N  P  D  V  Y  L  V  C  T  G  A  T  Q  D  Y  R  F  P  G  Y
          AATCCTGATGTTTATTTAGTATGCACGGGAGCTACTCAAGATTATCGATTCCCTGGATAT          6060

F  N  E  L  M  V  L  A  K  K  L  G  I  E  S  K  I  K  I  L
          TTTAATGAATTGATGGTTTTGGCAAAAAAGCTCGGAATTGAATCGAAAATTAAGATATTA          6120
```

Figure 8/5

```
           G  H  I  P  K  L  E  Q  I  E  L  I  K  N  C  I  A  V  I  Q
           GGGCATATACCTAAACTTGAACAAATTGAATTAATCAAAAATTGCATTGCTGTAATACAA          6180

P  T  L  F  E  G  G  P  G  G  G  V  T  F  D  A  I  A  L  G
           CCAACCTTATTTGAAGGCGGGCCTGGAGGGGGGGTAACATTTGACGCTATTGCATTAGGG          6240

K  K  V  I  L  S  D  I  D  V  N  K  E  V  N  C  G  D  V  Y
           AAAAAAGTTATACTATCTGACATAGATGTCAATAAAGAAGTTAATTGCGGTGATGTATAT          6300

F  F  Q  A  K  N  H  Y  S  L  N  D  A  M  V  K  A  D  E  S
           TTCTTTCAGGCAAAAAACCATTATTCATTAAATGACGCGATGGTAAAAGCTGATGAATCT          6360

K  I  F  Y  E  P  T  T  L  I  E  L  G  L  K  R  R  N  A  C
           AAAATTTTTTATGAACCTACAACTCTGATAGAATTGGGTCTCAAAAGACGCAATGCGTGT          6420

End of orf6
           A  D  F  L  L  D  V  V  K  Q  E  I  E  S  R  S   *
           GCAGATTTTCTTTTAGATGTTGTGAAACAAGAAATTGAATCCCGATCT TAATATATTCAA          6480

Start of orf7
                         M  T  K  V  A  L  I  T  G  V  T  G  Q  D  G  S  Y
           GAGGTATATAATGACTAAAGTCGCTCTTATTACAGGTGTAACTGGACAAGATGGATCTTA          6540

L  A  E  F  L  L  D  K  G  Y  E  V  H  G  I  K  R  R  A  S
           TCTAGCTGAGTTTTTGCTTGATAAAGGGTATGAAGTTCATGGTATCAAACGCCGAGCCTC          6600

S  F  N  T  E  R  I  D  H  I  Y  Q  D  P  H  G  S  N  P  N
           ATCTTTTAATACAGAACGCATAGACCATATTTATCAAGATCCACATGGTTCTAACCCAAA          6660

F  H  L  H  Y  G  D  L  T  D  S  S  N  L  T  R  I  L  K  E
           TTTTCACTTGCACTATGGAGATCTGACTGATTCATCTAACCTCACTAGAATTCTAAAGGA          6720

V  Q  P  D  E  V  Y  N  L  A  A  M  S  H  V  A  V  S  F  E
           GGTACAGCCAGATGAAGTATATAATTTAGCTGCTATGAGTCACGTAGCAGTTTCTTTTGA          6780

S  P  E  Y  T  A  D  V  D  A  I  G  T  L  R  L  L  E  A  I
           GTCTCCAGAATATACAGCCGATGTCGATGCAATTGGTACATTACGTTTACTGGAAGCAAT          6840

R  F  L  G  L  E  N  K  T  R  F  Y  Q  A  S  T  S  E  L  Y
           TCGCTTTTTAGGATTGGAAAACAAAACGCGTTTCTATCAAGCTTCAACCTCAGAATTATA          6900

G  L  V  Q  E  I  P  Q  K  E  S  T  P  F  Y  P  R  S  P  Y
           TGGACTTGTTCAGGAAATCCCTCAAAAAGAATCCACCCCTTTTTATCCTCGTTCCCCTTA          6960

A  V  A  K  L  Y  A  Y  W  I  T  V  N  Y  R  E  S  Y  G  I
           TGCAGTTGCAAAACTTTACGCATATTGGATCACGGTAAATTATCGAGAGTCATATGGTAT          7020

Y  A  C  N  G  I  L  F  N  H  E  S  P  R  R  G  E  T  F  V
           TTATGCATGTAATGGTATATTGTTCAATCATGAATCTCCACGCCGTGGAGAAACGTTTGT          7080

T  R  K  I  T  R  G  L  A  N  I  A  Q  G  L  E  S  C  L  Y
           AACAAGGAAAATTACTCGAGGACTTGCAAATATTGCACAAGGCTTGGAATCATGTTTGTA          7140

L  G  N  M  D  S  L  R  D  W  G  H  A  K  D  Y  V  R  M  Q
           TTTAGGGAATATGGATTCGTTACGAGATTGGGGACATGCAAAAGATTATGTTAGAATGCA          7200

W  L  M  L  Q  Q  E  Q  P  E  D  F  V  I  A  T  G  V  Q  Y
           ATGGTTGATGTTACAACAGGAGCAACCCGAAGATTTTGTGATTGCAACAGGAGTCCAATA          7260

S  V  R  Q  F  V  E  M  A  A  A  Q  L  G  I  K  M  S  F  V
           CTCAGTCCGTCAGTTTGTCGAAATGGCAGCAGCACAACTTGGTATTAAGATGAGCTTTGT          7320
```

Figure 8/6

```
              G   K   G   I   E   E   K   G   I   V   D   S   V   E   G   Q   D   A   P   G
            TGGTAAAGGAATCGAAGAAAAAGGCATTGTAGATTCGGTTGAAGGACAGGATGCTCCAGG        7380

V   K   P   G   D   V   I   V   A   V   D   P   R   Y   F   R   P   A   E   V
            TGTGAAACCAGGTGATGTCATTGTTGCTGTTGATCCTCGTTATTTCCGACCAGCTGAAGT        7440

D   T   L   L   G   D   P   S   K   A   N   L   K   L   G   W   R   P   E   I
            TGATACTTTGCTTGGAGATCCGAGCAAAGCTAATCTCAAACTTGGTTGGAGACCAGAAAT        7500

T   L   A   E   M   I   S   E   M   V   A   K   D   L   E   A   A   K   K   H
            TACTCTTGCTGAAATGATTTCTGAAATGGTTGCCAAAGATCTTGAAGCCGCTAAAAAACA        7560

Start of orf8, End of orf7
                                                           M   M   M   N   K
              S   L   L   K   S   H   G   F   S   V   S   L   A   L   E   *
            TTCTCTTTTAAAATCGCATGGTTTTTCTGTAAGCTTAGCTCTGGAATGATGATGAATAAG        7620

Q   R   I   F   I   A   G   H   Q   G   M   V   G   S   A   I   T   R   R   L
            CAACGTATTTTTATTGCTGGTCACCAAGGAATGGTTGGATCAGCTATTACCCGACGCCTC        7680

K   Q   R   D   D   V   E   L   V   L   R   T   R   D   E   L   N   L   L   D
            AAACAACGTGATGATGTTGAGTTGGTTTTACGTACTCGGGATGAATTGAACTTGTTGGAT        7740

S   S   A   V   L   D   F   F   S   S   Q   K   I   D   Q   V   Y   L   A   A
            AGTAGCGCTGTTTTGGATTTTTTTTCTTCACAGAAAATCGACCAGGTTTATTTGGCAGCA        7800

A   K   V   G   G   I   L   A   N   S   S   Y   P   A   D   F   I   Y   E   N
            GCAAAAGTCGGAGGTATTTTAGCTAACAGTTCTTATCCTGCCGATTTTATATATGAGAAT        7860

I   M   I   E   A   N   V   I   H   A   A   H   K   N   N   V   N   K   L   L
            ATAATGATAGAGGCGAATGTCATTCATGCTGCCCACAAAAATAATGTAAATAAACTGCTT        7920

F   L   G   S   S   C   I   Y   P   K   L   A   H   Q   P   I   M   E   D   E
            TTCCTCGGTTCGTCGTGTATTTATCCTAAGTTAGCACACCAACCGATTATGGAAGACGAA        7980

L   L   Q   G   K   L   E   P   T   N   E   P   Y   A   I   A   K   I   A   G
            TTATTACAAGGGAAACTTGAGCCAACAAATGAACCTTATGCTATCGCAAAAATTGCAGGT        8040

I   K   L   C   E   S   Y   N   R   Q   F   G   R   D   Y   R   S   V   M   P
            ATTAAATTATGTGAATCTTATAACCGTCAGTTTGGGCGTGATTACCGTTCAGTAATGCCA        8100

T   N   L   Y   G   P   N   D   N   F   H   P   S   N   S   H   V   I   P   A
            ACCAATCTTTATGGTCCAAATGACAATTTTCATCCAAGTAATTCTCATGTGATTCCGGCG        8160

L   L   R   R   F   H   D   A   V   E   N   N   S   P   N   V   V   V   W   G
            CTTTTGCGCCGCTTTCATGATGCTGTGGAAAACAATTCTCCGAATGTTGTTGTTTGGGGA        8220

S   G   T   P   K   R   E   F   L   H   V   D   D   M   A   S   A   S   I   Y
            AGTGGTACTCCAAAGCGTGAATTCTTACATGTAGATGATATGGCTTCTGCAAGCATTTAT        8280

V   M   E   M   P   Y   D   I   W   Q   K   N   T   K   V   M   L   S   H   I
            GTCATGGAGATGCCATACGATATATGGCAAAAAAATACTAAAGTAATGTTGTCTCATATC        8340

N   I   G   T   G   I   D   C   T   I   C   E   L   A   E   T   I   A   K   V
            AATATTGGAACAGGTATTGACTGCACGATTTGTGAGCTTGCGGAAACAATAGCAAAAGTT        8400

V   G   Y   K   G   H   I   T   F   D   T   T   K   P   D   G   A   P   R   K
            GTAGGTTATAAAGGGCATATTACGTTCGATACAACAAAGCCCGATGGAGCCCCTCGAAAA        8460

L   L   D   V   T   L   L   H   Q   L   G   W   N   H   K   I   T   L   H   K
            CTACTTGATGTAACGCTTCTTCATCAACTAGGTTGGAATCATAAAATTACCCTTCACAAG        8520
```

Figure 8/7

```
                                                                End of orf8
       G L E N T Y N W F L E N Q L Q Y R G *
       GGTCTTGAAAATACATACAACTGGTTTCTTGAAAACCAACTTCAATATCGGGGTAATAA        8580
Start of orf9
       M F L H S Q D F A T I V R S T P L I S I
       TGTTTTTACATTCCCAAGACTTTGCCACAATTGTAAGGTCTACTCCTCTTATTTCTATAG     8640

D L I V E N E F G E I L L G K R I N R P
       ATTTGATTGTGGAAAACGAGTTTGGCGAAATTTTGCTAGGAAAACGAATCAACCGCCCGG     8700

A Q G Y W F V P G G R V L K D E K L Q T
       CACAGGGCTATTGGTTCGTTCCTGGTGGTAGGGTGTTGAAAGATGAAAAATTGCAGACAG     8760

A F E R L T E I E L G I R L P L S V G K
       CCTTTGAACGATTGACAGAAATTGAACTAGGAATTCGTTTGCCTCTCTCTGTGGGTAAGT     8820

F Y G I W Q H F Y E D N S M G G D F S T
       TTTATGGTATCTGGCAGCACTTCTACGAAGACAATAGTATGGGGGGAGACTTTTCAACGC     8880

H Y I V I A F L L K L Q P N I L K L P K
       ATTATATAGTTATAGCATTCCTTCTTAAATTACAACCAAACATTTTGAAATTACCGAAGT     8940

S Q H N A Y C W L S R A K L I N D D D V
       CACAACATAATGCTTATTGCTGGCTATCGCGAGCAAAGCTGATAAATGATGACGATGTGC     9000

H Y N C R A Y F N N K T N D A I G L D N
       ATTATAATTGTCGCGCATATTTTAACAATAAAACAAATGATGCGATTGGCTTAGATAATA     9060

Start of orf10      End of orf9
                         M S D A P I I A V V M A G G T G S
       K D I I C L M R Q *
       AGGATATAATATGTCTGATGCGCCAATAATTGCTGTAGTTATGGCCGGTGGTACAGGCAG     9120

R L W P L S R E L Y P K Q F L Q L S G D
       TCGTCTTTGGCCACTTTCTCGTGAACTATATCCAAAGCAGTTTTTACAACTCTCTGGTGA     9180

N T L L Q T T L L R L S G L S C Q K P L
       TAACACCTTGTTACAAACGACTTTGCTACGACTTTCAGGCCTATCATGTCAAAAACCATT     9240

V I T N E Q H R F V V A E Q L R E I N K
       AGTGATAACAAATGAACAGCATCGCTTTGTTGTGGCTGAACAGTTAAGGGAAATAAATAA     9300

L N G N I I L E P C G R N T A P A I A I
       ATTAAATGGTAATATTATTCTAGAACCATGCGGGCGAAATACTGCACCAGCAATAGCGAT     9360

S A F H A L K R N P Q E D P L L L V L A
       ATCTGCGTTTCATGCGTTAAAACGTAATCCTCAGGAAGATCCATTGCTTCTAGTTCTTGC     9420

A D H V I A K E S V F C D A I K N A T P
       GGCAGACCACGTTATAGCTAAAGAAAGTGTTTTCTGTGATGCTATTAAAAATGCAACTCC     9480

I A N Q G K I V T F G I I P E Y A E T G
       CATCGCTAATCAAGGTAAAATTGTAACGTTTGGAATTATACCAGAATATGCTGAAACTGG     9540

Y G Y I E R G E L S V P L Q G H E N T G
       TTATGGGTATATTGAGAGAGGTGAACTATCTGTACCGCTTCAAGGGCATGAAAATACTGG     9600

F Y Y V N K F V E K P N R E T A E L Y M
       TTTTTATTATGTAAATAAGTTTGTCGAAAAGCCTAATCGTGAAACCGCAGAATTGTATAT     9660

T S G N H Y W N S G I F M F K A S V Y L
       GACTTCTGGTAATCACTATTGGAATAGTGGAATATTCATGTTTAAGGCATCTGTTTATCT     9720
```

Figure 8/8

```
         E   E   L   R   K   F   R   P   D   I   Y   N   V   C   E   Q   V   A   S   S
      TGAGGAATTGAGAAAATTTAGACCTGACATTTACAATGTTTGTGAACAGGTTGCCTCATC        9780

S   Y   I   D   L   D   F   I   R   L   S   K   E   Q   F   Q   D   C   P   A
      CTCATACATTGATCTAGATTTTATTCGATTATCAAAAGAACAATTTCAAGATTGTCCTGC        9840

E   S   I   D   F   A   V   M   E   K   T   E   K   C   V   V   C   P   V   D
      TGAATCTATTGATTTTGCTGTAATGGAAAAAACAGAAAAATGTGTTGTATGCCCTGTTGA        9900

I   G   W   S   D   V   G   S   W   Q   S   L   W   D   I   S   L   K   S   K
      TATTGGTTGGAGTGACGTTGGATCTTGGCAATCGTTATGGGACATTAGTCTAAAATCGAA        9960

T   G   D   V   C   K   G   D   I   L   T   Y   D   T   K   N   N   Y   I   Y
      AACAGGAGATGTATGTAAAGGTGATATATTAACCTATGATACTAAGAATAATTATATCTA       10020

S   E   S   A   L   V   A   A   I   G   I   E   D   M   V   I   V   Q   T   K
      CTCTGAGTCAGCGTTGGTAGCCGCCATTGGAATTGAAGATATGGTTATCGTGCAAACTAA       10080

D   A   V   L   V   S   K   K   S   D   V   Q   H   V   K   K   I   V   E   M
      AGATGCCGTTCTTGTGTCTAAAAAGAGTGATGTACAGCATGTAAAAAAAATAGTCGAAAT       10140

L   K   L   Q   Q   R   T   E   Y   I   S   H   R   E   V   F   R   P   W   G
      GCTTAAATTGCAGCAACGTACAGAGTATATTAGTCATCGTGAAGTTTTCCGACCATGGGG       10200

K   F   D   S   I   D   Q   G   E   R   Y   K   V   K   K   I   I   V   K   P
      AAAATTTGATTCGATTGACCAAGGTGAGCGATACAAAGTCAAGAAAATTATTGTGAAACC       10260

G   E   G   L   S   L   R   M   H   H   H   R   S   E   H   W   I   V   L   S
      TGGTGAGGGGCTTTCTTTAAGGATGCATCACCATCGTTCTGAACATTGGATCGTGCTTTC       10320

G   T   A   K   V   T   L   G   D   K   T   K   L   V   T   A   N   E   S   I
      TGGTACAGCAAAAGTAACCCTTGGCGATAAAACTAAACTAGTCACCGCAAATGAATCGAT       10380

Y   I   P   L   G   A   A   Y   S   L   E   N   P   G   I   I   P   L   N   L
      ATACATTCCCCTTGGCGCAGCGTATAGTCTTGAGAATCCGGGCATAATCCCTCTTAATCT       10440

I   E   V   S   S   G   D   Y   L   G   E   D   D   I   I   R   Q   K   E   R
      TATTGAAGTCAGTTCAGGGGATTATTTGGGAGAGGATGATATTATAAGACAGAAAGAACG       10500

End of orf10    Start of orf11
         Y   K   H   E   D   *     M   K   S   L   T   C   F   K   A   Y   D   I   R
      TTACAAACATGAAGAT TAACATATGAAATCTTTAACCTGCTTTAAAGCCTATGATATTCG       10560

G   K   L   G   E   E   L   N   E   D   I   A   W   R   I   G   R   A   Y   G
      CGGGAAATTAGGCGAAGAACTGAATGAAGATATTGCCTGGCGCATTGGGCGTGCCTATGG       10620

E   F   L   K   P   K   T   I   V   L   G   G   D   V   R   L   T   S   E   A
      CGAATTTCTCAAACCGAAAACCATTGTTTTAGGCGGTGATGTCCGCCTCACCAGCGAAGC       10680

L   K   L   A   K   G   L   Q   D   A   G   V   D   V   L   D   I   G
      GTTAAAACTGGCGCTTGCGAAAGGTTTACAGGATGCGGGCGTCGATGTGCTGGATATCGG       10740

M   S   G   T   E   E   I   Y   F   A   T   F   H   L   G   V   D   G   G   I
      TATGTCCGGCACCGAAGAGATCTATTTCGCCACGTTCCATCTCGGAGTGGATGGCGGCAT       10800

E   V   T   A   S   H   N   P   M   D   Y   N   G   M   K   L   V   R   E   G
      CGAAGTTACCGCCAGCCATAACCCGATGGATTACAACGGCATGAAGCTGGTGCGCGAAGG       10860

A   R   P   I   S   G   D   T   G   L   R   D   V   Q   R   L   A   E   A   N
      GGCTCGCCCGATCAGCGGTGATACCGGACTGCGCGATGTCCAGCGTCTGGCAGAAGCCAA       10920

D   F   P   P   V   D   E   T   K   R   G   R   Y   Q   Q   I   N   L   R   D
      TGACTTCCCTCCTGTCGATGAAACCAAACGTGGTCGCTATCAGCAAATCAATCTGCGTGA       10980
```

```
        A  Y  V  D  H  L  F  G  Y  I  N  V  K  N  L  T  P  L  K  L
    CGCTTACGTTGATCACCTGTTCGGTTATATCAACGTCAAAAACCTCACGCCGCTCAAGCT        11040

V  I  N  S  G  N  G  A  A  G  P  V  V  D  A  I  E  A  R  F
    GGTGATCAACTCCGGGAACGGCGCAGCGGGTCCGGTGGTGGACGCCATTGAAGCCCGATT        11100

K  A  L  G  A  P  V  E  L  I  K  V  H  N  T  P  D  G  N  F
    TAAAGCCCTCGGCGCACCGGTGGAATTAATCAAAGTACACAACACGCCGGACGGCAATTT        11160

P  N  G  I  P  N  P  L  L  P  E  C  R  D  D  T  R  N  A  V
    CCCCAACGGTATTCCTAACCCGCTGCTGCCGGAATGCCGCGACGACACCCGTAATGCGGT        11220

I  K  H  G  A  D  M  G  I  A  F  D  G  D  F  D  R  C  F  L
    CATCAAACACGGCGCGGATATGGGCATTGCCTTTGATGGCGATTTTGACCGCTGTTTCCT        11280

F  D  E  K  G  Q  F  I  E  G  Y  Y  I  V  G  L  L  A  E  A
    GTTTGACGAAAAAGGGCAGTTTATCGAGGGCTACTACATTGTCGGCCTGCTGGCAGAAGC        11340

F  L  E  K  N  P  G  A  K  I  I  H  D  P  R  L  S  W  N  T
    GTTCCTCGAAAAAAATCCCGGCGCGAAGATCATCCACGATCCACGTCTCTCCTGGAACAC        11400

V  D  V  V  T  A  A  G  G  T  P  V  M  S  K  T  G  H  A  F
    CGTTGATGTGGTGACTGCCGCAGGCGGCACCCCGGTAATGTCGAAAACCGGACACGCCTT        11460

I  K  E  R  M  R  K  E  D  A  I  Y  G  G  E  M  S  A  H  H
    TATTAAAGAACGTATGCGCAAGGAAGACGCCATCTACGGTGGCGAAATGAGCGCTCACCA        11520

Y  F  R  D  F  A  Y  C  D  S  G  M  I  P  W  L  L  V  A  E
    TTACTTCCGTGATTTCGCTTACTGCGACAGCGGCATGATCCCGTGGCTGCTGGTCGCCGA        11580

L  V  C  L  K  G  K  T  L  G  E  M  V  R  D  R  M  A  A  F
    ACTGGTGTGCCTGAAAGGAAAAACGCTGGGCGAAATGGTGCGCGACCGGATGGCGGCGTT        11640

P  A  S  G  E  I  N  S  K  L  A  Q  P  V  E  A  I  N  R  V
    TCCGGCAAGCGGTGAGATCAACAGCAAACTGGCGCAACCCGTTGAGGCAATTAATCGCGT        11700

E  Q  H  F  S  R  E  A  L  A  V  D  R  T  D  G  I  S  M  T
    GGAACAGCATTTTAGCCGCGAGGCGCTGGCGGTGGATCGCACCGATGGCATCAGCATGAC        11760

F  A  D  W  R  F  N  L  R  S  S  N  T  E  P  V  V  R  L  N
    CTTTGCCGACTGGCGCTTTAACCTGCGCTCCTCCAACACCGAACCGGTGGTGCGGTTGAA        11820

V  E  S  R  G  D  V  K  L  M  E  K  K  T  K  A  L  L  K  L
    TGTGGAATCACGCGGTGATGTAAAGCTAATGGAAAAGAAAACTAAAGCTCTTCTTAAATT        11880
            End of orf11
        L  S  E  *
    GCTAAGTGAGTGATTATTTACATTAATCATTAAGCGTATTTAAGATTATATTAAAGTAAT        11940

GTTATTGCGGTATATGATGAATATGTGGGCTTTTTTATGTATAACGACTATACCGCAACT        12000

Start of H-repeat
    TTATCTAGGAAAAGATTAATAGAAATAAAGTTTTGTACTGACCAATTTGCATTTCACGTC        12060

ACGATTGAGACGTTCCTTTGCTTAAGACATTTTTTCATCGCTTATGTAATAACAAATGTG        12120

CCTTATATAAAAAGGAGAACAAAATGGAACTTAAAATAATTGAGACAATAGATTTTTATT        12180

ATCCCTGTTTACGATATTATAGCCAAAGTTGTATCCTGCATCAGTCCTGCAATATTTCAC        12240

GAGTGCTTTGTTAACTGAATACATGTCTGCCATTTTCCAGATGATAACGACGTCATCGCA        12300

ATTGATGGTAAAACACTTCGGCACACTTATGACAAGAGTCGTCGCAGAGGAGTGGTTCAT        12360
```

```
GTCATTAGTGCGTTTCAGCAATGCACAGTCTGGTCCTCGGATAGATCAAGACGGATGAGA        12420

AACCTAATGCGTTCACAGTTATTCATGAACTTTCTAAAATGATGGGTATTAAAGGAAAAA        12480

TAATCATAACTGATGCGATGGCTTGCCAGAAAGATATTGCAGAGAAGATATAAAAACAGA        12540

GATGTGATTATTTATTCGCTGTAAAAGGAAATAAGAGTCGGCTTAATAGAGTCTTTGAGG        12600

AGATATTTACGCTGAAAGAATTAAATAATCCAAAACATGACAGTTACGCAATTAGTGAAA        12660

AGAGGCACGGCAGAGACGATGTCCGTCTTCATATTGTTTGAGATGCTCCTGATGAGCTTA        12720

TTGATTTCACGTTTGAATGGAAAGGGCTGCAGAATTTATGAATGGCAGTCCACTTTCTCT        12780

CAATAATAGCAGAGCAAAAGAAAGAATCCGAAATGACGATCAAATATTATATTAGATCTG        12840

CTGCTTTAACCGCAGAGAAGTTCGCCACAGTAAATCGAAATCACTGGCGCATGGAGAATA        12900

AGTTGCACAGTAGCCTGATGTGGTAATGAATGAAATCGACTATAATATAAGAAGGCGAGT        12960

TGCATTCGAATGATTTTCTAGAATGCGGCACATCGCTATTAATATCTGACAATGATAATG        13020

TATTCAAGGCAGGATTATCATGTAAGATGCGAAAAGCAGTCATGGACAGAAACTTCCTAG        13080
                                              End of the H-repeat
CGTCAGGCATTGCAGCGTGCGGGCTTTCATAATCTTGCAT TGGTTTTGATAAGATATTTC       13140
              Start of orf12
                   M  N  L  Y  G  I  F  G  A  G  S  Y  G  R  E
TTTGGAGATGGGAAAATGAATTTGTATGGTATTTTTGGTGCTGGAAGTTATGGTAGAGAA        13200

T  I  P  I  L  N  Q  Q  I  K  Q  E  C  G  S  D  Y  A  L  V
ACAATACCCATTCTAAATCAACAAATAAAGCAAGAATGTGGTTCTGACTATGCTCTGGTT        13260

F  V  D  D  V  L  A  G  K  K  V  N  G  F  E  V  L  S  T  N
TTTGTGGATGATGTTTTGGCAGGAAAGAAAGTTAATGGTTTTGAAGTGCTTTCAACCAAC       13320

C  F  L  K  A  P  Y  L  K  K  Y  F  N  V  A  I  A  N  D  K
TGCTTTCTAAAAGCCCCTTATTTAAAAAAGTATTTTAATGTTGCTATTGCTAATGATAAG       13380

I  R  Q  R  V  S  E  S  I  L  L  H  G  V  E  P  I  T  I  K
ATACGACAGAGAGTGTCTGAGTCAATATTATTACACGGGGTTGAACCAATAACTATAAAA       13440

H  P  N  S  V  V  Y  D  H  T  M  I  G  S  G  A  I  I  S  P
CATCCAAATAGCGTTGTTTATGATCATACTATGATAGGTAGTGGCGCTATTATTTCTCCC      13500

F  V  T  I  S  T  N  T  H  I  G  R  F  F  H  A  N  I  Y  S
TTTGTTACAATATCTACTAATACTCATATAGGGAGGTTTTTTCATGCAAACATATACTCA      13560

Y  V  A  H  D  C  Q  I  G  D  Y  V  T  F  A  P  G  A  K  C
TACGTTGCACATGATTGTCAAATAGGAGACTATGTTACATTTGCTCCTGGGGCTAAATGT      13620

N  G  Y  V  V  I  E  D  N  A  Y  I  G  S  G  A  V  I  K  Q
AATGGATATGTTGTTATTGAAGACAATGCATATATAGGCTCGGGTGCAGTAATTAAGCAG      13680

G  V  P  N  R  P  L  I  I  G  A  G  A  I  I  G  M  G  A  V
GGTGTTCCTAATCGCCCACTTATTATTGGCGCGGGAGCCATTATAGGTATGGGGGCTGTT      13740

V  T  K  S  V  P  A  G  I  T  V  C  G  N  P  A  R  E  M  K
GTCACTAAAAGTGTTCCTGCCGGTATAACTGTGTGCGGAAATCCAGCAAGAGAAATGAAA      13800
                End of orf12
  R  S  P  T  S  I  *
AGATCGCCAACATCTATT TAATGGGAATGCGAAAACACGTTCCAAATGGGACTAATGTTT     13860
```

Figure 8/11

```
AAAATATATATAATTTCGCTAATTTACTAAATTATGGCTTCTTTTTAAGCTATCCTTTAC    13920
TTAGTTATTACTGATACAGCATGAAATTTATAATACTCTGATACATTTTTATACGTTATT    13980
CAAGCCGCATATCTAGCGGTAACCCCTGACAGGAGTAAACAATG    14024
```

Figure 8/12

```
GTTGACAAATACCGACCGTATAATGAATCAAACGTTCTGGATTGGTATTTATCCAGGCTT      60

GACTACAGAGCATTTAGATTATGTCGTAAGTAAGTTTGAAGAATTTTTTGGTTTAAATTT     120
```

Start of abe

```
                   M  L  D  V  N  K  K  I  L  M  T  G  A  T
CTAATTTTTAGGATAGGATGCTTGATGTGAATAAGAAAATCCTAATGACTGGCGCTACTA     180

S  F  V  G  T  H  L  L  H  S  L  I  K  E  G  Y  S  I  I  A
GCTTTGTAGGTACCCATCTACTACATAGTCTCATAAAGGAAGGTTATAGTATTATTGCAT     240

L  K  R  P  I  T  E  P  T  I  I  N  T  L  I  E  W  L  N  I
TAAAGCGTCCTATAACCGAGCCAACGATTATCAATACCTTGATTGAATGGTTGAATATAC     300

Q  D  I  E  K  I  C  Q  S  S  M  N  I  H  A  I  V  H  I  A
AAGATATAGAAAAATATGTCAATCATCTATGAATATTCATGCGATTGTCCATATTGCAA     360

T  D  Y  G  R  N  R  T  P  I  S  E  Q  Y  K  C  N  V  L  L
CAGACTATGGTCGAAACAGAACCCCTATATCTGAACAATATAAATGTAATGTCCTATTAC     420

P  T  R  L  L  E  L  M  P  A  L  K  T  K  F  F  I  S  T  D
CAACAAGACTGCTTGAGTTAATGCCAGCGCTTAAAACGAAATTCTTTATTTCTACTGACT     480

S  F  F  G  K  Y  E  K  H  Y  G  Y  M  R  S  Y  M  A  S  K
CTTTTTTTGGGAAATATGAGAAGCACTATGGATATATGCGTTCTTACATGGCATCTAAAA     540

R  H  F  V  E  L  S  K  I  Y  V  E  E  H  P  D  V  C  F  I
GACATTTTGTAGAACTATCAAAATATACGTAGAGGAACATCCAGACGTTTGTTTTATAA     600

N  L  R  L  E  H  V  Y  G  E  R  D  K  A  G  K  I  I  P  Y
ATTTACGTTTAGAACATGTTTACGGTGAGAGGGATAAAGCAGGTAAAATAATCCCGTATG     660

V  I  K  K  M  K  N  N  E  D  I  D  C  T  I  A  R  Q  K  R
TTATCAAAAAAATGAAAAACAATGAAGATATTGATTGTACGATCGCCAGGCAGAAAAGAG     720

D  F  I  Y  I  D  D  V  V  S  A  Y  L  K  I  L  K  E  G  F
ATTTTATTTATATAGACGATGTTGTTTCGGCCTATTTGAAAATTTTAAAGGAGGGTTTTA     780

N  A  G  H  Y  D  V  E  V  G  T  G  K  S  I  E  L  K  E  V
ACGCTGGACACTATGATGTCGAGGTGGGGACTGGAAAATCGATAGAGCTAAAAGAAGTGT     840

F  E  I  I  K  K  E  T  H  S  S  S  K  I  N  Y  G  A  V  A
TTGAGATAATAAAAAAAGAAACGCATAGTAGTAGTAAGATAAATTATGGTGCAGTTGCGA     900

M  R  D  D  E  I  M  E  S  H  A  N  T  S  F  L  T  R  L  G
TGCGTGATGATGAGATTATGGAGTCACATGCAAATACCTCTTTCTTGACTCGATTAGGTT     960
```

End of abe    Start of wzx

```
                                                             M
 W  S  A  E  F  S  I  E  K  G  V  K  K  M  L  S  M  K  E  *
GGAGTGCCGAGTTTTCTATTGAGAAGGGTGTGAAAAAAATGTTGAGTATGAAAGAGTAAT    1020

N  R  I  I  R  M  L  G  V  D  K  A  I  R  Y  V  I  F  G  K
GAATCGTATTATTAGAATGTTAGGTGTAGATAAAGCAATTCGTTATGTTATTTTTGGTAA    1080

I  I  S  V  L  T  G  L  L  L  I  M  L  I  S  H  H  L  S  K
GATAATATCTGTATTAACGGGTTTACTGTTAATAATGTTAATATCACACCATTTATCTAA    1140

D  A  Q  G  Y  Y  Y  T  F  N  S  V  V  A  L  Q  I  I  F  E
AGACGCACAGGGCTATTATTATACATTTAATTCAGTAGTGGCACTACAGATAATATTTGA    1200
```

Figure 9/1

```
              L   G   L   S   T   V   I   I   Q   F   A   S   H   E   M   S   A   L   K   Y
           ATTGGGGCTATCAACGGTAATCATTCAATTCGCTAGCCATGAAATGTCAGCGTTAAAATA    1260

D   Y   S   E   R   D   I   I   G   E   S   K   N   K   Q   R   Y   L   S   L
           TGATTATTCTGAACGAGATATTATAGGTGAAAGTAAAAATAAGCAACGTTACCTATCGTT    1320

F   R   L   A   I   K   W   Y   A   V   I   A   L   L   I   I   L   I   V   G
           ATTTCGGTTGGCAATAAAATGGTATGCAGTAATAGCTTTGCTAATAATATTAATAGTCGG    1380

P   I   G   Y   V   F   F   T   Q   K   E   G   L   G   V   P   W   Q   G   A
           TCCCATCGGGTATGTTTTTTTTACGCAAAAAGAAGGCTTAGGTGTACCTTGGCAAGGGGC    1440

W   L   L   L   T   I   V   T   A   F   N   I   F   L   V   S   V   L   S   V
           ATGGTTATTATTAACAATAGTTACAGCTTTTAATATTTTTCTTGTTTCTGTACTTTCTGT    1500

A   E   G   S   G   L   I   T   D   V   N   K   M   R   M   Y   Q   S   L   L
           CGCTGAAGGGAGTGGGTTAATTACTGATGTGAATAAAATGAGAATGTATCAGTCGCTGTT    1560

A   G   I   L   A   V   S   L   L   I   S   G   F   G   L   Y   A   T   S   A
           AGCTGGTATATTGGCAGTAAGCTTACTTATTAGTGGCTTTGGACTATATGCTACGTCTGC    1620

I   A   I   S   G   T   I   I   F   S   I   F   S   Y   K   Y   F   K   K   I
           AATAGCTATTTCAGGGACTATCATATTCTCCATATTTTCATATAAGTATTTTAAAAAAAT    1680

F   L   Q   S   L   K   H   K   N   K   Y   T   E   G   G   I   S   W   V   N
           TTTCCTGCAATCTTTAAAGCATAAAAATAAATATACTGAAGGTGGTATTTCATGGGTTAA    1740

E   I   F   P   M   Q   W   R   I   A   L   S   W   M   S   G   Y   F   I   Y
           TGAAATATTTCCTATGCAATGGCGAATTGCTCTAAGTTGGATGTCAGGGTATTTTATTTA    1800

F   V   M   T   P   I   A   F   K   Y   F   G   A   I   Y   A   G   Q   L   G
           TTTTGTTATGACCCCCATTGCATTCAAATATTTCGGGGCTATATATGCAGGGCAGTTAGG    1860

M   S   L   T   C   N   M   V   M   A   T   G   L   A   W   I   S   T   K
           GATGTCTTTAACATTATGCAATATGGTAATGGCTACGGGCCTGGCTTGGATATCCACTAA    1920

Y   P   K   W   G   V   M   V   S   N   K   Q   L   A   E   L   S   K   S   F
           ATATCCAAAATGGGGAGTAATGGTTTCCAACAAACAGCTTGCGGAACTGAGTAAATCGTT    1980

K   S   A   V   M   Q   S   S   F   F   V   L   T   G   L   T   G   V   Y   I
           CAAAAGTGCAGTAATGCAATCATCCTTTTTTGTCTTGACAGGATTAACTGGTGTATACAT    2040

S   L   W   L   L   K   L   S   G   S   N   I   G   E   R   F   L   G   L   Q
           TTCATTATGGTTATTGAAATTATCTGGTTCAAACATTGGCGAGCGGTTTTTGGGATTGCA    2100

D   F   F   F   L   S   L   A   I   I   G   N   H   I   V   A   C   F   A   T
           GGATTTTTTCTTTTTATCTTTAGCAATTATTGGTAATCACATTGTAGCTTGCTTTGCAAC    2160

Y   I   R   A   H   K   T   E   K   M   T   L   A   S   C   I   M   A   L   L
           CTATATAAGAGCGCATAAAACTGAAAAAATGACATTGGCATCATGTATAATGGCTCTCTT    2220

T   I   T   T   M   L   F   V   A   Y   L   E   Y   S   R   F   Y   M   L   M
           GACTATAACTACAATGTTGTTTGTTGCATATTTAGAGTACTCGAGGTTCTACATGTTAAT    2280

Y   A   A   L   T   W   L   Y   F   V   P   Q   T   Y   I   I   F   K   R   F
                                                                    S   L   K   D
           GTATGCAGCACTAACGTGGTTATATTTTGTTCCTCAAACTTATATAATCTTTAAAAGATT    2340
```

Figure 9/2

```
                Start of wbaR   End of wzx
        K  S  S  Y  E  *
                        M  S  K  K  P  L  L  T  I  A  I  P  T  Y  N  R
CAAGAGTTCTTATGAGTAAAAAACCTCTTCTTACTATTGCTATTCCGACATATAACCGCT              2400

S  S  C  L  A  R  L  L  D  S  I  I  Q  Q  E  N  Y  C  H  D
CTTCATGTTTGGCTCGTTTACTTGATAGTATAATTCAACAGGAGAACTATTGTCATGATG              2460

E  L  E  V  I  V  C  D  N  A  S  T  D  E  T  A  R  I  A  K
AACTCGAGGTTATTGTTTGTGATAATGCTTCAACAGATGAAACAGCAAGAATAGCCAAGA              2520

S  G  L  D  K  I  R  N  S  T  Y  H  L  N  E  E  N  L  G  M
GTGGCTTAGATAAAATAAGAAATAGTACTTATCATCTAAATGAAGAAAACTTAGGAATGG              2580

D  G  N  F  Q  K  C  F  E  L  S  N  G  K  Y  L  W  M  I  G
ATGGTAACTTCCAGAAATGTTTTGAGTTATCAAATGGAAAATATCTTTGGATGATTGGCG              2640

D  D  D  L  I  V  K  N  G  I  S  K  V  F  S  I  L  K  S  R
ATGATGATCTAATAGTCAAAAATGGTATTTCGAAGGTTTTTTCGATATTAAAGTCCCGGC              2700

P  A  L  D  M  V  Y  V  N  S  A  A  K  T  E  L  N  Y  N  A
CTGCATTAGATATGGTGTATGTAAATTCAGCAGCAAAGACTGAGTTAAACTATAATGCTG              2760

D  V  R  T  S  F  Y  T  N  D  V  D  F  I  S  D  V  K  V  M
ATGTGAGGACGTCATTCTACACAAATGATGTAGATTTTATTTCAGACGTGAAAGTTATGT              2820

F  T  F  I  S  G  M  I  C  K  K  T  D  A  I  V  K  A  V  G
TCACGTTTATTTCTGGAATGATATGTAAGAAAACTGATGCAATTGTCAAAGCCGTTGGTA              2880

I  F  S  P  Q  T  T  G  K  Y  L  M  H  L  T  W  Q  L  P  L
TTTTCAGTCCGCAAACTACTGGAAAATATCTTATGCATTTAACATGGCAATTGCCATTAC              2940

L  K  Q  G  G  E  F  A  V  I  H  N  N  I  I  E  A  E  P  D
TTAAACAGGGTGGAGAGTTCGCAGTTATCCATAATAATATAATTGAGGCTGAGCCAGATA              3000

N  S  G  G  Y  H  L  Y  K  V  F  S  N  N  L  A  T  I  F  D
ATTCAGGTGGATATCATTTATATAAGGTTTTTTCTAATAATCTTGCGACAATCTTTGATG              3060

V  F  Y  P  R  E  H  R  V  S  K  R  V  R  A  S  A  C  L  F
TTTTTTATCCCAGAGAGCACCGTGTAAGTAAAAGAGTTCGCGCATCAGCATGTTTATTCT              3120

L  L  N  F  I  G  D  E  D  K  T  K  N  F  A  T  N  N  Y  L
TACTTAACTTCATAGGCGATGAAGATAAAACCAAAAATTTTGCTACAAATAATTATTTAA              3180

R  D  C  D  S  A  F  I  D  L  I  I  Y  K  Y  G  L  R  F  F
GAGATTGCGATAGTGCATTTATAGATTTAATTATATATAAATATGGGCTTAGGTTTTTCT              3240

Y  L  Y  P  K  T  V  P  L  F  R  K  I  K  Y  I  I  K  T  V
ATCTATATCCTAAAACTGTGCCTTTATTTAGAAAAATAAAATATATTATAAAGACGGTTT              3300

End of wbaR
 L  M  R  K  *
TAATGCGGAAATAAAAATTATTCAAGATGGTTTGCTGAAAACGACTTATAGGACTATCTA              3360

Start of wbaL
   M  F  V  Y  S  L  R  L  K  L  N  L  I  I  S  L  L  S  K  V
ATGTTTGTCTATAGTTTAAGATTAAAATTAAATCTTATCATATCATTATTGAGTAAAGTT              3420

R  R  K  S  K  A  K  F  L  V  L  L  S  G  Y  D  F  K  M  V
AGGCGGAAATCAAAAGCAAAGTTTCTTGTTCTGCTTAGCGGATATGATTTTAAAATGGTT              3480
```

Figure 9/3

```
          G   K   N   F   K   L   N   V   K   P   Y   S   A   K   N   N   T   S   S   K
          GGGAAGAATTTTAAATTGAATGTCAAACCTTACTCTGCAAAAAATAACACCTCTTCCAAA                      3540

W   G   S   M   R   V   G   D   N   C   W   I   E   A   V   Y   N   Y   G   D
          TGGGGTAGTATGCGGGTTGGTGATAACTGCTGGATTGAAGCTGTATATAATTATGGTGAT                      3600

E   K   F   E   P   Y   L   Y   I   G   D   R   I   C   L   S   D   N   V   H
          GAAAAATTTGAACCTTATTTGTACATAGGTGATCGTATATGTTTAAGTGATAATGTTCAT                      3660

I   S   C   V   S   C   L   I   L   E   N   D   I   L   I   G   S   K   V   Y
          ATTTCTTGCGTATCATGTTTAATTTTAGAAAACGATATATTAATTGGTAGCAAAGTTTAT                      3720

I   G   D   H   S   H   G   S   Y   K   V   C   S   P   K   I   E   P   P   A
          ATAGGCGATCATAGCCATGGCAGTTATAAAGTATGCAGTCCGAAAATAGAACCGCCAGCA                      3780

N   K   P   L   G   D   I   A   P   I   K   I   G   N   C   C   W   I   G   D
          AATAAGCCATTAGGTGATATTGCTCCTATTAAAATAGGTAATTGCTGCTGGATTGGAGAT                      3840

N   A   V   I   L   A   G   S   E   I   C   D   G   C   V   I   A   A   N   S
          AATGCAGTAATTCTGGCTGGTAGTGAAATTTGTGATGGCTGTGTAATCGCAGCTAATTCA                      3900

V   V   K   D   L   K   V   D   K   P   C   L   I   G   G   V   P   A   K   V
          GTCGTCAAGGATTTAAAAGTCGATAAGCCATGTTTAATTGGTGGGGTTCCTGCTAAAGTA                      3960
                               End of wbaL  Start of wbaQ
          I   K   V   F   *
                                      M   N   V   F   I   S   I   C   I   P   S   Y   N   R   A
          ATAAAGGTATTT TAAAATGAATGTTTTTATCAGTATTTGTATACCGTCTTATAATAGAGC                     4020

E   F   L   E   P   L   L   D   S   I   Y   N   Q   D   Y   C   L   K   N   N
          TGAGTTTTTAGAGCCACTACTGGATAGCATATATAATCAAGATTATTGTTTAAAGAATAA                      4080

D   F   E   V   I   V   C   E   D   K   S   P   Q   R   D   E   I   N   S   I
          TGATTTTGAGGTCATTGTTTGTGAAGATAAATCTCCACAGAGAGATGAGATAAACTCTAT                      4140

I   E   N   Y   K   A   K   N   N   K   Q   N   L   Y   V   N   F   N   E   D
          TATCGAAAACTATAAAGCAAAAAATAATAAACAAAATCTTTATGTTAATTTCAATGAAGA                      4200

N   L   G   Y   D   K   N   L   K   K   C   I   S   L   T   T   G   K   Y   C
          TAATTTAGGCTATGATAAGAATTTAAAAAAATGCATTAGTTTGACGACAGGTAAATATTG                      4260

M   I   M   G   N   D   D   L   L   A   D   G   A   L   S   K   I   V   K   V
          CATGATCATGGGCAACGATGATCTATTAGCAGATGGAGCGTTATCAAAAATAGTGAAAGT                      4320

L   K   A   N   P   E   I   V   L   A   T   R   A   Y   G   W   F   K   E   N
          TTTGAAGGCTAATCCTGAAATTGTATTGGCTACGCGAGCGTATGGTTGGTTTAAGGAAAA                      4380

P   N   E   L   C   D   T   V   R   H   L   T   D   D   T   L   F   Q   P   G
          TCCGAATGAGTTATGTGATACTGTTCGTCATTTAACAGACGATACTTTATTTCAGCCGGG                      4440

A   D   A   I   K   F   F   F   R   R   V   G   V   I   S   G   F   I   V   N
          GGCTGATGCCATTAAATTTTTCTTCCGTAGAGTTGGAGTTATTTCAGGCTTTATTGTCAA                      4500

A   E   K   A   K   K   L   S   S   D   L   F   D   G   R   L   Y   Y   Q   M
          TGCTGAAAAAGCAAAAAAACTATCGAGTGATTTATTTGATGGGCGTTTATATTATCAAAT                      4560

Y   L   A   G   M   L   M   A   E   G   Q   G   Y   Y   F   S   D   V   M   T
          GTACCTTGCTGGTATGCTAATGGCTGAAGGTCAGGGATACTATTTTAGCGACGTGATGAC                      4620
```

Figure 9/4

```
             L    S    R    D    T    E    A    P    D    F    G    N    A    G    T    E    K    G    V    F
ATTGTCGAGGGATACAGAGGCTCCTGACTTTGGTAACGCTGGAACTGAAAAAGGAGTTTT                                                      4680

T    P    G    G    Y    K    P    E    G    R    I    H    M    V    E    G    L    L    L    I
CACCCCGGGGGGGTATAAACCAGAGGGCCGTATACATATGGTTGAAGGCTTGTTGCTAAT                                                      4740

A    K    Y    I    E    D    T    T    K    I    D    G    V    Y    A    G    I    R    K    D
TGCAAAATATATAGAAGATACAACAAAAATTGATGGCGTTTATGCTGGAATTAGAAAAGA                                                      4800

L    A    N    Y    F    Y    P    Y    I    R    D    Q    L    D    L    P    L    Y    T    Y
CTTAGCGAACTATTTTTATCCTTATATTCGAGATCAACTCGACTTGCCTCTTTATACTTA                                                      4860

I    K    M    I    N    K    F    R    K    M    G    F    S    N    E    K    L    F    Y    V
TATTAAAATGATAAATAAATTTCGGAAAATGGGATTTTCAAATGAAAAGCTTTTCTATGT                                                      4920

H    A    F    L    G    Y    V    L    K    R    R    G    Y    D    A    L    I    K    Y    I
GCATGCCTTTTTAGGGTATGTACTAAAACGGAGGGGCTATGATGCTTTAATTAAATACAT                                                      4980
                                                              End of wbaQ
     R    S    K    K    G    G    T    P    R    L    G    I    *
TCGTAGCAAAAAAGGCGGTACTCCGCGTCTTGGTATTTAACCTCCACTTTCAAAAAATGT                                                      5040

TATGAATATACTTCTTGCTGCGATATTAGGCGTTAACTTATTTTCTCCATATATTAGTTC                                                      5100
              Start of wzy
                                M    L    P    F    P    P    G    A    I    L    R    D    V    L    N    V
GTGGATGGTGGGTATGCTGCCATTTCCACCAGGAGCAATCCTAAGGGATGTACTCAATGT                                                      5160

F    F    V    A    L    V    L    V    R    F    V    I    D    R    K    K    T    Y    F    P
ATTTTTTGTGGCGTTAGTGCTAGTTCGATTTGTCATTGATAGGAAAAAAACTTATTTCCC                                                      5220

L    V    F    T    I    F    S    W    S    A    V    I    L    W    V    I    A    L    T    I
GTTGGTTTTTACTATTTTTTCATGGTCGGCGGTAATACTATGGGTAATAGCGTTAACTAT                                                      5280

F    S    P    D    K    I    Q    A    I    M    G    G    R    S    Y    I    L    F    P    A
ATTCTCACCGGATAAAATTCAAGCAATTATGGGGGGGCGGAGTTATATTTTATTCCCGGC                                                      5340

V    F    I    A    L    V    I    L    K    V    S    Y    P    Q    S    L    N    I    E    K
AGTTTTTCATAGCATTAGTGATTTTAAAAGTATCATACCCGCAATCCTTAAATATTGAAA                                                      5400

I    V    C    Y    I    I    F    L    M    F    M    V    A    T    I    S    I    I    D    V
AATAGTTTGCTACATAATTTTTCTAATGTTTATGGTTGCGACAATATCTATTATTGATGT                                                      5460

L    M    N    G    E    F    I    K    L    L    G    Y    D    E    H    Y    A    G    E    Q
ACTAATGAATGGAGAGTTCATTAAATTGCTCGGATATGATGAGCATTATGCAGGAGAACA                                                      5520

L    N    L    I    N    S    Y    D    G    M    V    R    A    T    G    G    F    S    D    A
ATTAAACTTAATTAATAGCTATGATGGGATGGTCCGGGCTACAGGCGGTTTTAGTGATGC                                                      5580

L    N    F    G    Y    M    L    T    L    G    V    L    L    C    M    E    C    F    S    Q
TCTCAATTTTGGATATATGCTCACATTAGGTGTTTTGTTATGTATGGAGTGTTTTTCCCA                                                      5640

G    Y    K    R    L    L    M    L    I    I    S    F    V    L    F    I    A    I    C    M
AGGATATAAAGATTATTGATGCTTATTATTAGTTTTGTGCTATTTATAGCGATCTGCAT                                                       5700

S    L    T    R    G    A    I    L    V    A    A    L    I    Y    A    L    Y    I    I    S
GAGTCTTACTAGAGGAGCAATACTTGTTGCTGCGCTTATTTACGCACTTTATATAATTTC                                                     5760

N    R    K    M    L    F    C    G    I    T    L    F    V    I    I    I    P    V    L    A
AAATCGGAAGATGCTTTTTTGTGGAATAACTTTATTTGTAATAATTATACCCGTTTTAGC                                                     5820
```

Figure 9/5

```
        I   S   T   N   I   F   D   N   Y   T   E   Y   L   I   G   R   F   T   D   S
        AATTTCTACTAATATTTTTGACAACTATACAGAAATTTTGATCGGCAGGTTTACAGATTC         5880

S   Q   A   S   R   G   S   T   Q   G   R   I   D   M   A   I   N   S   L   N
        GTCTCAGGCATCGCGTGGATCTACACAGGGGCGGATAGATATGGCAATTAATTCATTAAA         5940

F   L   S   E   H   P   S   G   I   G   L   G   T   Q   G   S   G   N   M   L
        CTTCCTGTCAGAACATCCATCAGGTATAGGTCTGGGTACTCAAGGTTCAGGAAACATGCT         6000

S   V   K   D   N   R   L   N   T   D   N   Y   F   F   W   I   A   L   E   T
        TTCGGTAAAAGATAATAGGTTAAATACGGATAATTATTTTTTCTGGATCGCCCTTGAGAC         6060

G   I   I   G   L   I   I   N   I   I   Y   L   A   S   Q   F   Y   S   S   T
        TGGTATTATTGGCTTAATCATAAATATTATTTATCTGGCAAGTCAATTTTATTCTTCAAC         6120

L   L   N   R   I   Y   G   S   H   C   S   N   M   H   Y   R   L   Y   F   L
        TTTACTAAATAGAATATATGGCAGTCATTGTAGCAATATGCACTATAGATTATATTTTCT         6180

F   G   S   I   Y   F   I   S   A   A   L   S   S   A   P   S   S   S   T   F
        CTTTGGAAGTATATATTTTATAAGTGCAGCGTTAAGTTCAGCACCTTCGTCATCAACTTT         6240

S   I   Y   Y   W   T   V   L   A   L   I   P   F   L   K   L   T   N   R   R
        TTCTATATATTATTGGACAGTTTTAGCTTTGATTCCATTTTTAAAATTAACAAATAGACG         6300

End of wzy Start of wbaW
        C   T   R   *   M   N   N   K   K   V   L   M   D   I   S   W   S   N   K   G
        GTGCACGCGA TAATGAATAATAAAAAGGTTTTGATGGATATTAGTTGGTCTAATAAAGGG        6360

G   I   G   R   F   T   D   E   I   S   K   L   L   C   D   I   S   K   E   E
        GGGATTGGACGTTTTACTGATGAAATTTCTAAACTACTATGTGATATATCTAAGGAGGAA        6420

L   Y   R   K   C   A   S   P   L   A   P   L   G   L   A   V   N   I   F   L
        CTATATAGAAAATGTGCTTCTCCGCTGGCCCCATTAGGTTTAGCAGTCAATATTTTTCTG        6480

R   K   K   T   D   V   V   F   L   P   G   Y   I   P   P   L   F   C   S   K
        CGAAAGAAAACTGATGTGGTTTTTCTTCCTGGCTATATTCCACCACTTTTTTGTTCGAAA        6540

K   F   I   I   T   I   H   D   L   N   H   L   D   L   N   D   N   S   S   L
        AAGTTCATAATAACAATACATGATCTAAATCATCTGGATTTAAATGATAATTCCTCTCTT        6600

F   K   R   L   F   Y   N   F   I   I   K   R   G   C   R   K   A   Y   K   I
        TTTAAGAGGTTATTTTATAATTTTATAATAAAGCGCGGTTGTAGAAAAGCATATAAAATA        6660

F   T   V   S   N   F   S   K   E   R   I   V   A   W   S   G   V   N   P   N
        TTTACAGTTTCGAATTTTTCAAAAGAAAGAATAGTAGCATGGTCAGGTGTAAACCCTAAT        6720

K   I   V   T   V   Y   N   G   V   S   S   L   F   N   A   D   V   K   P   L
        AAAATAGTCACGGTATATAATGGGGTATCTAGTCTATTTAATGCCGATGTAAAACCATTG        6780

N   L   G   Y   K   Y   L   L   C   V   G   N   R   K   T   H   K   N   E   K
        AATTTAGGCTATAAATATTTGCTATGTGTAGGAAACAGAAAAACTCATAAGAATGAGAAG        6840

C   V   I   S   A   F   A   K   A   D   I   D   P   S   I   K   L   V   F   T
        TGTGTTATATCTGCCTTTGCCAAAGCAGATATTGATCCATCAATAAAACTCGTTTTTACT        6900

G   N   P   C   N   D   L   E   K   L   I   I   Q   H   G   L   S   E   R   V
        GGTAATCCTTGTAATGATTTAGAAAAACTAATAATACAACATGGTTTAAGTGAACGTGTA        6960
```

Figure 9/6

```
        K  F  F  G  F  V  S  E  K  D  L  P  S  L  Y  K  G  S  L  G
        AAGTTCTTTGGGTTCGTGTCTGAAAAAGATTTACCATCGTTATATAAGGGCTCGTTAGGA        7020

L  V  F  P  S  L  Y  E  G  F  G  L  P  V  V  E  G  M  A  C
        TTAGTTTTCCCTTCTTTATATGAAGGTTTTGGATTACCTGTAGTGGAGGGCATGGCCTGT        7080

G  I  P  V  L  T  S  L  T  S  S  L  P  E  V  A  G  D  A  A
        GGTATTCCTGTATTAACTTCTCTAACTTCATCATTGCCAGAGGTGGCTGGAGATGCAGCG        7140

I  L  V  D  P  L  S  E  D  A  I  T  K  G  I  S  R  L  I  N
        ATTCTTGTCGACCCTCTTTCGGAAGATGCTATTACTAAAGGAATTTCGAGGTTAATTAAT        7200

D  S  E  L  R  K  H  L  I  Q  K  G  L  L  R  A  K  R  F  N
        GATTCTGAACTTCGTAAGCATTTAATCCAAAAGGGGCTTTTGCGGGCAAAGAGGTTCAAT        7260

Start of wbaZ
        W  Q  N  V  V  S  E  I  E  M  V  L  T  E  A  C  D  G  N  K
                                                            M  E  I  N
        TGGCAAAACGTGGTTAGTGAGATTGAAATGGTACTGACAGAGGCATGTGATGGAAATAAA        7320
        End of wbaW
             *
        E  I  K  I  S  L  V  H  E  W  L  L  S  Y  A  G  S  E  Q  V
        TGAAATAAAAATATCTCTCGTTCATGAGTGGTTATTAAGTTATGCAGGCTCCGAACAGGT        7380

S  S  A  I  L  H  V  F  P  E  A  K  L  Y  S  V  V  D  F  L
        ATCATCTGCCATCCTGCATGTTTTTCCTGAAGCGAAGTTATATTCGGTGGTTGATTTTCT        7440

T  D  E  Q  R  R  H  F  L  G  K  Y  A  T  T  T  F  I  Q  N
        AACGGATGAACAAAGAAGACATTTTCTGGGGAAATATGCGACTACCACATTTATTCAAAA        7500

L  P  K  A  K  K  F  Y  Q  K  Y  L  P  L  M  P  L  A  I  E
        TTTACCTAAAGCTAAAAAATTTTACCAGAAATATTTACCACTAATGCCACTGGCTATTGA        7560

Q  L  D  L  S  D  A  N  I  I  I  S  S  A  H  S  V  A  K  G
        ACAACTTGATTTATCAGATGCTAATATCATCATTAGTAGCGCCCATTCCGTTGCAAAAGG        7620

V  I  S  G  P  D  Q  L  H  I  S  Y  V  H  S  P  I  R  Y  A
        TGTTATTTCCGGACCAGATCAGCTTCACATTAGCTATGTTCATTCTCCTATTCGATATGC        7680

W  D  L  Q  H  Q  Y  L  N  E  S  N  L  N  K  G  I  K  G  W
        GTGGGATTTACAGCATCAGTACCTTAATGAGTCTAACCTGAATAAAGGAATTAAAGGTTG        7740

L  A  K  W  L  L  H  K  I  R  I  W  D  S  R  T  A  N  G  V
        GTTAGCAAAATGGCTTCTTCACAAAATACGAATTTGGGATTCTCGAACCGCAAATGGGGT        7800

D  H  F  I  A  N  S  Q  Y  I  A  R  R  I  K  K  V  Y  R  R
        TGATCATTTTATAGCTAATTCTCAATATATCGCGCGTAGAATTAAAAAAGTATACAGACG        7860

E  A  S  V  I  Y  P  P  V  D  V  D  N  F  E  V  K  N  E  K
        TGAGGCTTCAGTTATATATCCGCCTGTAGATGTGGATAATTTTGAAGTAAAAAATGAAAA        7920

Q  D  Y  Y  F  T  A  S  R  M  V  P  Y  K  R  I  D  L  I  V
        GCAAGACTATTATTTCACAGCATCCCGTATGGTACCCTACAAACGTATTGATCTTATTGT        7980

E  A  F  S  K  M  P  E  K  K  L  V  V  I  G  D  G  P  E  M
        CGAAGCCTTTAGTAAAATGCCGGAAAAGAAATTAGTAGTTATTGGTGATGGACCGGAGAT        8040

K  K  I  K  S  K  A  T  D  N  I  K  L  L  G  Y  Q  S  F  P
        GAAAAAAATAAAGAGCAAGGCTACAGACAATATAAAATTGCTCGGTTATCAATCTTTTCC        8100
```

Figure 9/7

```
        V  L  K  E  Y  M  Q  S  A  R  A  F  V  F  A  A  E  E  D  F
      TGTTTTAAAAGAGTATATGCAGAGCGCCAGGGCGTTTGTTTTTGCAGCGGAAGAGGACTT      8160

G  I  I  P  V  E  A  Q  A  C  G  T  P  V  I  A  F  G  K  G
      TGGAATAATACCTGTCGAAGCTCAAGCTTGCGGTACCCCTGTTATTGCCTTTGGGAAGGG      8220

G  A  L  E  T  V  R  P  L  G  V  E  E  P  T  G  I  F  F  K
      TGGGGCCTTAGAAACCGTTCGCCCACTAGGTGTAGAGGAACCGACTGGCATTTTCTTCAA      8280

E  Q  N  I  A  S  L  H  E  A  V  S  E  F  E  K  N  A  S  F
      GGAACAGAATATTGCTTCTTTGCATGAAGCTGTTAGTGAATTTGAAAAAAATGCATCATT      8340

F  T  S  Q  A  C  R  K  N  A  E  K  F  S  R  S  R  F  E  Q
      TTTTACATCTCAGGCTTGTAGAAAAAATGCAGAAAAATTTTCTCGATCAAGATTTGAACA      8400

E  F  K  N  F  V  N  E  K  W  N  L  F  K  T  E  Q  I  I  K
      AGAATTTAAGAACTTTGTTAATGAAAAGTGGAATCTTTTCAAAACAGAACAGATTATTAA      8460

End of wbaZ Start of manC
                             M  S  K  L  I  P  V  I  M  A  G  G  I
        R  *
      ACGTTAATTATGGTTTATTGAATGTCTAAATTAATACCAGTAATAATGGCCGGTGGGATT      8520

G  S  R  L  W  P  L  S  R  E  E  H  P  K  Q  F  L  S  V  D
      GGTAGCCGTTTGTGGCCACTTTCACGTGAAGAGCATCCGAAACAGTTTTTAAGCGTAGAT      8580

G  E  L  S  M  L  Q  N  T  I  K  R  L  T  P  L  L  A  G  E
      GGTGAATTATCTATGCTGCAAAACACCATTAAAAGATTGACTCCTCTTTTGGCTGGAGAA      8640

P  L  V  I  C  N  D  S  H  R  F  L  V  A  E  Q  L  R  A  I
      CCTTTAGTCATTTGTAATGATAGTCACCGCTTCCTTGTCGCTGAACAACTTCGAGCTATA      8700

N  K  L  A  N  N  I  I  L  E  P  V  G  R  N  T  A  P  A  I
      AATAAACTAGCAAATAACATCATATTAGAGCCAGTGGGGCGTAATACAGCCCCAGCTATA      8760

A  L  A  A  F  C  S  L  Q  N  V  V  D  E  D  P  L  L  L  V
      GCGCTGGCCGCTTTTTGTTCACTTCAGAATGTCGTCGATGAAGACCCGCTTTTGCTTGTC      8820

L  A  A  D  H  V  I  R  D  E  K  V  F  L  K  A  I  N  H  A
      CTTGCTGCGGATCATGTCATCCGCGATGAGAAAGTGTTTCTTAAAGCTATCAATCACGCT      8880

E  F  F  A  T  Q  G  K  L  V  T  F  G  I  V  P  T  Q  A  E
      GAATTTTTTGCAACACAAGGTAAGCTAGTAACGTTTGGTATTGTACCCACACAGGCCGAA      8940

T  G  Y  G  Y  I  C  R  G  E  A  I  G  E  D  A  F  S  V  A
      ACTGGCTACGGTTATATTTGTAGAGGTGAAGCAATCGGGGAAGATGCTTTTTCTGTAGCC      9000

E  F  V  E  K  P  D  F  D  T  A  R  H  Y  V  E  S  E  K  Y
      GAATTTGTAGAGAAGCCTGATTTCGATACAGCGCGTCATTATGTAGAATCAGAGAAATAT      9060

Y  W  N  S  G  M  F  L  F  R  A  S  S  Y  L  Q  E  L  K  D
      TATTGGAACAGCGGTATGTTCCTATTTCGTGCAAGTAGTTACTTACAAGAATTAAAGGAT      9120

L  S  P  D  I  Y  Q  A  C  E  N  A  V  G  S  I  N  P  D  L
      CTGTCCCCCGATATTTACCAAGCATGTGAAAATGCGGTAGGGAGTATTAATCCTGATCTT      9180

D  F  I  R  I  D  K  E  A  F  A  M  C  P  S  D  S  I  D  Y
      GATTTTATCCGTATTGATAAAGAAGCATTCGCAATGTGCCCTAGTGATTCTATCGATTAT      9240
```

Figure 9/8

```
         A   V   M   E   H   T   R   H   A   V   V   V   P   M   N   A   G   W   S   D
        GCGGTAATGGAACATACTAGGCATGCAGTTGTCGTACCGATGAATGCCGGCTGGTCAGAT         9300

V   G   S   W   S   S   L   W   D   I   S   K   K   D   P   Q   R   N   V   L
        GTGGGGTCATGGTCTTCACTGTGGGATATTTCTAAGAAAGATCCACAACGTAATGTATTA         9360

H   G   D   I   F   A   Y   N   S   K   D   N   Y   I   Y   S   E   K   S   F
        CATGGCGATATTTTTGCATATAATAGTAAAGATAATTATATCTATTCTGAAAAATCGTTT         9420

I   S   T   I   G   V   N   N   L   V   I   V   Q   T   A   D   A   L   L   V
        ATTAGTACAATCGGAGTAAATAATTTAGTTATCGTGCAGACAGCAGATGCATTATTAGTA         9480

S   D   K   D   S   V   Q   D   V   K   K   V   V   D   Y   L   K   A   N   N
        TCTGATAAAGATTCAGTCCAGGATGTTAAAAAGTTGTTGATTATTTAAAAGCTAATAAT         9540

R   N   E   H   K   K   H   L   E   V   F   R   P   W   G   K   F   S   V   I
        AGAAACGAACATAAAAAACATTTAGAGGTTTTCCGACCGTGGGGAAAATTTAGCGTAATT         9600

H   S   G   D   N   Y   L   V   K   R   I   T   V   K   P   G   A   K   F   A
        CATAGTGGCGATAATTATTTAGTTAAAAGAATAACTGTTAAACCAGGCGCGAAGTTTGCT         9660

A   Q   M   H   L   H   R   A   E   H   W   I   V   V   S   G   T   A   C   I
        GCTCAGATGCATCTCCATCGTGCTGAGCATTGGATAGTGGTATCTGGTACTGCTTGTATT         9720

T   K   G   E   E   I   F   T   I   S   E   N   E   S   T   F   I   P   A   N
        ACTAAGGGGGAAGAAATTTTTACAATTTCGGAGAATGAATCAACATTTATACCTGCTAAT         9780

T   V   H   T   L   K   N   P   A   T   I   P   L   E   L   I   E   I   Q   S
        ACAGTTCATACGTTAAAAAACCCCGCGACTATTCCATTAGAACTAATAGAAATTCAATCT         9840

G   T   Y   L   A   E   D   D   I   I   R   L   E   K   H   S   G   Y   L   E
        GGCACCTATCTTGCGGAGGATGATATTATTCGCCTGGAGAAACATTCTGGATATCTGGAG         9900
          End of manC Start of manB
           *
                     M   K   N   I   Y   N   T   Y   D   V   I   N   K   S   G   I   N
        TAATGAATTGATGAAAAATATATATAATACTTACGATGTTATCAACAAATCTGGAATTAA         9960

F   G   T   S   G   A   R   G   L   V   T   D   F   T   P   E   V   C   A   R
        TTTTGGAACCAGTGGTGCCCGCGGCCTTGTTACCGATTTTACACCCGAAGTTTGCGCACG        10020

F   T   I   S   F   L   T   V   M   Q   Q   R   F   S   F   T   T   V   A   L
        ATTTACCATTTCCTTTTTTGACAGTAATGCAGCAAAGATTCTCATTTACAACGGTTGCGCT        10080

A   I   D   N   R   P   S   S   Y   A   M   A   Q   A   C   A   A   A   L   Q
        CGCAATTGATAATCGTCCAAGCAGTTACGCGATGGCTCAAGCTTGTGCCGCTGCTTTGCA        10140

E   K   G   I   K   T   V   Y   Y   G   V   I   P   T   P   A   L   A   H   Q
        AGAAAAAGGAATTAAAACCGTTTACTATGGCGTAATTCCAACACCTGCTTTAGCTCATCA        10200

S   I   S   D   K   V   P   A   I   M   V   T   G   S   H   I   P   F   D   R
        ATCAATTTCCGATAAAGTACCTGCAATCATGGTTACTGGCAGTCATATCCCTTTTGACCG        10260

N   G   L   K   F   Y   R   P   D   G   E   I   T   K   D   D   E   N   A   I
        TAATGGCCTGAAATTTTATAGACCAGATGGTGAAATTACTAAAGATGATGAGAATGCTAT        10320

I   H   V   D   A   S   F   M   Q   P   K   L   E   Q   L   T   I   S   T   I
        TATTCATGTTGATGCCTCATTTATGCAGCCTAAGCTTGAACAATTGACAATTTCCACAAT        10380
```

Figure 9/9

```
         A  A  R  N  Y  I  L  R  Y  T  S  L  F  P  M  P  F  L  K  N
        CGCTGCTAGAAATTATATTCTACGATATACCTCATTATTTCCAATGCCATTCTTGAAAAA   10440

K  R  I  G  I  Y  E  H  S  S  A  G  R  D  L  Y  K  T  L  F
        TAAGCGCATTGGAATTTATGAGCATTCTAGTGCGGGTCGTGATCTCTATAAGACGTTATT   10500

K  M  L  G  A  T  V  V  S  L  A  R  S  D  E  F  V  P  I  D
        CAAAATGTTGGGTGCTACAGTTGTTAGTTTAGCAAGGAGCGACGAATTTGTTCCTATTGA   10560

T  E  A  V  S  E  D  D  R  N  K  A  I  T  W  A  K  K  Y  Q
        TACTGAAGCTGTAAGTGAAGATGATAGAAATAAAGCAATCACATGGGCAAAAAAATATCA   10620

L  D  A  I  F  S  T  D  G  D  G  D  R  P  L  I  A  D  E  Y
        GTTAGATGCTATATTTTCAACTGATGGTGATGGAGATCGCCCTCTGATAGCTGACGAATA   10680

G  N  W  L  R  G  D  I  L  G  L  L  C  S  L  E  L  A  A  D
        TGGAAATTGGTTAAGAGGAGATATATTAGGCCTTCTGTGCTCTCTCGAATTAGCTGCTGA   10740

A  V  A  I  P  V  S  C  N  S  T  I  S  S  G  N  F  F  K  H
        TGCAGTCGCTATTCCTGTAAGCTGCAACAGTACAATCTCATCTGGTAACTTTTTTAAACA   10800

V  E  R  T  K  I  G  S  P  Y  V  I  A  A  F  A  K  L  S  A
        TGTGGAACGAACAAAGATTGGTTCACCCTATGTGATTGCAGCATTTGCTAAATTATCTGC   10860

N  Y  N  C  I  A  G  F  E  A  N  G  G  F  L  L  G  S  D  V
        AAACTATAATTGTATAGCTGGTTTTGAAGCGAATGGTGGCTTTCTGCTAGGTAGCGATGT   10920

Y  I  N  Q  R  L  L  K  A  L  P  T  R  D  A  L  L  P  A  I
        TTATATTAATCAGCGTTTACTTAAGGCATTACCAACACGTGATGCTTTATTACCTGCCAT   10980

M  L  L  F  G  S  K  D  K  S  I  S  E  L  V  K  K  L  P  A
        TATGCTTCTGTTTGGTAGCAAGGACAAAAGTATTAGTGAGCTTGTTAAAAAACTTCCTGC   11040

R  Y  T  Y  S  N  R  L  Q  D  I  S  V  K  T  S  M  S  L  I
        TCGCTATACCTATTCAAACAGATTACAGGATATAAGTGTTAAAACAAGTATGTCTTTAAT   11100

N  L  G  L  T  D  Q  E  D  F  L  Q  Y  I  G  F  N  K  H  H
        AAATCTTGGTCTGACAGATCAAGAGGATTTTTTGCAGTATATTGGTTTTAATAAACATCA   11160

I  L  H  S  D  V  T  D  G  F  R  I  T  I  D  N  N  N  I  I
        TATATTACATTCTGATGTTACTGATGGCTTTAGAATCACTATCGATAACAACAATATTAT   11220

H  L  R  P  S  G  N  A  P  E  L  R  C  Y  A  E  A  D  S  Q
        TCATTTACGACCTTCAGGCAATGCCCCTGAGTTGCGTTGCTATGCGGAGGCTGACTCGCA   11280

E  D  A  C  N  I  V  E  T  V  L  S  N  I  K  S  L  G  R
        AGAGGATGCATGTAATATTGTTGAAACTGTTCTCTCTAATATCAAAAGCAAACTGGGTAG   11340

End of manB
         A  *
        AGCTTAATGCTGTTGATAATAGAGCGTTTCTTTCCAGTAATACTTTGTCTGGTTATCTGG   11400

Start of wbaP
                                  M  D  R  F  D  N  K  Y  N  P  N  L
        TACCCAAGTTGAGGGTGAGAATTAAATGGATCGTTTTGATAATAAGTATAACCCAAATTT   11460

C  K  I  L  L  A  I  S  D  L  L  F  F  N  V  A  L  W  A  S
        ATGCAAAATATTATTGGCTATATCAGATTTACTGTTTTTTAATGTAGCCTTATGGGCATC   11520
```

Figure 9/10

```
    L  G  V  V  Y  L  I  F  D  E  V  Q  R  F  V  P  Q  E  Q  L
GTTAGGAGTTGTATATTTAATCTTTGATGAAGTTCAGCGATTTGTACCACAAGAGCAATT    11580

D  N  R  F  I  S  H  F  I  L  S  I  V  C  V  G  W  F  W  V
AGATAATCGATTTATATCACATTTTATTCTATCTATAGTATGCGTTGGATGGTTTTGGGT    11640

R  L  R  H  Y  T  Y  R  K  P  F  W  Y  E  L  K  E  V  I  R
TCGACTGCGTCACTATACATATCGAAAGCCATTCTGGTATGAGTTGAAAGAGGTTATTCG    11700

T  I  V  I  F  A  V  F  D  L  A  L  I  A  F  T  K  W  Q  F
TACTATCGTTATTTTTGCTGTGTTTGATTTGGCTTTAATTGCGTTTACAAAATGGCAGTT    11760

S  R  Y  V  W  V  F  C  W  T  F  A  I  I  L  V  P  F  F  R
TTCACGCTATGTCTGGGTGTTTTGTTGGACTTTTGCCATAATCCTGGTGCCTTTTTTTCG    11820

A  L  T  K  H  L  L  N  K  L  G  I  W  K  K  K  T  I  I  L
CGCACTTACAAAGCATTTATTGAACAAGCTAGGTATCTGGAAGAAAAAAACTATCATCCT    11880

G  S  G  Q  N  A  R  G  A  Y  S  A  L  Q  S  E  E  M  M  G
TGGGAGCGGACAGAATGCTCGTGGTGCATATTCTGCGCTGCAAAGTGAGGAGATGATGGG    11940

F  D  V  I  A  F  F  D  T  D  A  S  D  A  E  I  N  M  L  P
GTTTGATGTTATCGCTTTTTTTGATACGGATGCGTCAGATGCTGAAATAAATATGTTGCC    12000

V  I  K  D  T  E  T  I  W  D  L  N  R  T  G  D  V  H  Y  I
GGTGATAAAGGACACTGAGACTATTTGGGATTTAAATCGTACAGGTGATGTCCATTATAT    12060

L  A  Y  E  Y  T  E  L  E  K  T  H  F  W  L  R  E  L  S  K
CCTTGCTTATGAATACACCGAGTTGGAGAAAACACATTTTTGGCTACGTGAACTTTCAAA    12120

H  H  C  R  S  V  T  V  V  P  S  F  R  G  L  P  L  Y  N  T
ACATCATTGTCGTTCTGTTACTGTCGTCCCCTCGTTTAGAGGATTGCCATTATATAATAC    12180

D  M  S  F  I  F  S  H  E  V  M  L  L  R  I  Q  N  N  L  A
TGATATGTCTTTTATCTTTAGCCATGAAGTTATGTTATTAAGGATACAAAATAACTTGGC    12240

K  R  S  S  R  F  L  K  R  T  F  D  I  V  C  S  I  M  I  L
TAAAAGGTCGTCCCGTTTTCTCAAACGGACATTTGATATTGTTTGTTCAATAATGATTCT    12300

I  I  A  S  P  L  M  I  Y  L  W  Y  K  V  T  R  D  G  G  P
TATAATTGCATCACCACTTATGATTTATCTGTGGTATAAAGTTACTCGAGATGGTGGTCC    12360

A  I  Y  G  H  Q  R  V  G  R  H  G  K  L  F  P  C  Y  K  F
GGCTATTTATGGTCACCAGCGAGTAGGTCGGCATGGAAAACTTTTTCCATGCTACAAATT    12420

R  S  M  V  M  N  S
TCGTTCTATGGTTATGAATTC    12441
```

Figure 9/11

| | |
|---|---|
| GAATTCGGGAGGCGCAATGAAAGTCAGCTTTTTTCTGCTGAAATTTCCACTCTCATCGGA | 60 |
| AACCTTTGTGCTGAATCAGATTACTGCGTTTATTGATATGGGCCATGAGGTGGAGATTGT | 120 |
| CGCGTTACAAAAAGGCGATACCCAACATACTCACGCCGCCTGGGAGAAGTATGGCCTGGC | 180 |
| GGCGAAAACCCGCTGGTTACAGGATGAGCCCCAGGGACGGCTGGCGAAACTGCGCTACCG | 240 |
| GGCATGTAAAACGCTGCCGGGGCTGCATCGGGCGGCGACCTGGAAAGCGCTCAATTTTAC | 300 |
| CCGCTATGGCGATGAATCACGCAATTTGATCCTTTCCGCGATTTGCGCGCAGGTGAGCCA | 360 |
| GCCTTTTGTGGCGGATGTGTTTATCGCACACTTTGGTCCGGCGGGCGTGACGGCGGCCAA | 420 |
| ACTACGCGAACTGGGCGTGCTTCGCGGCAAAATCGCGACTATTTTCCACGGGATTGATAT | 480 |
| CTCTAGTCGTGAGGTGCTCAGTCATTACACGCCGGAGTATCAGCAGTTGTTTCGTCGTGG | 540 |
| CGATCTGATGCTGCCCATCAGCGATCTGTGGGCCGGTCGCCTGAAAAGTATGGGCTGTCC | 600 |
| GCCGGAAAAGATTGCCGTTTCGCGCATGGGCGTCGACATGACGCGTTTTACCCATCGTTC | 660 |
| GGTGAAAGCGCCAGGGATGCCGCTGGAGATGATTTCCGTCGCGCGCCTGACAGAAAAAAA | 720 |
| AGGCCTGCATGTGGCGATTGAAGCCTGTCGGCAACTGAAAGCACAGGGCGTGGCGTTTCG | 780 |
| CTACCGCATTCTGGGGATTGGCCCGTGGGAACGTCGGCTGCGCACGCTCATCGAGCAGTA | 840 |
| TCAGCTAGAGGATGTCATTGAGATGCCGGGGTTTAAACCGAGCCATGAAGTGAAGGCGAT | 900 |
| GCTGGATGACGCCGATGTTTTTTTGCTGCCGTCGATTACCGGTACGGATGGCGATATGGA | 960 |
| AGGTATTCCGGTAGCGCTGATGGAGGCGATGGCGGTAGGGATTCCCGTGGTATCTACCGT | 1020 |
| GCATAGCGGTATTCCGGAACTGGTGGAGGCCGGCAAATCCGGCTGGCTGGTGCCGGAAAA | 1080 |
| CGATGCGCAGGCGCTGGCGGCCCGACTCGCTGAGTTCAGCCGGATTGACCACGACACGCT | 1140 |
| GGAGTCGGTGATCACGCGCGCCCGTGAAAAAGTGGCGCAAGATTTTAATCAGCAGGCGAT | 1200 |
| TAATCGCCAGTTAGCCAGCCTGCTACAAACGATATAAACGAGGTGGTATGCCCGCGACTA | 1260 |
| AATTCTCCCGACGTACCCTCCTGACGGCAGGTTCTGCGCTTGCTGTTCTTCCTTTTCTGC | 1320 |
| GCGCCTTGCCGGTACAGGCGCGTGAACCTCGCGAGACCGTCGATATTAAGGATTATCCGG | 1380 |
| CGGATGACGGTATCGCCTCGTTCAAACAGGCCTTCGCCGACGGACAGACCGTGGTCGTAC | 1440 |
| CGCCAGGATGGGTGTGTGAAAATATCAATGCGGCGATAACGATTCCGGCGGGAAAAACGC | 1500 |
| TGCGGGTACAGGGCGCGGTGCGTGGGAATGGCCGGGGACGGTTTATTTTGCAGGACGGGT | 1560 |
| GTCAGGTGGTGGGGGAGCAGGGCGGCAGTCTGCACAATGTGACGCTGGATGTTCGCGGGT | 1620 |
| CGGACTGTGTGATTAAAGGCGTGGCGATGAGCGGCTTTGGCCCCGTCGCGCAAATTTTCA | 1680 |
| TCGGTGGTAAGGAACCGCAGGTGATGCGTAATCTCATTATCGATGACATCACCGTTACCC | 1740 |
| ACGCCAACTACGCCATTCTCCGCCAGGGATTTCATAACCAAATGGATGGCGCGCGGATTA | 1800 |
| CGCATAGCCGCTTTAGCGATTTACAGGGGGACGCCATTGAGTGGAATGTCGCGATTCACG | 1860 |
| ACCGCGACATCCTGATTTCCGATCATGTCATCGAACGCATTAATTGTACCAATGGCAAAA | 1920 |
| TCAACTGGGGGATCGGCATCGGGCTGGCGGGTAGCACCTATGACAACAGTTATCCTGAAG | 1980 |

Figure 10/1

```
ACCAGGCAGTAAAAAACTTTGTGGTGGCCAATATTACCGGATCTGATTGCCGACAGCTTG      2040
TGCACGTAGAAAATGGCAAACATTTCGTCATTCGCAATGTCAAAGCCAAAAACATCACGC      2100
CCGGTTTCAGTAAAAATGCGGGTATTGATAACGCAACGATCGCAATTTATGGCTGTGATA      2160
ATTTCGTCATTGATAATATTGATATGACGAATAGTGCCGGATGCTCATCGGCTATGGCG      2220
TCGTTAAAGGAAAATACCTGTCAATTCCGCAAAACTTTAAATTAAACGCTATTCGGTTGG      2280
ATAATCGCCAGGTTGCTTATAAATTACGCGGCATTCAAATTTCCTCCGGCAACACCCCCT      2340
CTTTTGTCGCCATCACCAATGTACGGATGACGCGTGCTACGCTGGAACTGCATAATCAAC      2400
CGCAGCACCTCTTTCTGCGCAATATCAACGTGATGCAAACTTCAGCGATTGGCCCGGCGT      2460
TAAAAATGCATTTCGATTTGCGTAAAGATGTACGTGGTCAATTTATGGCCCGCCAGGACA     2520
CGCTGCTTTCCCTCGCTAATGTTCATGCCATCAATGAAAACGGGCAGAGTTCCGTGGATA     2580
TCGACAGGATTAATCACCAAACCGTGAATGTCGAAGCAGTGAATTTTTCGCTGCCGAAGC     2640
GGGGAGGGTAAGTACCGCTATTTTTACGAAAATTCCTGGGAAAAGTTGTTCATACTTAA      2700
TGTTATGGTGCCGACTAAGACGTAATGTAGAGCGTGCCATCATTATCCCTGGCAGCAGAG     2760
TAATTCATGCTGGCGAAAACAAGCTAAAGAGCTATAATTCAGCAACCATTTTACAGGTGG     2820
AAGAAACAATGATGAATTTGAAAGCAGTTATACCGGTAGCGGGTTTGGGTATGCATATGT     2880
TGCCTGCCACCAAGGCAATCCCAAAAGAGATGCTACCGATCGTCGACAAGCCAATGATTC     2940
AGTACATTGTCGATGAGATTGTGGCTGCAGGGATCAAAGAAATCGTGCTGGTGACTCACG     3000
CGTCTAAAAACGCCGTTGAGAACCACTTCGACACCTCTTATGAACTTGAATCACTTCTTG     3060
AGCAGCGCGTTAAGCGTCAGCTTTTGGCGGAAGTGCAATCTATCTGCCCACCGGGCGTGA     3120
CGATTATGAACGTTCGCCAGGCGCAGCCGTTAGGGCTGGGGCATTCTATTCTGTGCGCGC     3180
GTCCGGTCGTGGGCGATAACCCTTTCATTGTGGTACTCCCGGATATTATTATCGATGATG     3240
CTACCGCCGATCCGCTGCGCTATAACCTTGCGGCGATGGTGGCGCGTTTCAATGAAACGG     3300
GTCGCAGCCAGGTGCTGGCGAAGCGCATGAAAGGTGATTTATCGGAGTATTCCGTTATCC     3360
AGACGAAAGAACCTCTGGATAATGAAGGCAAAGTCAGCCGGATTGTGGAGTTTATCGAAA     3420
AACCGGATCAGCCGCAGACGCTGGATTCCGATTTGATGGCGGTAGGCCGTTATGTGCTTT     3480
CAGCCGACATCTGGGCGGAACTGGAAAGAACCGAACCGGGCGCCTGGGGCCGCATCCAGC     3540
TCACCGATGCCATTGCTGAACTGGCGAAAAAACAGTCGGTTGACGCGATGCTAATGACGG     3600
GTGACAGCTATGACTGCGGTAAAAAATGGGCTACATGCAGGCATTTGTGAAGTACGGGC      3660
TGCGCAACCTGAAAGAAGGAGCCAAGTTCCGTAAGAGCATAGAGCAGCTTTTGCATGAAT     3720
AAGTATTAACAACCGTGATAAATGGTTGGTGATAAACATAATAACGGCAGTGAACATTCG     3780
AAGCGGCAAGTTGGCTGAAACGAGTGTTGACTGCCGTTTTAGTTTTGTATAAAGGGCTTA    3840
AGTAACAAGGGGTTATCTGGAGCATTTTAATGCTGATTTTATAAGATTAATCCTTGTTTC    3900
CGGATGCAATTAATAAGACAATTAGCGTTTAAGTTTTAGTGAGCTTTGCCCTGCTGGGCG    3960
```

Figure 10/2

```
AGGTTTGCAACAAGTCGATATGTACGCAGTGCACTGGTAGCTGATGAGCCAGGGGCGGTA    4020

GCGTGTGTAACGACTTGAGCAATTAATTTTTATTGGCAAATTAAATACCACATTAAATAC    4080

Start of rmlB
                V  K  I  L  I  T  G  G  A  G  F  I  G  S
GCCTTATGGAATAGAAAAGTGAAGATACTTATTACTGGCGGGGCAGGTTTTATTGGATCA    4140

A  V  V  R  H  I  I  K  N  T  Q  D  T  V  V  N  I  D  K  L
GCTGTTGTCCGCCATATTATTAAGAATACACAGGACACTGTAGTTAATATTGATAAATTA    4200

T  Y  A  G  N  L  E  S  L  S  D  I  S  E  S  N  R  Y  N  F
ACCTACGCCGGTAATCTTGAATCCCTTTCTGATATTTCTGAAAGTAATCGCTACAATTTT    4260

E  H  A  D  I  C  D  S  A  E  I  T  R  I  F  E  Q  Y  Q  P
GAACACGCGGATATTTGTGATTCCGCTGAAATAACGCGTATTTTTGAGCAGTACCAGCCG    4320

D  A  V  M  H  L  A  A  E  S  H  V  D  R  S  I  T  G  P  A
GACGCGGTGATGCATTTGGCTGCGGAAAGTCATGTGGACCGTTCGATTACCGGGCCAGCA    4380

A  F  I  E  T  N  I  V  G  T  Y  A  L  L  E  V  A  R  K  Y
GCATTTATTGAAACCAATATCGTCGGCACCTATGCACTTCTTGAAGTTGCGCGTAAATAC    4440

W  S  A  L  G  E  D  K  K  N  N  F  R  F  H  H  I  S  T  D
TGGTCTGCCCTTGGCGAAGATAAAAAAAATAATTTTCGTTTTCATCATATTTCCACTGAT    4500

E  V  Y  G  D  L  P  H  P  D  E  V  E  N  S  V  T  L  P  L
GAAGTTTACGGCGATTTACCGCATCCTGATGAAGTTGAAAACAGCGTTACGCTGCCGTTA    4560

F  T  E  T  T  A  Y  A  P  S  S  P  Y  S  A  S  K  A  S  S
TTTACTGAAACGACGGCATATGCGCCAAGTAGCCCCTATTCTGCGTCAAAAGCATCCAGC    4620

D  H  L  V  R  A  W  R  R  T  Y  G  L  P  T  I  V  T  N  C
GATCATTTAGTCCGTGCCTGGCGGCGTACCTATGGTCTACCAACGATCGTTACCAATTGT    4680

S  N  N  Y  G  P  Y  H  F  P  E  K  L  I  P  L  V  I  L  N
TCTAATAACTATGGCCCTTATCACTTCCCTGAAAAACTGATTCCGTTGGTCATTTTGAAC    4740

A  L  E  G  K  P  L  P  I  Y  G  K  G  D  Q  I  R  D  W  L
GCACTGGAAGGAAAGCCTTTGCCAATTTATGGCAAAGGGGATCAGATTCGCGATTGGCTA    4800

Y  V  E  D  H  A  R  A  L  H  M  V  V  T  E  G  K  A  G  E
TATGTAGAAGATCATGCTCGCGCGCTTCATATGGTAGTGACTGAAGGCAAGGCAGGGGAG    4860

T  Y  N  I  G  G  H  N  E  K  K  N  L  D  V  V  F  T  I  C
ACTTATAACATTGGTGGACACAATGAGAAGAAAAATCTCGATGTGGTATTTACCATCTGT    4920

D  L  L  D  E  I  V  P  K  A  T  S  Y  R  E  Q  I  T  Y  V
GATCTGCTGGATGAGATTGTACCCAAAGCGACTTCTTATCGTGAACAAATCACTTATGTC    4980

A  D  R  P  G  H  D  R  R  Y  A  I  D  A  G  K  I  S  R  E
GCGGATCGTCCGGGCCATGATCGTCGTTATGCCATTGATGCAGGTAAAATTAGCCGCGAA    5040

L  G  W  K  P  L  E  T  F  E  S  G  I  R  K  T  V  E  W  Y
TTAGGCTGGAAACCGCTGGAGACCTTTGAAAGCGGTATTCGTAAAACAGTGGAATGGTAC    5100

L  A  N  T  Q  W  V  N  N  V  K  S  G  A  Y  Q  S  W  I  E
CTTGCAAATACTCAATGGGTAAACAATGTTAAAAGTGGGGCGTATCAGAGTTGGATAGAA    5160

End of rmlB     Start of rmlD
    Q  N  Y  E  G  R  Q  *            M  N  I  L  L  F  G  K  T  G  Q  V
CAGAACTATGAAGGACGCCAGTAATGAATATCTTACTTTTTGGTAAGACAGGGCAAGTAG    5220
```

Figure 10/3

```
          G   W   E   L   Q   R   S   L   A   P   V   G   N   L   I   A   L   D   V   H
          GCTGGGAGTTGCAACGTTCTCTGGCACCGGTAGGGAATCTGATTGCCCTGGATGTCCATT            5280

S   K   E   F   C   G   D   F   S   N   P   K   G   V   A   E   T   V   R   K
          CAAAAGAGTTTTGCGGTGATTTTAGTAATCCGAAAGGCGTTGCCGAAACCGTTCGTAAGC            5340

L   R   P   D   V   I   V   N   A   A   A   H   T   A   V   D   K   A   E   S
          TTCGTCCCGATGTGATTGTTAACGCAGCAGCCCATACTGCAGTAGATAAAGCAGAGTCTG            5400

E   P   E   L   A   Q   L   L   N   A   T   S   V   E   A   I   A   K   A   A
          AACCAGAACTGGCGCAGTTACTTAACGCCACCAGTGTGGAAGCCATCGCTAAAGCAGCCA            5460

N   E   T   G   A   W   V   V   H   Y   S   T   D   Y   V   F   P   G   T   G
          ACGAAACTGGCGCATGGGTAGTGCATTATTCAACCGATTATGTATTTCCTGGTACCGGCG            5520

D   I   P   W   Q   E   T   D   A   T   S   P   L   N   V   Y   G   K   T   K
          ATATCCCATGGCAGGAAACGGACGCTACGTCGCCGCTGAATGTCTATGGCAAAACCAAAC            5580

L   A   G   E   K   A   L   Q   D   N   C   P   K   H   L   I   F   R   T   S
          TGGCGGGAGAAAAGGCCCTGCAGGATAACTGCCCTAAACACCTTATCTTCCGCACCAGTT            5640

W   V   Y   A   G   K   G   N   N   F   A   K   T   M   L   R   L   A   K   E
          GGGTTTATGCAGGTAAGGGCAATAATTTCGCAAAGACAATGCTTCGTCTGGCGAAAGAGC            5700

R   Q   T   L   S   V   I   N   D   Q   Y   G   A   P   T   G   A   E   L   L
          GTCAGACACTTTCAGTCATTAACGATCAGTACGGTGCGCCAACCGGTGCGGAATTACTGG            5760

A   D   C   T   A   H   A   I   R   V   A   L   N   K   P   E   V   A   G   L
          CTGACTGTACGGCGCATGCGATCCGTGTGGCGTTAAATAAACCAGAAGTCGCAGGTCTTT            5820

Y   H   L   V   A   G   G   T   T   T   W   H   D   Y   A   A   L   V   F   D
          ACCATCTGGTTGCCGGGGGAACCACAACCTGGCATGACTACGCGGCCTTAGTCTTTGACG            5880

E   A   R   K   A   G   I   T   L   A   L   T   E   L   N   A   V   P   T   S
          AGGCGCGCAAAGCAGGGATAACGCTTGCGCTGACTGAGCTTAATGCTGTGCCGACCAGCG            5940

A   Y   P   T   P   A   S   R   P   G   N   S   R   L   N   T   E   K   F   Q
          CCTACCCGACGCCGGCGAGCAGACCAGGCAATTCGCGTCTCAATACTGAAAAGTTTCAGC            6000

R   N   F   D   L   I   L   P   Q   W   E   L   G   V   K   R   M   L   T   E
          GTAATTTTGACCTTATTCTGCCTCAATGGGAATTAGGAGTTAAGCGTATGCTGACTGAAA            6060

End of rmlD
          M   F   T   T   T   T   I   *
          TGTTTACGACGACAACCATCTAATAAATTTAAATGCCCATCAGGGCATTTTCTATGAATG            6120

Start of rmlA
                            M   K   T   R   K   G   I   I   L   A   G   G   S   G   T   R   L
          AGAAATGGAAATGAAAACGCGTAAGGGCATTATTTTAGCGGGGGGCTCCGGCACCCGTCT            6180

Y   P   V   T   M   A   V   S   K   Q   L   L   P   I   Y   D   K   P   M   I
          TTATCCGGTGACCATGGCGGTAAGTAAGCAATTGCTACCAATTTATGATAAACCGATGAT            6240

Y   Y   P   L   S   T   L   M   L   A   G   I   R   D   I   L   I   I   S   T
          TTACTATCCCCTTTCCACGCTTATGCTGGCAGGCATTCGGGATATCCTGATCATCAGTAC            6300

P   Q   D   T   P   R   F   Q   Q   L   L   G   D   G   S   Q   W   G   L   N
          GCCACAGGACACGCCGCGTTTTCAACAACTGCTGGGAGACGGCAGCCAGTGGGGGCTGAA            6360

L   Q   Y   K   V   Q   P   S   P   D   G   L   A   Q   A   F   I   I   G   E
          TCTTCAATATAAAGTACAGCCAAGCCCGGATGGCTTAGCACAGGCGTTTATTATTGGTGA            6420

E   F   I   G   H   D   D   C   A   L   V   L   G   D   N   I   F   Y   G   H
          AGAGTTCATTGGTCATGATGATTGTGCATTAGTGCTGGGTGACAATATCTTCTATGGTCA            6480
```

Figure 10/4

```
           D  L  P  K  L  M  E  A  A  V  N  K  E  S  G  A  T  V  F  A
        TGATTTACCAAAGTTAATGGAAGCTGCCGTTAATAAAGAAAGTGGTGCTACCGTCTTCGC      6540

Y  H  V  N  D  P  E  R  Y  G  V  V  E  F  D  Q  K  G  T  A
        TTATCATGTAAACGATCCGGAGCGCTACGGTGTGGTTGAGTTTGACCAAAAGGGCACAGC      6600

V  S  L  E  E  K  P  L  Q  P  K  S  N  Y  A  V  T  G  L  Y
        CGTTAGTCTGGAAGAAAAACCATTACAACCGAAGAGTAATTACGCGGTAACGGGGCTGTA      6660

F  Y  D  N  S  V  V  E  M  A  K  N  L  K  P  S  A  R  G  E
        TTTTTATGATAATAGCGTGGTGGAGATGGCGAAAAATCTTAAGCCTTCCGCTCGCGGTGA      6720

L  E  I  T  D  I  N  R  I  Y  M  E  Q  G  R  L  S  V  A  M
        GTTAGAAATCACGGATATTAACCGTATCTATATGGAGCAGGGAAGATTGTCTGTCGCTAT      6780

M  G  R  G  Y  A  W  L  D  T  G  T  H  Q  S  L  I  E  A  S
        GATGGGGCGCGGTTATGCCTGGCTGGATACAGGGACGCATCAGAGTTTGATAGAGGCCAG      6840

N  F  I  A  T  I  E  E  R  Q  G  L  K  V  S  C  P  E  E  I
        TAATTTTATTGCAACCATCGAAGAACGCCAGGGGCTAAAAGTGTCCTGCCCGGAAGAGAT      6900

A  F  R  K  N  F  I  N  A  Q  Q  V  I  E  L  A  G  P  L  S
        CGCATTTCGTAAAAATTTTATAAATGCACAACAGGTTATAGAACTGGCCGGGCCATTATC      6960

End of rmlA  Start of rmlC
           K  N  D  Y  G  K  Y  L  L  K  M  V  K  G  L  *  V  M  I  V
        AAAAAATGATTATGGCAAATATTTGCTGAAGATGGTGAAAGGTTTA TAAGTGATGATTGT    7020

I  K  T  A  I  P  D  V  L  I  L  E  P  K  V  F  G  D  E  R
        GATTAAAACAGCAATACCAGATGTCTTGATCTTAGAGCCTAAAGTTTTTGGCGATGAGAG      7080

G  F  F  F  E  S  Y  N  Q  Q  T  F  E  E  L  I  G  R  K  V
        GGGATTCTTTTTTGAAAGTTATAACCAGCAGACCTTTGAAGAGTTGATTGGACGTAAAGT      7140

T  F  V  Q  D  N  H  S  K  S  K  K  N  V  L  R  G  L  H  F
        TACATTTGTTCAAGATAATCATTCAAAATCCAAAAAGAACGTACTCAGAGGGCTACATTT      7200

Q  R  G  E  N  A  Q  G  K  L  V  R  C  A  V  G  E  V  F  D
        TCAGAGAGGAGAAAATGCACAGGGGAAGTTAGTTCGTTGTGCTGTCGGTGAGGTTTTTGA      7260

V  A  V  D  I  R  K  E  S  P  T  F  G  Q  W  V  G  V  N  L
        TGTTGCGGTCGATATCCGAAAAGAATCGCCTACTTTTGGTCAATGGGTTGGTGTAAATCT      7320

S  A  E  N  K  R  Q  L  W  I  P  E  G  F  A  H  G  F  V  T
        GTCTGCTGAGAATAAGCGACAGCTTTGGATTCCAGAAGGTTTTGCTCATGGTTTTGTTAC      7380

L  S  E  Y  A  E  F  L  Y  K  A  T  N  Y  Y  S  P  S  S  E
        TCTTAGTGAGTATGCAGAGTTTCTGTACAAAGCAACTAATTATTACTCACCTTCATCGGA      7440

G  S  I  L  W  N  D  E  A  I  G  I  E  W  P  F  S  Q  L  P
        AGGTAGCATTCTATGGAATGATGAGGCAATAGGTATTGAATGGCCTTTTTCTCAGCTGCC      7500

End of rmlC
           E  L  S  A  K  D  A  A  A  P  L  L  D  Q  A  L     L  T  E  *
        TGAGCTTTCAGCAAAAGATGCTGCAGCACCTTTACTGGATCAAGCCTTGTTAACAGAG TA    7560

Start of ddhD
             V  S  H  I  I  K  I  F  P  S  N  I  E  F  S  G  R  E
        AGCATCGTGTCTCATATTATTAAGATTTTTCCATCAAATATTGAATTTTCCGGTAGAGAG     7620

D  E  S  I  L  D  A  A  L  S  A  G  I  H  L  E  H  S  C  K
        GATGAATCAATCCTCGATGCTGCGCTATCGGCTGGTATCCATCTTGAACATAGCTGCAAA      7680

A  G  D  C  G  I  C  E  S  D  L  L  A  G  E  V  V  D  S  K
        GCGGGTGATTGTGGTATCTGTGAGTCCGATTTGTTGGCGGGAGAAGTTGTTGACTCCAAA      7740
```

Figure 10/5

```
       G  N  I  F  G  Q  G  D  K  I  L  T  C  C  C  K  P  K  T  A
      GGTAATATTTTTGGACAGGGTGATAAAATACTAACCTGCTGCTGTAAACCTAAAACCGCC    7800

L  E  L  N  A  H  F  F  P  E  L  A  G  Q  T  K  K  I  V  P
      CTTGAGCTAAATGCGCATTTTTTTCCTGAACTAGCTGGACAGACAAAAAAAATTGTCCCA    7860

C  K  V  N  S  A  V  L  V  S  G  D  V  M  T  L  K  L  R  T
      TGCAAGGTAAATAGTGCTGTACTGGTTTCAGGCGATGTTATGACTTTGAAGTTACGCACA    7920

P  P  T  A  K  I  G  F  L  P  G  Q  Y  I  N  L  H  Y  K  G
      CCACCAACAGCAAAAATTGGCTTCCTTCCAGGGCAGTATATCAATTTACATTATAAAGGT    7980

V  T  R  S  Y  S  I  A  N  S  D  E  S  N  G  I  E  L  H  V
      GTAACTCGCAGTTATTCTATCGCTAATAGTGATGAGTCGAATGGTATTGAGTTGCATGTA    8040

R  N  V  P  N  G  Q  M  S  S  L  I  F  G  E  L  Q  E  N  T
      AGGAATGTTCCCAATGGTCAGATGAGTTCGCTCATTTTTGGGGAGTTACAAGAAAATACT    8100

L  M  R  I  E  G  P  C  G  T  F  F  I  R  E  S  D  R  P  I
      CTTATGCGCATTGAAGGGCCTTGCGGAACATTTTTTATTCGTGAAAGTGACAGACCTATA    8160

I  F  L  A  G  G  T  G  F  A  P  V  K  S  M  V  E  H  L  I
      ATCTTCCTTGCAGGCGGTACTGGATTCGCTCCAGTTAAATCAATGGTTGAGCATCTCATT    8220

Q  G  K  C  R  R  E  I  Y  I  Y  W  G  M  Q  Y  S  K  D  F
      CAGGGAAAATGTCGTCGTGAGATCTACATTTACTGGGGAATGCAATATAGTAAAGATTTT    8280

Y  S  A  L  P  Q  Q  W  S  E  Q  H  D  N  V  H  Y  I  P  V
      TACTCTGCATTACCGCAGCAGTGGAGTGAACAGCACGACAACGTTCATTATATCCCTGTT    8340

V  S  G  D  D  A  E  W  G  G  R  K  G  F  V  H  H  A  V  M
      GTTTCTGGTGATGACGCCGAATGGGGGGGAAGAAAGGGATTTGTCCATCATGCCGTGATG    8400

D  D  F  D  S  L  E  F  F  D  I  Y  A  C  G  S  P  V  M  I
      GATGATTTTGATTCTCTAGAGTTCTTCGATATATATGCATGTGGTTCACCTGTGATGATC    8460

D  A  S  K  K  D  F  M  M  K  N  L  S  V  E  H  F  Y  S  D
      GATGCCAGTAAAAAGGACTTTATGATGAAAAATCTCTCTGTAGAACATTTCTATTCTGAT    8520

End of ddhD   Start of ddhA
       A  F  T  A  S  N  N  I  E  D  N  L  *
                                                 M  K  A  V  I  L  A  G
      GCATTTACCGCATCTAATAATATTGAGGATAATTTATGAAAGCGGTCATCCTGGCTGGTG    8580

G  L  G  T  R  L  S  E  E  T  I  V  K  P  K  P  M  V  E  I
      GACTTGGTACCAGACTAAGTGAAGAAACAATTGTAAAACCAAAACCGATGGTAGAAATTG    8640

G  G  K  P  I  L  W  H  I  M  K  M  Y  S  V  H  G  I  K  D
      GTGGCAAGCCTATTCTTTGGCACATTATGAAAATGTATTCTGTGCATGGTATCAAGGATT    8700

F  I  I  C  C  G  Y  K  G  Y  V  I  K  E  Y  F  A  N  Y  F
      TTATTATCTGCTGTGGTTATAAAGGATATGTGATTAAAGAATATTTTGCGAACTACTTCC    8760

L  H  M  S  D  V  T  F  H  M  A  E  N  R  M  E  V  H  H  K
      TTCACATGTCAGATGTAACATTCCATATGGCTGAAAACCGTATGGAAGTTCACCATAAAC    8820

R  V  E  P  W  N  V  T  L  V  D  T  G  D  S  S  M  T  G  G
      GTGTTGAACCATGGAATGTCACATTGGTTGATACGGGTGATTCTTCAATGACTGGTGGTC    8880

R  L  K  R  V  A  E  Y  V  K  D  D  E  A  F  L  F  T  Y  G
      GTCTGAAACGTGTTGCTGAATACGTAAAAGATGACGAGGCTTTCCTGTTTACTTATGGTG    8940

D  G  V  A  D  L  D  I  K  A  T  I  D  F  H  K  A  H  G  K
      ATGGCGTTGCCGACCTTGATATCAAAGCGACTATCGATTTCCATAAGGCTCACGGTAAGA    9000
```

Figure 10/6

```
      K  A  T  L  T  A  T  F  P  P  G  R  F  G  A  L  D  I  R  A
      AAGCGACTTTAACAGCTACTTTTCCACCAGGACGCTTTGGCGCATTAGATATCCGAGCTG      9060

G  Q  V  R  S  F  Q  E  K  P  K  G  D  G  A  M  I  N  G  G
      GTCAGGTCCGGTCATTCCAGGAAAAACCGAAAGGCGATGGGGCAATGATCAATGGTGGTT      9120

F  F  V  L  N  P  S  V  I  D  L  I  D  N  D  A  T  T  W  E
      TCTTTGTGTTGAATCCATCGGTTATCGATCTCATCGATAACGATGCAACAACCTGGGAAC      9180

Q  E  P  L  M  T  L  A  Q  Q  G  E  L  M  A  F  E  H  P  G
      AAGAGCCATTAATGACATTGGCACAACAGGGGGAGTTAATGGCTTTTGAACACCCAGGTT      9240

F  W  Q  P  M  D  T  L  R  D  K  V  Y  L  E  G  L  W  E  K
      TCTGGCAGCCGATGGATACCCTACGTGATAAAGTTTACCTCGAAGGGCTGTGGGAAAAG      9300

End of ddhA   Start of ddhB
                                         M  I  D  K  N  F  W  Q  G
      G  K  A  P  W  K  T  W  E  *
      GTAAAGCTCCGTGGAAAACCTGGAGTAACTAGATGATTGATAAAAATTTTTGGCAAGGT      9360

K  R  V  F  V  T  G  H  T  G  F  K  G  S  W  L  S  L  W  L
      AAACGTGTATTCGTTACCGGCCATACTGGCTTTAAAGGAAGCTGGCTTTCGCTATGGCTG      9420

T  E  M  G  A  I  V  K  G  Y  A  L  D  A  P  T  V  P  S  L
      ACTGAAATGGGTGCAATTGTAAAAGGCTATGCACTTGATGCGCCAACTGTTCCAAGTTTA      9480

F  E  I  V  R  L  N  D  L  M  E  S  H  I  G  D  I  R  D  F
      TTTGAGATAGTGCGTCTTAATGATCTTATGGAATCTCATATTGGCGACATTCGTGATTTT      9540

E  K  L  R  N  S  I  A  E  F  K  P  E  I  V  F  H  M  A  A
      GAAAAGCTGCGCAATTCTATTGCAGAATTTAAGCCAGAAATTGTTTTCCATATGGCAGCC      9600

Q  P  L  V  R  L  S  Y  E  Q  P  I  E  T  Y  S  T  N  V  M
      CAGCCTTTAGTGCGCCTATCTTATGAACAGCCAATCGAAACATACTCAACAAATGTTATG      9660

G  T  V  H  L  L  E  T  V  K  Q  V  G  N  I  K  A  V  V  N
      GGTACTGTCCATTTGCTTGAAACAGTTAAGCAAGTAGGTAACATAAAGGCAGTCGTAAAT      9720

I  T  S  D  K  C  Y  D  N  R  E  W  V  W  G  Y  R  E  N  E
      ATCACCAGTGATAAGTGCTACGACAATCGTGAGTGGGTGTGGGGCTATCGTGAGAACGAA      9780

P  M  G  G  Y  D  P  Y  S  N  S  K  G  C  A  E  L  V  A  S
      CCCATGGGAGGGTACGATCCATACTCTAATAGTAAAGGTTGTGCAGAATTAGTCGCGTCT      9840

A  F  R  N  S  F  F  N  P  A  N  Y  E  Q  H  G  V  G  L  A
      GCATTCCGGAACTCATTCTTCAATCCTGCAAATTATGAGCAACATGGCGTTGGTTTGGCG      9900

S  V  R  A  G  N  V  I  G  G  G  D  W  A  K  D  R  L  I  P
      TCTGTGAGGGCTGGTAATGTCATAGGCGGAGGCGATTGGGCTAAAGACCGTTTAATTCCC      9960

D  I  L  R  S  F  E  N  N  Q  Q  V  I  I  R  N  P  Y  S  I
      GATATTCTGCGCTCATTTGAAAATAACCAGCAGGTTATTATTCGAAACCCATATTCTATC      10020

R  P  W  Q  H  V  L  E  P  L  S  G  Y  I  V  V  A  Q  R  L
      CGTCCCTGGCAGCATGTACTGGAGCCTCTTTCTGGTTACATTGTGGTGGCGCAACGCTTA      10080

Y  T  E  G  A  K  F  S  E  G  W  N  F  G  P  R  D  E  D  A
      TATACAGAAGGTGCTAAGTTTTCTGAAGGATGGAATTTCGGCCCGCGTGATGAAGATGCG      10140

K  T  V  E  F  I  V  D  K  M  V  T  L  W  G  D  D  A  S  W
      AAGACGGTCGAATTTATTGTTGACAAGATGGTCACGCTTTGGGGTGATGATGCAAGCTGG      10200

L  L  D  G  E  N  H  P  H  E  A  H  Y  L  K  L  D  C  S  K
      TTACTGGATGGTGAGAATCATCCTCATGAGGCACATTACCTGAAACTGGATTGCTCTAAA      10260
```

```
          A  N  M  Q  L  G  W  H  P  R  W  G  L  T  E  T  L  G  R  I
        GCAAATATGCAATTAGGATGGCATCCGCGTTGGGGATTGACTGAAACACTTGGTCGCATC      10320

V  K  W  H  K  A  W  I  R  G  E  D  M  L  I  C  S  K  R  E
        GTAAAATGGCATAAAGCATGGATTCGCGGCGAAGATATGTTGATTTGTTCAAAGCGTGAA      10380
                                               End of ddhB
          I  S  D  Y  M  S  A  T  T  R  *
        ATCAGCGACTATATGTCTGCAACTACTCGT TAAGAAAATAAGTTTAAGGAATCAAAGTAA     10440
        Start of ddhC
         M  T  A  N  N  L  R  E  Q  I  S  Q  L  V  A  Q  Y  A  N  E
        TGACAGCAAATAACCTGCGTGAGCAAATCTCTCAGCTTGTCGCTCAGTATGCGAATGAGG      10500

A  L  S  P  K  P  F  V  A  G  T  S  V  V  P  P  S  G  K  V
        CATTGAGCCCGAAACCTTTTGTTGCAGGTACAAGCGTTGTGCCTCCTTCCGGGAAGGTTA      10560

I  G  A  K  E  L  Q  L  M  V  E  A  S  L  D  G  W  L  T  T
        TTGGTGCCAAAGAGTTACAATTGATGGTTGAGGCGTCTCTTGATGGATGGCTAACTACTG      10620

G  R  F  N  D  A  F  E  K  K  L  G  E  F  I  G  V  P  H  V
        GTCGTTTCAATGATGCCTTTGAAAAAAAACTTGGGGAATTTATTGGGGTTCCTCATGTTT      10680

L  T  T  T  S  G  S  S  A  N  L  L  A  L  T  A  L  T  S  P
        TAACGACAACATCTGGCTCTTCGGCAAACTTGCTGGCACTGACTGCGCTGACTTCCCCAA      10740

K  L  G  E  R  A  L  K  P  G  D  E  V  I  T  V  A  A  G  F
        AATTAGGCGAGCGAGCTCTCAAACCTGGTGATGAGGTTATTACTGTCGCTGCTGGCTTCC      10800

P  T  T  V  N  P  A  I  Q  N  G  L  I  P  V  F  V  D  V  D
        CGACTACAGTTAACCCGGCGATCCAGAATGGTTTAATACCGGTATTCGTGGATGTTGATA      10860

I  P  T  Y  N  I  D  A  S  L  I  E  A  A  V  T  E  K  S  K
        TCCCGACATATAATATCGATGCCTCTCTCATTGAAGCTGCAGTTACTGAGAAATCAAAAG      10920

A  I  M  I  A  H  T  L  G  N  A  F  N  L  S  E  V  R  R  I
        CGATAATGATCGCTCATACACTCGGTAATGCATTTAACCTGAGTGAAGTTCGTCGGATTG      10980

A  D  K  Y  N  L  W  L  I  E  D  C  C  D  A  L  G  T  T  Y
        CCGATAAATATAACTTATGGTTGATTGAAGACTGCTGTGATGCCCTTGGGACGACTTATG      11040

E  G  Q  M  V  G  T  F  G  D  I  G  T  V  S  F  Y  P  A  H
        AAGGCCAGATGGTAGGTACCTTTGGTGACATCGGAACCGTTAGTTTTTATCCGGCTCACC      11100

H  I  T  M  G  E  G  G  A  V  F  T  K  S  G  E  L  K  K  I
        ATATCACAATGGGTGAAGGCGGTGCTGTATTCACCAAGTCAGGTGAACTGAAGAAAATTA      11160

I  E  S  F  R  D  W  G  R  D  C  Y  C  A  P  G  C  D  N  T
        TTGAGTCGTTCCGTGACTGGGGCCGGGATTGTTATTGTGCGCCAGGATGCGATAACACCT      11220

C  G  K  R  F  G  Q  Q  L  G  S  L  P  Q  G  Y  D  H  K  Y
        GCGGTAAACGTTTTGGTCAGCAATTGGGATCACTTCCTCAAGGCTATGATCACAAATATA      11280

T  Y  S  H  L  G  Y  N  L  K  I  T  D  M  Q  A  A  C  G  L
        CTTATTCCCACCTCGGATATAATCTCAAAATCACGGACATGCAGGCAGCATGTGGTCTGG      11340

A  Q  L  E  R  V  E  E  F  V  E  Q  R  K  A  N  F  S  Y  L
        CTCAGTTGGAGCGCGTAGAAGAGTTTGTAGAGCAGCGTAAAGCTAACTTTTCCTATCTGA      11400

K  Q  G  L  Q  S  C  T  E  F  L  E  L  P  E  A  T  E  K  S
        AACAGGGCTTGCAATCTTGCACTGAATTCCTCGAATTACCAGAAGCAACAGAGAAATCAG      11460

D  P  S  W  F  G  F  P  I  T  L  K  E  T  S  G  V  N  R  V
        ATCCATCCTGGTTTGGCTTCCCTATCACCCTGAAAGAAACTAGCGGTGTTAACCGTGTCG      11520
```

```
                E  L  V  K  F  L  D  E  A  K  I  G  T  R  L  L  F  A  G  N
              AACTGGTGAAATTCCTTGATGAAGCAAAAATCGGTACACGTTTACTGTTTGCTGGAAATC      11580

L  I  R  Q  P  Y  F  A  N  V  K  Y  R  V  V  G  E  L  T  N
          TGATTCGCCAACCGTATTTTGCTAATGTGAAATATCGTGTAGTGGGTGAGTTGACAAATA        11640

T  D  R  I  M  N  Q  T  F  W  I  G  I  Y  P  G  L  T  T  E
          CCGACCGTATAATGAATCAAACGTTCTGGATTGGTATTTATCCAGGCTTGACTACAGAGC        11700

End of ddhC
          H  L  D  Y  V  V  S  K  F  E  E  F  F  G  L  N  F  *
          ATTTAGATTATGTAGTTAGCAAGTTTGAAGAGTTCTTTGGTTTGAATTTCTAATTCAATT        11760

Start of abe
                              M  T  F  L  K  E  Y  V  I  V  S  G  A
          TATTCTATCTGGTGATTGCGATGACCTTTTTGAAAGAATATGTAATTGTCAGTGGGGCTT        11820

S  G  F  I  G  K  H  L  L  E  A  L  K  K  S  G  I  S  V  V
          CCGGCTTTATTGGTAAGCATTTACTCGAAGCGCTAAAAAAATCGGGGATTTCAGTTGTCG        11880

A  I  T  R  D  V  I  K  N  N  S  N  A  L  A  N  V  R  W  C
          CAATCACTCGAGATGTAATAAAAAATAATAGTAATGCATTAGCTAATGTTAGATGGTGCA        11940

S  W  D  N  I  E  L  L  V  E  E  L  S  I  D  S  A  L  I  G
          GTTGGGATAATATCGAATTATTAGTCGAGGAGTTATCAATTGATTCTGCATTAATTGGTA        12000

I  I  H  L  A  T  E  Y  G  H  K  T  S  S  L  I  N  I  E  D
          TCATTCATTTGGCAACAGAATATGGGCATAAAACATCATCTCTCATAAATATTGAAGATG        12060

A  N  V  I  K  P  L  K  L  L  D  L  A  I  K  Y  R  A  D  I
          CAAATGTTATAAAACCATTAAAGCTTCTTGATTTGGCAATAAAATATCGGGCGGATATCT        12120

F  L  N  T  D  S  F  F  A  K  K  D  F  N  Y  Q  H  M  R  P
          TTTTAAATACAGATAGTTTTTTTGCCAAGAAAGATTTTAATTATCAACATATGCGGCCTT        12180

Y  I  I  T  K  R  H  F  D  E  I  G  H  Y  Y  A  N  M  H  D
          ATATAATTACTAAAAGACACTTTGATGAAATTGGGCATTATTATGCTAATATGCATGACA        12240

I  S  F  V  N  M  R  L  E  H  V  Y  G  P  G  D  G  E  N  K
          TTTCATTTGTAAACATGCGATTAGAGCATGTATATGGGCCTGGGGATGGTGAAAATAAAT        12300

F  I  P  Y  I  I  D  C  L  N  K  K  Q  S  C  V  K  C  T  T
          TTATTCCATACATTATCGACTGCTTAAATAAAAAACAGAGTTGCGTGAAATGTACAACAG        12360

G  E  Q  I  R  D  F  I  F  V  D  D  V  V  N  A  Y  L  T  I
          GCGAACAGATAAGAGACTTTATTTTTGTAGATGATGTGGTAAATGCTTATTTAACTATAT        12420

L  E  N  R  K  E  V  P  S  Y  T  E  Y  Q  V  G  T  G  A  G
          TAGAAAATAGAAAAGAAGTACCTTCATATACTGAGTATCAAGTTGGAACTGGTGCTGGGG        12480

V  S  L  K  D  F  L  V  Y  L  Q  N  T  M  M  P  G  S  S  S
          TAAGTTTGAAAGATTTTCTGGTTTATTTGCAAAATACTATGATGCCAGGTTCATCGAGTA        12540

I  F  E  F  G  A  I  E  Q  R  D  N  E  I  M  F  S  V  A  N
          TATTTGAATTTGGTGCGATAGAGCAAAGAGATAATGAAATAATGTTCTCTGTAGCAAATA        12600

N  K  N  L  K  A  M  G  W  K  P  N  F  D  Y  K  K  G  I  E
          ATAAAAATTTAAAAGCAATGGGCTGGAAACCAAATTTCGATTATAAAAAGGAATTGAAG        12660

End of abe
          E  L  L  K  R  L  *
          AACTACTGAAACGGTTATGAGATTTTCATGATCTTTTAATAAATAAATCGTTAACAAATT        12720

Start of wzx
                                                                 V  K  V  Q  L  L
          AGTCGCGTTATGTTGTAAAAACTAAGTCGTTTAATTGCATAGTGAAAGTTCAATTGTTAA        12780
```

Figure 10/9

```
K  I  P  S  H  L  I  V  A  G  S  S  W  L  S  K  I  I  I  A
AAATTCCGAGTCATTTAATTGTTGCAGGTTCATCATGGTTATCCAAAATAATAATTGCCG      12840

G  V  Q  L  A  S  I  S  Y  L  I  S  M  L  G  E  E  K  Y  A
GGGTGCAGTTAGCAAGTATTTCATATCTTATTTCTATGCTAGGTGAAGAGAAATATGCAA      12900

I  F  S  L  L  T  G  L  L  V  W  C  S  A  V  D  F  G  I  G
TCTTTAGTTTGTTAACTGGTTTATTAGTATGGTGTAGCGCTGTTGATTTTGGCATAGGTA      12960

T  G  L  Q  N  Y  I  S  E  C  R  A  K  N  K  S  Y  D  A  Y
CAGGACTGCAAAATTATATATCAGAATGCAGAGCCAAAAACAAAAGTTATGATGCATATA      13020

I  K  S  A  L  H  L  S  F  I  A  I  I  F  F  I  A  L  F  Y
TTAAATCAGCATTACATCTAAGCTTTATAGCTATTATTTTTTTTATTGCTTTATTTTATA      13080

I  F  S  G  V  I  S  A  K  Y  L  S  S  F  H  E  V  L  Q  D
TTTTTTCTGGGGTAATTTCCGCTAAATATCTTTCTTCTTTTCATGAGGTATTACAGGACA      13140

K  T  R  M  L  F  F  T  S  C  L  V  F  S  S  I  G  I  G  A
AAACCAGAATGCTCTTTTTTACCTCATGTCTGGTTTTCAGTTCTATTGGAATCGGAGCTA     13200

I  A  Y  K  I  L  F  A  E  L  V  G  W  K  A  N  L  N  A
TTGCTTATAAAATACTTTTTGCCGAATTGGTCGGGTGGAAAGCTAATCTATTAAACGCAT     13260

L  S  Y  M  I  G  M  L  G  L  L  Y  I  Y  Y  R  G  I  S  V
TATCTTATATGATAGGTATGCTCGGCTTGCTATATATATACTATAGGGGATCTCAGTTG      13320

D  I  K  L  S  L  I  V  L  Y  L  P  V  G  M  I  S  L  C  Y
ACATAAAATTATCACTAATAGTCCTGTATCTTCCAGTGGGTATGATTTCATTGTGCTATA     13380

I  V  Y  R  Y  I  K  L  Y  H  V  K  T  T  K  S  H  Y  I  A
TTGTATATAGATACATAAAGCTTTATCATGTTAAAACAACAAAATCTCATTATATAGCAA    13440

I  L  R  R  S  S  G  F  F  L  F  T  L  L  S  I  V  V  L  Q
TTTTACGTAGATCTTCAGGGTTTTTTCTTTTTACTTTATTATCGATAGTGGTGCTTCAAA    13500

T  D  Y  M  V  I  S  Q  R  L  T  P  A  D  I  V  Q  Y  T  V
CAGATTATATGGTCATTTCTCAAAGGCTAACTCCTGCTGATATTGTTCAATATACAGTAA    13560

T  M  K  I  F  G  L  V  F  F  I  Y  T  A  I  L  Q  A  L  W
CGATGAAAATTTTTGGTTTAGTCTTTTTTATTTATACTGCTATTTTGCAAGCATTATGGC    13620

P  I  C  A  E  L  R  V  K  Q  Q  W  K  K  L  N  K  M  I  G
CTATATGTGCTGAATTGAGAGTCAAACAGCAATGGAAAAAACTTAACAAAATGATAGGTG   13680

V  N  I  L  L  G  S  L  Y  V  V  G  C  T  I  F  I  Y  L  F
TCAATATTTTGCTTGGCTCACTATATGTTGTTGGATGTACAATATTTATTTATTTATTTA   13740

K  E  Q  I  F  S  V  I  A  K  D  I  N  Y  Q  V  S  I  L  S
AAGAACAGATATTTTCAGTAATAGCCAAAGATATTAATTATCAAGTTTCTATTTTATCTT   13800

F  M  L  I  G  I  Y  F  C  I  R  V  W  C  D  T  Y  A  M  L
TTATGTTAATTGGCATATATTTCTGTATTCGCGTTTGGTGTGACACTTATGCAATGTTAT   13860

L  Q  S  M  N  Y  L  K  I  L  W  I  L  V  P  L  Q  A  I  I
TGCAAAGTATGAATTATTTAAAAATACTTTGGATATTAGTACCACTACAAGCAATAATTG   13920

G  G  I  A  Q  W  Y  F  S  S  T  L  G  I  S  G  V  L  L  G
GTGGAATAGCACAATGGTATTTTTCTAGTACGCTTGGAATCAGTGGAGTGCTGCTTGGCT   13980

L  I  I  S  F  A  L  T  V  F  W  G  L  P  L  T  Y  L  I  K
TGATTATATCTTTTGCTTTAACTGTTTTTTGGGGGCTTCCACTAACTTACTTAATTAAGG   14040
```

Figure 10/10

```
                End of wzx  Start of wbaV
A   N   K   G   *       M   L   I   S   F   C   I   P   T   Y   N   R   K   Q
CAAATAAGGGATAATCATATGCTTATATCATTTTGTATTCCAACTTATAATAGAAAACAA      14100

Y   L   E   E   L   L   N   S   I   N   N   Q   E   K   F   N   L   D   I   E
TATCTTGAAGAGTTGTTGAATAGTATAAATAATCAGGAAAAATTTAATTTAGATATTGAG      14160

I   C   I   S   D   N   A   S   T   D   G   T   E   E   M   I   D   V   W   R
ATATGTATATCAGATAATGCCTCTACTGATGGTACAGAGGAAATGATTGATGTTTGGAGG      14220

N   N   Y   N   F   P   I   I   Y   R   R   N   S   V   N   L   G   P   D   R
AACAATTATAATTTCCCAATAATATATCGGCGTAATAGCGTTAACCTTGGGCCAGATAGG     14280

N   F   L   A   S   V   S   L   A   N   G   D   Y   C   W   I   F   G   S   D
AATTTTCTTGCTTCAGTATCCCTTGCGAATGGGGATTATTGTTGGATATTTGGCAGTGAT     14340

D   A   L   A   K   D   S   L   A   I   L   Q   T   Y   L   D   S   Q   A   D
GATGCTCTTGCGAAAGACTCGTTAGCGATATTACAAACTTATCTCGATTCTCAAGCAGAT     14400

I   Y   L   C   D   R   K   E   T   G   C   D   L   V   E   I   R   N   P   H
ATATATTTATGTGACAGAAAAGAGACCGGGTGTGATTTAGTTGAGATTAGAAACCCTCAT     14460

R   S   W   L   R   T   D   D   E   L   Y   V   F   N   N   N   L   D   R   E
CGTTCTTGGCTCAGAACAGATGATGAACTTTATGTGTTTAATAATAATTTAGATAGGGAA     14520

I   Y   L   S   R   C   L   S   I   G   G   V   F   S   Y   L   S   S   L   I
ATCTATCTCAGTAGATGCTTATCTATTGGTGGTGTATTTAGCTATCTAAGTTCTTTAATA     14580

V   K   K   E   R   W   D   A   I   D   F   D   A   S   Y   I   G   T   S   Y
GTAAAAAAAGAACGATGGGATGCCATTGATTTTGATGCGTCCTATATTGGCACTTCCTAT     14640

P   H   V   F   I   M   M   S   V   F   N   T   P   G   C   L   L   H   Y   I
CCTCATGTATTTATCATGATGAGCGTATTTAATACGCCAGGGTGCCTTTTGCATTATATA     14700

S   K   P   L   V   I   C   R   G   D   N   D   S   F   E   K   K   G   K   A
TCAAAACCACTCGTAATATGCCGAGGAGATAATGATAGTTTCGAGAAGAAAGGAAAGGCC     14760

R   R   I   L   I   D   F   I   A   Y   L   K   L   A   N   D   F   Y   S   K
AGACGAATTTTAATTGATTTTATTGCATATTTAAAATTAGCTAATGATTTTTACAGTAAA     14820

N   I   S   L   K   R   A   F   E   N   V   L   L   K   E   R   P   W   L   Y
AATATATCTTTAAAACGAGCATTTGAAAATGTTTTGCTAAAAGAGAGACCATGGTTATAT     14880

T   T   L   A   M   A   C   Y   G   N   S   D   E   K   R   D   L   S   E   F
ACAACTTTGGCTATGGCATGTTATGGCAATAGTGATGAAAAAAGAGATTTATCTGAATTT     14940

Y   A   K   L   G   C   N   K   N   M   I   N   T   V   L   R   F   G   K   L
TATGCAAAGCTAGGTTGTAATAAAAATATGATCAACACTGTACTTCGATTTGGGAAACTA     15000
                                                                End of wbaV
A   Y   A   V   K   N   I   T   V   L   K   N   F   T   K   R   I   I   K   *
GCATATGCAGTGAAAAATATTACCGTGCTTAAGAATTTTACTAAACGGATAATTAAGTAG     15060

TAGTAAGTTATTATATTGAGATTAAATGTAGATTTAACCTTTCTGGATTCAGCTAGATTT     15120

ACGTTACTGACTTTTCTTTTTAATGAAAATCATATTTGATATATATAAATAAATTTGGAT     15180

AGCTTAACTACTTAGATGTTTTTTTTCTGGGAATGTTAGTATAATAATATATTTCTTTATG    15240

ATTGTTTTGTAGTGTTTTACTGCCGGTATTACATTAACTCTATTATTAAGAATTACACC     15300

TAGTGTAAGCTTCGTAATATTATTTATCCTTATGATTATTGCTTTAAAGATGCGTATGGA    15360

Start of wbaU
            M   I   V   N   L   S   R   L   G   K   S   G   T   G
AAAACGGAGAGCTATTCAATGATCGTAAACCTATCACGTTTAGGTAAAAGTGGTACGGGA     15420
```

Figure 10/11

```
  M  W  Q  -  Y  S  I  K  F  L  T  A  L  R  E  I  A  D  V  D  A
ATGTGGCAATACTCGATTAAATTTTTAACGGCACTGCGAGAAATAGCTGATGTTGACGCA    15480

I  I  C  S  K  V  H  A  D  Y  F  E  K  L  G  Y  A  V  V  T
ATAATCTGTAGCAAGGTACACGCTGATTATTTTGAAAAGCTCGGTTATGCAGTAGTTACT    15540

V  P  N  I  V  S  N  T  S  K  T  S  R  L  R  P  L  V  W  Y
GTTCCGAATATTGTTAGCAACACATCAAAAACATCGCGACTTAGACCATTAGTATGGTAT    15600

V  Y  S  Y  W  L  A  L  R  V  L  I  K  F  G  N  K  K  L  V
GTATATAGTTACTGGCTTGCGCTGAGGGTTTTAATTAAGTTTGGTAATAAAAAATTGGTG    15660

C  T  T  H  H  T  I  P  L  L  R  N  Q  T  I  T  V  H  D  I
TGTACTACACATCACACTATCCCCTTACTGAGAAACCAAACGATAACCGTACATGATATA    15720

R  P  F  Y  Y  P  D  S  F  I  Q  K  V  Y  F  R  F  L  L  K
AGACCTTTTTATTATCCAGATAGTTTTATTCAGAAAGTGTATTTTCGCTTTTTATTAAAA    15780

M  S  V  K  R  C  K  H  V  L  T  V  S  Y  T  V  K  D  S  I
ATGTCCGTTAAGCGATGTAAGCATGTTTTAACGGTATCTTATACCGTTAAAGATAGCATT    15840

A  K  T  Y  N  V  D  S  E  K  I  S  V  I  Y  N  S  V  N  K
GCTAAAACTTATAATGTAGATAGTGAGAAAATATCAGTAATTTATAATAGTGTTAATAAA    15900

S  D  F  I  Q  K  K  E  K  E  N  Y  F  L  A  V  G  A  S  W
TCTGATTTTATACAAAAAAAGAAAAAGAGAATTACTTTTTAGCTGTTGGTGCAAGTTGG    15960

P  H  K  N  I  H  S  F  I  K  N  K  K  V  W  S  D  S  Y  N
CCACATAAAAATATTCATTCATTCATAAAAAATAAAAAAGTTTGGTCTGACTCTTATAAT    16020

L  I  I  V  C  G  R  T  D  Y  A  M  S  L  Q  Q  M  V  V  D
TTAATTATTGTATGTGGTCGTACTGACTATGCAATGTCTCTCCAACAAATGGTCGTTGAT    16080

L  E  L  K  D  K  V  T  F  L  H  E  V  S  F  N  E  L  K  I
CTGGAACTAAAAGATAAAGTGACTTTTTTTACATGAAGTCTCATTTAATGAATTAAAGATT    16140

L  Y  S  K  A  Y  A  L  V  Y  P  S  I  D  E  G  F  G  I  P
TTATATTCTAAAGCCTACGCGCTTGTTTATCCATCTATTGATGAGGGTTTTGGTATACCT    16200

P  I  E  A  M  A  S  N  T  P  V  I  V  S  D  I  P  V  F  H
CCTATTGAAGCGATGGCATCAAATACTCCAGTTATAGTGTCCGATATACCAGTATTTCAT    16260

E  V  L  T  N  G  A  L  Y  V  N  P  D  D  E  K  S  W  Q  S
GAAGTGTTAACCAATGGTGCATTATATGTGAATCCGGATGATGAAAAAAGCTGGCAGAGT    16320

A  I  K  N  I  E  Q  L  P  D  A  I  S  R  F  N  N  Y  V  A
GCAATTAAAAATATAGAGCAGTTGCCTGATGCAATTTCCCGATTTAACAACTATGTCGCA    16380

End of wbaU
  R  Y  D  F  D  N  M  K  Q  M  V  G  N  W  L  A  E  S  K  *
CGGTATGACTTTGATAATATGAAGCAGATGGTTGGCAATTGGTTGGCGGAATCAAAA TAA   16440

Start of wbaN
  M  K  I  T  L  I  I  P  T  Y  N  A  G  S  L  W  P  N  V  L
ATGAAAATAACATTAATTATTCCCACATATAATGCAGGGTCGCTTTGGCCTAATGTTCTG    16500

D  A  I  K  Q  Q  T  I  Y  P  D  K  L  I  V  I  D  S  G  S
GATGCGATTAAGCAGCAAACTATATATCCGGATAAATTGATTGTTATAGACTCAGGTTCT    16560

K  D  E  T  V  P  L  A  S  D  L  K  N  I  S  I  F  N  I  D
AAAGATGAAACGGTTCCGTTAGCCTCAGACCTGAAAAATATATCAATATTTAATATTGAC    16620

S  K  D  F  N  H  G  G  T  R  N  L  A  V  A  K  T  L  D  A
TCTAAAGATTTTAATCATGGAGGAACCAGAAATTTAGCAGTTGCAAAAACTCTGGACGCT    16680
```

```
  D  V  I  I  F  L  T  Q  D  A  I  L  A  D  S  D  A  I  K  N
GATGTTATAATTTTTCTAACGCAAGATGCAATTCTCGCGGATTCGGATGCAATTAAAAAT    16740

L  V  Y  Y  F  S  D  P  L  I  A  A  V  C  G  R  Q  L  P  H
TTGGTTTATTATTTTTCAGATCCATTGATAGCAGCGGTTTGTGGTAGACAACTTCCTCAT    16800

K  D  A  N  P  L  A  V  H  A  R  N  F  N  Y  S  S  K  S  I
AAAGATGCTAATCCCCTTGCAGTGCATGCCAGAAATTTTAATTATAGTTCAAAATCTATT    16860

V  K  S  K  A  D  I  E  K  L  G  I  K  T  V  F  M  S  N  S
GTTAAAAGTAAGGCAGATATAGAAAAATTGGGTATTAAAACTGTATTTATGTCCAATTCT    16920

F  A  A  Y  R  R  S  V  F  E  E  L  S  G  F  P  E  H  T  I
TTTGCTGCCTATCGCCGTTCCGTTTTTGAAGAGTTAAGTGGGTTTCCTGAACATACAATT    16980

L  A  E  D  M  F  M  A  A  K  M  I  Q  A  G  Y  K  V  A  Y
CTTGCCGAGGATATGTTTATGGCGGCTAAGATGATTCAGGCGGGTTATAAGGTCGCCTAC    17040

C  A  E  A  V  V  R  H  S  H  N  Y  T  P  R  E  E  F  Q  R
TGCGCTGAAGCGGTGGTAAGACACTCCCATAATTATACCCCGCGAGAAGAGTTTCAACGA    17100

Y  F  D  T  G  V  F  H  A  C  S  P  W  I  Q  R  D  F  G  G
TATTTTGATACTGGTGTATTTCATGCTTGTTCTCCGTGGATTCAGCGTGACTTTGGCGGA    17160

A  G  G  E  G  F  R  F  V  K  S  E  I  Q  F  L  L  K  N  A
GCCGGTGGTGAGGGTTTCCGCTTCGTAAAATCAGAGATTCAATTCCTGCTTAAAAATGCA    17220

P  F  W  I  P  R  A  L  L  T  T  F  A  K  F  L  G  Y  K  L
CCGTTCTGGATTCCAAGAGCTTTATTAACAACCTTTGCTAAATTCTTGGGTTACAAATTA    17280

G  K  H  W  Q  S  L  P  L  S  T  C  R  Y  F  S  M  Y  K  S
GGCAAGCATTGGCAATCTTTACCGTTGTCTACATGTCGCTATTTTAGCATGTACAAGAGT    17340

End of wbaN  Start of manC
  Y  W  N  N  I  Q  Y  S  S  S  K  E  I  K  *  M  S  F  L  P
TATTGGAATAATATCCAATATTCTTCGTCAAAAGAGATAAAA TAAATGTCTTTTCTTCCC    17400

V  I  M  A  G  G  T  G  S  R  L  W  P  L  S  R  E  Y  H  P
GTAATTATGGCTGGCGGCACAGGTAGCCGTTTATGGCCGCTTTCACGCGAATATCATCCG    17460

K  Q  F  L  S  V  E  G  K  L  S  M  L  Q  N  T  I  K  R  L
AAGCAGTTTCTAAGCGTTGAAGGTAAACTATCAATGCTGCAAAATACTATAAAGCGATTA    17520

A  S  L  S  T  E  E  P  V  V  I  C  N  D  R  H  R  F  L  V
GCTTCACTTTCTACAGAAGAACCCGTTGTCATTTGCAATGACAGACACCGTTTCTTAGTC    17580

A  E  Q  L  R  E  I  D  K  L  A  N  N  I  I  L  E  P  V  G
GCTGAACAACTCCGTGAAATTGACAAGTTAGCAAATAATATTATTCTCGAACCGGTAGGC    17640

R  N  T  A  P  A  I  A  L  A  A  F  C  A  L  Q  N  A  D  N
CGTAATACTGCACCAGCGATCGCTCTTGCCGCGTTTTGTGCGCTCCAGAATGCTGATAAT    17700

A  D  P  L  L  L  V  L  A  A  D  H  V  I  Q  D  E  I  A  F
GCTGATCCTCTTTTGTTGGTTCTTGCTGCAGATCATGTGATTCAGGATGAAATAGCTTTT    17760

T  K  A  V  R  H  A  E  E  Y  A  A  N  G  K  L  V  T  F  G
ACGAAAGCTGTCAGACATGCTGAAGAATACGCTGCAAATGGTAAGCTTGTAACTTTTGGT    17820

I  V  P  T  H  A  E  T  G  Y  G  Y  I  R  R  G  E  L  I  G
ATTGTTCCAACGCATGCTGAAACGGGTTATGGATATATTCGTCGTGGTGAGTTGATAGGA    17880

N  D  A  Y  A  V  A  E  F  V  E  K  P  D  I  D  T  A  G  D
AATGACGCTTATGCAGTGGCTGAATTTGTGGAGAAACCGGATATCGATACCGCCGGTGAC    17940

Y  F  K  S  G  K  Y  Y  W  N  S  G  M  F  L  F  R  A  S  S
TATTTCAAATCAGGGAAATATTACTGGAATAGCGGTATGTTTTTATTTCGTGCAAGCTCT    18000
```

Figure 10/13

```
          Y   L   N-  E   L   K   Y   L   S-  P   E   I   Y   K   A   C   E   K   A   V
         TATTTAAACGAATTAAAGTATTTATCACCTGAAATTTATAAAGCTTGTGAAAAGGCGGTA       18060

G   H   I   N   P   D   L   D   F   I   R   I   D   K   E   E   F   M   S   C
         GGACATATAAATCCCGATCTTGATTTTATTCGTATTGATAAAGAAGAGTTTATGTCATGC       18120

P   S   D   S   I   D   Y   A   V   M   E   H   T   Q   H   A   V   V   I   P
         CCGAGTGATTCTATCGATTATGCAGTTATGGAGCACACACAGCATGCGGTGGTGATACCA       18180

M   S   A   G   W   S   D   V   G   S   W   S   S   L   W   D   I   S   N   K
         ATGAGCGCTGGCTGGTCGGATGTGGGTTCCTGGTCCTCACTTTGGGATATATCGAATAAA       18240

D   H   Q   R   N   V   L   K   G   D   I   F   A   H   A   C   N   D   N   Y
         GATCATCAGAGAAATGTTTTAAAAGGAGATATTTTCGCACATGCTTGTAATGATAATTAC       18300

I   Y   S   E   D   M   F   I   S   A   I   G   V   S   N   L   V   I   V   Q
         ATTTATTCCGAAGATATGTTTATAAGTGCGATTGGTGTAAGCAATCTTGTCATTGTTCAA       18360

T   T   D   A   L   L   V   A   N   K   D   T   V   Q   D   V   K   K   I   V
         ACAACAGACGCTTTACTGGTGGCTAATAAAGATACAGTACAAGATGTTAAAAAAATTGTC       18420

D   Y   L   K   R   N   D   R   N   E   Y   K   Q   H   Q   E   V   F   R   P
         GATTATTTAAAACGGAATGATAGGAACGAATATAAACAACATCAAGAAGTTTTCCGCCCC       18480

W   G   K   Y   N   V   I   D   S   G   K   N   Y   L   V   R   C   I   T   V
         TGGGGAAAATATAATGTGATTGATAGCGGCAAAAATTACCTCGTTCGATGTATCACTGTT       18540

K   P   G   E   K   F   V   A   Q   M   H   H   H   R   A   E   H   W   I   V
         AAGCCGGGTGAGAAATTTGTGGCGCAGATGCATCACCACCGGGCTGAGCATTGGATAGTA       18600

L   S   G   T   A   R   V   T   K   G   E   Q   T   Y   M   V   S   E   N   E
         TTATCCGGGACTGCTCGTGTTACAAAGGGAGAGCAGACTTATATGGTTTCTGAAAATGAA       18660

S   T   F   I   P   P   N   T   I   H   A   L   E   N   P   G   M   T   P   L
         TCAACATTTATTCCTCCGAATACTATTCACGCGCTGGAAAATCCTGGAATGACCCCCCTG       18720

K   L   I   E   I   Q   S   G   T   Y   L   G   E   D   D   I   I   R   L   E
         AAGTTAATTGAGATTCAATCAGGTACCTATCTTGGTGAGGATGATATTATTCGTTTAGAA       18780

Start of manB    End of manC
                                             M   N   V   V   N   N   S   R   D   V
          Q   R   S   G   F   S   K   E   W   T   N   E   R   S   *
         CAACGTTCTGGATTTTCGAAGGAGTGGACTAATGAACGTAGTTAATAATAGCCGTGATGT       18840

I   Y   S   S   G   I   V   F   G   T   S   G   A   R   G   L   V   K   D   F
         TATTTATTCATCAGGTATTGTGTTTGGAACGAGTGGGGCTCGCGGTCTTGTAAAAGATTT       18900

T   P   Q   V   C   A   A   F   T   V   S   F   V   A   V   M   Q   E   H   F
         TACACCTCAGGTATGTGCTGCTTTTACGGTTTCATTTGTTGCCGTTATGCAGGAACATTT       18960

S   F   D   T   V   A   L   A   I   D   N   R   P   S   S   Y   G   M   A   Q
         TTCCTTTGATACCGTAGCATTGGCAATAGATAATCGTCCAAGTAGTTATGGGATGGCTCA       19020

A   C   A   A   A   L   A   D   K   G   V   N   C   I   F   Y   G   V   V   P
         GGCGTGTGCTGCTGCATTGGCGGATAAAGGCGTTAACTGTATTTTTTATGGAGTGGTACC       19080

T   P   A   L   A   F   Q   S   M   S   D   N   M   P   A   I   M   V   T   G
         AACCCCAGCTTTGGCCTTTCAGTCTATGTCTGACAATATGCCTGCGATAATGGTTACGGG       19140

S   H   I   P   F   E   R   N   G   L   K   F   Y   R   P   D   G   E   I   T
         AAGTCATATTCCATTCGAGCGGAACGGCCTCAAGTTTTATCGTCCTGATGGTGAAATCAC       19200

K   H   D   E   A   A   I   L   S   V   E   D   T   C   S   H   L   E   L   K
         GAAACATGATGAGGCTGCGATCCTTAGTGTTGAAGATACGTGCAGCCATTTAGAGCTTAA       19260
```

Figure 10/14

```
      E   L   I   V   S   E   M   A   A   V   N   Y   I   S   R   Y   T   S   L   F
    AGAACTCATAGTTTCAGAAATGGCTGCTGTTAATTATATATCTCGTTATACATCTTTATT              19320

S   T   P   F   L   K   N   K   R   I   G   I   Y   E   H   S   S   A   G   R
    TTCTACTCCATTCCTGAAAAATAAGCGTATTGGTATTTACGAACATTCAAGCGCTGGGCG              19380

D   L   Y   K   P   L   F   I   A   L   G   A   E   V   V   S   L   G   R   S
    TGATCTTTATAAGCCTTTATTTATTGCATTGGGGGCTGAAGTCGTTAGCTTGGGTAGAAG              19440

D   N   F   V   P   I   D   T   E   A   V   S   K   E   D   R   E   K   A   R
    CGATAATTTTGTACCTATAGATACAGAGGCTGTAAGCAAAGAGGATCGGGAAAAAGCTCG              19500

S   W   A   K   E   F   D   L   D   A   I   F   S   T   D   G   D   G   D   R
    CTCATGGGCTAAAGAGTTCGATTTAGATGCCATATTCTCGACAGATGGGGATGGTGATCG              19560

P   L   I   A   D   E   A   G   E   W   L   R   G   D   I   L   G   L   L   C
    CCCTCTTATTGCTGATGAGGCCGGTGAGTGGCTAAGAGGCGATATACTAGGTCTATTATG              19620

S   L   A   L   D   A   E   A   V   A   I   P   V   S   C   N   S   I   I   S
    TTCACTTGCATTGGATGCAGAAGCCGTCGCTATTCCTGTTAGTTGTAACAGCATAATTTC              19680

S   G   R   F   F   K   H   V   K   L   T   K   I   G   S   P   Y   V   I   E
    TTCTGGCCGCTTTTTTTAAACATGTTAAGCTTACAAAAATTGGCTCGCCTTATGTTATCGA             19740

A   F   N   E   L   S   R   S   Y   S   R   I   V   G   F   E   A   N   G   G
    AGCTTTTAATGAATTATCGCGGAGTTATAGTCGTATTGTCGGTTTTGAAGCCAATGGCGG              19800

F   L   L   G   S   D   I   C   I   N   E   Q   N   L   H   A   L   P   T   R
    TTTTTTTATTAGGAAGCGACATCTGTATTAACGAGCAGAATCTTCATGCCTTACCAACTCG             19860

D   A   V   L   P   A   I   M   L   L   Y   K   S   R   N   T   S   I   S   A
    TGATGCTGTATTACCAGCAATAATGCTGCTTTACAAAAGTAGGAATACCAGCATTAGCGC              19920

L   V   N   E   L   P   T   R   Y   T   H   S   D   R   L   Q   G   I   T   T
    TTTAGTCAATGAACTCCCAACTCGTTACACCCATTCTGACAGATTACAGGGGATTACAAC              19980

D   K   S   Q   S   L   I   S   M   G   R   E   N   L   S   N   L   L   S   Y
    TGATAAAAGTCAATCCTTAATTAGTATGGGCAGAGAAAATCTGAGCAACCTCTTAAGCTA              20040

I   G   L   E   N   E   G   A   I   S   T   D   M   T   D   G   M   R   I   T
    TATTGGTTTGGAGAATGAAGGTGCAATTTCTACAGATATGACAGATGGTATGCGAATTAC              20100

L   R   D   G   C   I   V   H   L   R   A   S   G   N   A   P   E   L   R   C
    TTTACGTGATGGATGTATTGTGCATTTGCGCGCTTCTGGTAATGCACCTGAGTTACGCTG              20160

Y   A   E   A   N   L   L   N   R   A   Q   D   L   V   N   T   T   L   A   N
    CTATGCAGAAGCTAATTTATTAAATAGGGCTCAGGATCTTGTAAATACAACGCTTGCTAA              20220
                                                End of manB
      I   K   K   R   C   L   L   *
    TATTAAAAAACGATGCTTGCTGTAAAAAAATTGAATGTTATTTACTTAATATGCCTATTT              20280
                                                Start of wbaP
                                          M   D   N   I   D   N   K   Y
    TATTTACATTATGCACGGTCAGAGGGTGAGGATTAAATGGATAATATTGATAATAAGTAT              20340

N   P   Q   L   C   K   I   F   L   A   I   S   D   L   I   F   F   N   L   A
    AATCCACAGCTATGTAAAATTTTTTTGGCTATATCGGATTTGATTTTTTTTAATTTAGCC              20400

L   W   F   S   L   G   C   V   Y   F   I   F   D   Q   V   Q   R   F   I   P
    TTATGGTTTTCATTAGGATGTGTCTATTTTATTTTTGATCAAGTACAGCGATTTATTCCT              20460

Q   D   Q   L   D   T   R   V   I   T   H   F   I   L   S   V   V   C   V   G
    CAAGACCAATTAGATACAAGAGTTATTACGCATTTTATTTTGTCAGTAGTATGTGTCGGT              20520
```

Figure 10/15

```
       W  F  W  I  R  L  R  H  Y  T  I  R  K  P  F  W  Y  E  L  K
      TGGTTTTGGATTCGTTTGCGACATTATACTATCCGCAAGCCATTTTGGTATGAGTTAAAA    20580

E  I  F  R  T  I  V  I  F  A  I  F  D  L  A  L  I  A  F  T
      GAAATTTTTCGTACGATCGTTATTTTTGCTATATTTGATTTGGCTCTGATAGCGTTTACA    20640

K  W  Q  F  S  R  Y  V  W  V  F  C  W  T  F  A  L  I  L  V
      AAATGGCAGTTTTCACGCTATGTCTGGGTGTTTTGTTGGACTTTTGCCCTAATCCTGGTG    20700

P  F  F  R  A  L  T  K  H  L  L  N  K  L  G  I  W  K  K  K
      CCTTTTTTTCGCGCACTTACAAAGCATTTATTGAACAAGCTAGGTATCTGGAAGAAAAAA    20760

T  I  I  L  G  S  G  Q  N  A  R  G  A  Y  S  A  L  Q  S  E
      ACTATCATCCTGGGGAGCGGACAGAATGCTCGTGGTGCATATTCTGCGCTGCAAAGTGAG    20820

E  M  M  G  F  D  V  I  A  F  F  D  T  D  A  S  D  A  E  I
      GAGATGATGGGGTTTGATGTTATCGCTTTTTTTGATACGGATGCGTCAGATGCTGAAATA    20880

N  M  L  P  V  I  K  D  T  E  I  I  W  D  L  N  R  T  G  D
      AATATGTTGCCGGTGATAAAGGATACTGAGATTATTTGGGATTTAAATCGTACAGGTGAT    20940

V  H  Y  I  L  A  Y  E  Y  T  E  L  E  K  T  H  F  W  L  R
      GTCCATTATATCCTTGCTTATGAATACACCGAGTTGGAGAAAACACATTTTTGGCTACGT    21000

E  L  S  K  H  H  C  R  S  V  T  V  V  P  S  F  R  G  L  P
      GAACTTTCAAAACATCATTGTCGTTCTGTTACTGTAGTCCCCTCGTTTAGAGGATTGCCA    21060

L  Y  N  T  D  M  S  F  I  F  S  H  E  V  M  L  L  R  I  Q
      TTATATAATACTGATATGTCTTTTATCTTTAGCCATGAAGTTATGTTATTAAGGATACAA    21120

N  N  L  A  K  R  S  S  R  F  L  K  R  T  F  D  I  V  C  S
      AATAACTTGGCTAAAAGGTCGTCCCGTTTTCTCAAACGGACATTTGATATTGTTTGTTCA    21180

I  M  I  L  I  I  A  S  P  L  M  I  Y  L  W  Y  K  V  T  R
      ATAATGATTCTTATAATTGCATCACCACTTATGATTTATCTGTGGTATAAAGTTACTCGA    21240

D  G  G  P  A  I  Y  G  H  Q  R  V  G  R  H  G  K  L  F  P
      GATGGTGGTCCGGCTATTTATGGTCACCAGCGAGTAGGTCGGCATGGAAAACTTTTTCCA    21300

C  Y  K  F  R  S  M  V  M  N  S  Q  E  V  L  K  E  L  L  A
      TGCTACAAATTTCGTTCTATGGTTATGAATTCTCAAGAGGTACTAAAAGAACTTTTGGCT    21360

N  D  P  I  A  R  A  E  W  E  K  D  F  K  L  K  N  D  P  R
      AACGATCCTATTGCCAGGGCTGAATGGGAGAAAGATTTTAAACTGAAAAATGATCCTCGA    21420

I  T  A  V  G  R  F  I  R  K  T  S  L  D  E  L  P  Q  L  F
      ATCACAGCTGTAGGTCGATTTATACGTAAAACTAGCCTTGATGAGTTGCCACAACTTTTT    21480

N  V  L  K  G  D  M  S  L  V  G  P  R  P  I  V  S  D  E  L
      AATGTACTAAAAGGTGATATGAGCCTGGTTGGACCACGACCTATCGTTTCGGATGAACTG    21540

E  R  Y  C  D  D  V  D  Y  Y  L  M  A  K  P  G  M  T  G  L
      GAGCGTTATTGTGATGATGTTGATTATTATTTGATGGCAAAGCCGGGCATGACAGGTCTA    21600

W  Q  V  S  G  R  N  D  V  D  Y  D  T  R  V  Y  F  D  S  W
      TGGCAAGTGAGTGGGCGTAATGATGTTGATTATGACACTCGTGTTTATTTTGATTCCTGG    21660

Y  V  K  N  W  T  L  W  N  D  I  A  I  L  F  K  T  A  K  V
      TATGTTAAAAACTGGACGCTTTGGAATGATATTGCCATTCTGTTTAAAACAGCGAAAGTT    21720
                                End of wbaP
       V  L  R  R  D  G  A  Y  *
      GTTTTGCGGCGAGATGGTGCGTAT TAAGCTTACCGAGAAGTACTGAATAATAATTGTATA    21780

AATTAGCCTGCGTAAAATCTGAACGCATCAATCGCTACCTTAATATCATACCTTTGAGTT    21840
```

Figure 10/16

```
AACATACTATTCACCTTTAACCTGCCATGACCGTTTGTGGCAGGGTTTCCACACCTGACA    21900

GGAGTATGTAATGTCCAAGCAACAGATCGGCGTCGTCGGTATGGCAGTGATGGGGCGCAA    21960

CCTCGCGCTCAACATCGAAAGCCGTGGTTATACCGTCTCCGTTTTCAACCGCTCCCGTGA    22020

AAAGACCGAAGAAGTGATTGCCGAGAATCCCGGCAAAAAGCTGGTGCCTTATTACACGGT    22080
```

NUCLEIC ACID-BASED METHODS OF DETECTING BACTERIAL O-ANTIGENS

TECHNICAL FIELD

The invention relates to novel nucleotide sequences located in a gene cluster which controls the synthesis of a bacterial polysaccharide antigen, especially an O antigen, and the use of those nucleotide sequences for the detection of bacteria which express particular polysaccharide antigens (particularly O antigens) and for the identification of the polysaccharide antigens (particularly O antigens) of those bacteria.

BACKGROUND ART

Enteropathogenic *E. coli* strains are well known causes of diarrhoea and haemorrhagic colitis in humans and can lead to potentially life threatening sequelae including haemolytic uremic syndrome and thrombotic thrombocytopaenic purpura. Some of these strains are commonly found in livestock and infection in humans is usually a consequence of consumption of contaminated meat or dairy products which have been improperly processed. The O specific polysaccharide component (the "O antigen") of lipopolysaccharide is known to be a major virulence factor of enteropathogenic *E. coli* strains.

The *E. coli* O antigen is highly polymorphic and 166 different forms of the antigen have been defined; Ewing, W. H. [in Edwards and Ewings "Identification of the Enterobacteriacea" Elsevier. Amsterdam (1986)] discusses 128 different O antigens while Lior H. (1994) extends the number to 166 [in "Classification of *Escherichia coli* In *Escherichia coli* in domestic animals and humans pp31–72. Edited by C. L. Gyles CAB International]. The genus *Salmonella enterica* has 46 known O antigen types [Popoff M. Y. et al (1992) "Antigenic formulas of the *Salmonella enterica* serovars" 6th revision WHO Collaborating Centre for Reference and Research on *Salmonella enterica*, Institut Pasteur Paris France].

An important step in determining the biosynthesis of O antigens-and therefore the mechanism of the polymorphism has been to characterise the gene clusters controlling O antigen biosynthesis. The genes specific for the synthesis of the O antigen are generally located in a gene cluster at map position 45 minutes on the chromosome of *E. coli* K-12 [Bachmann, B. J. 1990 "Linkage map of *Escherichia coli* K-12". Milcrobiol. Rev. 54:130–197], and at the corresponding position in *S. enterica* LT2 [Sanderson et al (1995) "Genetic map of *Salmonella enterica* typhimurium", Edition VIII Microbiol. Rev. 59: 241–303]. In both cases the O antigen gene cluster is close to the gnd gene as is the case in other strains of *E. coli* and *S. enterica* [Reeves P. R. (1994) "Biosynthesis and assemby of lipopolysaccharide, 281–314. in A. Neuberger and L. L. M. van Deenen (eds) "Bacterial cell wall, new comprehensive biochemistry" vol 27 Elsevier Science Publishers]. These genes encode enzymes for the synthesis of nucleotide diphosphate sugars and for assembly of the sugars into oligosaccharide units and in general for polymerisation to O antigen.

The *E. coli* O antigen gene clusters for a wide range of *E. coli* O antigens have been cloned but the O7, O9, O16 and O111 O antigens have been studied in more detail with only O9 and O16 having been fully characterised with regard to nucleotide sequence to date [Kido N., Torgov V. I., Sugiyama T., Uchiya K., Sugihara H., Komatsu T., Kato N. & Jann K. (1995) "Expression of the O9 polysaccharide of *Escherichia coli*: sequencing of the *E. coli* O9 rfb gene cluster, characterisation of mannosyl transferases, and evidence for an ATP-binding cassette transport system" J. of Bacteriol. 177 2178–2187; Stevenson G., Neal B., Liu D., Hobbs M., Packer N. H., Batley M., Redmond J. W., Lindguist L. & Reeves PR (1994) "Structure of the O antigen of *E. coli* K12 and the sequence of its rfb gene cluster" J. of Bacteriol. 176 4144–4156; Jayaratne, P. et al. (1991) "Cloning and analysis of duplicated rfbM and rfbK genes involved in the formation of GDP-mannose in *Escherichia coli* O9:K30 and participation of rfb genes in the synthesis of the group 1 K30 capsular polysaccharide" J. Bacteriol. 176: 3126–3139; Valvano, M. A. and Crosa, J. H.(1989)"Molecular cloning and expression in *Escherichia coli* K-12 of chromosomal genes determining the O7 lipopolysaccharide antigen of a human invasive strain of *E. coli* O7:K1". Inf and Immun. 57:937–943; Marolda C. L. And Valvano, M. A. (1993). "Identification, expression, and DNA sequence of the GDP-mannose biosynthesis genes encoded by the O7 rfb gene cluster of strain VW187 (*Eschericia coli* O7:K1)". J. Bacteriol. 175:148–158.1].

Bastin D. A., et al. 1991 ["Molecular cloning and expression in *Escherichia coli* K-12 of the rfb gene cluster determining the O antigen of an *E. coli* O111 strain". Mol. Microbiol. 5:9 2223–2231] and Bastin D. A. and Reeves, P. R. [(1995)"Sequence and analysis of the O antigen gene (rfb)cluster of *Escherichia coli* O111". Gene 164: 17–23] isolated chromosomal DNA encoding the *E. coli* 0111 rfb region and characterised a 6962 bp fragment of *E. coli* 0111 rfb. Six open reading frames (orfs) were identified in the 6962 bp partial fragment and the alignment of the sequences of these orfs revealed homology with genes of the GDP-mannose pathway, rfbK and rfbM, and other rfb and cps genes.

The nucleotide sequences of the loci which control expression of *Salmonella enterica* B, A, D1, D2, D3, C1, C2 and E O antigens have been characterised [Brown, P. K., L. K. Romana and P. R. Reeves (1991) "Cloning of the rfb gene cluster of a group C2 *Salmonella enterica*": comparison with the rfb regions of groups B and D Mol. Microbiol. 5:1873–1881; Jiang, X.-M., B. Neal, F. Santiago, S. J. Lee, L. K. Romana, and P. R. Reeves (1991) "Structure and sequence of the rfb (O antigen) gene cluster of *Salmonella enterica* serovar typhimurium (LT2)". Mol. Microbiol. 5:692–713; Lee, S. J., L. K. Romana, and P. R. Reeves (1992) "Sequences and structural analysis of the rfb (O antigen)gene cluster from a group C1 *Salmonella enterica* enterica strain" J. Gen. Microbiol. 138: 1843–1855; Lui, D., N. K. Verma, L. K. Romana, and P. R. Reeves (1991) "Relationship among the rfb regions of *Salmonella enterica* serovars A, B and D" J. Bacteriol. 173: 4814–4819; Verma, N. K., and P. Reeves (1989) "Identification and sequence of rfbS and rfbE, which determine the antigenic specificity of group A and group D *Salmonella entericae*" J. Bacteriol. 171: 5694–5701; Wang, L., L. K. Romana, and P. R. Reeves (1992) "Molecular analysis of a *Salmonella enterica* enterica group E1 rfb gene cluster: O antigen and the genetic basis of the major polymorphism" Genetics 130: 429–443; Wyk, P., and P. Reeves (1989). "Identification and sequence of the gene for abequose synthase, which confers antigenic specificity on group B *Salmonella entericae*: homology with galactose epimerase" J. Bacteriol. 171: 5687–5693,; Xiang, S. H., M. Hobbs, and P. R. Reeves. 1994 Molecular analysis of the rfb gene luster of a group D2 *Salmonella enterica* strain: evidence for its origin from an insertion sequence-mediated recombination event between group E and D1 strains. J. Bacteriol. 176: 4357–4365; Curd, H., D. Liu and P. R. Reeves, 1998. Relationships among the O antigen *Salmonella enterica* groups B, D1, D2, and D3. J. Bacteriol. 180: 1002–1007.).

Of the closely related *Shigella* (which really can be considered to be part of *E. coli*) *S. dysenteriae* and *S. flexneri* O antigens have been fully sequenced and are next to gnd. [Klena JD & Schnaitman CA (1993) "Function of the rfb gene cluster and the rfe gene in the synthesis of O antigen by *Shigella dysenteriae* 1" Mol. Microbiol. 9 393–402; Morona R., Mavris M., Fallarino A. & Manning P. (1994) "Characterisation of the rifc region of *Shigella flexneri*" J.Bacteriol 176: 733–747].

Inasmuch as the O antigen of enteropathogenic *E. coli* strains and the O antigen of *Salmonella enterica* strains are major virulence factors and are highly polymorphic, there is a real need to develop highly specific, sensitive, rapid and inexpensive diagnostic assays to detect *E. coli* and assays to detect *S. enterica*. There is also a real need to develop diagnostic assays to identify the O antigens of *E. coli* strains and assays to identify the O antigens of *S. enterica* strains. With regard to the detection of *E. coli* these needs extend beyond EHFC (enteropathogenic haemorrhagic *E. coli*) strains but this is the area of greatest need. There is interest in diagnostics for ETEC (enterotoxigenic *E. coli*) etc in *E. coli*.

The first diagnostic systems employed in this field used large panels of antisera raised against *E. coli* O antigen expressing strains or *S. enterica* O antigen expressing strains. This technology has inherent difficulties associated with the preparation, storage and usage of the reagents, as well as the time required to achieve a meaningful diagnostic result.

Nucleotide sequences derived from the O antigen gene clusters of *S. enterica* strains have been used to determine *S. enterica* O antigens in a PCR assay [Luk, J. M. C. et al. (1993) "Selective amplification of abequose and paratose synthase genes (rfb) by polymerase chain reaction for identification of *S. enterica* major serogoups (A, B, C2, and D)", J. Clin. Microbiol. 31:2118–2123 ]. The prior complete nucleotide sequence characterisation of the entire rfb locus of serovars Typhimurium, Paratyphi A, Typhi, Muenchen, and Anatum; representing groups B, A, D1, C2 and E1 respectively enabled Luk et al. to select oligonucleotide primers specific for those serogroups. Thus the approach of Luk et al. was based on aligning known nucleotide sequences corresponding to CDP-abequose and CDP-paratose synthesis genes within the O antigen regions of *S. enterica* serogroups E1, D1, A, B and C2 and exploiting the observed nucleotide sequence differences in order to identify serotype-specific oligonucleotides.

In an attempt to determine the O antigen serotype of a Shiga-like toxin producing *E. coli* strain, Paton, A. W., et al. 1996 ["Molecular microbiological investigation of an outbreak of Hemolytic-Uremic Syndrome caused by dry fermented sausage contaminated with Shiga-like toxin producing *Escherichia coli*". J. Clin. Microbiol. 34: 1622–1627], used oligonucleotides derived from the wbdI (orf6) region, which were believed to be specific to the *E. coli* O111 antigen and which were derived from *E. coli* O111 sequence, in a PCR diagnostic assay. Unpublished reports indicate that the approach of Paton et al. is deficient in that the nucleotide sequences derived from wbdI may not specifically identify the O111 antigen and in fact lead to detection of false positive results. Paton et al. disclose the detection of 5 O111 antigen isolates by PCR when in fact from only 3 of those isolates did they detect bacteria which reacted with O111 specific antiserum.

DESCRIPTION OF THE INVENTION

Whilst not wanting to be held to a particular hypothesis, the present inventors now believe that the reported false positives found with the Paton et al. method are due to the fact that the nucleic acid molecules employed by Paton et al. were derived from genes which have a putative function as a sugar pathway gene, [Bastin D. A. and Reeves, P. R. (1995) Sequence and analysis of the O antigen gene(rfb) cluster of *Escherichia coli* O111. Gene 164: 17–23] which they now believe to lack the necessary nucleotide sequence specificity to identify the *E. coli* O antigen. The inventors now believe that many of the nucleic acid molecules derived from sugar pathway genes expressed in *S. enterica* or other enterobacteria are also likely to lack the necessary nucleotide sequence specificity to identify specific O antigens or specific serotypes.

In this regard it is important to note that the genes for the synthesis of a polysaccharide antigen include those related to the synthesis of the sugars present in the antigen (sugar pathway genes) and those related to the manipulation of those sugars to form the polysaccharide. The present invention is predominantly concerned with the latter group of genes, particularly the assembly and transport genes such as transferase, polymerase and flippase genes.

The present inventors have surprisingly found that the use of nucleic acid molecules derived from particular assembly and transport genes, particularly transferase, wzx and wzy genes, within O antigen gene clusters can improve the specificity of the detection and identification of O antigens. The present inventors believe that the invention is not necessarily limited to the detection of the particular O antigens which are encoded by the nucleic acid molecules exemplified herein, but has broad application for the detection of bacteria which express an O antigen and the identification of O antigens in general. Further because of the similarities between the gene clusters involved in the synthesis of O antigens and other polymorphic polysaccharide antigens, such as bacterial capsular antigens, the inventors believe that the methods and molecules of the present invention are also applicable to these other polysaccharide antigens.

Accordingly, in one aspect the present invention relates to the identification of nucleic acid molecules which are useful for the detection and identification of specific bacterial polysaccharide antigens.

The invention provides a nucleic acid molecule derived from: a gene encoding a transferase; or a gene encoding an enzyme for the transport or processing of a polysaccharide or oligosaccharide unit, including a wzx gene, wzy gene, or a gene with a similar function; the gene being involved in the synthesis of a particular bacterial polysaccharide antigen, wherein the sequence of the nucleic acid molecule is specific to the particular bacterial polysaccharide antigen.

Polysaccharide antigens, such as capsular antigens of *E. coli* (Type I and Type II), the Virulence capsule of *S. enterica* sv *Typhi* and the capsules of species such as *Streptococcus pneumoniae* and *Staphylococcus albus* are encoded by genes which include nucleotide sugar pathway genes, sugar transferase genes and genes for the transport and processing of the polysaccharide or oligosaccharide unit. In some cases these are wzx or wzy but in other cases they are quite different because a different processing pathway is used. Examples of other gene clusters include the gene clusters for an extracellular polysaccharide of *Streptococcus thermothilus*, an exopolysaccharide of *Rhizobium melilotti* and the K2 capsule of *Klebsiella pneumoniae*. These all have genes which by experimental analysis, comparison of nucleotide sequence or predicted protein structure, can be seen to include nucleotide sugar pathway genes, sugar transferase genes and genes for oligosaccharide or polysaccharide processing.

In the case of the *E. coli* K-12 colanic acid capsule gene cluster [Stevenson et al (1996) "Organization of the *Escherichia coli* K-12 gene cluster responsible for production of the extracellular polysaccharide colanic acid". J. Bacteriol 178: 4885–4893] genes from the three classes were identified either provisionally or definitively. Colanic acid capsule is classified with the Type I capsule of *E. coli*.

The present inventors believe that, in general, transferase genes and genes for oligosaccharide processing will be more specific for a given capsule than the genes coding for the nucleotide sugar synthetic pathways as most sugars present in such capsules occur in the capsules of different serotypes. Thus the nucleotide sugar synthesis pathway genes could now be predicted to be common to more than one capsule type.

As elaborated below the present inventors recognise that there may be polysaccharide antigen gene clusters which share transferase genes and/or genes for oligosaccharide or polysaccharide processing so that completely random selection of nucleotide sequences from within these genes may still lead to cross-reaction; an example with respect to capsular antigens is provided by the *E. coli* type II capsules for which only transferase genes are sufficiently specific. However, the present inventors in light of their current results nonetheless consider the transferase genes or genes controlling oligosaccharide or polysaccharide processing to be superior targets for nucleotide sequence selection for the specific detection and characterisation of polysaccharide antigen types. Thus where there is similarity between particular genes, selection of nucleotide sequences from within other transferase genes or genes for oligosaccharide or polysaccharide processing from within the relevant gene cluster will still provide specificity, or alternatively the use of combinations of nucleotide sequences will provied the desired specificity. The combinations of nucleotide sequences may include nucleotide sequences derived from pathway genes together with nucleotide sequences derived from transferase, wzx or wzy genes.

Thus the invention also provides a panel of nucleic acid molecules wherein the nucleic acid molecules are derived from a combination of genes encoding transferases and/or enzymes for the transport or processing of a polysaccharide or oligosaccharide unit including wzx or wzy genes; wherein the combination of genes is specific to the synthesis of a particular bacterial polysaccharide antigen and wherein the panel of nucleic acid molecules is specific to a bacterial polysaccharied antigen. In another preferred form, the nucleic acid molecules are derived from a combination of genes encoding transferases and/or enzymes for the transport or processing of a polysaccharide or oligosaccharide unit including wzx or wzy genes, together with nucleic acid molecules derived from pathway genes.

In a second aspect the present invention relates to the identification of nucleic acid molecules which are useful for the detection of bacteria which express O antigens and for the identification of the O antigens of those bacteria in diagnostic assays.

The invention provides a nucleic acid molecule derived from: a gene encoding a transferase; or a gene encoding an enzyme for the transport or processing of a polysaccharide or oligosaccharide unit such as a wzx or wzy gene, the gene being involved in the synthesis of a particular bacterial O antigen, wherein the sequence of the nucleic acid molecule is specific to the particular bacterial O antigen.

The nucleic acids of the invention may be variable in length. In one embodiment they are from about 10 to about 20 nucleotides in length.

In one preferred embodiment, the invention provides a nucleic acid molecule derived from: a gene encoding a transferase; or a gene encoding an enzyme for the transport or processing of a polysaccharide or oligosaccharide unit including a wzx or wzy gene the gene being involved in the synthesis of an O antigen expressed by *E. coli*, wherein the sequence of the nucleic acid molecule is specific to the O antigen.

In one more preferred embodiment, the sequence of the nucleic acid molecule is specific to the nucleotide sequence encoding the O111 antigen (SEQ ID NO:1). More preferably, the sequence is derived from a gene selected from the group consisting of wbdh (nucleotide position 739 to 1932 of SEQ ID NO:1), wzx (nucleotide position 8646 to 9911 of SEQ ID NO:1), wzy (nucleotide position 9901 to 10953 of SEQ ID NO:1), wbdM (nucleotide position 11821 to 12945 of SEQ ID NO:1) and fragments of those molecules of at least 10–12 nucleotides in length. Particularly preferred nucleic acid molecules are those set out in Table 5 and 5A, with respect to the above mentioned genes.

In another more preferred embodiment, the sequence of the nucleic acid molecule is specific to the nucleotide sequence encoding the 0157 antigen (SEQ ID NO:2). More preferably the sequence is derived from a gene selected from the group consisting of wbdN (nucleotide position 79 to 861 of SEQ ID NO:2), wbdO, (nucleotide position 2011 to 2757 of SEQ ID NO:2), wbdP (nucleotide position 5257 to 6471 of SEQ ID NO:2)), wbdR (13156 to 13821 of SEQ ID NO:2), wzx (nucleotide position 2744 to 4135 of SEQ ID NO:2) and wzy (nucleotide position 858 to 2042 of SEQ ID NO:2). Particularly preferred nucleic acid molecules are those set out in Table 6 and 6A.

The invention also provides in a further preferred embodiment a nucleic acid molecule derived from: a gene encoding a transferase; or a gene encoding an enzyme for the transport or processing of a polysaccharide or oligosaccharide unit including a wzx or wzy gene; the gene being involved in the synthesis of an O antigen expressed by *Salmonella enterica*, wherein the sequence of the nucleic acid molecule is specific to the O antigen.

In one more preferred form of this embodiment, the sequence of the nucleic acid molecule is specific to the nucleotide sequence encoding the *S. enterica* C2 antigen (SEQ ID NO:3). More preferably the sequence of the nucleic acid molecule is derived from a gene selected from the group consisting of wbaR (nucleotide position 2352 to 3314 of SEQ ID NO:3), wbaL (nucleotide position 3361 to 3875 of SEQ ID NO:3), wbaQ (nucleotide position 3977 to 5020 of SEQ ID NO:3), wbaW (nucleotide position 6313 to 7323 of SEQ ID NO:3), wbaZ (nucleotide position 7310 to 8467 of SEQ ID NO:3), wzx (nucleotide position 1019 to 2359 of SEQ ID NO:3)and wzy (nucleotide position 5114 to 6313 of SEQ ID NO:3). Particularly preferred nucleic acid molecules are those set out in Table 7.

In another more preferred form of this embodiment, the sequence of the nucleic acid molecule is specific to the nucleotide sequence encoding the *S. enterica* B antigen (SEQ ID NO:4). More preferably the sequence is derived from wzx (nucleotide position 12762 to 14054 of SEQ ID NO:4) or wbav (nucleotide position 14059 to 15060 of SEQ ID NO:4). Particularly preferred nucleic acid molecules are those set out in Table 8 which are derived from wzx and wbaV genes.

In a further more preferred form of this embodiment, the sequence of the nucleic acid molecule is specific to the *S. enterica* D3 O antigen and is derived from the wzy gene.

In yet a further preferred form of this embodiment, the sequence of the nucleic acid molecule is specific to the *S. enterica* E1 O antigen and is derived from the wzx gene.

While transferase genes, or genes coding for the transport or processing of a polysaccharide or oligosaccharide unit, such as a wzx or wzy gene, are superior targets for specific detection of individual O antigen types there may well be individual genes or parts of them within this group that can be demonstrated to be the same or closely related, between different O antigen types such that cross-reactions can occur. Cross reactions should be avoided by the selection of a different target within the group or the use of multiple targets within the group.

Further, it is recognised that there are cases where O antigen gene clusters have arisen from recombination of at least two strains such that the unique O antigen type is provided by a combination of gene products shared with at least two other O antigen types. The recognised example of this phenomenon is the *S. enterica* O antigen serotype D2 which has genes from D1 and E1 but none unique to D2. In these circumstances the detection of the O antigen type can still be achieved in accordance with the invention, but requires the use of a combination of nucleic acid molecules to detect a specific combination of genes that exists only in that particular O antigen gene cluster.

Thus, the invention also provides a panel of nucleic acid molecules wherein the nucleic acid molecules are derived from genes encoding transferases and/or enzymes for the transport or processing of a polysaccharide or oligosaccharide unit including wzx or wzy genes, wherein the panel of nucleic acid molecules is specific to a bacterial O antigen. Preferably the particular bacterial O antigen is expressed by *S enterica*. More preferably, the panel of nucleic acid molecules is specific to the D2 O antigen and is derived from the E1 wzy gene and the D1 wzx gene.

The combinations of nucleotide sequences may include nucleotide sequences derived from pathway genes, together with nucleotide sequences derived from transferase, wzx or wzy genes.

Thus, the invention also provides a panel of nucleic acid molecules, wherein the nucleic acid molecules are derived from genes encoding transferases and/or enzymes for the transport or processing of a polysaccharide or oligosaccharide unit including wzx or wzy genes, and sugar pathway genes, wherein the panel of nucleic acid molecules is specific to a particular bacterial O antigen. Preferably the O antigen is expressed *S. enterica*.

Further it is recognised that there may be instances where spurious hybridisation will arise through initial selection of a sequence found in many different genes but this is typically recognisable by, for instance, comparison of band sizes against controls in PCR gels, and an alternative sequence can be selected.

The present inventors believe that based on the teachings of the present invention and available information concerning polysaccharide antigen gene clusters (including O antigen gene clusters), and through use of experimental analysis, comparison of nucleic acid sequences or predicted protein structures, nucleic acid molecules in accordance with the invention can be readily derived for any particular polysaccharide antigen of interest. Suitable bacterial strains can typically be acquired commercially from depositary institutions.

As mentioned above there are currently 166 defined *E. coli* O antigens while the *S. enterica* has 46 known O antigen types [Popoff M. Y. et al (1992) "Antigenic formulas of the *Salmonella serovars*" 6th revision WHO Collaborating centre for Reference and Research on *Salmonella*, Institut Pasteur Paris France]. Many other genera of bacteria are known to have O antigens and these include *Citrobacter, Shigella, Yersinia, Plesiomonas, Vibrio* and *Proteus*.

Samples of the 166 different *E. coli* O antigen serotypes are available from Statens Serum Institut, Copenhagen, Denmark.

The 46 *S. enterica* serotypes are available from Institute of Medical and Veterinary Science, Adelaide, Australia.

In another aspect, the invention relates to a method of testing a sample for the presence of one or more bacterial polysaccharide antigens comprising contacting the sample with at least one oligonucleotide molecule capable of specifically hybridising to: (i) a gene encoding a transferase, or (ii) a gene encoding an enzyme for transport or processing of oligosaccharide or polysaccharide units, including a wzx or wzy gene; wherein said gene is involved in the synthesis of the bacterial polysaccharide antigen; under conditions suitable to permit the at least one oligonucleotide molecule to specifically hybridise to at least one such gene of any bacteria expressing the particular bacterial polysaccharide antigen present in the sample and detecting any specifically hybridised oligonucleotide molecules.

Where a single specific oligonucleotide molecule is unavailable a combination of molecules hybridising specifically to the target region may be used. Thus the invention provides a panel of nucleic acid molecules for use in the method of testing of the invention, wherein the nucleic acid molecules are derived from genes encoding transferases and/or enzymes for the transport or processing of a polysaccharide or oligosaccharide unit including wzx or wzy genes, wherein the panel of nucleic acid molecules is specific to a particular bacterial polysaccharide. The panel of nucleic acid molecules can include nucleic acid molecules derived from sugar pathway genes where necessary.

In another aspect, the invention relates to a method of testing a sample for the presence of one or more bacterial polysaccharide antigens comprising contacting the sample with at least one pair of oligonucleotide molecules, with at least one oligonucleotide molecule of the pair capable of specifically hybridising to: (i) a gene encoding a transferase, or (ii) a gene encoding an enzyme for transport or processing oligosaccharide or polysaccharide units, including a wzx or wzy gene; wherein said gene is involved in the synthesis of the bacterial polysaccharide antigen; under conditions suitable to permit the at least one oligonucleotide molecule of the pair of molecules to specifically hybridise to at least one such gene of any bacteria expressing the particular bacterial polysaccharide antigen present in the sample and detecting any specifically hybridised oligonucleotide molecules.

The pair of oligonucleotide molecules may both hybridise to the same gene or to different genes. Only one oligonucleotide molecule of the pair need hybridise specifically to sequence specific for the particular antigen type. The other molecule can hybridise to a non-specific region.

Where the particular polysaccharide antigen gene cluster has arisen through recombination, the at least one pair of oligonucleotide molecules may be selected to be capable of hybridising to a specific combination of genes in the cluster specific to that polysaccharide antigen, or multiple pairs may be selected to provide hybridisation to the specific combination of genes. Even where all the genes in a particular cluster are unique, the method may be carried out using nucleotide molecules which recognise a combination of genes within the cluster.

Thus the invention provides a panel containing pairs of nucleic acid molecules for use in the method of testing of the invention, wherein the pairs of nucleic acid molecules are derived from genes encoding transferases and/or enzymes for the transport or processing of a polysaccharide or oligosaccharide unit including wzx or wzy genes, wherein the panel of nucleic acid molecules is specific to a particular bacterial polysaccharide antigen. The panel of nucleic acid molecules can include pairs of nucleic acid molecules derived from sugar pathway genes where necessary.

In another aspect, the invention relates to a method of testing a sample for the presence of one or more particular bacterial O antigens comprising contacting the sample with at least one oligonucleotide molecule capable of specifically hybridising to: (i) a gene encoding an O antigen transferase, or (ii) a gene encoding an enzyme for transport or processing of the oligosaccharide or polysaccharide unit, including a wzx or wzy gene; wherein said gene is involved in the synthesis of the particular O antigen; under conditions suitable to permit the at least one oligonucleotide molecule to specifically hybridise to at least one such gene of any bacteria expressing the particular bacterial O antigen present in the sample and detecting any specifically hybridised oligonucleotide molecules. Preferably the bacteria are *E. coli* or *S. enterica*. More preferably, the *E. coli* express the 0157 serotype or the 0111 serotype. More preferably the *S. enterica* express the C2 or B serotype. Preferably, the method is a Southern blot method. More preferably, the nucleic acid molecule is labelled and hybridisation of the nucleic acid molecule is detected by autoradiography or detection of fluorescence.

The inventors envisage circumstances where a single specific oligonucleotide molecule is unavailable. In these circumstances a combination of molecules hybridising specifically to the target region may be used. Thus the invention provides a panel of nucleic acid molecules for use in the method of testing of the invention, wherein the nucleic acid molecules are derived from genes encoding transferases and/or enzymes for the transport or processing of a polysaccharide or oligosaccharide unit including wzx or wzy genes, wherein the panel of nucleic acid molecules is specific to a particular bacterial O antigen. Preferably the particular bacterial O antigen is expressed by *S. enterica*. The panel of nucleic acid molecules can include nucleic acid molecules derived from sugar pathway genes where necessary.

In another aspect, the invention relates to a method of testing a sample for the presence of one or more particular bacterial O antigens comprising contacting the sample with at least one pair of oligonucleotide molecules with at least one oligonucleotide molecule of the pair being capable of specifically hybridising to: (i) a gene encoding an O antigen transferase, or (ii) a gene encoding an enzyme for transport or processing of the oligosaccharide or polysaccharide unit, including a wzx or wzy gene; wherein said gene is involved in the synthesis of the particular O antigen; under conditions suitable to permit the at least one oligonucleotide molecule to specifically hybridise to at least one such gene of any bacteria expressing the particular bacterial O antigen present in the sample and detecting any specifically hybridised oligonucleotide molecules.

Preferably the bacteria are *E coli* or *S. enterica*. More preferably, the *E. coli* are of the 0111 or the 0157 serotype. More preferably the *S. enterica* express the C2 or B serotype. Preferably, the method is a polymerase chain reaction method. More preferably the oligonucleotide molecules for use in the method of the invention are labelled. Even more preferably the hybridised oligonucleotide molecules are detected by electrophoresis. Preferred oligonucleotides for use with 0111 which provide for specific detection of 0111 are illustrated in Table 5 and 5A with respect to the genes wbdH, wzx, wzy and wbdM. Preferred oligonucleotide molecules for use with O157 which provide for specific detection of O157 are illustrated in Table 6 and 6A.

With respect to serotypes C2 and B, suitable oligonucleotide molecules can be selected from appropriate regions described in column 3 of Tables 7 and 8.

The inventors envisage rare circumstances whereby two genetically similar gene clusters encoding serologically different O antigens have arisen through recombination of genes or mutation so as to generate polymorphic variants. In these circumstances multiple pairs of oligonucleotides may be selected to provide hybridisation to the specific combination of genes. The invention thus provides a panel containing pairs of nucleic acid molecules for use in the method of testing of the invention, wherein the pairs of nucleic acid molecules are derived from genes encoding transferases and/or enzymes for the transport or processing of a polysaccharide or oligosaccharide unit including wzx or wzy genes, wherein the panel of nucleic acid molecules is specific to a particular bacterial O antigen. Preferably the particular bacterial O antigen is expressed by *S. enterica*. The panel of nucleic acid molecules can include pairs of nucleic acid molecules derived from sugar pathway genes where necessary.

In another aspect, the invention relates to a method for testing a food derived sample for the presence of one or more particular bacterial O antigens comprising contacting the sample with at least one pair of oligonucleotide molecules with at least one oligonucleotide molecule of the pair being capable of specifically hybridising to: (i) a gene encoding an O antigen transferase, or (ii) a gene encoding an enzyme for transport or processing of the oligosaccharide or polysaccharide unit, including a wzx or wzy gene; wherein the gene is involved in the synthesis of the particular O antigen; under conditions suitable to permit the at least one oligonucleotide molecule to specifically hybridise to at least one such gene of any bacteria expressing the particular bacterial polysaccharide antigen present in the sample and detecting any specifically hybridised oligonucleotide molecules. Preferably the bacteria are *E. coli* or *S. enterica*. More preferably, the *E. coli* are of the 0111 or 0157 serotype. More preferably the *S. enterica* are of the C2 or B serotype. Preferably, the method is a polymerase chain reaction method. More preferably the oligonucleotide molecules for use in the method of the invention are labelled. Even more preferably the hybridised oligonucleotide molecules are detected by electrophoresis.

In another aspect the present invention relates to a method for testing a faecal derived sample for the presence of one or more particular bacterial O antigens comprising contacting the sample with at least one pair of oligonucleotide molecules with at least one oligonucleotide molecule of the pair being capable of specifically hybridising to: (i) a gene encoding an O antigen transferase, or (ii) a gene encoding an enzyme for transport or processing of the oligosaccharide or polysaccharide unit, including a wzx or wzy gene; wherein said gene is involved with synthesis of the particular O antigen; under conditions suitable to permit the at least one oligonucleotide molecule to specifically hybridise to at least one of said gene of any bacteria expressing the particular bacterial O antigen present in the sample and detecting any specifically hybridised oligonucleotide molecules. Preferably the bacteria are E. coli or S. enterica. More preferably, the E. coli are of the O111 or O157 serotype. More preferably, the S. enterica are of the C2 or B serotype. Preferably, the method is a polymerase chain reaction method. More preferably the oligonucleotide molecules for use in the method of the invention are labelled. Even more preferably the hybridised oligonucleotide molecules are detected by electrophoresis.

In another aspect, the present invention relates to a method for testing a sample derived from a patient for the presence of one or more particular bacterial O antigens comprising contacting the sample with at least one pair of oligonucleotide molecules with at least one oligonucleotide molecule of the pair being capable of specifically hybridising to: (i) a gene encoding an O antigen transferase, or (ii) a gene encoding an enzyme for transport or processing of the oligosaccharide or polysaccharide unit, including a wzx or wzy gene; wherein said gene is involved in the synthesis of the particular O antigen; under conditions suitable to permit the at least one oligonucleotide molecule to specifically hybridise to at least one such gene of any bacteria expressing the particular bacterial O antigen present in the sample and detecting any specifically hybridised oligonucleotide molecules. Preferably the bacteria are E. coli or S. enterica. More preferably, the E. coli are of the O111 or O157 serotype. More preferably, the S. enterica are of the C2 or B serotype. Preferably, the method is a polymerase chain reaction method. More preferably the oligonucleotide molecules for use in the method of the invention are labelled. Even more preferably the hybridised oligonucleotide molecules are detected by electrophoresis.

In the above described methods it will be understood that where pairs of oligonucleotides are used one of the oligonucleotide sequences may hybridise to a sequence that is not from a transferase, wzx or wzy gene. Further where both hybridise to one of these gene products they may hybridise to the same or a different one of these genes.

In addition it will be understood that where cross reactivity is an issue a combination of oligonucleotides may be chosen to detect a combination of genes to provide specificity.

The invention further relates to a diagnostic kit which can be used for the detection of bacteria which express bacterial polysaccharide antigens and the identification of the bacterial polysaccharide type of those bacteria.

Thus in a further aspect, the invention relates to a kit comprising a first vial containing a first nucleic acid molecule capable of specifically hybridising to: (i) a gene encoding a transferase, or (ii) a gene encoding an enzyme for transport or processing oligosaccharide or polysaccharide, including a wzx or wzy gene, wherein the said gene is involved in the synthesis of a bacterial polysaccharide. The kit may also provide in the same or a separate vial a second specific nucleic acid capable of specifically hybridising to: (i) a gene encoding a transferase, or (ii) a gene encoding an enzyme for transport or processing oligosaccharide or polysaccharide, including a wzx or wzy gene, wherein the said gene is involved in the synthesis of a bacterial polysaccharide, wherein the sequence of the second nucleic acid molecule is different from the sequence of the first nucleic acid molecule.

In a further aspect the invention relates to a kit comprising a first vial containing a first nucleic acid molecule capable of specifically hybridising to: (i) a gene encoding a transferase, or (ii) a gene encoding an enzyme for transport or processing oligosaccharide or polysaccharide including wzx or wzy, wherein the said gene is involved in the synthesis of a bacterial O antigen. The kit may also provide in the same or a separate vial a second specific nucleic acid capable of specifically hybridising to: (i) a gene encoding a transferase, or (ii) a gene encoding an enzyme for transport or processing oligosaccharide or polysaccharide including wzx or wzy, wherein the said gene is involved in the synthesis of O antigen, wherein the sequence of the second nucleic acid molecule is different from the sequence of the first nucleic acid molecule. Preferably the first and second nucleic acid sequences are derived from E. coli or the first and second nucleic acid sequences are derived from S. enterica.

The present inventors provide full length sequence of the O157 gene cluster for the first time and recognise that from this sequence of this previously uncloned full gene cluster appropriate recombinant molecules can be generated and -continued NOMENCLATURE
Synonyms for *E. coli* O111 rfb

| Current names | Our names | Bastin et al. 1991 |
|---|---|---|
| manB | orf5 | rfbK* |
| wbdJ | orf6 | orf6.7* |
| wbdK | orf7 | orf7.7* |
| wzx | orf8 | orf8.9 and rfbX* |
| wzy | orf9 | |
| wbdL | orf10 | |
| wbdM | orf11 | |

*Nomenclature according to Bastin D.A., et al. 1991 "Molecular cloning and expression in *Escherichia coli* K-12 of the rfb gene cluster determining the O antigen of an *E. coli* O111 strain". Mol. Microbiol. 5:9 2223–2231.

| Other Synonyms | |
|---|---|
| wzy | rfc |
| wzx | rfbX |
| rmlA | rfbA |
| rmlB | rfbB |
| rmlC | rfbC |
| rmlD | rfbD |
| glf | orf6* |
| wbbI | orf3#, orf8* of *E. coli* K-12 |
| wbbJ | orf2#, orf9* of *E. coli* K-12 |
| wbbK | orf1#, orf10* of *E. coli* K-12 |
| wbbL | orf5#, orf 11* of *E. coli* K-12 |

Nomenclature according to Yao, Z. And M. A. Valvano 1994. "Genetic analysis of the O-specific lipopolysaccharide biosynthesis region (rfb) of *Escherichia coli* K-12 W3110: identification of genes the confer groups-specificty to Shigella flexineri serotypes Y and 4a". J. Bacteriol. 176: 4133–4143.
*Nomenclature according to Stevenson et al. 1994. "Structure of the O-antigen of *E. coli* K-12 and the sequence of its rfb gene cluster". J. Bacteriol 176: 4144–4156.
• *S. enterica* is a name introduced in 1987 to replace the many other names such as *Salmonella typhi* and *Salmonella typhimurium*, the old species names becoming serovar names as in *S. enterica* sv Typhi. However, the traditional names are still widely used.
• The O antigen genes of many species were given rfb names (rfbA etc) and the O antigen gene cluster was often referred to as the rfb cluster. There are now new names for the rfb genes as shown in the table. Both terminologies have been used herein, depending on the source of the information.

BRIEF DESCRIPTION OF DRAWINGS

FIG. 7 shows the nucleotide sequence of the *E. coli* O111 O antigen gene cluster. Note: (1) The first and last three bases of a gene are underlined and of italic respectively.; (2) The region which was previously sequenced by Bastin and Reeves 1995 "Sequence and anlysis of the O antigen gene (rfb) cluster of *Eschericia coli* o111" Gene 164: 17–23 is marked.

FIG. 8 shows the nucleotide sequence of the *E. coli* O157 O antigen gene cluster. Note: (1) The first and last three bases of a gene (region) are underlined and of italic respectively (2) The region previously sequenced by Bilge et al. 1996 "Role of the *Eschericia coli* O157-H7O side chain in adherence and analysis of an rfb locus". Inf. and Immun 64:4795–4801 is marked.

FIG. 9 shows the nucleotide sequence of *S. enterica* serogroup C2 O antigen gene cluster. Note:

Figure 1:
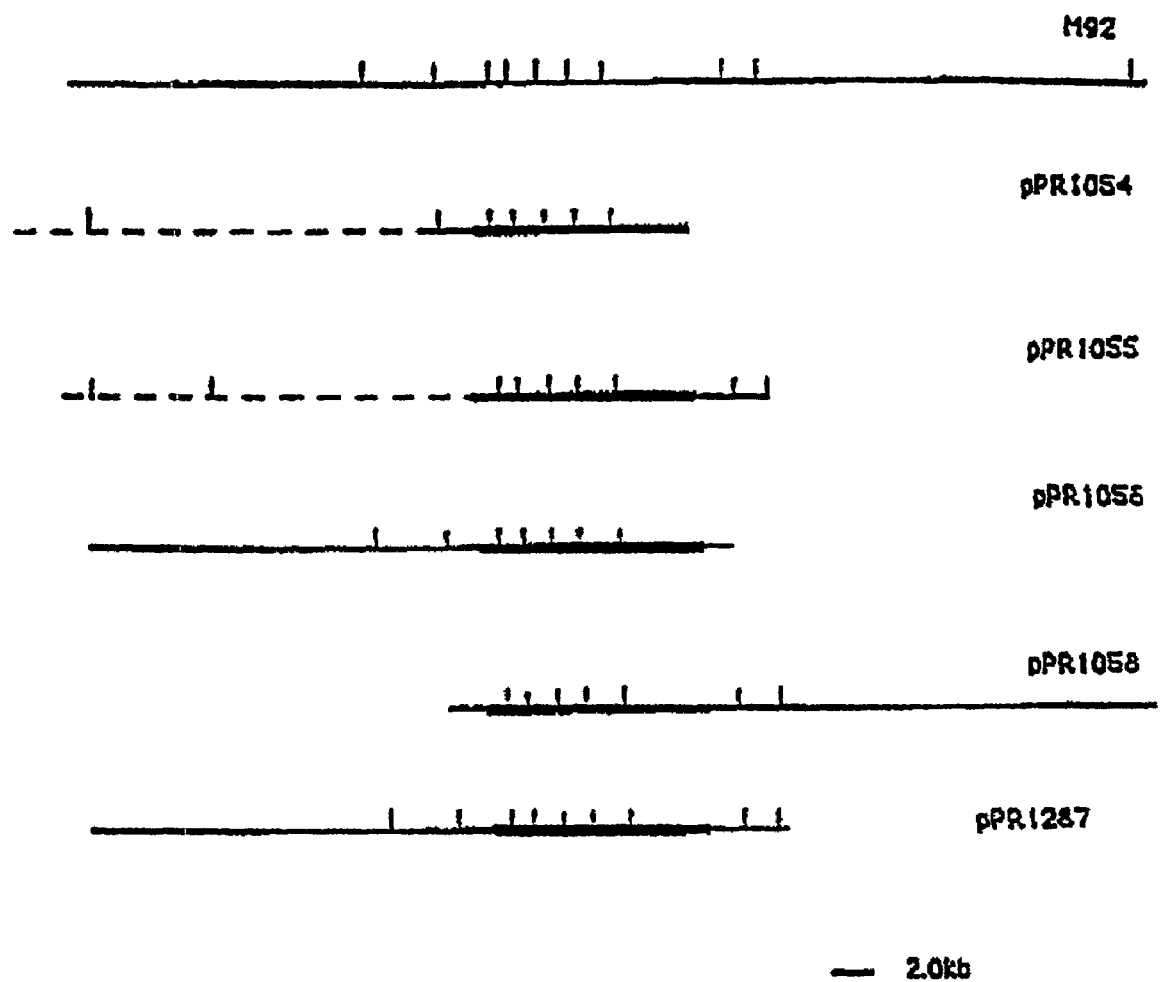
FIG. 1 shows Eco R1 restriction maps of cosmid clones pPR1054, pPR1055, pPR1056, pPR1058, pPR1287 which are subclones of *E. coli* O111 O antigen gene cluster. The thickened line is the region common to all clones Broken lines show segments that are non-contiguous on the chromosome. The deduced restriction map for *E. coli* strain M92 is shown above.

(1) The numbering is as in Brown et al. 1992. "Molecular analysis of the rfb gene cluster of *Salmonella* serovar muenchen (strain M67): the genetic basis of the polymorphism between groups C2 and B". Mol. Microbiol. 6: 1385–1394(2) The first and last three bases of a gene are underlined and in italics respectively.(3) Only that part of the group C2 gene cluster, which differs from that of group B, was sequenced and is presented here.

FIG. 10 shows the nucleotide sequence of *S. enterica* serogroup B O antigen gene cluster Note: (1) The numbering is as in Jiang et al. 1991. "Structure and sequence of the rfb (O antigen) gene cluster of *Salmonella* serovar typhimurium (strain LT2)". Mol. Microbiol. 5: 695–713. The first gene in the O antigen gene cluster is rmlB which starts at base 4099. (2) The first and last three bases of a gene are underlined and in italics respectively.

BEST METHOD FOR CARRYING OUT THE INVENTION

Materials and Methods-part 1

The experimental procedures for the isolation and characterisation of the *E. coli* O111 O antigen gene cluster (position 3,021–9,981) are according to Bastin D. A., et al. 1991 "Molecular cloning and expression in *Escherichia coli* K-12 of the rfb gene cluster determining the O antigen of an *E. coli* O111 strain". Mol. Microbiol. 5:9 2223–2231 and Bastin D. A. and Reeves, P. R. 1995 "Sequence and analysis of the O antigen gene (rfb) cluster of *Escherichia coli* O111". Gene 164: 17–23.

A. Bacterial strains and growth media

Bacteria were grown in Luria broth supplemented as required.

B. Cosmids and phage

Cosmids in the host-strain x2819 were repackaged in vivo. Cells were grown in 250mL flasks containing 30 mL of culture, with moderate shaking at 30° C. to an optical density of 0.3 at 580 nm. The defective lambda prophage was induced by heating in a water bath at 45° C. for 15min followed by an incubation at 37° C. with vigorous shaking for 2hr. Cells were then lysed by the addition of 0.3 mL chloroform and shaking for a further 10 min. Cell debris were removed from 1 mL of lysate by a 5 min spin in a microcentrifuge, and the supernatant removed to a fresh microfuge tube. One drop of chloroform was added then shaken vigorously through the tube contents.

C. DNA preparation

Chromosomal DNA was prepared from bacteria grown overnight at 37° C. in a volume of 30 mL of Luria broth. After harvesting by centrifugation, cells were washed and resuspended in 10 mL of 50 mM Tris-HCl pH 8.0. EDTA was added and the mixture incubated for 20 min. Then lysozyme was added and incubation continued for a further 10 min. Proteinase K, SDS, and ribonuclease were then added and the mixture incubated for up to 2 hr for lysis to occur. All incubations were at 37° C. The mixture was then heated to 65° C. and extracted once with 8 mL of phenol at the same temperature. The mixture was extracted once with 50 mL of phenol/chloroform/iso-amyl alcohol at 4° C. Residual phenol was removed by two ether extractions. DNA was precipitated with 2 vols. of ethanol at 4° C., spooled and washed in 70% ethanol, resuspended in 1–2mL of TE and dialysed. Plasmid and cosmid DNA was prepared by a modification of the Birnboim and Doly method (Birnhoim, H. C. And Doly, J. (1979) A rapid alkaline extraction procedure for screening recombinant plasmid DNA Nuci. Acid Res. 7:1513–1523. The volume of culture was 10 nmL and the lysate was extracted with phenol/chloroform/iso-amyl alcohol before precipitation with isopropanol. Plasmid DNA to be used as vector was isolated on a continuous caesium chloride gradient following alkaline lysis of cells grown in 1 L of culture.

D. Enzymes and buffers

Restriction endonucleases and DNA T4 ligase were purchased from Boehringer Mannheim (Castle Hill, NSW, Australia)or Pharmacia LKB (Melbourne, VIC Australia). Restriction enzymes were used in the recommended commercial buffer.

E. Construction of a gene bank.

Individual aliquots of M92 chromosomal DNA (strain Stoke W, from Statens Serum Institut, 5 Artillerivej, 2300 Copenhagen S, Denmark) were partially digested with 0.2U Sau3A1 for 1–15 mins. Aliquots giving the greatest proportion of fragments in the size range of approximately 40–50 kb were selected and ligated to vector pPR691 previously digested with BamH1and PvuII. Ligation mixtures were packaged in vitro with packaging extract. The host strain for transduction was x2819 and recombinants were selected with kanamycin.

F. Serological procedures.

Colonies were screened for the presence of the O111 antigen by immunblotting. Colonies were grown overnight, up to 100 per plate then transferred to nitrocellulose discs and lysed with 0.5N HCl. Polyoxyethylene (20)-sorbitan monolaurate (TWEEN 20) was added to TBS at 0.05% final concentration for blocking, incubating and washing steps. Primary antibody was E. coli O group 111antiserm, diluted 1:800. The secundary antibody was goat anti-rabbit IgG labelled with horseradish peroxidase diluted 1:5000. The staining substrate was 4-chloro-1-naptol. Slide agglutination was performed according to the standard procedure.

G. Recombinant DNA methods.

Restriction mapping was based on a combination of standard methods including single and double digests and sub-cloning. Deletion derivatives of entire cosmids were produced as follows: aliquots of 1.8 µg of cosmid DNA were digested in a volume of 20 µl with 0.25U of restriction enzyme for 5–80 min. One half of each aliquot was used to check the degree of digestion on an agarose gel. The sample which appeared to give a representative range of fragments was ligated at 4° C. overnight and transformed by the $CaCl_2$ method into JM109. Selected plasmids were transformed into sφ174 by the same method. P4657 was transformed with pPR1244 by electroporation.

H. DNA hybridisation

Probe DNA was extracted from agarose gels by electro-elution and was nick-translated using [α-32P]-dCTP. Chromosomal or plasmid DNA was electrophoresed in 0.8% agarose and transferred to a nitrocellulose membrane. The hybridisation and pre-hybridisation buffers contained either 30% or 50% formamide for low and high stringency probing respectively. Incubation temperatures were 42° C. and 37° C. for pre-hybridisation and hybridisation respectively. Low stringency washing of filters consisted of 3×20 min washes in 2 ×SSC and 0.1% SDS. High-stringency washing consisted of 3×5 min washes in 2 ×SSC and 0.1% SDS at room temperature, a 1hr wash in 1 ×SSC and 0.1% SDS at 58° C. and 15 min wash in 0.1 ×SSC and 0.1% SDS at 58° C.

I. Nucleotide Sequencing of E. coli 0111 O Antigen Gene Cluster (position 3,021–9,981)

Nucleotide sequencing was performed using an ABI 373 automated sequencer (CA, USA). The region between map positions 3.30 and 7.90 was sequenced using uni-directional exonuclease III digestion of deletion families made in PT7T3190 from clones pPR1270 and pPR1272. Gaps were filled largely by cloning of selected fragments into M13mp18 or M13mp19. The region from map positions 7.90–10.2 was sequenced from restriction fragments in M13mp18 or M13mp19. Remaining gaps in both the regions were filled by priming from synthetic oligonucleotides complementary to determined positions along the sequence, using a single stranded DNA template in M13 or phagemid The oligonucleotides were designed after analysing the adjacent sequence. All sequencing was performed by the chain termination method. Sequences were aligned using SAP [Staden, R., 1982 "Automation of the computer handling of gel reading data produced by the shotgun method of DNA sequencing". Nuc. Acid Res. 10: 4731–4751; Staden, R., 1986 "The current status and portability of our sequence handling software". Nuc. Acid Res. 14: 217–231]. The program NIP [Staden, R. 1982 "An interactive graphics program for comparing and aligning nucleic acid and amino acid sequence". Nuc. Acid Res. 10: 2951–2961] was used to find open reading frames and translate them into proteins.

J. Isolation of Clones Carrying E. Coli O111 O Antigen Gene Cluster.

The E. coli O antigen gene cluster was isolated according to the method of Bastin D. A., et al. [1991 "Molecular cloning and expression in Escherichia coli K-12 of the rfb gene cluster determining the O antigen of an E. coli O111 strain". Mol. Microbiol. 5(9), 2223–2231]. Cosmid gene banks of M92 chromosomal DNA were established in the in vivo packaging strain x2819. From the genomic bank, $3.3×10^3$ colonies were screened with E. coli 0111 antiserum using an immuno-blotting procedure: 5 colonies (pPR1054, pPR1055, pPR1056, pPR1058 and pPR1287) were positive. The cosmids from these strains were packaged in vivo into lambda particles and transduced into the E. coli deletion mutant Sφ174 which lacks all O antigen genes. In this host strain, all plasmids gave positive agglutination with 0111 antiserum. An Eco R1 restriction map of the 5 independent cosmids showed that they have a region of approximately 11.5 kb in common (FIG. 1). Cosmid pPR1058 included sufficient flanking DNA to identify several chromosomal markers linked to O antigen gene cluster and was selected for analysis of the O antigen gene cluster region.

K. Restriction Mapping of Cosmid pPR1058

Figure 2:
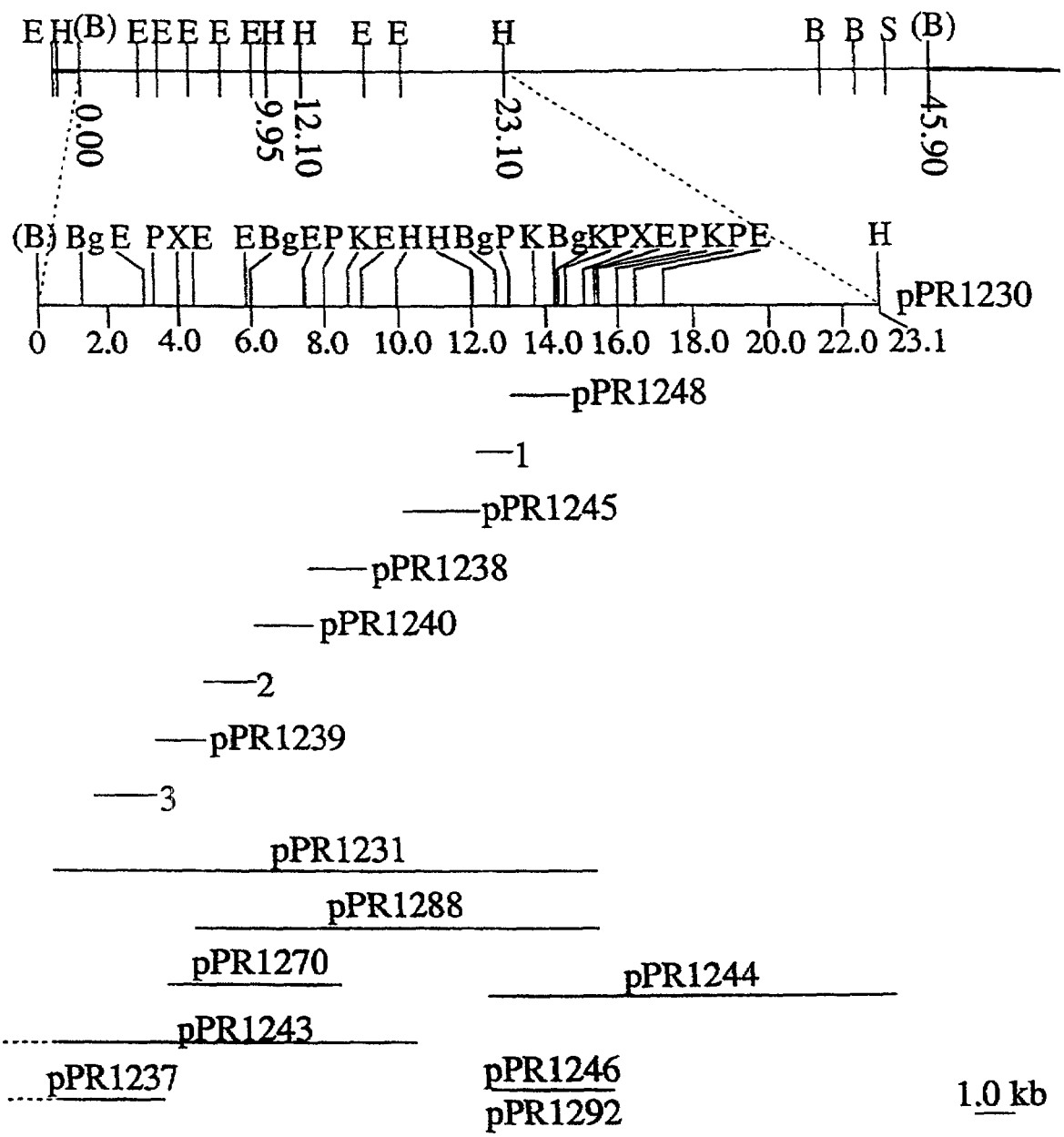
FIG. 2 shows a restriction mapping analysis of *E. coli* O111 O antigen gene cluster within the cosmid clone pPR1058. Restriction enzymes are: (B: BamH1; Bg: BglII, E: EcoR1; H: HindIII; K: KpnI; P: PstI; S: SalI and X: Xho1. Plasmids pPR1230, pPR1231, and pPR1288 are deletion derivatives of pPR1058. Plasmids pPR 1237, pPR1238, pPR1239 and pPR1240 are in pUC19. Plasmids pPR1243, pPR1244, pPR1245, pPR1246 and pPR1248 are in pUC18, and pPR1292 is in pUC19. Plasmid pPR1270 is in pT7T319U. Probes 1, 2 and 3 were isolated as internal fragments of pPR1246, pPR1243 and pPR1237 respectively. Dotted lines indicate that subclone DNA extends to the left of the map into attached vector.

Cosmid pPR1058 was mapped in two stages. A preliminary map was constructed first, and then the region between map positions 0.00 and 23.10 was mapped in detail, since it was shown to be sufficient for O111 antigen expression. Restriction sites for both stages are shown in FIG. 2. The region common to the five cosmid clones was between map positions 1.35 and 12.95 of pPR1058.

To locate the O antigen gene cluster within pPR1058, pPR1058 cosmid was probed with DNA probes covering O antigen gene cluster flanking regions from *S. enterica* LT2 and *E. coli* K-12. Capsular polysaccharide (cps) genes lie upstream of O antigen gene cluster while the gluconate dehydrogenase (gnd) gene and the histidine (his) operon are downstream, the latter being further from the O antigen gene cluster. The probes used were pPR472 (3.35kb), carrying the gnd gene of LT2, pPR685(5.3kb) carrying two genes of the cps cluster, cpsB and cpsG of LT2, and K350 (16.5kb) carrying all of the his operon of K-12. Probes hybridised as follows: pPR472 hybridised to 1.55kb and 3.5 kb (including 2.7 kb of vector) fragments of PstI and HindIII double digests of pPR1246 (a HindIII/EcoR1subclone derived from pPR1058, FIG. 2), which could be located at map positions 12.95–15.1; pPR685 hybridized to a 4.4 kb EcoR1 fragment of pPR1058 (including 1.3 kb of vector) located at map position 0.00–3.05; and K350 hybridised with a 32 kb EcoR1 fragment of pPR1058 (including 4.0 kb of vector), located at map position 17.30–45.90. Subclones containing the presumed gnd region complemented a gnd edd strain GB23152. On gluconate bromothymol blue plates, pPR1244 and pPR1292 in this host strain gave the green colonies expected of a gnd edd genotype. The his phenotype was restored by plasmid pPR1058 in the his deletion strain Sφ174 on minimal medium plates, showing that the plasmid carries the entire his operon.

It is likely that the O antigen gene cluster region lies between gnd and cps, as in other *E. coli* and *S. enterica* strains, and hence between the approximate map positions 3.05 and 12.95. To confirm this, deletion derivatives of pPR1058 were made as follows: first, pPR1058 was partially digested with HindIII and self ligated. Transformants were selected for kanamycin resistance and screened for expression of O111 antigen. Two colonies gave a positive reaction. EcoR1digestion showed that the two colonies hosted identical plasmids, one of which was designated pPR1230, with an insert which extended from map positions 0.00 to 23.10. Second pPR1058 was digested with Sal1 and partially digested with Xho1 and the compatible ends were re-ligated. Transformants were selected with kanamycin and screened for O111 antigen expression. Plasmid DNA of 8 positively reacting clones was checked using EcoR1 and Xho1 digestion and appeared to be identical. The cosmid of one was designated pPR1231. The insert of pPR1231 contained the DNA region between map positions 0.00 and 15.10. Third, pPR1231 was partially digested with Xho1, self-ligated, and transformants selected on spectinomycin/streptomycin plates. Clones were screened for kanamycin sensitivity and of 10 selected, all had the DNA region from the Xho1 site in the vector to the Xho1 site at position 4.00 deleted. These clones did not express the O111 antigen, showing that the Xho1 site at position 4.00 is within the O antigen gene cluster. One clone was selected and named pPR1288. Plasmids pPR1230, pPR1231, and pPR1288 are shown in FIG. 2.

Figure 3:
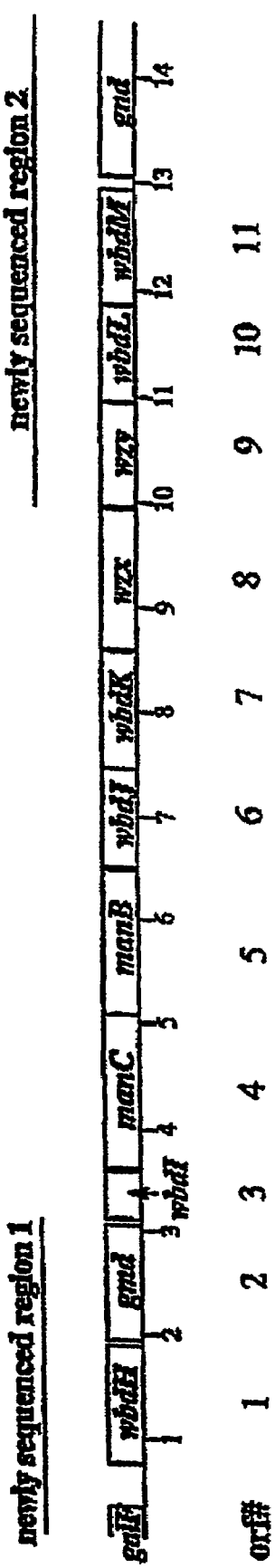
FIG. 3 shows the structure of *E. coli* O111 O antigen gene cluster.

L. Analysis of the *E. coli* O111 O antigen gene cluster (position 3,021–9,981) nucleotide sequence data Bastin and Reeves [1995 "Sequence and analysis of the O antigen gene (rfb) cluster of *Escherichia coli* O111". Gene 164: 17–23] partially characterised the *E. coli* O111 O antigen gene cluster by sequencing a fragment from map position 3,021–9,981. FIG. 3 shows the gene organisation of position 3,021–9,981 of *E. coli* O111 O antigen gene cluster. orf3 and orf6 have high level amino acid identity with wcaH and wcaG (46.3% and 37.2% respectively), and are likely to be similar in function to sugar biosynthetic pathway genes in the *E. coli* K-12 colanic gene cluster. orf4 and orf5 show high levels of amino acid homology to manC and manB genes respectively. orf7 shows high level homology with rfbH which is an abequose pathway gene. orf8 encodes a protein with 12 transmembrane segments and has similarity in secondary structure to other wzx ,ens and is likely therefore to be the O antigen flippase gene.

Materials and Methods-part 2

A. Nucleotide Sequencing of 1 to 3,020 and 9,982 to 14,516 of the *E. Coli* O111 O Antigen Gene Cluster The sub clones which contained novel nucleotide sequences, pPR1231(map position 0 and 1,510), pPR1237 (map position −300 to 2,744), pPR1239 (map position 2,744 to 4,168), pPR1245 (map, position 9,736 to 12,007) and pPR1246 (map position 12,007 to 15,300) (FIG. 2), were characterised as follows: the distal ends of the inserts of pPR1237, pPR1239 an pPR1245 were sequenced using the M13 forward and reverse primers located in the vector. PCR walking was carried out to sequence further into each insert using primers based on the sequence data and the primers were tagged with M13 forward or reverse primer sequences for sequencing. This PCR walking procedure was repeated until the entire insert was sequenced. pPR1246 was characterised from position 12,007 to 14,516. The DNA of these sub clones was sequenced in both directions. The sequencing reactions were performed using the dideoxy termination method and thermocycling and reaction products were analysed using flourescent dye and an ABI automated sequencer (CA, USA).

B. Analysis of the *E. Coli* O111 O Antigen Gene Cluster (Positions 1 to 3,020 and 9,982 to 14,516 of SEQ ID NO:1) Nucleotide Sequence Data.

The gene organisation of regions of *E. coli* O111 O antigen gene cluster which were not characterised by Bastin and Reeves [1995 "Squence and analysis of the O antigen gene (rfb) cluster of *Escherichia coli* O111."Gene 164: 17–23],(positions 1 to 3,020 and 9,982 to 14,516) is shown in FIG. 3. Thereare two open reading frames in region 1. Four open reading frames are predicted in region 2. The position of each gene is listed in Table 5.

The deduced amino acid sequence of orf1 (wbdH) shares about 64% similarity with that of the rfp gene of *Shigella dysenteriae*. Rfp and WbdH have very similar hydrophobicity plots and both have a very convincing predicted transmembrane segment in a corresponding position. rfp is a galactosyl transferase involved in the synthesis of LPS core, thus wbdH is likely to be a galactosyl transferase gene. orf2 has 85.7% identity at amino acid level to the gmd gene identified in the *E. coli* K-12 colanic acid gene cluster and is likely to be a gmd gene. orf9 encodes a protein with 10 predicted transmembrane segments and a large cytoplasmic loop. This inner membrane topology is a characteristic feature of all known O antigen polymerases thus it is likely that orf9 encodes an O antigen polymerase gene, wzy. orf10 (wbdL) has a deduced amino acid sequence with low homology with Lsi2 of *Neisseria gonorrhoeae*. Lsi2 is responsible for adding GlcNAc to galactose in the synthesis of lipooligosaccharide. Thus it is likely that wbdL is either a colitose or glucose transferase gene. orf11 (wbdM) shares high level nucleotide and amino acid similarity with TrsE of *Yersinia enterocholitica*. TrsE is a putative sugar transferase thus it is likely that wbdM encodes the colitose or glucose transferase.

In summary three putative transferase genes and an O antigen polymerase gene were identified at map position 1 to 3,020 and 9,982 to 14,516 of *E. coli* O111 O antigen gene cluster. A search of GenBank has shown that there are no genes with significant similarity at the nucleotide sequence level for two of the three putative transferase genes or the polymerase gene. SEQ ID NO:1 and FIG. 7 provide the nucleotide sequence of the O111 antigen gene cluster.

Materials and Methods-part 3

A. PCR Amplification of O157 Antigen gene Cluster from an *E. Coli* O157:H7 Strain (Strain C664–1992, from Statens Serum Institut, 5 Artillerivej, 2300, Copenhagen S, Denmark).

*E. coli* O157 O antigen gene cluster was amplified by using long PCR (Cheng et al. 1994, "Effective amplification of long targets from cloned inserts and human and genomic DNA" P.N.A.S. USA 91: 5695–569) with one primer (primer #412: att ggt agc tgt aag cca agg gcg gta gcg t (SEQ ID NO:5)) based on the JumpStart sequence usually found in the promoter region of O antigen gene clusters (Hobbs, et al. 1994 "The JumpStart sequence: a 39 bp element common to several polysaccharide gene dusted" Mol. Microbiol. 12: 855–856), and another primer #482 (cac tgc cat acc gac gac gcc gat ctg ttg ctt gg (SEQ ID NO:6)) based on the gnd gene usually found downstream of the O antigen gene cluster. Long PCR was carried out using the Expand Long Template PCR System from Boehringer Mannheim (Castle Hill NSW Australia), and products, 14 kb in length, from several reactions were combined and purified using the Promega Wizard PCR preps DNA purification System (Madison WI USA). The PCR product was then extracted with phenol and twice with ether, precipitated with 70% ethanol, and resuspended in 40 µL of water.

B. Construction of a Random DNase I Bank:

Two aliquots containing about 150 ng of DNA each were subjected to DNase I digestion using the Novagen DNase I Shotgun Cleavage (Madison Wis. USA) with a modified protocol as described. Each aliquot was diluted into 45 µl of 0.05 M Tris -HCl (pH7.5), 0.05 mg/mL BSA and 10 mM MnCl$_2$ 5 µL of 1:3000 or 1:4500 dilution of DNaseI (Novagen) (Madison Wis. USA) in the same buffer was added into each tube respectively and 10µl of stop buffer (100mM EDTA), 30% glycerol, 0.5% Orange G, 0.075% xylene and cyanol (Novagen) (Madison Wis. USA) was added after incubation at 15° C. for 5 min. The DNA from the two DNaseI reaction tubes were then combined and fractionated on a 0.8% LMT agarose gel, and the gelsegment with DNA of about 1 kb in size (about 1.5 mL agarose) was excised. DNA was extracted from agarose using Promega Wizard PCR Preps DNA Purification (Madison Wis. USA) and resuspended in 200 µL water, before being extracted with phenol and twice with ether, and precipitated. The DNA was then resuspended in 17.25 µL water and subjected to T4 DNA polymerase repair and single dA tailing using the Novagen Single dA Tailing Kit (Madison Wis. USA). The reaction product (85 µl containing about 8 ng DNA) was then extracted with chloroform:isoamyl alcohol (24:1) once and ligated to 3×10$^{-3}$ pmol PGEM-T (Promega) (Madison Wis. USA) in a total volume of 100 µL. Ligation was carried out overnight at 4° C. and the ligated DNA was precipitated and resuspended in 20 µL water before being electroporated into *E. coli* strain JM109 and plated out on BCIG-IPTG plates to give a bank.

C. Sequencing

DNA templates from clones of the bank were prepared for sequencing using the 96-well format plasmid DNA miniprep kit from Advanced Genetic Technologies Corp (Gaithersburg Md. USA) The inserts of these clones were sequenced from one or both ends using the standard M13 sequencing primer sites located in the pGEM-T vector. Sequencing was carried out on an ABI377 automated sequencer (CA USA) as described above, after carrying out the sequencing reaction on an ABI Catalyst (CA USA). Sequence gaps and areas of inadequate coverage were PCR amplified directly from O157 chromosomal DNA using primers based on the already obtained sequencing data and sequenced using the standard M13 sequencing primer sites attached to the PCR primers.

Figure 4:
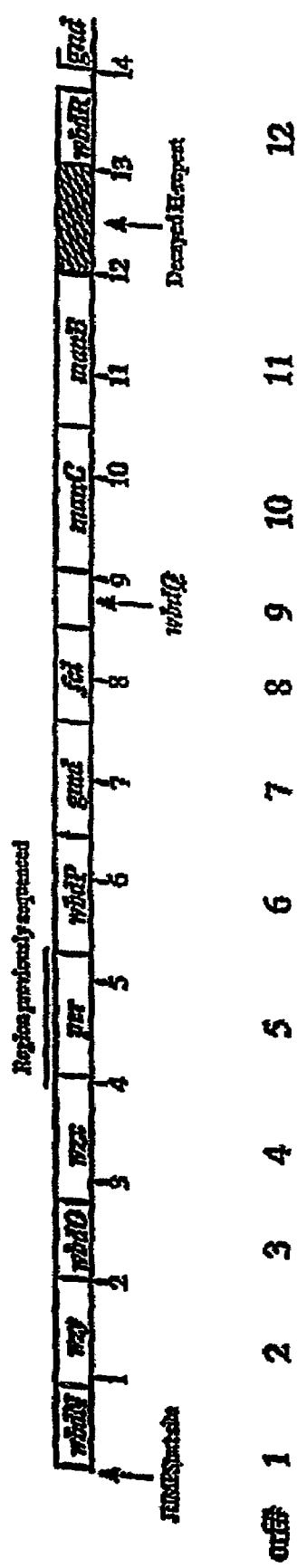
FIG. 4 shows the structure of *E. coli* O157 O antigen gene cluster.
Figure 5:
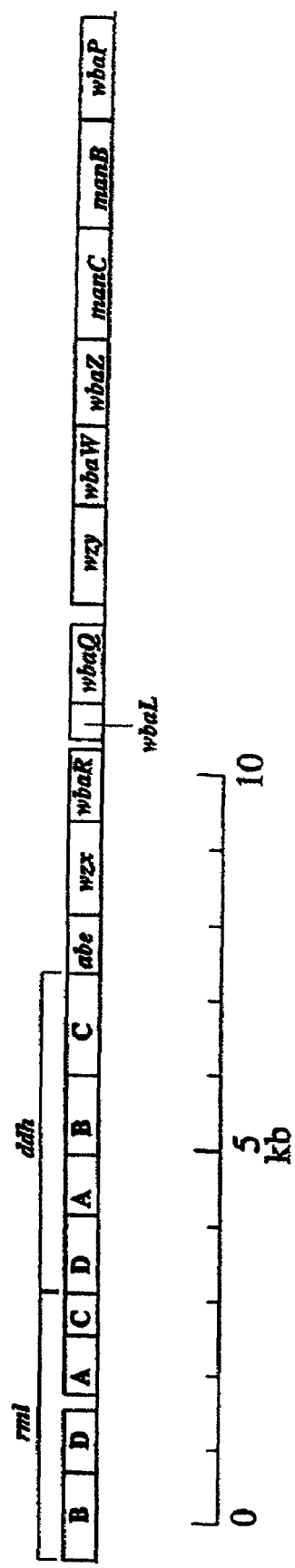
FIG. 5 shows the structure *S. enterica* locus encoding the serogroup C2 O antigen gene cluster.
Figure 6:
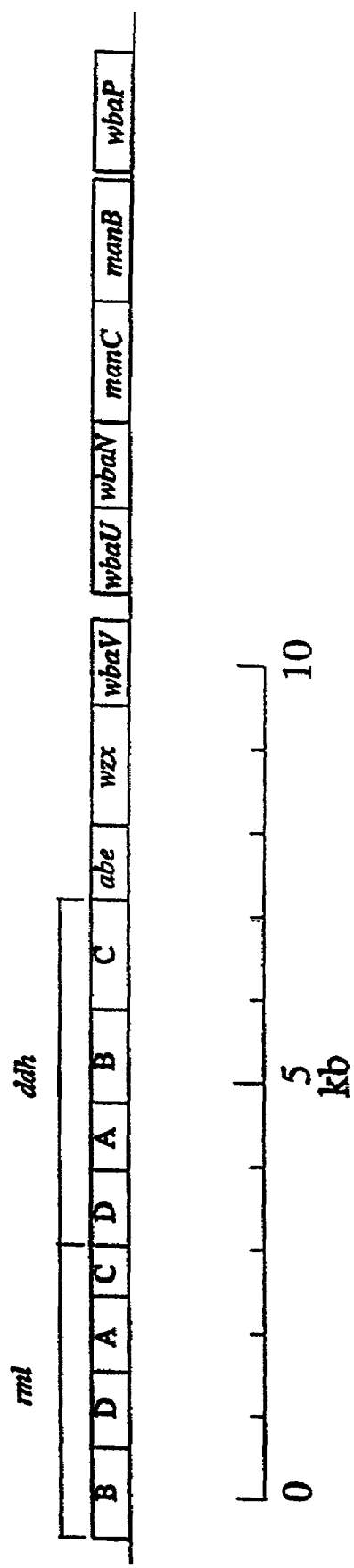
FIG. 6 shows the structure *S. enterica* locus encoding the serogroup B O antigen gene cluster.

D. Analysis of the *E. Coli* O157 O Antigen Gene Cluster Nucleotide Sequence Data Sequence data were processed and analysed using the Staden programs [Staden, R., 1982 "Automation of the computer handling of gel reading data produced by the shotgun method of DNA sequencing." Nuc. Acid Res. 10: 4731–4751; Staden, R., 1986 "The current status and portability of our sequence handling software". Nuc. Acid Res. 14: 217–231; Staden, R. 1982 "An interactive graphics program for comparing and aligning nucleic acid and amino acid sequence". Nuc. Acid Res. 10: 2951–2961]. FIG. 4 shows the structure of *E. coli* O157 O antigen gene cluster. Twelve open reading frames were predicted from the sequence data, and the nucleotide and amino acid sequences of all these genes were then used to search the GenBank database for indication of possible function and specificity of these genes. The position of each gene is listed in Table 6. The nucleotide sequence is presented in SEQ ID NO:2 and FIG. 8.

orfs 10 and 11 showed high level identity to manC and manB and were named manC and manb respectively. orf7 showed 89% identity (at amino acid level) to the gmd gene of the *E. coli* colanic acid capsule gene cluster (Stevenson G., K. et al. 1996 "Organisation of the *Escherichia coli* K-12 gene cluster responsible for production of the extracellular polysaccharide colanic acid".J. Bacteriol. 178:4885–4893) and was named gmd. orf8 showed 79% and 69% identity (at amino acid level) respectively to wcaG of the *E. coli* colanic acid capsule gene cluster and to wbcJ (orf14.8) gene of the *Yersinia enterocolitica* O8 O antigen gene cluster (Zhang, L. et al. 1997 "Molecular and chemical characterization of the lipopolysaccharide O-antigen and its role in the virulence of *Y. enterocolitica* serotype O8"Mol. Microbiol. 23:63–76). Colanic acid and the *Yersinia* O8 O antigen both contain fucose as does the O157 O antigen. There are two enzymatic steps required for GDP-L-fucose synthesis from GDP-4-keto-6-deoxy-D-mannose, the product of the gmd gene product. However, it has been shown recently (Tonetti, M et al. 1996 Synthesis of GDP-L-fucose by the human FX protein J. Biol. Chem. 271:27274–27279) that the human FX protein has "significant homology" with the wcaG gene (referred to as Yefb in that paper), and that the FX protein carries out both reactions to convert GDP-4-keto-6-deoxy-D-mannose to GDP-L-fucose. We believe that this makes a very strong case for orf8 carrying out these two steps and propose to name the gene fcl. In support of the one enzyme carrying out both functions is the observation that there are no genes other than manB, manC, gmd and fcl with similar levels of similarity between the three bacterial gene clusters for fucose containing structures.

orf5 is very similar to wbeE (rfbE) of *Vibrio cholerae* O1, which is thought to be the perosamine synthetase, which converts GDP-4-keto-6-deoxy-D-mannose to GDP-perosamine (Stroeher, U.H et al. 1995 "A putative pathway for perosamine biosynthesis is the first function encoded within the rfb region of *Vibrio choleraef*"O1. Gene 166: 33–42). *V. cholerae* O1 and *E. coli* O157 O antigens contain perosamine and N-acetyl-perosamine respectively. The *V. cholerae* O1 manA, manB, gmd and wbeE genes are the only genes of the *V. cholerae* O1 gene cluster with significant similarity to genes of the *E. coli* O157 gene cluster and we believe that our observations both confirm the prediction made for wbe of *V. cholerae*, and show that orf5 of the O157 gene cluster encodes GDP-perosamine synthetase. orf5 is therefore named per. orf5 plus about 100 bp of the upstream region (postion 4022–5308)was previously sequenced by Bilge, S.S. et al. [1996 "Role of the *Escherichia coli* O157-H7 O side chain in adherence and analysis of an rfb locus".Infect. Immun. 64:4795–4801].

orf12 shows high level similarity to the conserved region of about 50 amino acids of various members of an acetyl-transferase family (Lin, W., et al. 1994 "Sequence analysis and molecular characterisation of genes required for the biosynthesis of type 1 capsular polysaccharide in *Staphylococcus aureus*". J. Bateriol. 176: 7005–7016) and we believe it is the N-acetyltransferase to convert GDP-perosamine to GDP-perNAc. orf12 has been named wbdR.

The genes manB, manC, gmd, fcl, per and wbdR account for all of the expected biosynthetic pathway genes of the O157 gene cluster.

The remaining biosynthetic step(s) required are for synthesis of UDP-GalNAc from UDP-Glc. It has been proposed (Zhang, L., et al. 1997 "Molecular and chemical characterisation of the lipopolysaccharide O-antigen and its role in the virulence of *Yersinia enterocolitica* serotype O8".Mol. Microbiol. 23:63–76) that in *Yersinia enterocolitica* UDP-GalNAc is synthesised from UDP-GlcNAc by a homologue of galactose epimerase (GalE), for which there is a galE like gene in the *Yersinia enterocolitica* O8 gene cluster. In the case of O157 there is no galE homologue in the gene cluster and it is not clear how UDP-GalNAc is synthesised. It is possible that the galactose epimerase encoded by the galE gene in the gal operon, can carry out conversion of UDP-GlcNAc to UDP-GalNAc in addition to conversion of UDP-Glc to UDP-Gal. There do not appear to be any gene(s) responsible for UDP-GalNAc synthesis in the O157 gene cluster.

orf4 shows similarity to many wzx genes and is named wzx and orf2 which shows similarity of secondary structure in the predicted protein to other wzy genes and is for that reason named wzy.

The orf1, orf3 and orf6 gene products all have characteristics of transferases, and have been named wbdN, wbdO and wbdp respectively. The O157 O antigen has 4 sugars and 4 transferases are expected. The first transferase to act would put a sugar phosphate onto undecaprenol phosphate. The two transferases known to perform this function, WbaP (RfbP) and WecA (Rfe) transfer galactose phosphate and N-acetyl-glucosamine phosphate respectively to undecaprenol phosphate. Neither of these sugars is present in the O157 structure.

Further, none of the presumptive transferases in the O157 gene cluster has the transmembrane segments found in WecA and WbaP which transfer a sugar phosphate to undecaprenol phosphate and expected for any protein which transferred a sugar to undecaprenol phosphate which is embedded within the membrane.

The WecA gene which transfers GlcNAc-P to undecaprenol phosphate is located in the Enterobactereal Common Antigen (ECA) gene cluster and it functions in ECA synthesis in most and perhaps all *E. coli* strains, and also in O antigen synthesis for those strains which have GlcNAc as the first sugar in the O unit.

It appears that WecA acts as the transferase for addition of GalNAc-1-P to undecaprenol phosphate for the *Yersinia enterocolitica* O8 O antigen [Zhang et al. 1997 "Molecular and chemical characterisation of the lipopolysaccharide O antigen and its role in the virulence of *Yersinia enterocolitica* serotype O8Mol. Microbiol. 23: 63–76.] and perhaps does so here as the O157 structure includes GalNAc. WecA has also been reported to add Glucose-1-P phosphate to undecaprenol phosphate in *E. coli* O8 and O9 strains, and an alternative possibility for transfer of the first sugar to undecaprenol phosphate is WecA mediated transfer of glucose, as there is a glucose residue in the O157 O antigen. In either case the requisite number of transferase genes are present if GalNAc or Glc is transferred by WecA and the side chain Glc is transferrd by a transferase outside of the O antigen gene cluster.

orf9 shows high level similarity (44% identity at amino acid level, sa engt) with wcah gene of the *E. coli* colanic acid capsule gene cluster. The function of this gene is unknown, and we give off orf9 the name wbdQ.

The DNA between manB and wdbR has strong sequence similarity to one of the H-repeat units of *E. coli* K12. Both of the inverted repeat sequences flanking this region are still recognisable, each with two of the 11 bases being changed. The H-repeat associated protein encoding gene located within this region has a 267 base deletion and mutations in various positions. It seems that the H-repeat unit has been associated with this gene cluster for a long period of time since it translocated to the gene cluster, perhaps playing a role in assembly of the gene cluster ashas been proposed in other cases.

Materials and Methods - part 4

To test our hypothesis that O antigen genes for transferases and the wzx, wzy genes were more specific than pathway genes for diagnostic PCR, we first carried out PCR using primers for all the *E. coli* 016 O antigen genes (Table 4). The PCR was then carried out using PCR primers for *E. coli* O111 transferase, wzx and wzy genes (Table 5, 5A). PCR was also carried out using PCR primers for the *E. coli* 0157 transferase, wzx and wzy genes (Table 6, 6A).

Chromosomal DNA from the 166 serotypes of *E. coli* available from Statens Serum Institut, 5 Artillerivej, 2300 Copenhagen Denmark was isolated using the Promega Genomic (Madison Wis. USA) isolation kit. Note that 164 of the serogroups are described by Ewing W. H.: Edwards and Ewings "Identification of the Enterobacteriacea" Elsevier, Amsterdam 1986 and that they are numbered 1–171 with numbers 31, 47, 67, 72, 93, 94 and 122 no longer valid. Of the two serogroup 19 strains we used 19ab strain F8188–41. Lior H. 1994 ["Classification of *Eschericia coli* In *Esche-* ricia coli in domestic animals and humans pp 31–72. Edited by C. L. Gyles CAB international] adds two more numbered 172 and 173 to give the 166 serogroups used. Pools containing 5 to 8 samples of DNA per pool were made. Pool numbers 1 to 19 (Table 1) were used in the *E. coli* 0111 and 0157 assay. Pool numbers 20 to 28 were also used in the 0111 assay, and pool numbers 22 to 24 contained *E. coli* 0111 DNA and were used as positive controls (Table 2). Pool numbers 29 to 42 were also used in the 0157 assay, and pool numbers 31 to 36 contained *E. coli* 0157 DNA, and were used as positive controls (Table 3). Pool numbers 2 to 20, 30, 43 and 44 were used in the *E. coli* O16 assay (Tables 1 to 3). Pool number 44 contained DNA of *E. coli* K-12 strains C600 and WGI and was used as a positive control as between them they have all of the *E. coli* K-12 O16 O antigen genes.

PCR reactions were carried out under the following conditions: denaturing 94° C./30"; annealing, temperature varies (refer to Tables 4 to 8)/30"; extension, 72° C./1'; 30 cycles. PCR reaction was carried out in an volume of 25μL for each pool. After the PCR reaction, 10μL PCR product from each pool was run on an agarose gel to check for amplified DNA.

Each *E. coli* and *S. enterica* chromosomal DNA sample was checked by gel electrophoresis for the presence of chromosomal DNA and by PCR amplification of the *E. coli* or *S. enterica* mdh gene using oligonucleotides based on *E. coli* K-12 or *Salmonella enterica* LT2 [Boyd et al. (1994) "Molecular genetic basis of allelic polymorphism in malate degydrogenase (mdh) in natural populations of *Escherichia coli* and *Salmonella enterica*" Proc. Nat. Acad. Sci. USA. 91:1280–1284.] Chromosomal DNA samples from other bacteria were only checked by gel electrophoresis of chromosomal DNA.

A. Primers based on *E. Coli* O16 O Antigen Gene Cluster Sequence.

The O antigen gene cluster of *E. coli* O16 was the only typical *E. coli* O antigen gene cluster that had been fully sequenced prior to that of O111, and we chose it for testing our hypothesis. One pair of primers for each gene was tested against pools 2 to 20, 30 and 43 of *E. coli* chromosomal DNA. The primers, annealing temperatures and functional information for each gene are listed in Table 4.

For the five pathway genes, there were 17/21, 13/21, 0/21, 0/21, 0/21 positive pools for rmlB, rmlD, rmlA, rmlC and glf respectively (Table 4). For the wzx, wzy and three transferase genes there were no positives amongst the 21 pools of *E. coli* chromosomal DNA tested (Table 4). In each case the #44 pool gave a positive result.

B Primers Based on the *E. Coli* 0111 O Antigen Gene Clsuter Sequence.

One to four pairs of primers for each of the transferase, wzx and wzy genes of O111 were tested against the pools 1 to 21 of *E. coli* chromosomal DNA (Table 5). For wbdh, four pairs of primers, which bind to various regions of this gene, were tested and found to be specific for O111 as there was no amplified DNA of the correct size in any of those 21 pools of *E. coli* chromosomal DNA tested. Three pairs of primers for wbdM were tested, and they are all specific although primers #985/#986 produced a band of the wrong size from one pool. Three pairs of primers for wzx were tested and they all were specific. Two pairs of primers were betlted for wzy, both are specific although #980/#983 gave a band of the wrong size in all pools. One pair of primers for wbdL was tested and found unspecific and therefore further test was carried out. Thus, wzx, wzy and two of the three transferase genes are highly specific to O111. Bands of the wrong size found in amplified DNA are assumed to be due to chance hybridisation of genes widely present in *E. coli*. The primers, annealing temperatures and positions for each gene are in (Table 5).

The 0111 assay was also performed using pools including DNA from O antigen expressing *Yersinia pseudotuberculosis, Shiaella boydii* and *Salmonella enterica* strains (Table 5A). None of the oligonucleotides derived from wbdH, wzx, wzy or wbdM gave amplified DNA of the correct size with these pools. Notably, pool number 25 ncludes *S. enterica* Adelaide which has the same O antigen as *E. coli* 0111: this pool did not give a positive PCR result for any primers tested indicating that these genes are highly specifiic for *E. coli* 0111.

Each of the 12 pairs binding to wbdH, wzx, wzy and wbdM produces a band a predicted size with the pools containing 0111 DNA (pool number 22 to 24). As pools 22 to 24 included DNA from all strains present in pool 21 plus 0111 strain DNA (Table 2), we conclude that the 12 pairs of primers all give a positive PCR test with each of three unrelated 0111 strains but not with any other strains tested. Thus these genes are highly specific for *E. coli* O111.

C. Primers Based on the *E. Coli* 0157 O Antigen Gene Cluster Sequence.

Two or three primer pairs for each of the transferase, wzx and wzy genes of O157 were tested against *E. coli* chromosomal DNA of pools 1 to 19, 29 and 30 (Table 6). For wbdN, three pairs of primers, which bind to various regions of this gene, were tested and found to be specific for O157 as there was no amplified DNA in any of those 21 pools of *E. coli* chromosomal DNA tested. Three pairs of primers for wbdO were tested, and they are all specific although primers #1211/#1212 produced two or three bands of the wrong size from all pools. Three pairs of primers were tested for wbdP and they all were specific. Two pairs of primers were tested for wbdR and they were all specific. For wzy, three pairs of primers were tested and all were specific although primer pair #1203/#1204 produced one or three bands of the wrong size in each pool. For wzx, two pairs of primers were tested and both were specific although primer pair #1217/#1218 produced 2 bands of wrong size in 2 pools, and 1 band of wrong size in 7 pools. Bands of the wrong size found in amplified DNA are assumed to be due to chance hybridisation of genes widely present in *E. coli*. The primers, annealing temperatures and function information for each gene are in Table 6.

The 0157 assay was also performed using pools 37 to 42, including DNA from O antigen expressing *Yersinia pseudotuberculosis, Shiaella boydii, Yersinia enterocolitica* 09, *Brucella abortus* and *Salmonella enterica* strains (Table 6A). None of the oligonucleotides derived from wbdN, wzy, wbdO, wzx, wbdP or wbdr reacted specifically with these pools, except that primer pair #1203/#1204 produced two bands with *Y. enterocolitica* O9 and one of the bands is of the same size with that from the positive control. Primer pair #1203/#1204 binds to wzy. The predicted secondary structures of Wzy proteins are generally similar, although there is very low similarity at amino acid or DNA level among the sequenced wzy genes. Thus, it is possible that *Y. enterolcolitica* O9 has a wzy gene closely related to that of *E. coli* O157. It is also possible that this band is due to chance hybridization of another gene, as the other two wzy primer pairs (#1205/#1206 and #1207/#1208) did not produce any band with *Y. enterocolitica* O9. Notably, pool number 37 includes *S. enterica* Landau which has the same O antigen as *E. coli* O157, and pool 38 and 39 contain DNA of *B*.

*abortus* and *Y. enterocolitica* O9 which cross react serologically with *E. coli* O157. This result indicates that these genes are highly O157 specific, although one primer pair may have cross reacted with *Y. enterocolitica* O9.

Each of the 16 pairs binding to wbdN, wzx, wzy, wbdO, wbdP and wbdR produces a band of predicted size with the pools containing O157 DNA (pools number 31 to 36). As pool 29 included DNA from all strains present in pools 31 to 36 other than O157 strain DNA (Table 3), we conclude that the 16 pairs of primers all give a positive PCR test with each of the five unrelated O157 strains.

Thus PCR using primers based on genes wbdN, wzy, wbdO, wzx, wbdP and wbdR is highly specific for *E. coli* O157, giving positive results with each of six unrelated O157 strains while only one primer pair gave a band of the expected size with one of three strains with O antigens known to cross-react serologically with *E. coli* O157.

D. Primers Based on the *Salmonella Enterica* Serotype C2 and B O Antigen Gene Cluster Sequences.

We also performed a PCR using primers for the *S. enterica* C2 and B serogroup transferases, wzx, wzy and genes (Tables 7 to 9). The nucleotide sequences of C2 and B O antigen gene clusters are listed as SEQ ID NO: 3 (FIG. 9) and SEQ ID NO:4 (FIG. 10) respectively. Chromosomal DNA from all the 46 serotypes of *Salmonella enterica* (Table 9) was isolated using the Promega Genomic isolation kit, 7 pools of 4 to 8 samples per pool were made. *Salmonella enterica* serotype B or C2 DNA was omitted from the pool for testing primers of 46 respective serotypes but added to a pool containing 6 other samples to give pool number 8 for use as a positive control.

PCR reactions were carried out under the following conditions: denaturing, 94° C./30"; annealing, temperature varies (see below)/30"; extension, 72° C./1'; 30 cycles. PCR reaction was carried out in a volume of 25μL for each pool. After the PCR reaction, 10μL PCR product from each pool was run on an agarose gel to check for amplified DNA. For pools which gave a band of correct size, PCR was repeated using individual chromosomal samples of that pool, and agarose gel was run to check for amplified DNA from each sample.

The *Salmonella enterica* serotype B O antigen gene cluster (of strain LT2) was the first O antigen gene cluster to be fully sequenced, and the function of each gene has been identified experimentally [Jiang, X. M., Neal, B., Santiago, F., Lee, S. J., Romana, L. K., and Reeves, P. R. (1991) "Structure and sequence of the rfb (O antigen) gene cluster of *Salmonella* serovar typhimurium (strain LT2)." Mol. Microbiol. 5(3), 695–713; Liu, D., Cole, R., and Reeves, P. R. (1996). "An O antigen processing function for Wzx (RfbX): a promising candidate for O-unit flippase" J. Bacteriol., 178(7),2102–2107; Liu, D., Haase, A. M., Lindqvist, L., Lindberg, A. A., and Reeves, P. R. (1993). "Glycosyl transferases of O-antigen biosynthesis in *S. enterica*: identification and characterisation of transferase genes of groups B, C2 and E1." J. Bacteriol., 175, 3408–3413; Liu, D., Lindquist, L., and Reeves P. R. (1995). "Transferases of O-antigen biosynthesis in *Salmonella enterica*:dideoxyhexosyl transferases of groups B and C2 and acetyltransferase of group C2." J. Bacteriol. 177, 4084–4088; Romana, L. K., Santiago, F S., and Reeves, P. R. (1991). "High level expression and purification dThymidine-diphospho-D-glucose 4,6 dehydratase (rfbB) from *Salmonella* serovar typhimurium LT2." BBRC, 174, 846–852]. One pair of primers for each of the pathway genes and wbaP was tested against the pools of *Salmonella enterica* DNA, two to three pairs of primers for each of the other transferases and wzx genes were also tested. See Table 8 for a list of primers and functional information of each gene, as well as the annealing temperature of the PCR reaction for each pair of primers.

For pathway genes of group B strain LT2, there are 19/45, 14/45, 15/45, 12/45, 6/45, 6/45, 6/45, 6/45, 1/45, 9/45, 8/45 positives for rmlB, zmlD, rmlA, rmlC, ddhD, ddhA, ddhb, ddhC, abe, manC, and manB repsectively (Table 9).

For the LT2 wzx gene we used three primer pairs each of which gave 1/45 positive. For the 4 transferase genes we used a total of 9 primer pairs. 2 primer pairs for wbaV gave 2/90 positives. For 3 primer pairs of wbaN, 11/135 gave a positive result. For the wbaP primer pair 10/45 gave a positive result (Table 9).

The experimental data show that oligonucleotides derived from the wzx and wbaV group B O antigen genes are specific for group B O antigen amongst all 45 *Salmonella enterica* O antigen groups except O group 67. The oligonucleotides derived from *Salmonella enterica* B group wbaN and wbaU genes detected B group O antigen and also produced positive results with groups A, D1 and D3. WbaU encodes a transferase for a Mannose α(1–4) Mannose linkage and is expressed in groups A, B and D1 while wbaN, which encodes a transferase for Rhamnose α(1–3) Galactose linkage is present in groups A, B, D1, D2, D3 and E1. This accounts for the positive results with the group B wbau and wbaN genes. The wbaN gene of groups E and D2 has considerable sequence differences from that of groups A, B, D1 and D3 and this accounts for the positive results only with groups B, D1 and D3.

The *Salmonella enterica* B primers derived from wzx and transferase genes produced a positive result with *Salmonella enterica* 067. We find that *Salmonella enterica* O67 has all the genes of the group B O antigen cluster. There are several possible explanations for this finding including the possibility that the gene cluster is not functional due to mutation and the group 067 antigenicity is due to another antigen, or the O antigen is modified after synthesis such that its antigenicity is changed. *Salmonella enterica* 067 would therefore be scored as *Salmonella enterica* group B in the PCR diagnostic assay. However, this is of little importance because *Salmonella enterica* 067 is a rare O antigen and only one (serovar Crossness) of the 2324 known serovars has the 067 serotype [Popoff M. Y. et al (1992) "Antigenic formulas of the *Salmonella enterica* serovars" 6th revision WHO Collaborating Centre for Reference and Research on *Salmonella enterica*, Institut Pasteur Paris France], and serovar Crossness had only been isolated once [M. Popoff, personal communication].

The *Salmonella enterica* B primers derived from wbaP reacted with group A, C2, D1, D2, D3, E1, 54, 55, 67 and E4 O antigen groups. WbaP encodes the galactosyl transferase which initiates O unit synthesis by transfer of Galactose phosphate to the lipid carrier Undecaprenol phosphate. This reaction is common to the synthesis of several O antigens. As such wbaP is distinguished from other transferases of the invention as it does not make a linkage within an O antigen.

We also tested 20 primer pairs for the wzx, wzy and 5 transferase genes of serotype C2 and found no positives in all the 7 pools (Table 7).

Groups A, B, D1, D2, D3, C2 and E1 share many genes in common. Some of these genes occur with more than one sequence in which case each specific sequence can be named after one of the serogroups in which it occurs. The distribution of these sequence specificities is shown in Table 10. The inventors have aligned the nucleotide sequences of

*Salmonella enterica* wzy, wzx genes and transferase genes so as to determine specific combinations of nucleic acid molecules which can be employed to specifically detect and identify the *Salmonella enterica* groups A, B, D1, D2, D3, C2 and E1 (Table 10). The results show that many of the O antigen groups can be detected and identified using a single specific nucleic acid molecule although other groups in particular D2 and E1, and A and D1 require a panel of nucleic acid molecules derived from a combination of genes.

It will be understood that in carrying out the methods of the invention with respect to the testing of particular sample types including samples from food, patients and faeces the samples are prepared by routine techniques routinely used in the preparation of such samples for DNA based testing.

TABLE 1

| Pool No. | Strains of which chromosonal DNA included in the pool | Source* |
|---|---|---|
| 1 | *E. coli* type strains for O serotypes 1, 2, 3, 4, 10, 16, 18 and 39 | IMVS[a] |
| 2 | *E. coli* type strains for O serotypes 40, 41, 48, 49, 71, 73, 88 and 100 | IMVS |
| 3 | *E. coli* type strains for O serotypes 102, 109, 119, 120, 121, 125, 126 and 137 | IMVS |
| 4 | *E. coli* type strains for O serotypes 138, 139, 149, 7, 5, 6, 11 and 12 | IMVS |
| 5 | *E. coli* type strains for O serotypes 13, 14, 15, 17, l9ab, 20, 21 and 22 | IMVS |
| 6 | *E. coli* type strains for O serotypes 23, 24, 25, 26, 27, 28, 29 and 30 | IMVS |
| 7 | *E. coli* type strains for O serotypes 32, 33, 34, 35, 36, 37, 38 and 42 | IMVS |
| 8 | *E. coli* type strains for O serotypes 43, 44, 45, 46, 50, 51, 52 and 53 | IMVS |
| 9 | *E. coli* type strains for O serotypes 54, 55, 56, 57, 58, 59, 60 and 61 | IMVS |
| 10 | *E. coli* type strains for O serotypes 62, 63, 64, 65, 66, 68, 69 and 70 | IMVS |
| 11 | *E. coli* type strains for O serotypes 74, 75, 76, 77, 78, 79, 80 and 81 | IMVS |
| 12 | *E. coli* type strains for O serotypes 82, 83, 84, 85, 86, 87, 89 and 90 | IMVS |
| 13 | *E. coli* type strains for O serotypes 91, 92, 95, 96, 97, 98, 99 and 101 | IMVS |
| 14 | *E. coli* type strains for O serotypes 103, 104, 105, 106, 107, 108 and 110 | IMVS |
| 15 | *E. coli* type strains for O serotypes 112, 162, 113, 114, 115, 116, 117 and 118 | IMVS |
| 16 | *E. coli* type strains for O serotypes 123, 165, 166, 167, 168, 169, 170 and 171 | See b |
| 17 | *E. coli* type strains for O serotypes 172, 173, 127, 128, 129, 130, 131 and 132 | See c |
| 18 | *E. coli* type strains for O serotypes 133, 134, 135, 136, 140, 141, 142 and 143 | IMVS |
| 19 | *E. coli* type strains for O serotypes 144, 145, 146, 147, 148, 150, 151 and 152 | IMVS |

*
[a]Institute of Medical and Veterinary Science, Adelaide, Australia
b 123 from IMVS; the rest from Statens Serum Institut, Copenhagen, Denmark
c 172 and 173 from Statens Serum Institut, Copenhagen, Denmark, the rest from IMVS

TABLE 2

| Pool No. | Strains of which chromosonal DNA included in the pool | Source* |
|---|---|---|
| 20 | *E. coli* type strains for O serotypes 153, 154, 155, 156, 157, 158, 159 and 160 | IMVS |
| 21 | *E. coli* type strains for O serotypes 161, 163, 164, 8, 9 and 124 | IMVS |
| 22 | As pool #21, plus *E. coli* 0111 type strain Stoke W. | IMVS |
| 23 | As pool #21, plus *E. coil* 0111:H2 strain C1250–1991 | See d |
| 24 | As pool #21, plus *E. coli* 0111:H12 strain C156–1989 | See e |
| 25 | As pool #21, plus *S. enterica* serovar Adelaide | See f |
| 26 | *Y. pseudotuberculosis* strains of O groups IA, IIA, IIB, IIC, III, IVA, IVB, VA, VB, VI and VII | See g |
| 27 | *S. boydii* strains of serogroups 1, 3, 4, 5, 6, 8, 9, 10, 11, 12, 14 and 15 | See h |
| 28 | *S. enterica* strains of serovars (each representing a different O group) Typhi, Montevideo, Ferruch, Jangwani, Raus, Hvittingfoss, Waycross, Dan, Dugbe, Basel, 65,:i:e,n,z,15 and 52:d:e,n,x,z15 | IMVS |

*
d C1250–1991 from Statens Serum Institut, Copenhagen, Denmark
e C156–1989 from Statens Serum Institut, Copenhagen, Denmark
f *S. enterica* serovar Adelaide from IMVS
g Dr. S. Aleksic of Institute of Hygiene, Germany
h Dr. J. Lefebvre of Bacterial Identification Section, Laboratoroie de Santè Publique duQuèbec, Canada

TABLE 3

| Pool No. | Strains of which chromosonal DNA included in the pool | Source* |
|---|---|---|
| 29 | *E. coli* type strains for O serotypes 153, 154, 155, 156, 158, 159 and 160 | IMVS |
| 30 | *E. coli* type strains for O serotypes 161, 163, 164, 8, 9, 111 and 124 | IMVS |
| 31 | As pool #29, plus *E. coli* O157 type strain A2 (O157:H19) | IMVS |
| 32 | As pool #29, plus *E. coli* O157:H16 strain C475–89 | See d |
| 33 | As pool #29, plus *E. coli* O157:H45 strain C727–89 | See d |
| 34 | As pool #29, plus *E. coli* O157:H2 strain C252–94 | See d |
| 35 | As pool #29, plus *E. coli* O157:H39 strain C258–94 | See d |
| 36 | As pool #29, plus *E. coli* O157:H26 | See e |
| 37 | As pool #29, plus *S. enterica* serovar Landau | See f |
| 38 | As pool #29, plus *Brucella abortus* | See g |
| 39 | As pool #29, plus *Y. enterocolitica* O9 | See h |
| 40 | *Y. pseudotuberculosis* strains of O groups IA, IIA, IIB, IIC, III, IVA, IVB, VA, VB, VI and VII | See i |
| 41 | *S. boydii* strains of serogroups 1, 3, 4, 5, 6, 8, 9, 10, 11, 12, 14 and 15 | See j |
| 42 | *S. enterica* strains of serovars (each representing a different O group) Typhi, Montevideo, Ferruch, Jangwani, Raus, Hvittingfoss, Waycross, Dan, Dugbe, Basel, 65:i:e,n,z15 and 52:d:e,n,x,z15 | IMVS |
| 43 | *E. coli* type strains for O serotypes 1, 2, 3, 4, 10, 18 and 29 | IMVS |
| 44 | As pool #43, plus *E. coli* K-12 strains C600 and WG1 | IVMS See k |

*
d O157 strains from Statens Serum Institut, Copenhagen, Denmark
e O157:H26 from Dr. R. Brown of Royal Children's Hospital, Melbourne, Victoria
f *S. enterica* serovar Landau from Dr. M. Poppoff of Institut Pasteur, Paris, France
g *B. Abortus* from the culture collection of The University of Sydney, Sydney, Australia
h *Y. enterocolitica* O9 from Dr. K. Bettelheim of Victorian Infectious Diseases Reference Laboratory Victoria, Australia.
i Dr. S. Aleksic of Institute of Hygiene, Germany
j Dr. J. Lefebvre of Bacterial Identification Section, Laboratoroie de Santè Publique du Quèbec, Canada
k Strains C600 and WG1 from Dr. B.J. Backmann of Department of Biology, Yale University, USA.

TABLE 4

PCR assay result using primers based on the *E. coli* serotype O16 (strain K-12) O antigen gene cluster sequence

| Gene | Function | Base positions of the gene | Forward primer (base positions) | Reverse primer (base positions) | Length of the PCR fragment | Number of pools (out of 21) giving band of correct size | Annealing temperature of the PCR |
|---|---|---|---|---|---|---|---|
| rmlB* | TDP-rhamnose pathway | 90–1175 | #1064(91–109) | #1065(1175–1157) | 1085 bp | 17 | 60° C. |
| rmlD* | TDP-rhamnose pathway | 1175–2074 | #1066(1175–1193) | #1067(2075–2058) | 901 bp | 13 | 60° C. |
| rmlA* | TDP-rhamnose pathway | 2132–3013 | #1068(2131–2148) | #1069(3013–2995) | 883 bp | 0 | 60° C. |
| rmlC* | TDP-rhamnose pathway | 3013–3570 | #1070(3012–3029) | #1071(3570–3551) | 559 bp | 0 | 60° C. |
| gtf* | Galactofuranose pathway | 4822–5925 | #1074(4822–4840) | #1075(5925–5908) | 1104 bp | 0 | 55° C. |
| wzx* | Flippase | 3567–4814 | #1072(3567–3586) | #1073(4814–4797) | 1248 bp | 0 | 55° C. |
| wzy* | O polymerase | 5925–7091 | #1076(5925–5944) | #1077(7091–7074) | 1167 bp | 0 | 60° C. |
| wbbI* | Galactofuranosyl transferase | 7094–8086 | #1078(7094–7111) | #1079(8086–8069) | 993 bp | 0 | 50° C. |
| wbbJ* | Acetyltransferase | 8067–8654 | #1080(8067–8084) | #1081(8654–8632) | 588 bp | 0 | 60° C. |
| wbbK** | Glucosyl transferase | 5770–6888 | #1082(5770–5787) | #1083(6888–6871) | 1119 bp | 0 | 55° C. |
| wbbL*** | Rhamnosyltransferase | 679–1437 | #1084(679–697) | #1085(1473–1456) | 795 bp | 0**** | 55° C. |

*,,*Base positions based on GenBank entry U09876, U03041 and L19537 respectively
****19 pools giving a band of wrong size

TABLE 5

PCR assay data using O111 primers

| Gene | Base positions of the gene according to SEQ ID NO: 1 | Forward primer (base positions) | Reverse primer (base positions) | Length of the PCR fragment | Number of pools (out of 21) giving band of correct size | Annealing temperature of the PCR |
|---|---|---|---|---|---|---|
| wbdH | 739–1932 | #866(739–757) | #867(1941–1924) | 1203 bp | 0 | 60° C. |
|  |  | #976(925–942) | #978(1731–1714) | 807 bp | 0 | 60° C. |
|  |  | #976(925–942) | #979(1347–1330) | 423 bp | 0 | 60° C. |
|  |  | #977(1165–1182) | #978(1731–1714) | 567 bp | 0 | 60° C. |
| wzx | 8646–9911 | #969(8646–8663) | #970(9908–9891) | 1263 bp | 0 | 50° C. |
|  |  | #1060(8906–8923) | #1062(9468–9451) | 563 bp | 0 | 60° C. |
|  |  | #1061(9150–9167) | #1063(9754–9737) | 605 bp | 0 | 50° C. |

TABLE 5-continued

PCR assay data using O111 primers

| Gene | Base positions of the gene according to SEQ ID NO: 1 | Forward primer (base positions) | Reverse primer (base positions) | Length of the PCR fragment | Number of pools (out of 21) giving band of correct size | Annealing temperature of the PCR |
|---|---|---|---|---|---|---|
| wzy | 9901–10953 | #900(9976–9996) | #901(10827–10807) | 852 bp | 0 | 60° C. |
|  |  | #980(10113–10130) | #983(10484–10467) | 372 bp | 0* | 61° C. |
| wbdL | 10931–11824 | #870(10931–10949) | #871(11824–11796) | 894 bp | 7 | 60° C. |
| wbdM | 11821–12945 | #868(11821–11844) | #869(12945–12924) | 1125 bp | 0 | 60° C. |
|  |  | #984(12042–12059) | #987(12447–12430) | 406 bp | 0 | 60° C. |
|  |  | #985(12258–12275) | #986(12698–12681) | 441 bp | 0** | 65° C. |

*Giving a band of wrong size in all pools
**One pool giving a band of wrong size

TABLE 5A

PCR specificity test data using O111 primers

| Gene | Base positions of the gene according to SEQ ID NO: 1 | Forward primer (base positions) | Reverse primer (base positions) | Length of the PCR Fragment | Number of pools (pools no. 25–28) giving band of correct size | Annealing Temperature of the PCR |
|---|---|---|---|---|---|---|
| wbdH | 739–1932 | #866(739–757) | #867(1941–1924) | 1203 bp | 0* | 60° C. |
|  |  | #976(925–942) | #978(1731–1714) | 807 bp | 0 | 60° C. |
|  |  | #976(925–942) | #979(1347–1330) | 423 bp | 0 | 60° C. |
|  |  | #977(1165–1182) | #978(1731–1714) | 567 bp | 0 | 60° C. |
| wzx | 8646–9911 | #969(8646–8663) | #970(9908–9891) | 1263 bp | 0 | 55° C. |
|  |  | #1060(8906–8923) | #1062(9468–9451) | 563 bp | 0 | 60° C. |
|  |  | #1061(9150–9167) | #1063(9754–9737) | 605 bp | 0* | 50° C. |
| wzy | 9901–10953 | #900(9976–9996) | #901(10827–10807) | 852 bp | 0 | 60° C. |
|  |  | #980(10113–10130) | #983(10484–10467) | 372 bp | 0** | 60° C. |
| wbdL | 10931–11824 | #870(10931–10949) | #871(11824–11796) | 894 bp | 0 | 60° C. |
| wbdM | 11821–12945 | #868(11821–11844) | #869(12945–12924) | 1125 bp | 0 | 60° C. |
|  |  | #984(12042–12059) | #987(12447–12430) | 406 bp | 0 | 60° C. |
|  |  | #985(12258–12275) | #986(12698–12681) | 441 bp | 0* | 65° C. |

*1 pool giving a band of wrong size
**2 pools giving 3 bands of wrong sizes, 1 pool giving 2 bands of wrong sizes

TABLE 6

PCR results using primers based on the E. coli O157 sequence

| Gene | Function | Base position of the gene according to SEQ ID NO: 2 | Forward primer (base position) | Reverse primer (base position) | Length of the PCR fragment | Number of pools (out of 21) giving band of correct size | Annealing Temperature of the PCR |
|---|---|---|---|---|---|---|---|
| wbdN | Sugar transferase | 79–861 | #1197(79–96) | #1198(861–844) | 783 | 0 | 55° C. |
|  |  |  | #1199(184–201) | #1200(531–514) | 348 | 0 | 55° C. |
|  |  |  | #1201(310–327) | #1202(768–751) | 459 | 0 | 55° C. |
| wzy | O antigen | 858–2042 | #1203(858–875) | #1204(2042–2025) | 1185 | 0* | 50° C. |
|  |  |  | #1205(1053–1070) | #1206(1619–1602) | 567 | 0 | 63° C. |
|  |  |  | #1207(1278–1295) | #1208(1913–1896) | 636 | 0 | 60° C. |
| wbdO | Sugar transferase | 2011–2757 | #1209(2011–2028) | #1210(2757–2740) | 747 | 0 | 50° C. |
|  |  |  | #1211(2110–2127) | #1212(2493–2476) | 384 | 0** | 62° C. |
|  |  |  | #1213(2305–2322) | #1214(2682–2665) | 378 | 0 | 60° C. |
| wzx | O antigen flippase | 2744–4135 | #1215(2744–2761) | #1216(4135–4118) | 1392 | 0 | 50° C. |
|  |  |  | #1217(2942–2959) | #1218(3628–3611) | 687 | 0*** | 63° C. |
| wbdP | Sugar transferase | 5257–6471 | #1221(5257–5274) | #1222(6471–6454) | 1215 | 0 | 55° C. |
|  |  |  | #1223(5440–5457) | #1224(5973–5956) | 534 | 0 | 55° C. |
|  |  |  | #1225(5707–5724) | #1226(6231–6214) | 525 | 0 | 55° C. |
| wbdR | N-acetyl transferase | 13156–13821 | #1229(13261–13278) | #1230(13629–13612) | 369 | 0 | 55° C. |
|  |  |  | #1231(13384–13401) | #1232(13731–13714) | 348 | 0 | 60° C. |

*3 bands of wrong size in one pool, 1 band of wrong size in all other pools
**3 bands of wrong sizes in 9 pools, 2 bands of wrong size in all other pools
***2 bands of wrong sizes in 2 pools, 1 band of wrong size in 7 pools

TABLE 6A

PCR results using primers based on the *E. coli* O157 sequence

| Gene | Function | Base position of the gene according to SEQ ID NO: 2 | Forward primer (base positions) | Reverse primer (base positions) | Length of the PCR fragment | Number or pools (pools no. 37–42) giving band of correct size | Annealing temperature of the PCR |
|---|---|---|---|---|---|---|---|
| wbdN | Sugar transferase | 79–861 | #1197(79–96) | #1198(861–844) | 783 | 0* | 55° C. |
|  |  |  | #1199(184–201) | #1200(531–514) | 348 | 0* | 55° C. |
|  |  |  | #1201(310–327) | #1202(768–751) | 459 | 0 | 61° C. |
| wzy | O antigen polymerase | 858–2042 | #1203(858–875) | #1204(2042–2025) | 1185 | 1** | 50° C. |
|  |  |  | #1205(1053–1070) | #1206(1619–1602) | 567 | 0*** | 60° C. |
|  |  |  | #1207(1278–1295) | #1208(1913–1896) | 636 | 0 | 60° C. |
| wbdO | Sugar transferase | 2011–2757 | #1209(2011–2028) | #1210(2757–2740) | 747 | 0 | 50° C. |
|  |  |  | #1211(2110–2127) | #1212(2493–2476) | 384 | 0**** | 61° C. |
|  |  |  | #1213(2305–2322) | #1214(2682–2665) | 378 | 0 | 60° C. |
| wzx | O antigen flippase | 2744–4135 | #1215(2744–2761) | #1216(4135–4118) | 1392 | 0 | 50° C. |
|  |  |  | #1217(2942–2959) | #1218(3628–3611) | 687 | 0 | 63° C. |
| wbdP | Sugar transferase | 5257–6471 | #1221(5257–5274) | #1222(6471–6454) | 1215 | 0 | 55° C. |
|  |  |  | #1223(5440–5457) | #1224(5973–5956) | 534 | 0* | 60° C. |
|  |  |  | #1225(5707–5724) | #1226(6231–6214) | 525 | 0 | 55° C. |
| wbdR | N-acetyl transferase | 13156–13821 | #1229(13261–13278) | #1230(13629– | 369 | 0 | 50° C. |
|  |  |  | #1231(13384–13401) | #1232(13731– | 348 | 0 | 60° C. |

*1 band of wrong size in one pool
**pool #39 giving two bands, one band of correct size, the other band of wrong size in another pool
***2 bands of wrong sizes in one pool
****3 bands of wrong sizes in 2 pools, 2 bands of wrong sizes in 2 other pools

TABLE 7

PCR assay data using primers based on the *Salmonella enterica* serotype C2 (strain M67) O antigen gene cluster sequence

| Gene | Function | Base positions of the gene according to SEQ ID NO: 3 | Forward primer (base position) | Reverse primer (base position) | Length of the PCR fragment | Number of pools (out of 7) giving band of correct size | Annealing temperature of the PCR |
|---|---|---|---|---|---|---|---|
| wzx | Flippase | 1019–2359 | #1144(1019–1036) | #1145(1414–1397) | 396 bp | 0 | 55° C. |
|  |  |  | #1146(1708–1725) | #1147(2170–2153) | 463 bp | 0 | 55° C. |
|  |  |  | #1148(1938–1955) | #1149(2356–2339) | 419 bp | 0 | 55° C. |
| wbaR | Abequosyl transferase | 2352–3314 | #1150(2352–2369) | #1151(2759–2742) | 408 bp | 0 | 55° C. |
|  |  |  | #1152(2601–2618) | #1153(3047–3030) | 447 bp | 0 | 55° C. |
|  |  |  | #1154(2910–2927) | #1155(3311–3294) | 402 bp | 0 | 55° C. |
| wbaL | Acetyl transferase | 3361–3875 | #1156(3361–3378) | #1157(3759–3742) | 399 bp | 0 | 55° C. |
|  |  |  | #1158(3578–3595) | #1159(3972–3955) | 395 bp | 0 | 50° C. |
| wbaQ | Rhamnosyl | 3977–5020 | #1160(3977–3994) | #1161(4378–4361) | 402 bp | 0 | 55° C. |
|  |  |  | #1162(4167–4184) | #1163(4774–4757) | 608 bp | 0 | 55° C. |
|  |  |  | #1164(4603–4620) | #1165(5017–5000) | 415 bp | 0* | 60° C. |
| wzy | O polymerase | 5114–6313 | #1166(5114–5131) | #1167(5515–5498) | 402 bp | 0** | 55° C. |
|  |  |  | #1168(5664–5681) | #1169(6112–6095) | 449 bp | 0 | 55° C. |
|  |  |  | #1170(5907–5924) | #1171(6310–6293) | 404 bp | 0 | 55° C. |
| wbaW | Mannosyl transferase | 6313–7323 | #1172(6313–6330) | #1173(6805–6788) | 493 bp | 0 | 50° C. |
|  |  |  | #1174(6697–6714) | #1175(7068–7051) | 372 bp | 0 | 55° C. |
|  |  |  | #1176(6905–6922) | #1177(7320–7303) | 416 bp | 0 | 55° C. |
| wbaZ | Mannosyl transferase | 7310–8467 | #1178(7310–7327) | #1179(7775–7758) | 466 bp | 0 | 50° C. |
|  |  |  | #1180(7530–7547) | #1181(7907–7890) | 378 bp | 0 | 55° C. |
|  |  |  | #1182(8007–8024) | #1183(8464–8447) | 458 bp | 0 | 55° C. |

*Positive pool gives another band, which is also present in another pool. All other pools gave bands of wrong size.
**Band of wrong size in 6 other pools.

TABLE 8

PCR primers based on the *Salmonella enterica* serotype B (strain LT2) O antigen gene cluster sequence

| Gene | Function | Base position of the gene according to SEQ ID NO: 4 | Forward primer (base position) | Reverse primer (base position) | Length of the PCR fragment | Annealing temperature of the PCR |
|---|---|---|---|---|---|---|
| rmlB | TDP-rhamnose pathway | 4099–5184 | #1094(4100–4117) | #1095(4499–4482) | 400 bp | 55° C. |
| rmlD | TDP-rhamnose pathway | 5184–6083 | #1092(5186–5203) | #1093(5543–5526) | 358 bp | 50° C. |
| rmlA | TDP-rhamnose pathway | 6131–7009 | #1090(6531–6548) | #1091(6837–6820) | 308 bp | 55° C. |
| rmlC | TDP-rhamnose pathway | 7010–7561 | #1088(7013–7030) | #1089(7372–7355) | 360 bp | 55° C. |
| ddhD | CDP-abequose pathway | 7567–8559 | #1112(7567–7584) | #1113(7970–7953) | 404 bp | 55° C. |
| ddhA | CDP-adequose pathway | 8556–9329 | #1114(8556–8573) | #1115(8975–8958) | 420 bp | 60° C. |

TABLE 8-continued

PCR primers based on the *Salmonella enterica* serotype B (strain LT2) O antigen gene cluster sequence

| Gene | Function | Base position of the gene according to SEQ ID NO: 4 | Forward primer (base position) | Reverse primer (base position) | Length of the PCR fragment | Annealing temperature of the PCR |
|---|---|---|---|---|---|---|
| ddhB | CDP-adequose pathway | 9334–10413 | #1116(9334–9351) | #1117(9816–9799) | 483 bp | 45° C. |
| ddhC | CDP-adequose pathway | 10440–11753 | #1118(10440–10457) | #1119(10871–10854) | 432 bp | 60° C. |
| abe | CDP-adequose pathway | 11781–12680 | #1100(12008–12025) | #1101(12388–12371) | 381 bp | 55° C. |
| wzx | Flippase | 12762–14054 | #1120(12762–12779) | #1121(13150–13133) | 389 bp | 55° C. |
|  |  |  | #1122(12993–13010) | #1123(13417–13400) | 425 bp | 55° C. |
|  |  |  | #1124(13635–13652) | #1125(14051–14034) | 417 bp | 55° C. |
| wbaV | Abequosyl transferase | 14059–15060 | #1126(14059–14076) | #1127(14421–14404) | 363 bp | 45° C. |
|  |  |  | #1128(14688–14705) | #1129(15057–15040) | 370 bp | 45° C. |
| wbaU | Mannosyl transferase | 15379–16440 | #1130(15379–15396) | #1131(15768–15751) | 390 bp | 60° C. |
|  |  |  | #1132(15850–15867) | #1133(16262–16245) | 413 bp | 50° C. |
|  |  |  | #1134(16027–16044) | #1135(16437–16420) | 411 bp | 60° C. |
| wbaN | Rhamnosyl transferase | 16441–17385 | #1136(16441–16458) | #1137(16851–16834) | 411 bp | 45° C. |
|  |  |  | #1138(16630–16647) | #1139(17087–17070) | 458 bp | 55° C. |
|  |  |  | #1140(16978–16995) | #1141(17382–17365) | 405 bp | 50° C. |
| manC | GDP-mannose pathway | 17386–18825 | #1098(17457–17474) | #1099(18143–18126) | 687 bp | 60° C. |
| mabB | GDP-mannose pathway | 18812–20245 | #1096(18991–19008) | #1097(19345–19328) | 355 bp | 55° C. |
| wbaP | Galactosyl transferase | 20317–21747 | #1142(20389–20406) | #1143(20709–20692) | 321 bp | 55° C. |

TABLE 9

PCR results using LT2 primers*

| Strain name | O group | 1094 – 1095 rmlB | 1092 – 1093 rmlD | 1090 – 1091 rmlA | 1088 – 1089 rmlC | 1112 – 1113 ddhD | 1114 – 1115 ddhA | 1116 – 1117 ddhB | 1118 – 1119 ddhC | 1100 – 1101 abe | 1120 – 1121 wzx | 1122 – 1123 wzx | 1124 – 1125 wzx | 1126 – 1127 wbaV |
|---|---|---|---|---|---|---|---|---|---|---|---|---|---|---|
| M8 | A | y | y | y | y | y | y | y | y |  |  |  |  |  |
| P9003 | B | y | y | y | y | y | y | y | y | y | y | y | y | y |
| M40 | C1 |  |  |  |  |  |  |  |  |  |  |  |  |  |
| M67 | C2 | y | y | y | y | y | y | y | y |  |  |  |  |  |
| M18 | D1 | y | y | y | y | y | y | y | y |  |  |  |  |  |
| M388 | D2 | y |  | y | y | y | y | y | y |  |  |  |  |  |
| M344 | D3 | y | y | y | y | y | y | y | y |  |  |  |  |  |
| M32 | E1 | y | y | y | y |  |  |  |  |  |  |  |  |  |
| M324 | F | y | y | y | y |  |  |  |  |  |  |  |  |  |
| M258 | G |  |  |  |  |  |  |  |  |  |  |  |  |  |
| M252 | H |  |  |  |  |  |  |  |  |  |  |  |  |  |
| M264 | I |  |  |  |  |  |  |  |  |  |  |  |  |  |
| M254 | J |  |  |  |  |  |  |  |  |  |  |  |  |  |
| M255 | K |  |  |  |  |  |  |  |  |  |  |  |  |  |
| M7 | L |  |  |  |  |  |  |  |  |  |  |  |  |  |
| M269 | M | y | y | y |  |  |  |  |  |  |  |  |  |  |
| M270 | N |  |  |  |  |  |  |  |  |  |  |  |  |  |
| M95 | O |  |  |  |  |  |  |  |  |  |  |  |  |  |
| M260 | P |  |  |  |  |  |  |  |  |  |  |  |  |  |
| M273 | Q | y |  |  |  |  |  |  |  |  |  |  |  |  |
| M261 | R |  |  |  |  |  |  |  |  |  |  |  |  |  |
| M282 | S |  |  |  |  |  |  |  |  |  |  |  |  |  |
| M287 | T | y | y | y | y |  |  |  |  |  |  |  |  |  |
| M295 | U |  |  |  |  |  |  |  |  |  |  |  |  |  |
| M289 | V |  |  |  |  |  |  |  |  |  |  |  |  |  |
| M296 | W |  |  |  |  |  |  |  |  |  |  |  |  |  |
| M278 | X |  |  |  |  |  |  |  |  |  |  |  |  |  |
| M298 | Y |  |  |  |  |  |  |  |  |  |  |  |  |  |
| M93 | Z |  |  |  |  |  |  |  |  |  |  |  |  |  |
| M291 | 51 |  |  |  |  |  |  |  |  |  |  |  |  |  |
| M309 | 52 |  |  |  |  |  |  |  |  |  |  |  |  |  |
| M303 | 53 | y | y | y |  |  |  |  |  |  |  |  |  |  |
| M292 | 54 | y | y | y | y |  |  |  |  |  |  |  |  |  |
| M304 | 56 | y |  |  |  |  |  |  |  |  |  |  |  |  |
| M293 | 57 | y | y | y |  |  |  |  |  |  |  |  |  |  |
| M305 | 58 |  |  |  |  |  |  |  |  |  |  |  |  |  |
| M285 | 59 | y | y | y | y |  |  |  |  |  |  |  |  |  |
| M306 | 60 | y |  |  |  |  |  |  |  |  |  |  |  |  |
| M328 | 61 |  |  |  |  |  |  |  |  |  |  |  |  |  |
| M330 | 65 |  |  |  |  |  |  |  |  |  |  |  |  |  |
| M322 | 66 |  |  |  |  |  |  |  |  |  |  |  |  |  |
| M1408 | 33 |  |  |  |  |  |  |  |  |  |  |  |  |  |
| M1409 | 62 |  |  |  |  |  |  |  |  |  |  |  |  |  |

TABLE 9-continued

PCR results using LT2 primers*

| | | | | | | | | | | | | | | |
|---|---|---|---|---|---|---|---|---|---|---|---|---|---|---|
| M1410 | 63 | y | | | | | | | | | | | | |
| M1413 | 67 | y | y | y | y | y | y | y | y | y | y | y | y | y |
| M74 | E4 | y | y | y | y | | | | | | | | | |

| Strain name | O group | 1128 – 1129 wbaV | 1130 – 1131 wbaU | 1132 – 1133 wbaU | 1134 – 1135 wbaU | 1136 – 1137 wbaN | 1138 – 1139 wbaN | 1140 – 1141 wbaN | 1098 – 1099 mmC | 1096 – 1097 mmB | 1142 – 1143 wbap |
|---|---|---|---|---|---|---|---|---|---|---|---|
| M8 | A | | y | y | y | y | y | y | y | y | y |
| P9003 | B | y | y | y | y | y | y | y | y | y | y |
| M40 | C1 | | | | | | | | | | |
| M67 | C2 | | | | | | | | y | y | y |
| M18 | D1 | | y | y | y | y | y | y | y | y | y |
| M388 | D2 | | | | | | | | y | y | y |
| M344 | D3 | | y | y | | | y | y | y | | y |
| M32 | E1 | | | | | | | | y | y | y |
| M324 | F | | | | | | | | | | |
| M258 | G | | | | | | | | | | |
| M252 | H | | | | | | | | | | |
| M264 | I | | | | | | | | | | |
| M254 | J | | | | | | | | | | |
| M255 | K | | | | | | | | | | |
| M7 | L | | | | | | | | | | |
| M269 | M | | | | | | | | | | |
| M270 | N | | | | | | | | | | |
| M95 | O | | | | | | | | | | |
| M260 | P | | | | | | | | | | |
| M273 | Q | | | | | | | | | | |
| M261 | R | | | | | | | | | | |
| M282 | S | | | | | | | | | | |
| M287 | T | | | | | | | | | | |
| M295 | U | | | | | | | | | | |
| M289 | V | | | | | | | | | | |
| M296 | W | | | | | | | | | | |
| M278 | X | | | | | | | | | | |
| M298 | Y | | | | | | | | | | |
| M93 | Z | | | | | | | | | | |
| M291 | 51 | | | | | | | | | | |
| M309 | 52 | | | | | | | | | | |
| M303 | 53 | | | | | | | | | | |
| M292 | 54 | | | | | | | | y | y | y |
| M304 | 56 | | | | | | | | | | |
| M293 | 57 | | | | | | | | | | |
| M305 | 58 | | | | | | | | | | |
| M285 | 59 | | | | | | | | | | |
| M306 | 60 | | | | | | | | | | |
| M328 | 61 | | | | | | | | | | |
| M330 | 65 | | | | | | | | | | |
| M322 | 66 | | | | | | | | | | |
| M1408 | 33 | | | | | | | | | | y |
| M1409 | 62 | | | | | | | | | | |
| M1410 | 63 | | | | | | | | | | |
| M1413 | 67 | y | y | y | y | y | y | y | y | y | y |
| M74 | E4 | | | | | | | | y | y | y |

*y indicates a positive PCR result. Blank indicates a negative result.

TABLE 10

Gene specificities in *Salmonella enterica* serogroups

| | Genes | | | | | | | | | | |
|---|---|---|---|---|---|---|---|---|---|---|---|
| Serogroup | wzy | wzx | wbaP | wbaU | wbaN | wbaV | wbaO | wbaW | wbaZ | wbaQ | wbaR |
| A | B | D | B | B | B | D | — | — | — | — | — |
| B | B | B | B | B | B | B | — | — | — | — | — |
| D1 | B | D | B | B | B | D | — | — | — | — | — |
| D2 | E1 | D | B | — | E1 | D | E1 | — | — | — | — |
| D3 | D3 | D | B | B | B | D | — | — | — | — | — |
| C2 | C2 | C2 | B | — | — | — | — | C2 | C2 | C2 | C2 |
| E1 | E1 | E1 | B | — | E1 | — | E1 | — | — | — | — |

— means 'not present'

The invention claimed is:

1. A method of testing a sample for the presence of *E. coli* encoding bacterial polysaccharide O-antigen serotype O111, the method comprising the steps of:
 (a) providing a sample to be tested;
 (b) providing at least one oligonucleotide molecule which is about 17 to 28 nucleotides in length, and hybridizes using highly stringent wash conditions, to a nucleic acid sequence selected from the group consisting of:
  wbdH (nucleotide positions 739 to 1932 of SEQ ID NO:1);
  wzx (nucleotide positions 8646 to 9911 of SEQ ID NO:1) wzy (nucleotide positions 9901 to 10953 of SEQ ID NO:1); and
  wbdM (nucleotide positions 11821 to 12945 of SEQ ID NO:1)
 or to at least one nucleic acid sequence complementary to the group consisting of:
  wbdH (nucleotide positions 739 to 1932 of SEQ ID NO:1);
  wzx (nucleotide positions 8646 to 9911 of SEQ ID NO:1)
  wzy (nucleotide positions 9901 to 10953 of SEQ ID NO:1); and
  wbdM (nucleotide positions 11821 to 12945 of SEQ ID NO:1),
 (c) contacting said sample with said at least one oligonucleotide molecule to permit said oligonucleotide molecule to hybridize under said highly stringent wash conditions to said nucleic acid sequence when present in said sample; and
 (d) detecting any hybridized oligonucleotide molecules, wherein detection of said hybridized oligonucleotide molecules indicates the presence of said *E. coli* in said sample.

2. The method as claimed in claim 1, wherein step (b) involves providing one pair of oligonucleotide molecules, and wherein at least one oligonucleotide molecule of said pair hybridizes to one of said nucleic acid sequence.

3. The method as claimed in claim 2, wherein said pair of oligonucleotide molecules is a pair of polymerase chain reaction primers.

4. The method as claimed in claim 1, wherein said at least one oligonucleotide molecule is selected from the group consisting of positions 739–757 of SEQ ID NO:1, positions 925–942 of SEQ ID NO:1, positions 1165–1182 of SEQ ID NO:1, positions 8646–8663 of SEQ ID NO:1, positions 8906–8923 of SEQ ID NO:1, positions 9150–9167 of SEQ ID NO:1, positions 9976–9996 of SEQ ID NO:1, positions 10113–10130 of SEQ ID NO:1, positions 11821–11844 of SEQ ID NO:1, positions 12042–10259 of SEQ ID NO:1, positions 12258–12275 of SEQ ID NO:1, positions 1941–1924 of SEQ ID NO:1, positions 1731–1714 of SEQ ID NO:1, positions 1347–1330 of SEQ ID NO:1, positions 9908–9891 of SEQ ID NO:1, positions 9468–9451 of SEQ ID NO:1, positions 9754–9737 of SEQ ID NO:1, positions 10827–10807 of SEQ ID NO:1, positions 10484–10467 of SEQ ID NO:1, positions 12945–12924 of SEQ ID NO:1, positions 12447–12430 of SEQ ID NO:1and positions 12698–12681 of SEQ ID NO:1.

5. A method of testing a sample for the presence of *E. coli* encoding bacterial polysaccharide O-antigen serotype 0157, the method comprising the steps of:
 (a) providing a sample to be tested;
 (b) providing at least one oligonucleotide molecule which is about 17 to 28 nucleotides in length and hybridizes using highly stringent wash conditions, to a nucleic acid sequence selected from the group consisting of:
  wbdN (nucleotide position 79 to 861 of SEQ ID NO:2);
  wbdO (nucleotide positions 2011 to 2757 of SEQ ID NO:2);
  wbdP (nucleotide positions 5365 to 6471 of SEQ ID NO:2);
  wbdR (nucleotide positions 13156 to 13821 of SEQ ID NO:2);
  wzx (nucleotide positions 2744 to 3109 of SEQ ID NO:2); and
  wzy (nucleotide positions 858 to 2042 of SEQ ID NO:2),
 or to at least one nucleic acid sequence complementary to the group consisting of:
  wbdN (nucleotide position 79 to 861 of SEQ ID NO:2);
  wbdO (nucleotide positions 2011 to 2757 of SEQ ID NO:2);
  wbdP (nucleotide positions 5365 to 6471 of SEQ ID NO:2);
  wbdR (nucleotide positions 13156 to 13821 of SEQ ID NO:2);
  wzx (nucleotide positions 2744 to 3109 of SEQ ID NO:2); and
  wzy (nucleotide positions 858 to 2042 of SEQ ID NO:2),
 (c) contacting said sample with said at least one oligonucleotide molecule to permit said oligonucleotide molecule to hybridize under said highly stringent wash conditions to said nucleic acid sequence when present in said sample; and
 (d) detecting any hybridized oligonucleotide molecules, wherein detection of said hybridized oligonucleotide molecules indicates the presence of said *E. coli* in said sample.

6. The method as claimed in claim 5, wherein step (b) involves providing one pair of oligonucleotide molecules, and wherein at least one oligonucleotide molecule of said pair hybridizes to one of said nucleic acid sequence.

7. The method as claimed in claim 6, wherein said pair of oligonucleotide molecules is a pair of polymerase chain reaction primers.

8. The method as claimed in claim 5, wherein said at least one oligonucleotide molecule is selected from the group consisting of positions 79–96 of SEQ ID NO:2, positions 184–201 of SEQ ID NO:2, positions 310–327 of SEQ ID NO:2, positions 858–875 of SEQ ID NO:2, positions 1053–1070 of SEQ ID NO:2, positions 1278–1295 of SEQ ID NO:2, positions 2011–2028 of SEQ ID NO:2, positions 2110–2127 of SEQ ID NO:2, positions 2305–2322 of SEQ ID NO:2, positions 2744–2761 of SEQ ID NO:2, positions 2942–2959 of SEQ ID NO:2, positions 5440–5457 of SEQ ID NO:2, positions 5707–5724 of SEQ ID NO:2, positions 13261–13278 of SEQ ID NO:2, positions 13384–13401 of SEQ ID NO:2, positions 861–844 of SEQ ID NO:2, positions 531–514 of SEQ ID NO:2, positions 768–751 of SEQ ID NO:2, positions 2042–2025 of SEQ ID NO:2, positions 1619–1602 of SEQ ID NO:2, positions 1913–1896 of SEQ ID NO:2, positions 2757–2740 of SEQ ID NO:2, positions 2493–2476 of SEQ ID NO:2, positions 2682–2665 of SEQ ID NO:2, positions 6471–6454 of SEQ ID NO:2, positions 5973–5956 of SEQ ID NO:2, positions 6231–6214 of SEQ ID NO:2, positions 13629–13612 of SEQ ID NO:2 and positions 13731–13714 of SEQ ID NO:2.

9. A method of testing a sample for the presence of *S. enterica* encoding bacterial polysaccharide O-antigen serotype C2, the method comprising the steps of:
(a) providing a sample to be tested;
(b) providing at least one oligonucleotide molecule which is about 17 to 28 nucleotides in length, and hybridizes using highly stringent wash conditions, to a nucleic acid sequence selected from the group consisting of:

wbaR (nucleotide positions at 2352 to 3314 of SEQ ID NO:3);

wbaL (nucleotide positions 3361 to 3875 of SEQ ID NO:3);

wbaQ (nucleotide positions 3977 to 5020 of SEQ ID NO:3);

wbaW (nucleotide positions 6313 to 7323 of SEQ ID NO:3);

wbaZ (nucleotide positions 7310 to 8467 of SEQ ID NO:3);

wzx (nucleotide positions 1019 to 2359 of SEQ ID NO:3); and wzy (nucleotide positions 5114 to 6313 of SEQ ID NO:3), or to at least one nucleic acid sequence complementary to the group consisting of:

wbaR (nucleotide positions at 2352 to 3314 of SEQ ID NO:3);

wbaL (nucleotide positions 3361 to 3875 of SEQ ID NO:3);

wbaQ (nucleotide positions 3977 to 5020 of SEQ ID NO:3);

wbaW (nucleotide positions 6313 to 7323 of SEQ ID NO:3);

wbaZ (riucleotide positions 7310 to 8467 of SEQ ID NO:3);

wzx (nucleotide positions 1019 to 2359 of SEQ ID NO:3); and wzy (nucleotide positions 5114 to 6313 of SEQ ID NO:3), (c) contacting said sample with said at least one oligonucleotide molecule to permit said oligonucleotide molecule to hybridize under said highly stringent wash conditions to said nucleic acid sequence when present in said sample; and (d) detecting any hybridized oligonucleotide molecules, wherein detection of said hybridized oligonucleotide molecules indicates the presence of said *S. enteria* in said sample.

10. The method as claimed in claim 9, wherein step (b) involves providing one pair of oligonucleotide molecules, and wherein at least one oligonucleotide molecule of the pair hybridizes to one of said nucleic acid sequence.

11. The method as claimed in claim 10, wherein said pair of oligonucleotide molecules is a pair of polymerase chain reaction primers.

12. The method as claimed in claim 9, wherein said at least one oligonucleotide molecule is selected from the group consisting of positions 1019–1036 of SEQ ID NO:3, positions 1708–1725 of SEQ ID NO:3, positions 1938–1955 of SEQ ID NO:3, positions 2352–2369 of SEQ ID NO:3, positions 2601–2618 of SEQ ID NO:3, positions 2910–2927 of SEQ ID NO:3, positions 3361–3378 of SEQ ID NO:3, positions 3578–3595 of SEQ ID NO:3, positions 3977–3994 of SEQ ID NO:3, positions 4167–4184 of SEQ ID NO:3, positions 4603–4620 of SEQ ID NO:3, positions 5114–5131 of SEQ ID NO:3, positions 5664–5681 of SEQ ID NO:3, positions 5907–5924 of SEQ ID NO:3, positions 6313–6330 of SEQ ID NO:3, positions 6697–6714 of SEQ ID NO:3, positions 6905–6922 of SEQ ID NO:3, positions 7310–7327 of SEQ ID NO:3, positions 7530–7547 of SEQ ID NO:3, positions 8007–8024 of SEQ ID NO:3, positions 1414–1397 of SEQ ID NO:3, positions 2170–2153 of SEQ ID NO:3, positions 2356–2339 of SEQ ID NO:3, positions 2759–2742 of SEQ ID NO:3, positions 3047–3030 of SEQ ID NO:3, positions 3311–3294 of SEQ ID NO:3, positions 3759–3742 of SEQ ID NO:3, positions 4378–4361 of SEQ ID NO:3, positions 4774–4757 of SEQ ID NO:3, positions 5017–5000 of SEQ ID NO:3, positions 5515–5498 of SEQ ID NO:3, positions 6112–6095 of SEQ ID NO:3, positions 6310–6293 of SEQ ID NO:3, positions 6805–6788 of SEQ ID NO:3, positions 7068–7051 of SEQ ID NO:3, positions 7320–7303 of SEQ ID NO:3, positions 7775–7758 of SEQ ID NO:3, positions 7907–7890 of SEQ ID NO:3 and positions 8464–8447 of SEQ ID NO:3.

13. A method of testing a sample for the presence of *S. enteria* encoding bacterial polysaccharide O-antigen serotype B, the method comprising the steps:

(a) providing a sample to be tested;

(b) providing at least one oligonucleotide molecule which is about 17 to 28 nucleotides in length and hybridizes using highly stringent wash conditions to a nucleic acid sequence selected from the group consisting of:

wzx (nucleotide positions 12762 to 14054 of SEQ ID NO: 4); and wbaV (nucleotide positions 14059 to 15060 of SEQ ID NO: 4), or to at least one nucleic acid sequence complementary to the group consisting of:

wzx (nucleotide positions 12762 to 14054 of SEQ ID NO: 4); and wbaV (nucleotide positions 14059 to 15060 of SEQ ID NO: 4), (c) contacting said sample with said at least one oligonucleotide molecule to permit said oligonucleotide molecule to hybridize under said highly stringent wash conditions to said nucleic acid sequence when present in said genomic DNA; and (d) detecting any hybridized oligonucleotide molecules, wherein detection of said hybridized oligonucleotide molecules indicates the presence of said *S. enteria* in said samples.

14. The method as claimed in claim 13, wherein step (b) involves providing one pair of oligonucleotide molecules, and wherein at least one oligonucleotide molecule of said pair hybridizes to one of said nucleic acid sequence.

15. The method as claimed in claim 14, wherein said pair of oligonucleotide molecules is a pair of polymerase chain reaction primers.

16. The method as claimed in claim 13, wherein said at least one oligonucleotide molecule is selected from the group consisting of positions 12762–12779 of SEQ ID NO:4, positions 12993–13010 of SEQ ID NO:4, positions 13635–13652 of SEQ ID NO:4, positions 14059–14076 of SEQ ID NO:4, positions 14688–14705 of SEQ ID NO:4, positions 13150–13133 of SEQ ID 140:4, positions 13417–13400 of SEQ ID NO:4, positions 14051–14034 of SEQ ID NO:4, positions 14421–14404 of SEQ ID NO:4, and positions 15057–15040 of SEQ ID NO:4.

17. The method as claimed in any one of claims 1, 5, 9 or 13, wherein the method further comprises providing at least one further oligonucleotide molecule, said further oligonucleotide molecule hybridizes using highly stringent wash conditions to a sugar-pathway gene specific to the bacterial strain to be detected, wherein said sugar-pathway gene is selected from the group consisting of rmlB, rmlD, rmlA, rmlC, gtf, manC, manB, ddhD, ddhA, ddhB, ddhC and abe, and contacting said further oligonucleotide molecule with said sample to permit said further oligonucleotide molecule to hybridize under said highly stringent wash conditions to said sugar-pathway gene, and detecting any specifically hybridized oligonucleotide molecules.

18. The method according to any one of claims 1, 5, 9 or 13, wherein the hybridized oligonucleotide molecules are detected by Southern blot analysis.

19. The method as claimed in any one of claims 3, 7, 11 or 15, wherein the method is performed using a polymerase chain reaction.

20. The method as claimed in any one of claims 1, 5, 9 or 13, wherein said sample is a food derived sample.

21. The method as claimed in any one of claims 1, 5, 9 or 13, wherein said sample is a faecal derived sample.

22. The method as claimed in any one of claims 1, 5, 9 or 13, wherein said sample is derived from a patient.

* * * * *

SEQUENCE LISTING

<160> NUMBER OF SEQ ID NOS: 4

<210> SEQ ID NO 1
<211> LENGTH: 14516
<212> TYPE: DNA
<213> ORGANISM: Escherichia coli

<400> SEQUENCE: 1

| | | | | | |
|---|---|---|---|---|---|
| gatctgatgg | ccgtagggcg | ctacgtgctt | tctgctgata | tctgggctga | gttggaaaaa | 60 |
| actgctccag | gtgcctgggg | acgtattcaa | ctgactgatg | ctattgcaga | gttggctaaa | 120 |
| aaacagtctg | ttgatgccat | gctgatgacc | ggcgacagct | acgactgcgg | taagaagatg | 180 |
| ggctatatgc | aggcattcgt | taagtatggg | ctgcgcaacc | ttaaagaagg | ggcgaagttc | 240 |
| cgtaagagca | tcaagaagct | actgagtgag | tagagattta | cacgtctttg | tgacgataag | 300 |
| ccagaaaaaa | tagcggcagt | taacatccag | gcttctatgc | tttaagcaat | ggaatgttac | 360 |
| tgccgttttt | tatgaaaaat | gaccaataat | aacaagttaa | cctaccaagt | ttaatctgct | 420 |
| ttttgttgga | ttttttcttg | tttctggtcg | catttggtaa | gacaattagc | gtgagtttta | 480 |
| gagagttttg | cgggatctcg | cggaactgct | cacatctttg | gcatttagtt | agtgcactgg | 540 |
| tagctgttaa | gccaggggcg | gtagcttgcc | taattaattt | ttaacgtata | catttattct | 600 |
| tgccgcttat | agcaaataaa | gtcaatcgga | ttaaacttct | tttccattag | gtaaaagagt | 660 |
| gtttgtagtc | gctcagggaa | attggttttg | gtagtagtac | ttttcaaatt | atccattttc | 720 |
| cgatttagat | ggcagttgat | gttactatgc | tgcatacata | tcaatgtata | ttatttactt | 780 |
| ttagaatgtg | atatgaaaaa | aatagtgatc | ataggcaatg | tagcgtcaat | gatgttaagg | 840 |
| ttcaggaaag | aattaatcat | gaatttagtg | aggcaaggtg | ataatgtata | ttgtctagca | 900 |
| aatgattttt | ccactgaaga | tcttaaagta | ctttcgtcat | ggggcgttaa | gggggttaaa | 960 |
| ttctctctta | actcaaaggg | tattaatcct | tttaaggata | taattgctgt | ttatgaacta | 1020 |
| aaaaaaattc | ttaaggatat | ttccccagat | attgtatttt | catattttgt | aaagccagta | 1080 |
| atatttggaa | ctattgcttc | aaagttgtca | aaagtgccaa | ggattgttgg | aatgattgaa | 1140 |
| ggtctaggta | atgccttcac | ttattataag | ggaaagcaga | ccacaaaaac | taaaatgata | 1200 |
| aagtggatac | aaattctttt | atataagtta | gcattaccga | tgcttgatga | tttgattcta | 1260 |
| ttaaatcatg | atgataaaaa | agatttaatc | gatcagtata | atattaaagc | taaggtaaca | 1320 |
| gtgttaggtg | ggattggatt | ggatcttaat | gagttttcat | ataaagagcc | accgaaagag | 1380 |
| aaaattacct | ttatttttat | agcaaggtta | ttaagagaga | aaggatatt | tgagtttatt | 1440 |
| gaagccgcaa | agttcgttaa | gacaacttat | ccaagttctg | aatttgtaat | tttaggaggt | 1500 |
| tttgagagta | ataatccttt | ctcattacaa | aaaaatgaaa | ttgaatcgct | aagaaaagaa | 1560 |
| catgatctta | tttatcctgg | tcatgtggaa | atgttcaag | attggttaga | gaaaagttct | 1620 |
| gttttttgttt | tacctacatc | atatcgagaa | ggcgtaccaa | gggtgatcca | agaagctatg | 1680 |
| gctattggta | gacctgtaat | aacaactaat | gtacctgggt | gtagggatat | aataaatgat | 1740 |
| ggggtcaatg | gcttttttgat | acctccattt | gaattaatt | tactggcaga | aaaaatgaaa | 1800 |
| tattttattg | agaataaaga | taagtactc | gaaatgggc | ttgctggaag | gagtttgca | 1860 |
| gaaaaaaact | ttgatgcttt | tgaaaaaaat | aatagactag | catcaataat | aaaatcaaat | 1920 |
| aatgattttt | gacttgagca | gaaattattt | atatttcaat | ctgaaaaata | aaggctgtta | 1980 |
| ttatgaataa | agtggcatta | attactggta | tcactgggca | agatggctcc | tatttggcag | 2040 |

-continued

```
aattattgtt agaaaaaggt tatgaagttc atggtattaa acgccgtgca tcttcattta    2100
atactgagcg agtggatcac atctatcagg attcacattt agctaatcct aaacttttc     2160
tacactatgg cgatttgaca gatacttcca atctgacccg tattttaaaa gaagttcaac    2220
cagatgaagt ttacaatttg gggcgatga gccatgtagc ggtatcattt gagtcaccag     2280
aatacactgc tgatgttgat gcgataggaa cattgcgtct tcttgaagct atcaggatat    2340
tggggctgga aaaaagaca aaattttatc aggcttcaac ttcagagctt tatggtttgg    2400
ttcaagaaat tccacaaaaa gagactacgc cattttatcc acgttcgcct tatgctgttg    2460
caaaattata tgcctattgg atcactgtta attatcgtga gtcttatggt atgtttgcct    2520
gcaatggtat tctctttaac cacgaatcac ctcgccgtgg cgagaccttt gttactcgta    2580
aaataacacg cgggatagca aatattgctc aaggtcttga taaatgctta tacttgggaa    2640
atatggattc tctgcgtgat tgggacatg ctaaggatta tgtcaaaatg caatggatga    2700
tgctgcagca agaaactcca aagattttg taattgctac aggaattcaa tattctgtcc    2760
gtgagtttgt cacaatggcg gcagagcaag taggcataga gttagcattt gaaggtgagg    2820
gagtaaatga aaaggtgtt gttgtttcgg tcaatggcac tgatgctaaa gctgtaaacc    2880
cgggcgatgt aattatatct gtagatccaa ggtattttag gcctgcagaa gttgaaacct    2940
tgcttggcga tcctactaat gcgcataaaa aattaggatg gagccctgaa attacattgc    3000
gtgaaatggt aaagaaatg gtttccagcg atttagcaat agcgaaaaag aacgtcttgc     3060
tgaaagctaa taacattgcc actaatattc cgcaagaata aaaagataa tacattaaat    3120
aattaaaaat ggtgctagat ttattagtac cattattttt ttttgggtga ctaatgttta    3180
ttacatcaga taaatttaga gaattatca agttagttcc attagtatca attgatctgc     3240
taattgaaaa cgagaatggt gaatatttat ttggtcttag gaataatcga ccggccaaaa    3300
attatttttt tgttccaggt ggtaggattc gcaaaaatga atctattaaa aatgctttta    3360
aaagaatatc atctatggaa ttaggtaaag agtatggtat ttcaggaagt gttttttaatg   3420
gtgtatggga acatttctat gatgatggtt ttttttctga aggcgaggca acacattata    3480
tagtgctttg ttacacactg aaagttctta aaagtgaatt gaatctccca gatgatcaac    3540
atcgtgaata ccttttggcta actaaacacc aaataaatgc taaacaagat gttcataact    3600
attcaaaaaa ttattttttg taatttttat taaaaattaa tatgcgagag aattgtatgt    3660
ctcaatgtct ttaccctgta attattgccg gaggaaccgg aagccgtcta tggccgttgt    3720
ctcgagtatt ataccctaaa caatttttaa atttagttgg ggattctaca atgttgcaaa    3780
caacaattac gcgtttggat ggcatcgaat gcgaaaatcc aattgttatc tgcaatgaag    3840
atcaccgatt tattgtagca gagcaattac gacagattgg taagctaacc aagaatatta    3900
tacttgagcc gaaaggccgt aatactgcac ctgccatagc tttagctgct tttatcgctc    3960
agaagaataa tcctaatgac gaccctttat tattagtact tgcggcagac cactctataa    4020
ataatgaaaa agcatttcga gagtcaataa taaaagctat gccgtatgca acttctggga    4080
agttagtaac atttggaatt attccggaca cggcaaatac tggttatgga tatattaaga    4140
gaagttcttc agctgatcct aataaagaat tcccagcata taatgttgcg agtttgtag    4200
aaaaaccaga tgttaaaaca gcacaggaat atatttcgag tgggaattat tactggaata    4260
gcggaatgtt tttatttcgc gccagtaaat atcttgatga actacggaaa tttagaccag    4320
atatttatca tagctgtgaa tgtgcaaccg ctacagcaaa tatagatatg gactttgtcc    4380
```

-continued

```
gaattaacga ggctgagttt attaattgtc ctgaagagtc tatcgattat gctgtgatgg    4440
aaaaaacaaa agacgctgta gttcttccga tagatattgg ctggaatgac gtgggttctt    4500
ggtcatcact ttgggatata agccaaaagg attgccatgg taatgtgtgc catggggatg    4560
tgctcaatca tgatggagaa aatagttta tttactctga gtcaagtctg gttgcgacag    4620
tcggagtaag taatttagta attgtccaaa ccaaggatgc tgtactggtt gcggaccgtg    4680
ataaagtcca aaatgttaaa aacatagttg acgatctaaa aaagagaaaa cgtgctgaat    4740
actacatgca tcgtgcagtt tttcgcccctt ggggtaaatt cgatgcaata gaccaaggcg    4800
atagatatag agtaaaaaaa ataatagtta aaccaggaga agggttagat ttaaggatgc    4860
atcatcatag ggcagagcat tggattgttg tatccggtac tgctaaagtt tcactaggta    4920
gtgaagttaa actattagtt tctaatgagt ctatatatat ccctcaggga gcaaaatata    4980
gtcttgagaa tccaggcgta ataccttttgc atctaattga agtaagttct ggtgattacc    5040
ttgaatcaga tgatatagtg cgttttactg acagatataa cagtaaacaa ttcctaaagc    5100
gagattgata aatatgaata aaataacttg cttcaaagca tatgatatac gtgggcgtct    5160
tggtgctgaa ttgaatgatg aaatagcata tagaattggt cgcgcttatg gtgagttttt    5220
taaacctcaa actgtagttg tgggaggaga tgctcgctta acaagtgaga gtttaaagaa    5280
atcactctca aatgggctat gtgatgcagg cgtaaatgtc ttagatcttg gaatgtgtgg    5340
tactgaagag atatattttt ccacttggta tttaggaatt gatggtggaa tcgaggtaac    5400
tgcaagccat aatccaattg attataatgg aatgaaatta gtaaccaaag gtgctcgacc    5460
aatcagcagt gacacaggtc tcaaagatat acaacaatta gtagagagta ataattttga    5520
agagctcaac ctagaaaaaa aagggaatat taccaaaatat tccacccgag atgcctacat    5580
aaatcatttg atgggctatg ctaatctgca aaaataaaa aaaatcaaaa tagttgtgaa    5640
ttctgggaat ggtgcagctg gtcctgttat tgatgctatt gaggaatgct ttttacggaa    5700
caatattccg attcagtttg taaaaataaa taatacaccc gatggtaatt ttccacatgg    5760
tatccctaat ccattactac ctgagtgcag agaagatacc agcagtgcgg ttataagaca    5820
tagtgctgat tttggtattg catttgatgg tgattttgat aggtgttttt tctttgatga    5880
aaatggacaa tttattgaag gatactacat tgttggttta ttagcggaag ttttttttagg    5940 gaaatatcca aacgcaaaaa tcattcatga tcctcgcctt atatggaata ctattgatat    6000
cgtagaaagt catggtggta tacctataat gactaaaacc ggtcatgctt acattaagca    6060
aagaatgcgt gaagaggatg ccgtatatgg cggcgaaatg agtgcgcatc attatttttaa    6120 agattttgca tactgcgata gtggaatgat tccttggatt ttaatttgtg aacttttgag    6180
tctgacaaat aaaaaattag gtgaactggt ttgtggttgt ataaacgact ggccggcaag    6240
tggagaaata aactgtacac tagacaatcc gcaaaatgaa atagataaat tatttaatcg    6300
ttacaaagat agtgccttag ctgttgatta cactgatgga ttaactatgg agttctctga    6360
ttggcgtttt aatgttagat gctcaaatac agaacctgta gtacgattga atgtagaatc    6420
taggaataat gctattctta tgcaggaaaa aacagaagaa attctgaatt ttatatcaaa    6480
ataaatttgc acctgagttc ataatgggaa caagaaatat atgaaagtac ttctgactgg    6540
ctcaactggc atggttggta agaatatatt agagcatgat agtgcaagta aatataatat    6600
acttactcca accagctctg atttgaattt attagataaa aatgaaatag aaaaattcat    6660
gcttatcaac atgccagact gtattataca tgcagcggga ttagtggag gcattcatgc    6720 aaatataagc aggccgtttg attttctgga aaaaaatttg cagatggtt taaatttagt    6780
```

```
ttccgtcgca aaaaaactag gtatcaagaa agtgcttaac ttgggtagtt catgcatgta    6840
cccaaaaac tttgaagagg ctattcctga gaaagctctg ttaactggtg agctagaaga    6900
aactaatgag ggatatgcta ttgcgaaaat tgctgtagca aaagcatgcg aatatatatc   6960
aagagaaaac tctaattatt tttataaaac aattatccca tgtaatttat atgggaaata   7020
tgataaattt gatgataact cgtcacatat gattccggca gttataaaaa aaatccatca   7080
tgcgaaaatt aataatgtcc cagagatcga aatttggggg gatggtaatt cgcgccgtga   7140
gtttatgtat gcagaagatt tagctgatct tattttttat gttattccta aaatagaatt   7200
catgcctaat atggtaaatg ctggtttagg ttacgattat tcaattaatg actattataa   7260
gataattgca gaagaaattg gttatactgg gagttttttct catgatttaa caaaaccaac   7320
aggaatgaaa cggaagctag tagatatttc attgcttaat aaaattggtt ggtcaagtca   7380
ctttgaactc agagatggca tcagaaagac ctataattat tacttggaga atcaaaataa   7440
atgattacat acccacttgc tagtaatact tgggatgaat atgagtatgc agcaatacag   7500
tcagtaattg actcaaaaat gtttaccatg ggtaaaaagg ttgagttata tgagaaaaat   7560
tttgctgatt tgtttggtag caaatatgcc gtaatggtta gctctggttc tacagctaat   7620
ctgttaatga ttgctgccct tttcttcact aataaaccaa aacttaaaag aggtgatgaa   7680
ataatagtac ctgcagtgtc atggtctacg acatattacc ctctgcaaca gtatggctta   7740
aaggtgaagt ttgtcgatat caataaagaa actttaaata ttgatatcga tagtttgaaa   7800
aatgctattt cagataaaac aaaagcaata ttgacagtaa attttattagg taatcctaat   7860
gattttgcaa aaataaatga gataataaat aatagggata ttatcttact agaagataac   7920
tgtgagtcga tgggcgcggt ctttcaaaat aagcaggcag gcacattcgg agttatgggt   7980
accttagtt cttttactc tcatcatata gctacaatgg aagggggctg cgtagttact    8040
gatgatgaag agctgtatca tgtattgttg tgccttcgag ctcatggttg gacaagaaat   8100
ttaccaaaag agaatatggt tacaggcact aagagtgatg atattttcga gagtcgtttt   8160
aagtttgttt taccaggata caatgttcgc ccacttgaaa tgagtggtgc tattgggata   8220
gagcaactta aaaagttacc aggttttata tccaccagac gttccaatgc acaatatttt   8280
gtagataaat ttaaagatca tccattcctt gatatacaaa aagaagttgg tgaaagtagc   8340
tggtttggtt tttccttcgt tataaaggag ggagctgcta ttgagaggaa gagtttagta   8400
aataatctga tctcagcagg cattgaatgc cgaccaattg ttactgggaa ttttctcaaa   8460
aatgaacgtg ttttgagtta ttttgattac tctgtacatg atacggtagc aaatgccgaa   8520
tatatagata gaatggtttt ttttgtcgga aaccaccaga tacctttgtt taatgaaata   8580
gattatctac gaaaagtatt aaaataacta acgaggcact ctatttcgaa tagagtgcct   8640
ttaagatggt attaacagtg aaaaaaattt tagcgtttgg ctattctaaa gtactaccac   8700
cggttattga acagtttgtc aatccaattt gcatcttcat tatcacacca ctaatactca   8760
accacctggg taagcaaagc tatggtaatt ggattttatt aattactatt gtatcttttt   8820
ctcagttaat atgtggagga tgttccgcat ggattgcaaa atcattgca gaacagagaa    8880
ttcttagtga tttatcaaaa aaaaatgctt tacgtcaaat ttcctataat ttttcaattg   8940
ttattatcgc atttgcggta ttgatttctt ttcttatatt aagtatttgt ttcttcgatg   9000
ttgcgaggaa taattcttca ttcttattcg cgattattat ttgtggtttt tttcaggaag   9060
ttgataattt atttagtggt gcgctaaaag gttttgaaaa atttaatgta tcatgttttt   9120
```

```
ttgaagtaat tacaagagtg ctctgggctt ctatagtaat atatggcatt tacggaaatg   9180
cactcttata ttttacatgt ttagccttta ccattaaagg tatgctaaaa tatattcttg   9240
tatgtctgaa tattaccggt tgtttcatca atcctaattt taatagagtt gggattgtta   9300
atttgttaaa tgagtcaaaa tggatgtttc ttcaattaac tggtggcgtc tcacttagtt   9360
tgtttgatag gctcgtaata ccattgattt tatctgtcag taaactggct tcttatgtcc   9420
cttgccttca actagctcaa ttgatgttca ctctttctgc gtctgcaaat caaatattac   9480
taccaatgtt tgctagaatg aaagcatcta acacatttcc ctctaattgt ttttttaaaa   9540
ttctgcttgt atcactaatt tctgttttgc cttgtcttgc gttattcttt tttggtcgtg   9600
atatattatc aatatggata aaccctacat tgcaactga aaattataaa ttaatgcaaa    9660
ttttagctat aagttacatt ttattgtcaa tgatgacatc ttttcatttc ttgttattag   9720
gaattggtaa atctaagctt gttgcaaatt taaatctggt tgcagggctc gcacttgctg   9780
cttcaacgtt aatcgcagct cattatggcc tttatgcaat atctatggta aaataatat    9840 atccggcttt tcaattttat tacctttatg tagcttttgt ctatttttaat agagcgaaaa  9900 atgtctattg atttactttt ttcaattact gaaatcgcaa ttgttttttc ttgcactatt   9960
tacatattta ctcaatgttt gttaatgcgg aggatctatt tagataaaag tattttaatt  10020
cttttatgct tgctcttttt tttagtaatc attcaacttc ctgagcttaa tgtaaacggt  10080
ttggtcgatt ctttaaagtt atcactgcct ttattgatgg tctttatcgc ttttcaaaaa  10140
ccgaaattat gcttgtgggt tattattgca ttgttgtttt tgaactctgc atttaattt   10200 ttatatttaa agacattcga taagtttagc tcatttcctt ttactttttt tatattgctg  10260
ttttacttgt ttagattggg aattggtaat ttaccggttt ataaaaataa aaattttac   10320 gcgttgattt ttctctttat attaatagac ataatgcagt cattgttaat aaattatagg  10380
gggcagattt tatattccgt aatttgcatc ctgatacttg tgtttaaagt taatttaaga  10440
aaaaagattc catactttttt tttaatgctg ccagttttat atgtaattat tatggcttat  10500
attggtttta attatttcaa taaggcgta acttttttg aacctacagc aagtaatatt   10560
gaacgtacgg ggatgatata ttatttggtt tcacagcttg gtgattatat attccatggt  10620
atggggacat taaatttctt aaataacggc ggacaatata agacgttata tggacttcca  10680
tcattaattc ctaatgaccc tcatgatttt ttattacggt tctttataag tattggtgtg  10740
ataggagcat tggtttatca ttctatattt tttgtttttt ttaggagaat atctttctta  10800
ttatatgaga gaaatgctcc tttcattgtt gtaagttgtt tgttactgtt acaagttgtg  10860
ttaatttata cattaaaccc ttttgatgct tttaatcgat tgatttgcgg gcttacagtt  10920
ggagttgttt atggatttgc aaaaattaga taagtatacc tgtaatggaa atttagacgc  10980
tccacttgtt tcaataatca ttgcaactta taattctgaa cttgatatag ctaagtgttt  11040
gcaatcggta actaatcaat cttataagaa tattgaaatc ataataatgg atggaggatc  11100
ttctgataaa acgcttgata ttgcaaaatc gtttaaagac gaccgaataa aaatagtttc  11160
agagaaagat cgtggaattt atgatgcctg gaataaagca gttgatttat ccattggtga  11220
ttgggtagca tttattggtt cagatgatgt ttactatcat acagatgcaa ttgcttcatt  11280
gatgaagggg gttatggtat ctaatggcgc ccctgtggtt tatgggagga cagcgcacga  11340
aggtcccgat aggaacatat ctggattttc aggcagtgaa tggtacaacc taacaggatt  11400
taagtttaat tattacaaat gtaatttacc attgcccatt atgagcgcaa tatattctcg  11460
tgatttcttc agaaacgaac gttttgatat taaattaaaa attgttgctg acgctgattg  11520
```

-continued

```
gtttctgaga tgtttcatca aatggagtaa agagaagtca ccttatttta ttaatgacac   11580 gaccccctatt gttagaatgg gatatggtgg ggtttcgact gatatttctt ctcaagttaa   11640
aactacgcta gaaagtttca ttgtacgcaa aaagaataat atatcctgtt taaacataca   11700
gctgattctt agatatgcta aaattctggt gatggtagcg atcaaaaata tttttggcaa   11760
taatgtttat aaattaatgc ataacgggta tcattcccta aagaaaatca agaataaaat   11820
atgaagattg tttatataat aaccgggctt acttgtggtg gagccgaaca ccttatgacg   11880
cagttagcag accaaatgtt tatacgcggg catgatgtta atattatttg tctaactggt   11940
atatctgagg taaagccaac acaaaatatt aatattcatt atgttaatat ggataaaaat   12000
tttagaagct ttttagagc tttatttcaa gtaaaaaaaa taattgtcgc cttaaagcca   12060
gatataatac atagtcatat gtttcatgct aatattttta gtcgttttat taggatgctg   12120
attccagcgg tgcccctgat atgtaccgca cacaacaaaa atgaaggtgg caatgcaagg   12180
atgttttgtt atcgactgag tgatttttta gcttctatta ctacaaatgt aagtaaagag   12240
gctgttcaag agtttatagc aagaaaggct acacctaaaa ataaaatagt agagattccg   12300
aattttatta atacaaataa atttgatttt gatattaatg tcagaaagaa aacgcgagat   12360
gcttttaatt tgaaagacag tacagcagta ctgctcgcag taggaagact tgttgaagca   12420
aaagactatc cgaacttatt aaatgcaata aatcatttga ttctttcaaa aacatcaaat   12480
tgtaatgatt ttatttttgct tattgctggc gatggcgcat taagaaataa attattggat   12540
ttggtttgtc aattgaatct tgtggataaa gttttcttct tggggcaaag aagtgatatt   12600
aaagaattaa tgtgtgctgc agatcttttt gttttgagtt ctgagtggga aggttttggt   12660
ctcgttgttg cagaagctat ggcgtgtgaa cgtcccgttg ttgctaccga ttctggtgga   12720
gttaaagaag tcgttggacc tcataatgat gttatccctg tcagtaatca tattctgttg   12780
gcagagaaaa tcgctgagac acttaaaata gatgataacg caagaaaaat aataggtatg   12840
aaaaatagag aatatattgt ttccaatttt tcaattaaaa cgatagtgag tgagtgggag   12900
cgcttatatt ttaaatattc caagcgtaat aatataattg attgaaaata taagtttgta   12960
ctctggatgc aatagtttct ctatgctgtt tttttactgg ctccgtattt ttacttatag   13020
ctggattttg ttatatatca gtattaatct gtctcaactt catctagact acattcaagc   13080
cgcgcatgcg tcgcgcggtg actacacctg acaggagtat gtaatgtcca agcaacagat   13140
cggcgtcgtc ggtatggcag tgatggggcg caacctggcg ctcaacatcg aaagccgcgg   13200
ttataccgtc tccatcttca accgctcccg cgagaaaact gaagaagttg ttgccgagaa   13260
cccggataag aaactggttc cttattacac ggtgaaagag ttcgtcgagt ctcttgaaac   13320
cccacgtcgt atcctgttaa tggtaaaagc agggggcggga actgatgctg ctatcgattc   13380
cctgaagccg tatctggata aaggcgacat cattattgat ggtggcaaca ccttcttcca   13440
ggacactatc cgtcgtaacc gtgaactgtc cgcggaaggc tttaacttca tcggtaccgg   13500
cgtgtccggc ggtgaagagg gcgccctgaa aggcccatct atcatgccag gtggccagaa   13560
agaagcgtat gagctggttg cgcctatcct gaccaagatt gctgcggttg ctgaagatgg   13620
cgaaccatgt ataacttaca tcggtgctga cggtgcgggt cactacgtga agatggtgca   13680
caacggtatc gaatatggcg atatgcagct gattgctgaa gcctattctc tgcttaaagg   13740
cggccttaat ctgtctaacg aagagctggc aaccactttt accgagtgga atgaaggcga   13800
gctaagtagc tacctgattg acatcaccaa agacatcttc accaaaaaag atgaagaggg   13860
```

```
taaatacctg gttgatgtga tcctggacga agctgcgaac aaaggcaccg gtaaatggac   13920
cagccagagc tctctggatc tgggtgaacc gctgtcgctg atcaccgaat ccgtattcgc   13980
tcgctacatc tcttctctga agaccagcg cattgcggca tctaaagtgc tgtctggtcc   14040
gcaggctaaa ctggctggtg ataaagcaga gttcgttgag aaagtccgtc gcgcgctgta   14100
cctgggtaaa atcgtctctt atgcccaagg cttctctcaa ctgcgtgccg cgtctgacga   14160
atacaactgg gatctgaact acggcgaaat cgcgaagatc ttccgcgcgg gctgcatcat   14220
tcgtgcgcag ttcctgcaga aaattactga cgcgtatgct gaaaacaaag gcattgctaa   14280
cctgttgctg gctccgtact tcaaaaatat cgctgatgaa tatcagcaag cgctgcgtga   14340
tgtagtggct tatgctgtgc agaacggtat tccggtaccg accttctctg cagcggtagc   14400
ctactacgac agctaccgtt ctgcggtact gccggctaat ctgattcagg cacagcgtga   14460
ttacttcggt gcgcacacgt ataaacgcac tgataaagaa ggtgtgttcc acaccg       14516

<210> SEQ ID NO 2
<211> LENGTH: 14024
<212> TYPE: DNA
<213> ORGANISM: Escherichia coli

<400> SEQUENCE: 2
gtaaccaagg gcggtacgtg cataaatttt aatgcttatc aaaactatta gcattaaaaa     60
tatataagaa attctcaaat gaacaaagaa accgtttcaa taattatgcc cgtttacaat    120
ggggccaaaa ctataatctc atcagtagaa tcaattatac atcaatctta tcaagatttt    180
gttttgtata tcattgacga ttgtagcacc gatgatacat tttcattaat caacagtcga    240
tacaaaaaca atcagaaaat aagaatattg cgtaacaaga caaatttagg tgttgcagaa    300
agtcgaaatt atggaataga aatggccacg gggaaatata tttcttttg tgatgcggat    360 gatttgtggc acgagaaaaa attagagcgt caaatcgaag tgttaaataa tgaatgtgta    420
gatgtggtat gttctaatta ttatgttata gataacaata gaaatattgt tggcgaagtt    480
aatgctcctc atgtgataaa ttatagaaaa atgctcatga aaactacat agggaatttg     540 acaggaatct ataatgccaa caattgggt aagttttatc aaaaaaagat tggtcacgag    600
gattatttga tgtggctgga ataattaat aaaacaaatg gtgctatttg tattcaagat    660
aatctggcgt attacatgcg ttcaaataat tcactatcgg gtaataaaat taaagctgca    720
aaatggacat ggagtatata tagagaacat ttacatttgt cctttccaaa aacattatat    780
tattttttat tatatgcttc aaatggagtc atgaaaaaaa taacacattc actattaagg    840
agaaaggaga ctaaaagtg aagtcagcgg ctaagttgat tttttattc ctatttacac      900 tttatagtct ccagttgtat ggggttatca tagatgatcg tataacaaat tttgatacaa    960
aggtattaac tagtattata attatatttc agattttttt tgttttatta ttttatctaa   1020
cgattataaa tgaaagaaaa cagcagaaaa atttatcgt gaactgggag ctaaagttaa    1080
tactcgtttt ccttttgtg actatagaaa ttgctgctgt agttttattt cttaaagaag    1140
gtattcctat atttgatgat gatccagggg gggctaaact tagaatagct gaaggtaatg   1200
gactttacat tagatatatt aagtattttg gtaatatagt tgtgtttgca ttaattattc   1260
tttatgatga gcataaattc aaacagagga ccatcatatt tgtatatttt acaacgattg   1320
ctttatttgg ttatcgttct gaattggtgt tgctcattct tcaatatata ttgattacca   1380
atatcctgtc aaaggataac cgtaatccta aataaaaag aataataggg tatttttat     1440 tggtagggt tgtatgctcg ttgttttatc taagtttagg acaagacgga gaacaaaatg    1500
```

-continued

```
actcatataa taatatgtta aggataatta ataggttaac aatagagcaa gttgaaggtg    1560
ttccatatgt tgtttctgaa tctattaaga acgatttctt tccgacacca gagttagaaa    1620
aggaattaaa agcaataata aatagaatac agggaataaa gcatcaagac ttattttatg    1680
gagaacggtt acataaacaa gtatttggag acatgggagc aaatttttta tcagttacta    1740
cgtatggagc agaactgtta gttttttttg gttttctctg tgtattcatt atccctttag    1800
ggatatatat acctttttat cttttaaaga gaatgaaaaa aacccatagc tcgataaatt    1860
gcgcattcta ttcatatatc attatgattt tattgcaata cttagtggct gggaatgcat    1920
cggccttctt ttttggtcct tttctctccg tattgataat gtgtactcct ctgatcttat    1980
tgcatgatac gttaaagaga ttatcacgaa atgaaaatat cagttataac tgtgacttat    2040
aataatgctg aagggttaga aaaaacttta agtagtttat caattttaaa aataaaacct    2100
tttgagatta ttatagttga tggcggctct acagatggaa cgaatcgtgt cattagtaga    2160
tttactagta tgaatattac acatgtttat gaaaaagatg aagggatata tgatgcgatg    2220
aataagggcc gaatgttggc caaaggcgac ttaatacatt atttaaacgc cggcgatagc    2280
gtaattggag atatatataa aaatatcaaa gagccatgtt tgattaaagt tggccttttc    2340
gaaaatgata aacttctggg attttcttct ataacccatt caaatacagg gtattgtcat    2400 caagggtga ttttcccaaa gaatcattca gaatatgatc taaggtataa aatatgtgct    2460
gattataagc ttattcaaga ggtgtttcct gaagggttaa gatctctatc tttgattact    2520
tcgggttatg taaatatga tatggggga gtatcttcaa aaaaagaat tttaagagat    2580 aaagagcttg ccaaaattat gtttgaaaaa aataaaaaaa accttattaa gtttattcca    2640
atttcaataa tcaaaatttt attccctgaa cgtttaagaa gagtattgcg gaaaatgcaa    2700
tatatttgtc taactttatt cttcatgaag aatagttcac catatgataa tgaataaaat    2760
caaaaaaata cttaaatttt gcactttaaa aaaatatgat acatcaagtg ctttaggtag    2820
agaacaggaa aggtacagga ttatatcctt gtctgttatt tcaagtttga ttagtaaaat    2880
actctcacta ctttctctta tattaactgt aagtttaact ttaccttatt taggacaaga    2940
gagatttggt gtatggatga ctattaccag tcttggtgct gctctgacat ttttggactt    3000
aggtatagga aatgcattaa caaacaggat cgcacattca tttgcgtgtg caaaaatt    3060 aaagatgagt cggcaaatta gtggtgggct cactttgctg gctggattat cgtttgtcat    3120
aactgcaata tgctatatta cttctggcat gattgattgg caactagtaa taaaaggtat    3180
aaacgagaat gtgtatgcag agttacaaca ctcaattaaa gtctttgtaa tcatatttgg    3240
acttggaatt tattcaaatg gtgtgcaaaa agtttatatg ggaatacaaa aagcctatat    3300
aagtaatatt gttaatgcca tatttatatt gttatctatt attactctag taatatcgtc    3360
gaaactacat gcgggactac cagtttttaat tgtcagcact cttggtattc aatacatatc    3420
gggaatctat ttaacaatta atcttattat aaagcgatta ataaagttta caaaagttaa    3480
catacatgct aaaagagaag ctccatattt gatattaaac ggtttttttct tttttatttt    3540 acagttaggc actctggcaa catggagtgg tgataacttt ataatatcta acatttggg    3600 tgttacttat gttgctgttt ttagcattac acagagatta tttcaaatat ctacggtccc    3660
tcttacgatt tataacatcc cgttatgggc tgcttatgca gatgctcatg cacgcaatga    3720
tactcaattt ataaaaaaga cgctcagaac atcattgaaa atagtgggta tttcatcatt    3780
cttattggcc ttcatattag tagtgttcgg tagtgaagtc gttaatattt ggacagaagg    3840
```

```
aaagattcag gtacctcgaa cattcataat agcttatgct ttatggtctg ttattgatgc    3900 ttttttcgaat acatttgcaa gcttttaaa tggtttgaac atagttaaac aacaaatgct    3960
tgctgttgta acattgatat tgatcgcaat tccagcaaaa tacatcatag ttagccattt    4020
tgggttaact gttatgttgt actgcttcat ttttatatat attgtaaatt actttatatg    4080
gtataaatgt agttttaaaa acatatcga tagacagtta aatataagag gatgaaaatg    4140
aaatatatac cagtttacca accgtcattg acaggaaaag aaaaagaata tgtaaatgaa    4200
tgtctggact caacgtggat ttcatcaaaa ggaaactata ttcagaagtt tgaaaataaa    4260
tttgcggaac aaaccatgt gcaatatgca actactgtaa gtaatggaac ggttgctctt    4320
catttagctt tgttagcgtt aggtatatcg gaaggagatg aagttattgt tccaacactg    4380
acatatatag catcagttaa tgctataaaa tacacaggag ccacccccat tttcgttgat    4440
tcagataatg aaacttggca aatgtctgtt agtgacatag aacaaaaaat cactaataaa    4500
actaaagcta ttatgtgtgt ccatttatac ggacatccat gtgatatgga acaaattgta    4560
gaactggcca aaagtagaaa tttgtttgta attgaagatt gcgctgaagc ctttggttct    4620
aaatataaag gtaaatatgt gggaacattt ggagatattt ctacttttag cttttttgga    4680
aataaaacta ttactacagg tgaaggtgga atggttgtca cgaatgacaa aacactttat    4740
gaccgttgtt tacattttaa aggccaagga ttagctgtac ataggcaata ttggcatgac    4800
gttataggct acaattatag gatgacaaat atctgcgctg ctataggatt agcccagtta    4860
gaacaagcta atgattttat atcacgaaaa cgtgaaattg ctgatattta taaaaaaaat    4920
atcaacagtc ttgtacaagt ccacaaggaa agtaaagatg ttttttcacac ttattggatg    4980 gtctcaattc taactaggac cgcagaggaa agagaggaat taaggaatca ccttgcagat    5040
aaactcatcg aaacaaggcc agttttttac cctgtccaca cgatgccaat gtactcggaa    5100
aaatatcaaa agcaccctat agctgaggat cttggttggc gtggaattaa tttacctagt    5160
ttccccagcc tatcgaatga gcaagttatt tatatttgtg aatctattaa cgaatttat    5220 agtgataaat agcctaaaat attgtaaagg tcattcatga aaattgcgtt gaattcagat    5280
ggattttacg agtggggcgg tggaattgat tttattaaat atattctgtc aatattagaa    5340
acgaaaccag aaatatgtat cgatattctt ttaccgagaa atgatataca ttctcttata    5400
agagaaaaag catttccttt taaagtata ttaaaagcaa ttttaaagag ggaaaggcct    5460
cgatggattt cattaaatag atttaatgag caatactata gagatgcctt tacacaaaat    5520
aatatagaga cgaatcttac ctttattaaa agtaagagct ctgcctttta ttcatatttt    5580
gatagtagcg attgtgatgt tattcttcct tgcatgcgtg ttccttcggg aaatttgaat    5640
aaaaaagcat ggattggtta tatttatgac tttcaacact gttactatcc ttcatttttt    5700
agtaagcgag aaatagatca aaggaatgtg ttttttaaat tgatgctcaa ttgcgctaac    5760
aatattattg ttaatgcaca ttcagttatt accgatgcaa ataaatatgt tgggaattat    5820
tctgcaaaac tacattctct tccatttagt ccatgccctc aattaaaatg gttcgctgat    5880
tactctggta atattgccaa atataatatt gacaaggatt attttataat ttgcaatcaa    5940
ttttggaaac ataaagatca tgcaactgct tttagggcat ttaaaattta tactgaatat    6000
aatcctgatg tttatttagt atgcacggga gctactcaag attatcgatt ccctggatat    6060
tttaatgaat tgatggtttt ggcaaaaaag ctcggaattg aatcgaaaat taagatatta    6120 ggcatatac ctaaacttga acaaattgaa ttaatcaaaa attgcattgc tgtaatacaa    6180
ccaaccttat ttgaaggcgg gcctggaggg ggggtaacat ttgacgctat tgcattaggg    6240
```

-continued

```
aaaaaagtta tactatctga catagatgtc aataaagaag ttaattgcgg tgatgtatat    6300
ttctttcagg caaaaaacca ttattcatta aatgacgcga tggtaaaagc tgatgaatct    6360
aaaatttttt atgaacctac aactctgata gaattgggtc tcaaaagacg caatgcgtgt    6420
gcagattttc ttttagatgt tgtgaaacaa gaaattgaat cccgatctta atatattcaa    6480
gaggtatata atgactaaag tcgctcttat tacaggtgta actggacaag atggatctta    6540
tctagctgag ttttttgctt gataaagggta tgaagttcat ggtatcaaac gccgagcctc    6600
atcttttaat acagaacgca tagaccatat ttatcaagat ccacatggtt ctaacccaaa    6660
ttttcacttg cactatggag atctgactga ttcatctaac ctcactagaa ttctaaagga    6720
ggtacagcca gatgaagtat ataatttagc tgctatgagt cacgtagcag tttcttttga    6780
gtctccagaa tatacagccg atgtcgatgc aattggtaca ttacgtttac tggaagcaat    6840
tcgcttttta ggattggaaa acaaaacgcg tttctatcaa gcttcaacct cagaattata    6900
tggacttgtt caggaaatcc ctcaaaaaga atccacccct ttttatcctc gttcccctta    6960
tgcagttgca aaactttacg catattggat cacggtaaat tatcgagagt catatggtat    7020
ttatgcatgt aatggtatat tgttcaatca tgaatctcca cgccgtggag aaacgtttgt    7080
aacaaggaaa attactcgag gacttgcaaa tattgcacaa ggcttggaat catgtttgta    7140
tttagggaat atggattcgt tacgagattg gggacatgca aaagattatg ttagaatgca    7200
atggttgatg ttacaacagg agcaacccga agattttgtg attgcaacag gagtccaata    7260
ctcagtccgt cagtttgtcg aaatggcagc agcacaactt ggtattaaga tgagcttgt    7320 tggtaaagga atcgaagaaa aaggcattgt agattcggtt gaaggacagg atgctccagg    7380
tgtgaaacca ggtgatgtca ttgttgctgt tgatcctcgt tatttccgac cagctgaagt    7440
tgatactttg cttggagatc cgagcaaagc taatctcaaa cttggttgga gaccagaaat    7500
tactcttgct gaaatgattt ctgaaatggt tgccaaagat cttgaagccg ctaaaaaaca    7560 ttctcttttta aaatcgcatg gttttttctgt aagcttagct ctggaatgat gatgaataag    7620
caacgtattt ttattgctgg tcaccaagga atggttggat cagctattac ccgacgcctc    7680
aaacaacgtg atgatgttga gttggttta cgtactcggg atgaattgaa cttgttggat    7740
agtagcgctg ttttggatt ttttttcttca cagaaaatcg accaggttta tttggcagca    7800
gcaaaagtcg gaggtatttt agctaacagt tcttatcctg ccgatttat atatgagaat    7860 ataatgatag aggcgaatgt cattcatgct gcccacaaaa ataatgtaaa taaactgctt    7920
ttcctcggtt cgtcgtgtat ttatcctaag ttagcacacc aaccgattat ggaagacgaa    7980
ttattacaag ggaacttga gccaacaaat gaacttatg ctatcgcaaa aattgcaggt    8040
attaaattat gtgaatctta taccgtcag tttgggcgtg attaccgttc agtaatgcca    8100
accaatcttt atggtccaaa tgacaatttt catccaagta attctcatgt gattccggcg    8160
cttttgcgcc gctttcatga tgctgtggaa acaattctc cgaatgttgt tgtttgggga    8220
agtggtactc caaagcgtga attcttacat gtagatgata tggcttctgc aagcattat    8280 gtcatggaga tgccatacga tatatggcaa aaaaatacta agtaatgtt gtctcatatc    8340 aatattggaa caggtattga ctgcacgatt tgtgagcttg cggaaacaat agcaaaagtt    8400
gtaggttata aagggcatat tacgttcgat acaacaaagc ccgatggagc ccctcgaaaa    8460
ctacttgatg taacgcttct tcatcaacta ggttggaatc ataaaattac ccttcacaag    8520
ggtcttgaaa atacatacaa ctggtttctt gaaaaccaac ttcaatatcg ggggtaataa    8580
```

```
tgttttttaca ttcccaagac tttgccacaa ttgtaaggtc tactcctctt atttctatag    8640
atttgattgt ggaaaacgag tttggcgaaa ttttgctagg aaaacgaatc aaccgcccgg    8700
cacagggcta ttggttcgtt cctggtggta gggtgttgaa agatgaaaaa ttgcagacag    8760
cctttgaacg attgacagaa attgaactag gaattcgttt gcctctctct gtgggtaagt    8820
tttatggtat ctggcagcac ttctacgaag acaatagtat gggggggagac ttttcaacgc    8880 attatatagt tatagcattc cttcttaaat tacaaccaaa cattttgaaa ttaccgaagt    8940
cacaacataa tgcttattgc tggctatcgc gagcaaagct gataaatgat gacgatgtgc    9000
attataattg tcgcgcatat tttaacaata aaacaaatga tgcgattggc ttagataata    9060
aggatataat atgtctgatg cgccaataat tgctgtagtt atggccggtg gtacaggcag    9120
tcgtctttgg ccactttctc gtgaactata tccaaagcag tttttacaac tctctggtga    9180
taacaccttg ttacaaacga ctttgctacg actttcaggc ctatcatgtc aaaaaccatt    9240
agtgataaca aatgaacagc atcgctttgt tgtggctgaa cagttaaggg aaataaataa    9300
attaaatggt aatattattc tagaaccatg cgggcgaaat actgcaccag caatagcgat    9360
atctgcgttt catgcgttaa aacgtaatcc tcaggaagat ccattgcttc tagttcttgc    9420
ggcagaccac gttatagcta aagaaagtgt tttctgtgat gctattaaaa atgcaactcc    9480
catcgctaat caaggtaaaa ttgtaacgtt tggaattata ccagaatatg ctgaaactgg    9540
ttatgggtat attgagagag gtgaactatc tgtaccgctt caagggcatg aaaatactgg    9600
tttttattat gtaaataagt ttgtcgaaaa gcctaatcgt gaaaccgcag aattgtatat    9660
gacttctggt aatcactatt ggaatagtgg aatattcatg tttaaggcat ctgtttatct    9720
tgaggaattg agaaaattta gacctgacat ttacaatgtt tgtgaacagg ttgcctcatc    9780
ctcatacatt gatctagatt ttattcgatt atcaaaagaa caatttcaag attgtcctgc    9840
tgaatctatt gattttgctg taatggaaaa aacagaaaaa tgtgttgtat gccctgttga    9900
tattggttgg agtgacgttg gatcttggca atcgttatgg gacattagtc taaaatcgaa    9960
aacaggagat gtatgtaaag gtgatatatt aacctatgat actaagaata attatatcta   10020
ctctgagtca gcgttggtag ccgccattgg aattgaagat atggttatcg tgcaaactaa   10080
agatgccgtt cttgtgtcta aaaagagtga tgtacagcat gtaaaaaaaa tagtcgaaat   10140
gcttaaattg cagcaacgta cagagtatat tagtcatcgt gaagttttcc gaccatgggg   10200
aaaatttgat tcgattgacc aaggtgagcg atacaaagtc aagaaaatta ttgtgaaacc   10260
tggtgagggg ctttcttaa ggatgcatca ccatcgttct gaacattgga tcgtgctttc   10320
tggtacagca aaagtaaccc ttggcgataa aactaaacta gtcaccgcaa atgaatcgat   10380
atacattccc cttggcgcag cgtatagtct tgagaatccg gcataatcc ctcttaatct   10440 tattgaagtc agttcagggg attatttggg agaggatgat attataagac agaaagaacg   10500
ttacaaacat gaagattaac atatgaaatc tttaacctgc tttaaagcct atgatattcg   10560
cgggaaatta ggcgaagaac tgaatgaaga tattgcctgg cgcattgggc gtgcctatgg   10620
cgaatttctc aaaccgaaaa ccattgtttt aggcggtgat gtccgcctca ccagcgaagc   10680
gttaaaactg gcgcttgcga aggtttacaa ggatgcgggc gtcgatgtgc tggatatcgg   10740
tatgtccggc accgaagaga tctatttcgc cacgttccat ctcggagtgg atggcggcat   10800
cgaagttacc gccagccata acccgatgga ttacaacggc atgaagctgg tgcgcgaagg   10860
ggctcgcccg atcagcggtg ataccggact gcgcgatgtc cagcgtctgg cagaagccaa   10920
tgacttccct cctgtcgatg aaaccaaacg tggtcgctat cagcaaatca atctgcgtga   10980
```

```
cgcttacgtt gatcacctgt tcggttatat caacgtcaaa aacctcacgc cgctcaagct    11040
ggtgatcaac tccgggaacg gcgcagcggg tccggtggtg gacgccattg aagcccgatt    11100
taaagccctc ggcgcaccgg tggaattaat caaagtacac aacacgccgg acggcaattt    11160
ccccaacggt attcctaacc cgctgctgcc ggaatgccgc gacgacaccc gtaatgcggt    11220
catcaaacac ggcgcggata tgggcattgc ctttgatggc gattttgacc gctgtttcct    11280
gtttgacgaa aaagggcagt ttatcgaggg ctactacatt gtcggcctgc tggcagaagc    11340
gttcctcgaa aaaatcccg gcgcgaagat catccacgat ccacgtctct cctggaacac    11400
cgttgatgtg gtgactgccg caggcggcac cccggtaatg tcgaaaaccg gacacgcctt    11460
tattaaagaa cgtatgcgca aggaagacgc catctacggt ggcgaaatga gcgctcacca    11520
ttacttccgt gatttcgctt actgcgacag cggcatgatc ccgtggctgc tggtcgccga    11580
actggtgtgc ctgaaaggaa aaacgctggg cgaaatggtg cgcgaccgga tggcggcgtt    11640
tccggcaagc ggtgagatca acagcaaact ggcgcaaccc gttgaggcaa ttaatcgcgt    11700
ggaacagcat tttagccgcg aggcgctggc ggtggatcgc accgatggca tcagcatgac    11760 cttttgccgac tggcgcttta acctgcgctc ctccaacacc gaaccggtgg tgcggttgaa    11820
tgtggaatca cgcggtgatg taaagctaat ggaaaagaaa actaaagctc ttcttaaatt    11880
gctaagtgag tgattattta cattaatcat taagcgtatt taagattata ttaaagtaat    11940
gttattgcgg tatatgatga atatgtgggc ttttttatgt ataacgacta taccgcaact    12000
ttatctagga aaagattaat agaaataaag ttttgtactg accaatttgc atttcacgtc    12060
acgattgaga cgttcctttg cttaagacat ttttcatcg cttatgtaat aacaaatgtg    12120
ccttatataa aaaggagaac aaaatggaac ttaaaataat tgagacaata gattttatt    12180 atccctgttt acgatattat agccaaagtt gtatcctgca tcagtcctgc aatatttcac    12240
gagtgctttg ttaactgaat acatgtctgc cattttccag atgataacga cgtcatcgca    12300
attgatggta aaacacttcg gcacacttat gacaagagtc gtcgcagagg agtggttcat    12360
gtcattagtg cgtttcagca atgcacagtc tggtcctcgg atagatcaag acggatgaga    12420
aacctaatgc gttcacagtt attcatgaac tttctaaaat gatgggtatt aaggaaaaa    12480 taatcataac tgatgcgatg gcttgccaga aagatattgc agagaagata taaaaacaga    12540
gatgtgatta tttattcgct gtaaaaggaa ataagagtcg gcttaataga gtctttgagg    12600
agatatttac gctgaaagaa ttaaataatc aaaacatga cagttacgca attagtgaaa    12660
agaggcacgg cagagacgat gtccgtcttc atattgtttg agatgctcct gatgagctta    12720
ttgatttcac gtttgaatgg aaagggctgc agaatttatg aatggcagtc cactttctct    12780
caataatagc agagcaaaag aaagaatccg aaatgacgat caaatattat attagatctg    12840
ctgctttaac cgcagagaag ttcgccacag taaatcgaaa tcactggcgc atggagaata    12900
agttgcacag tagcctgatg tggtaatgaa tgaaatcgac tataatataa aaggcgagt    12960 tgcattcgaa tgattttcta gaatgcggca catcgctatt aatatctgac aatgataatg    13020
tattcaaggc aggattatca tgtaagatgc gaaaagcagt catggacaga aacttcctag    13080
cgtcaggcat tgcagcgtgc gggctttcat aatcttgcat tggttttgat aagatatttc    13140
tttggagatg ggaaaatgaa tttgtatggt attttttggtg ctggaagtta tggtagagaa    13200
acaataccca ttctaaatca acaaataaag caagaatgtg gttctgacta tgctctggtt    13260
tttgtggata tgtttttggc aggaaagaaa gttaatggtt ttgaagtgct ttcaaccaac    13320
```

```
tgctttctaa aagcccctta tttaaaaaag tattttaatg ttgctattgc taatgataag    13380
atacgacaga gagtgtctga gtcaatatta ttacacgggg ttgaaccaat aactataaaa    13440
catccaaata gcgttgttta tgatcatact atgataggta gtggcgctat tatttctccc    13500
tttgttacaa tatctactaa tactcatata gggaggtttt tcatgcaaa catatactca    13560 tacgttgcac atgattgtca ataggagac tatgttacat ttgctcctgg ggctaaatgt     13620
aatggatatg ttgttattga agacaatgca tatataggct cgggtgcagt aattaagcag    13680
ggtgttccta atcgcccact tattattggc gcgggagcca ttataggtat ggggctgtt    13740 gtcactaaaa gtgttcctgc cggtataact gtgtgcggaa atccagcaag agaaatgaaa    13800
agatcgccaa catctattta atgggaatgc gaaaacacgt tccaaatggg actaatgttt    13860
aaaatatata taatttcgct aatttactaa attatggctc cttttttaagc tatcctttac    13920 ttagttatta ctgatacagc atgaaattta taatactctg atacattttt atacgttatt    13980
caagccgcat atctagcggt aaccctgac aggagtaaac aatg                     14024

<210> SEQ ID NO 3
<211> LENGTH: 12441
<212> TYPE: DNA
<213> ORGANISM: Salmonella enterica

<400> SEQUENCE: 3
gttgacaaat accgaccgta taatgaatca acgttctgg attggtattt atccaggctt       60
gactacagag catttagatt atgtcgtaag taagtttgaa gaattttttg gtttaaattt      120
ctaattttta ggataggatg cttgatgtga ataagaaaat cctaatgact ggcgctacta     180
gctttgtagg tacccatcta ctacatagtc tcataaagga aggttatagt attattgcat     240
taaagcgtcc tataaccgag ccaacgatta tcaataccct gattgaatgg ttgaatatac     300
aagatataga aaaaatatgt caatcatcta tgaatattca tgcgattgtc catattgcaa     360
cagactatgg tcgaaacaga accctatat ctgaacaata taaatgtaat gtcctattac      420
caacaagact gcttgagtta atgccagcgc ttaaaacgaa attctttatt tctactgact     480 cttttttttgg gaaatatgag aagcactatg gatatatgcg ttcttacatg gcatctaaaa    540
gacattttgt agaactatca aaaatatacg tagaggaaca tccagacgtt tgttttataa    600
atttacgttt agaacatgtt tacggtgaga gggataaagc aggtaaaata atcccgtatg     660
ttatcaaaaa aatgaaaaac aatgaagata ttgattgtac gatcgccagg cagaaaagag    720 attttatttta tatagacgat gttgtttcgg cctatttgaa aattttaaag gagggtttta    780
acgctggaca ctatgatgtc gaggtgggga ctggaaaatc gatagagcta aaagaagtgt     840
ttgagataat aaaaaaagaa acgcatagta gtagtaagat aaattatggt gcagttgcga    900
tgcgtgatga tgagattatg gagtcacatg caaataccctc tttcttgact cgattaggtt    960
ggagtgccga gttttctatt gagaagggtg tgaaaaaaat gttgagtatg aaagagtaat    1020
gaatcgtatt attagaatgt taggtgtaga taaagcaatt cgttatgtta tttttggtaa    1080
gataatatct gtattaacgg gtttactgtt aataatgtta atatcacacc atttatctaa    1140
agacgcacag ggctattatt atacatttaa ttcagtagtg gcactacaga taatatttga     1200
attggggcta tcaacggtaa tcattcaatt cgctagccat gaaatgtcag cgttaaaata    1260
tgattattct gaacgagata ttataggtga agtaaaaat aagcaacgtt acctatcgtt     1320
atttcggttg gcaataaaat ggtatgcagt aatagctttg ctaataatat taatagtcgg    1380
tcccatcggg tatgtttttt ttacgcaaaa agaaggctta ggtgtaccctt ggcaagggc   1440
```

-continued

```
atggttatta ttaacaatag ttacagcttt taatattttt cttgtttctg tactttctgt    1500
cgctgaaggg agtgggttaa ttactgatgt gaataaaatg agaatgtatc agtcgctgtt    1560
agctggtata ttggcagtaa gcttacttat tagtggcttt ggactatatg ctacgtctgc    1620
aatagctatt tcagggacta tcatattctc catattttca tataagtatt ttaaaaaaat    1680
tttcctgcaa tctttaaagc ataaaaataa atatactgaa ggtggtattt catgggttaa    1740
tgaaatattt cctatgcaat ggcgaattgc tctaagttgg atgtcagggt atttttattta   1800 ttttgttatg accccccattg cattcaaata tttcggggct atatatgcag ggcagttagg    1860
gatgtcttta acattatgca atatggtaat ggctacgggc ctggcttgga tatccactaa    1920
atatccaaaa tggggagtaa tggtttccaa caaacagctt gcggaactga gtaaatcgtt    1980
caaaagtgca gtaatgcaat catccttttt tgtcttgaca ggattaactg gtgtatacat    2040
ttcattatgg ttattgaaat tatctggttc aaacattggc gagcggtttt tgggattgca    2100 ggatttttc ttttttatctt tagcaattat tggtaatcac attgtagctt gctttgcaac    2160
ctatataaga gcgcataaaa ctgaaaaaat gacattggca tcatgtataa tggctctctt    2220
gactataact acaatgttgt tgttgcata tttagagtac tcgaggttct acatgttaat     2280
gtatgcagca ctaacgtggt tatattttgt tcctcaaact tatataatct ttaaaagatt    2340
caagagttct tatgagtaaa aacctcttc ttactattgc tattccgaca tataaccgct     2400
cttcatgttt ggctcgttta cttgatagta taattcaaca ggagaactat tgtcatgatg    2460
aactcgaggt tattgtttgt gataatgctt caacagatga acagcaaga atagccaaga     2520 gtggcttaga taaaataaga aatagtactt atcatctaaa tgaagaaaac ttaggaatgg    2580
atggtaactt ccagaaatgt tttgagttat caaatgaaa atatctttgg atgattggcg     2640
atgatgatct aatagtcaaa atggtatttt cgaaggtttt ttcgatatta aagtcccggc    2700
ctgcattaga tatggtgtat gtaaattcag cagcaaagac tgagttaaac tataatgctg    2760
atgtgaggac gtcattctac acaaatgatg tagatttat ttcagacgtg aaagttatgt     2820
tcacgtttat ttctggaatg atatgtaaga aaactgatgc aattgtcaaa gccgttggta    2880
ttttcagtcc gcaaactact ggaaaatatc ttatgcattt aacatggcaa ttgccattac    2940
ttaaacaggg tggagagttc gcagttatcc ataataatt aattgaggct gagccagata    3000
attcaggtgg atatcattta taaggtttt tttctaataa tcttgcgaca atctttgatg      3060
ttttttatcc cagagagcac cgtgtaagta aaagagttcg cgcatcagca tgtttattct    3120
tacttaactt cataggcgat gaagataaaa ccaaaaattt tgctacaaat aattatttaa    3180
gagattgcga tagtgcattt atagatttaa ttatatataa atatgggctt aggttttttct   3240 atctatatcc taaaactgtg cctttattta gaaaaataaa atatattata aagacggttt    3300
taatgcggaa ataaaaatta ttcaagatgg tttgctgaaa acgacttata ggactatcta    3360
atgtttgtct atagtttaag attaaaatta aatcttatca tatcattatt gagtaaagtt    3420
aggcggaaat caaaagcaaa gtttcttgtt ctgcttagcg gatatgattt taaaatggtt    3480
gggaagaatt ttaaattgaa tgtcaaacct tactctgcaa aaaataacac ctcttccaaa    3540
tggggtagta tgcgggttgg tgataactgc tggattgaag ctgtatataa ttatggtgat    3600
gaaaaatttg aaccttattt gtacataggt gatcgtatat gtttaagtga taagtgttcat  3660 atttcttgcg tatcatgttt aatttttagaa acgatatat taattggtag caaagtttat    3720
ataggcgatc atagccatgg cagttataaa gtatgcagtc cgaaaataga accgccagca    3780
```

```
aataagccat taggtgatat tgctcctatt aaaataggta attgctgctg gattggagat   3840
aatgcagtaa ttctggctgg tagtgaaatt tgtgatggct gtgtaatcgc agctaattca   3900
gtcgtcaagg atttaaaagt cgataagcca tgtttaattg gtggggttcc tgctaaagta   3960
ataaaggtat tttaaaatga atgttttat cagtatttgt ataccgtctt ataatagagc    4020
tgagttttta gagccactac tggatagcat atataatcaa gattattgtt taaagaataa   4080
tgattttgag gtcattgttt gtgaagataa atctccacag agagatgaga taaactctat   4140
tatcgaaaac tataaagcaa aaataataa acaaaatctt tatgttaatt tcaatgaaga    4200
taatttaggc tatgataaga atttaaaaaa atgcattagt ttgacgacag gtaaatattg   4260
catgatcatg ggcaacgatg atctattagc agatggagcg ttatcaaaaa tagtgaaagt   4320
tttgaaggct aatcctgaaa ttgtattggc tacgcgagcg tatggttggt ttaaggaaaa   4380
tccgaatgag ttatgtgata ctgttcgtca tttaacagac gatactttat ttcagccggg   4440
ggctgatgcc attaaatttt tcttccgtag agttggagtt atttcaggct ttattgtcaa   4500
tgctgaaaaa gcaaaaaaac tatcgagtga tttatttgat gggcgtttat attatcaaat   4560
gtaccttgct ggtatgctaa tggctgaagg tcagggatac tattttagcg acgtgatgac   4620
attgtcgagg gatacagagg ctcctgactt tggtaacgct ggaactgaaa aaggagtttt   4680
caccccgggg gggtataaac cagagggccg tatacatatg gttgaaggct tgttgctaat   4740
tgcaaaatat atagaagata caacaaaaat tgatggcgtt tatgctggaa ttagaaaaga   4800
cttagcgaac tattttatc cttatattcg agatcaactc gacttgcctc tttatactta    4860
tattaaaatg ataaataaat ttcggaaaat gggattttca aatgaaaagc ttttctatgt   4920
gcatgccttt ttagggtatg tactaaaacg gagggctat gatgctttaa ttaaatacat    4980
tcgtagcaaa aaaggcggta ctccgcgtct tggtatttaa cctccacttt caaaaaatgt   5040
tatgaatata cttcttgctg cgatattagg cgttaactta ttttctccat atattagttc   5100
gtggatggtg ggtatgctgc catttccacc aggagcaatc ctaagggatg tactcaatgt   5160
attttttgtg gcgttagtgc tagttcgatt tgtcattgat aggaaaaaaa cttatttccc   5220
gttggttttt actatttttt catggtcggc ggtaatacta tgggtaatag cgttaactat   5280
attctcaccg gataaaattc aagcaattat gggggggcgg agttatattt tattcccggc   5340
agttttcata gcattagtga ttttaaaagt atcatacccg caatccttaa atattgaaaa   5400
aatagtttgc tacataattt ttctaatgtt tatggttgcg acaatatcta ttattgatgt   5460
actaatgaat ggagagttca ttaaattgct cggatatgat gagcattatg caggagaaca   5520
attaaactta attaatagct atgatgggat ggtccgggct acaggcggtt ttagtgatgc   5580
tctcaatttt ggatatatgc tcacattagg tgtttgtta tgtatggagt gttttttccca   5640 aggatataaa agattattga tgcttattat tagttttgtg ctatttatag cgatctgcat   5700
gagtcttact agaggagcaa tacttgttgc tgcgcttatt tacgcacttt atataaattc   5760
aaatcggaag atgcttttt gtggaataac tttatttgta ataattatac ccgttttagc   5820
aatttctact aatattttg acaactatac agaaattttg atcggcaggt ttacagattc   5880
gtctcaggca tcgcgtggat ctacacaggg gcggatagat atggcaatta attcattaaa   5940
cttcctgtca gaacatccat caggtatagg tctgggtact caaggttcag gaacatgct    6000 ttcggtaaaa gataataggt taaatacgga taattatttt ttctggatcg cccttgagac   6060
tggtattatt ggcttaatca taaatattat ttatctggca agtcaatttt attcttcaac   6120
tttactaaat agaatatatg gcagtcattg tagcaatatg cactatagat tatatttct    6180
```

```
ctttggaagt atatatttta taagtgcagc gttaagttca gcaccttcgt catcaacttt    6240
ttctatatat tattggacag ttttagcttt gattccattt ttaaaattaa caaatagacg    6300
gtgcacgcga taatgaataa taaaaaggtt ttgatggata ttagttggtc taataaaggg    6360
gggattggac gttttactga tgaaatttct aaactactat gtgatatatc taaggaggaa    6420
ctatatagaa aatgtgcttc tccgctggcc ccattaggtt tagcagtcaa tattttctg     6480 cgaaagaaaa ctgatgtggt ttttcttcct ggctatattc caccacttt  ttgttcgaaa    6540 aagttcataa taacaataca tgatctaaat catctggatt taaatgataa ttcctctctt    6600
tttaagaggt tattttataa ttttataata agcgcggtt  gtagaaaagc atataaaata    6660
tttacagttt cgaattttc  aaaagaaaga atagtagcat ggtcaggtgt aaaccctaat    6720
aaaatagtca cggtatataa tggggtatct agtctattta atgccgatgt aaaaccattg    6780
aatttaggct ataaatattt gctatgtgta ggaaacagaa aaactcataa gaatgagaag    6840
tgtgttatat ctgcctttgc caaagcagat attgatccat caataaaact cgttttact    6900 ggtaatcctt gtaatgattt agaaaaacta ataatacaac atggtttaag tgaacgtgta    6960
aagttctttg ggttcgtgtc tgaaaaagat ttaccatcgt tatataaggg ctcgttagga    7020
ttagttttcc cttctttata tgaaggtttt ggattacctg tagtggaggg catggcctgt    7080
ggtattcctg tattaacttc tctaacttca tcattgccag aggtggctgg agatgcagcg    7140
attcttgtcg accctctttc ggaagatgct attactaaag gaatttcgag gttaattaat    7200
gattctgaac ttcgtaagca tttaatccaa aagggggctt tgcgggcaaa gaggttcaat    7260
tggcaaaacg tggttagtga gattgaaatg gtactgacag aggcatgtga tggaaataaa    7320
tgaaataaaa atatctctcg ttcatgagtg gttattaagt tatgcaggct ccgaacaggt    7380
atcatctgcc atcctgcatg ttttcctga  agcgaagtta tattcggtgg ttgattttct    7440
aacggatgaa caaagaagac atttctggg  gaaatatgcg actaccacat ttattcaaaa    7500
tttacctaaa gctaaaaaat tttaccagaa atatttacca ctaatgccac tggctattga    7560
acaacttgat ttatcagatg ctaatatcat cattagtagc gcccattccg ttgcaaaagg    7620
tgttatttcc ggaccagatc agcttcacat tagctatgtt cattctccta ttcgatatgc    7680
gtgggattta cagcatcagt accttaatga gtctaacctg aataaaggaa ttaaaggttg    7740
gttagcaaaa tggcttcttc acaaaatacg aatttgggat tctcgaaccg caaatggggt    7800
tgatcatttt atagctaatt ctcaatatat cgcgcgtaga attaaaaaag tatacagacg    7860
tgaggcttca gttatatatc cgcctgtaga tgtggataat tttgaagtaa aaaatgaaaa    7920
gcaagactat tatttcacag catcccgtat ggtaccctac aaacgtattg atcttattgt    7980
cgaagccttt agtaaaatgc cggaaaagaa attagtagtt attggtgatg gaccggagat    8040
gaaaaaaata aagagcaagg ctacagacaa tataaaattg ctcggttatc aatcttttcc    8100
tgttttaaaa gagtatatgc agagcgccag ggcgtttgtt tttgcagcgg aagaggactt    8160
tggaataata cctgtcgaag ctcaagcttg cggtacccct gttattgcct ttgggaaggg    8220
tggggcctta gaaaccgttc gcccactagg tgtagaggaa ccgactggca ttttcttcaa    8280
ggaacagaat attgcttctt tgcatgaagc tgttagtgaa tttgaaaaaa atgcatcatt    8340
ttttacatct caggcttgta gaaaaaatgc agaaaaattt tctcgatcaa gatttgaaca    8400
agaatttaag aactttgtta atgaaaagtg gaatctttt  aaaacagaac agattattaa    8460
acgttaatta tggtttattg aatgtctaaa ttaataccag taataatggc cggtgggatt    8520
```

```
ggtagccgtt tgtggccact ttcacgtgaa gagcatccga aacagttttt aagcgtagat   8580
ggtgaattat ctatgctgca aaacaccatt aaaagattga ctcctctttt ggctggagaa   8640
cctttagtca tttgtaatga tagtcaccgc ttccttgtcg ctgaacaact tcgagctata   8700
aataaactag caaataacat catattagag ccagtggggc gtaatacagc cccagctata   8760
gcgctggccg cttttttgttc acttcagaat gtcgtcgatg aagacccgct tttgcttgtc   8820
cttgctgcgg atcatgtcat ccgcgatgag aaagtgtttc ttaaagctat caatcacgct   8880
gaattttttg caacacaagg taagctagta acgtttggta ttgtacccac acaggccgaa   8940
actggctacg gttatatttg tagaggtgaa gcaatcgggg aagatgcttt ttctgtagcc   9000
gaatttgtag agaagcctga tttcgataca gcgcgtcatt atgtagaatc agagaaatat   9060
tattggaaca gcgtatgtt cctatttcgt gcaagtagtt acttacaaga attaaaggat   9120
ctgtcccccg atatttacca agcatgtgaa aatgcggtag ggagtattaa tcctgatctt   9180
gattttatcc gtattgataa agaagcattc gcaatgtgcc ctagtgattc tatcgattat   9240
gcggtaatgg aacatactag gcatgcagtt gtcgtaccga tgaatgccgg ctggtcagat   9300
gtggggtcat ggtcttcact gtgggatatt tctaagaaag atccacaacg taatgtatta   9360
catggcgata ttttttgcata taatagtaaa gataattata tctattctga aaaatcgttt   9420
attagtacaa tcggagtaaa taatttagtt atcgtgcaga cagcagatgc attattagta   9480
tctgataaag attcagtcca ggatgttaaa aaagttgttg attatttaaa agctaataat   9540
agaaacgaac ataaaaaaca tttagaggtt ttccgaccgt gggggaaaatt tagcgtaatt   9600
catagtggcg ataattattt agttaaaaga ataactgtta aaccaggcgc gaagtttgct   9660
gctcagatgc atctccatcg tgctgagcat tggatagtgg tatctggtac tgcttgtatt   9720
actaaggggg aagaaatttt tacaatttcg gagaatgaat caacatttat acctgctaat   9780
acagttcata cgttaaaaaa ccccgcgact attccattag aactaataga aattcaatct   9840
ggcacctatc ttgcggagga tgatattatt cgcctggaga acattctgg atatctggag   9900
taatgaattg atgaaaaata tatataatac ttacgatgtt atcaacaaat ctggaattaa   9960
ttttggaacc agtggtgccc gcggccttgt taccgatttt acacccgaag tttgcgcacg  10020
atttaccatt tccttttga cagtaatgca gcaaagattc tcatttacaa cggttgcgct  10080
cgcaattgat aatcgtccaa gcagttacgc gatggctcaa gcttgtgccg ctgctttgca  10140
agaaaaagga attaaaaccg tttactatgg cgtaattcca acacctgctt tagctcatca  10200
atcaatttcc gataaagtac ctgcaatcat ggttactggc agtcatatcc cttttgaccg  10260
taatggcctg aaatttata gaccagatgg tgaaattact aaagatgatg agaatgctat  10320
tattcatgtt gatgcctcat ttatgcagcc taagcttgaa caattgacaa tttccacaat  10380
cgctgctaga aattatattc tacgatatac ctcattattt ccaatgccat tcttgaaaaa  10440
taagcgcatt ggaattatg agcattctag tgcgggtcgt gatctctata agacgttatt  10500
caaaatgttg ggtgctacag ttgttagttt agcaaggagc gacgaatttg ttcctattga  10560
tactgaagct gtaagtgaag atgatagaaa taaagcaatc acatgggcaa aaaaatatca  10620
gttagatgct atattttcaa ctgatggtga tggagatcgc cctctgatag ctgacgaata  10680
tggaaattgg ttaagaggag atatattagg ccttctgtgc tctctcgaat tagctgctga  10740
tgcagtcgct attcctgtaa gctgcaacag tacaatctca tctggtaact ttttttaaaca  10800
tgtggaacga acaaagattg gttcaccctta tgtgattgca gcatttgcta aattatctgc  10860
aaactataat tgtatagctg gttttgaagc gaatggtggc tttctgctag gtagcgatgt  10920
```

-continued

```
ttatattaat cagcgtttac ttaaggcatt accaacacgt gatgctttat tacctgccat    10980
tatgcttctg tttggtagca aggacaaaag tattagtgag cttgttaaaa aacttcctgc    11040
tcgctatacc tattcaaaca gattacagga tataagtgtt aaaacaagta tgtctttaat    11100
aaatcttggt ctgacagatc aagaggattt tttgcagtat attggtttta ataaacatca    11160
tatattacat tctgatgtta ctgatggctt tagaatcact atcgataaca acaatattat    11220
tcatttacga ccttcaggca atgcccctga gttgcgttgc tatgcggagg ctgactcgca    11280
agaggatgca tgtaatattg ttgaaactgt tctctctaat atcaaaagca aactgggtag    11340
agcttaatgc tgttgataat agagcgtttc tttccagtaa tactttgtct ggttatctgg    11400
tacccaagtt gagggtgaga attaaatgga tcgttttgat aataagtata acccaaattt    11460
atgcaaaata ttattggcta tatcagattt actgtttttt aatgtagcct tatgggcatc    11520
gttaggagtt gtatatttaa tctttgatga agttcagcga tttgtaccac aagagcaatt    11580
agataatcga tttatatcac attttattct atctatagta tgcgttggat ggttttgggt    11640
tcgactgcgt cactatacat atcgaaagcc attctggtat gagttgaaag aggttattcg    11700
tactatcgtt atttttgctg tgtttgattt ggctttaatt gcgtttacaa aatggcagtt    11760
ttcacgctat gtctgggtgt tttgttggac ttttgccata atcctggtgc ctttttttcg    11820
cgcacttaca aagcatttat tgaacaagct aggtatctgg aagaaaaaaa ctatcatcct    11880
tgggagcgga cagaatgctc gtggtgcata ttctgcgctg caaagtgagg agatgatggg    11940
gtttgatgtt atcgcttttt ttgatacgga tgcgtcagat gctgaaataa atatgttgcc    12000
ggtgataaag gacactgaga ctatttggga tttaaatcgt acaggtgatg tccattatat    12060
ccttgcttat gaatacaccg agttggagaa aacacatttt tggctacgtg aactttcaaa    12120
acatcattgt cgttctgtta ctgtcgtccc ctcgtttaga ggattgccat tatataatac    12180
tgatatgtct tttatcttta gccatgaagt tatgttatta aggatacaaa ataacttggc    12240
taaaaggtcg tcccgttttc tcaaacggac atttgatatt gtttgttcaa taatgattct    12300
tataattgca tcaccactta tgatttatct gtggtataaa gttactcgag atggtggtcc    12360
ggctatttat ggtcaccagc gagtaggtcg gcatggaaaa ctttttccat gctacaaatt    12420
tcgttctatg gttatgaatt c                                              12441
```

<210> SEQ ID NO 4
<211> LENGTH: 22080
<212> TYPE: DNA
<213> ORGANISM: Salmonella enterica

<400> SEQUENCE: 4

```
gaattcggga ggcgcaatga aagtcagctt ttttctgctg aaatttccac tctcatcgga     60
aacctttgtg ctgaatcaga ttactgcgtt tattgatatg gccatgagg tggagattgt    120
cgcgttacaa aaaggcgata cccaacatac tcacgccgcc tgggagaagt atggcctggc    180
ggcgaaaacc cgctggttac aggatgagcc ccagggacgg ctggcgaaac tgcgctaccg    240
ggcatgtaaa acgctgccgg ggctgcatcg ggcggcgacc tggaaagcgc tcaattttac    300
ccgctatggc gatgaatcac gcaatttgat cctttccgcg atttgcgcgc aggtgagcca    360
gccttttgtg gcggatgtgt ttatcgcaca ctttggtccg gcgggcgtga cggcggccaa    420
actacgcgaa ctgggcgtgc ttcgcggcaa aatcgcgact attttccacg ggattgatat    480
ctctagtcgt gaggtgctca gtcattacac gccggagtat cagcagttgt ttcgtcgtgg    540
```

```
cgatctgatg ctgcccatca gcgatctgtg ggccggtcgc ctgaaaagta tgggctgtcc     600
gccggaaaag attgccgttt cgcgcatggg cgtcgacatg acgcgtttta cccatcgttc     660
ggtgaaagcg ccagggatgc cgctggagat gatttccgtc gcgcgcctga cagaaaaaaa     720
aggcctgcat gtggcgattg aagcctgtcg gcaactgaaa gcacagggcg tggcgtttcg     780
ctaccgcatt ctgggattg gcccgtggga acgtcggctg cgcacgctca tcgagcagta     840
tcagctagag gatgtcattg agatgccggg gttaaaccg agccatgaag tgaaggcgat     900
gctggatgac gccgatgttt ttttgctgcc gtcgattacc ggtacggatg cgatatgga     960
aggtattccg gtagcgctga tggaggcgat ggcggtaggg attcccgtgg tatctaccgt    1020
gcatagcggt attccggaac tggtggaggc cggcaaatcc ggctggctgg tgccggaaaa    1080
cgatgcgcag cgcgctggcg cccgactcgc tgagttcagc cggattgacc acgacacgct    1140
ggagtcggtg atcacgcgcg cccgtgaaaa agtggcgcaa gatttttaatc agcaggcgat    1200
taatcgccag ttagccagcc tgctacaaac gatataaacg aggtggtatg cccgcgacta    1260
aattctcccg acgtaccctc ctgacggcag gttctgcgct tgctgttctt ccttttctgc    1320
gcgccttgcc ggtacaggcg cgtgaacctc gcgagaccgt cgatattaag gattatccgg    1380
cggatgacgg tatcgcctcg ttcaaacagg ccttcgccga cggacagacc gtggtcgtac    1440
cgccaggatg ggtgtgtgaa aatatcaatg gcgcgataac gattccggcg ggaaaaacgc    1500
tgcgggtaca gggcgcggtg cgtgggaatg gccggggacg gtttattttg caggacgggt    1560
gtcaggtggt gggggagcag ggcggcagtc tgcacaatgt gacgctggat gttcgcgggt    1620
cggactgtgt gattaaaggc gtggcgatga gcggctttgg ccccgtcgcg caaattttca    1680
tcggtggtaa ggaaccgcag gtgatgcgta atctcattat cgatgacatc accgttaccc    1740
acgccaacta cgccattctc cgccagggat ttcataacca aatggatggc gcgcggatta    1800
cgcatagccg ctttagcgat ttacagggg acgccattga gtggaatgtc gcgattcacg    1860
accgcgacat cctgatttcc gatcatgtca tcgaacgcat taattgtacc aatggcaaaa    1920
tcaactgggg gatcggcatc gggctggcg gtagcaccta tgacaacagt tatcctgaag    1980
accaggcagt aaaaaacttt gtggtggcca atattaccgg atctgattgc cgacagcttg    2040
tgcacgtaga aaatggcaaa catttcgtca ttcgcaatgt caaagccaaa aacatcacgc    2100
ccggtttcag taaaaatgcg ggtattgata acgcaacgat cgcaatttat ggctgtgata    2160
atttcgtcat tgataatatt gatatgacga atagtgccgg gatgctcatc ggctatggcg    2220
tcgttaaagg aaaatacctg tcaattccgc aaaactttaa attaaacgct attcggttgg    2280
ataatcgcca ggttgcttat aaattacgcg gcattcaaat ttcctccggc aacacccct    2340
cttttgtcgc catcaccaat gtacggatga gcgcgtgctac gctggaactg cataatcaac    2400
cgcagcacct ctttctgcgc aatatcaacg tgatgcaaac ttcagcgatt ggcccggcgt    2460
taaaaatgca tttcgatttg cgtaaagatg tacgtggtca atttatgcc cgccaggaca    2520
cgctgctttc cctcgctaat gttcatgcca tcaatgaaaa cgggcagagt ccgtggata    2580
tcgacaggat taatcaccaa accgtgaatg tcgaagcagt gaattttcg ctgccgaagc    2640
ggggagggta agtaccgcta ttttttacgaa aattcctggg aaaagttgt tcatacttaa    2700
tgttatggtg ccgactaaga cgtaatgtag agcgtgccat cattatccct ggcagcagag    2760
taattcatgc tggcgaaaac aagctaaaga gctataattc agcaaccatt ttacaggtgg    2820
aagaaacaat gatgaatttg aaagcagtta taccggtagc ggggtttgggt atgcatatgt    2880
tgcctgccac caaggcaatc ccaaaagaga tgctaccgat cgtcgacaag ccaatgattc    2940
```

```
agtacattgt cgatgagatt gtggctgcag ggatcaaaga aatcgtgctg gtgactcacg    3000
cgtctaaaaa cgccgttgag aaccacttcg acacctctta tgaacttgaa tcacttcttg    3060
agcagcgcgt taagcgtcag cttttggcgg aagtgcaatc tatctgccca ccgggcgtga    3120
cgattatgaa cgttcgccag gcgcagccgt tagggctggg gcattctatt ctgtgcgcgc    3180
gtccggtcgt gggcgataac cctttcattg tggtactccc ggatattatt atcgatgatg    3240
ctaccgccga tccgctgcgc tataaccttg cggcgatggt ggcgcgtttc aatgaaacgg    3300
gtcgcagcca ggtgctggcg aagcgcatga aaggtgattt atcggagtat tccgttatcc    3360
agacgaaaga acctctggat aatgaaggca aagtcagccg gattgtggag tttatcgaaa    3420
aaccggatca gccgcagacg ctggattccg atttgatggc ggtaggccgt tatgtgcttt    3480
cagccgacat ctgggcggaa ctggaaagaa ccgaaccggg cgcctggggc cgcatccagc    3540
tcaccgatgc cattgctgaa ctggcgaaaa acagtcggt tgacgcgatg ctaatgacgg     3600
gtgacagcta tgactgcggt aaaaaaatgg gctacatgca ggcatttgtg aagtacgggc    3660
tgcgcaacct gaaagaagga gccaagttcc gtaagagcat agagcagctt ttgcatgaat    3720
aagtattaac aaccgtgata aatggttggt gataaacata ataacggcag tgaacattcg    3780
aagcggcaag ttggctgaaa cgagtgttga ctgccgtttt agttttgtat aaagggctta    3840
agtaacaagg ggttatctgg agcattttaa tgctgatttt ataagattaa tccttgtttc    3900
cggatgcaat taataagaca attagcgttt aagttttagt gagctttgcc ctgctgggcg    3960
aggtttgcaa caagtcgata tgtacgcagt gcactggtag ctgatgagcc aggggcggta    4020
gcgtgtgtaa cgacttgagc aattaatttt tattggcaaa ttaaatacca cattaaatac    4080
gccttatgga atagaaaagt gaagatactt attactggcg gggcaggttt tattggatca    4140
gctgttgtcc gccatattat taagaataca caggacactg tagttaatat tgataaatta    4200
acctacgccg gtaatcttga atccctttct gatatttctg aaagtaatcg ctacaatttt    4260
gaacacgcgg atatttgtga ttccgctgaa ataacgcgta ttttgagca gtaccagccg     4320 gacgcggtga tgcatttggc tgcggaaagt catgtggacc gttcgattac cgggccagca    4380
gcatttattg aaaccaatat cgtcggcacc tatgcacttc ttgaagttgc gcgtaaatac    4440
tggtctgccc ttggcgaaga taaaaaaaat aattttcgtt ttcatcatat ttccactgat    4500
gaagtttacg gcgatttacc gcatcctgat gaagttgaaa acagcgttac gctgccgtta    4560
tttactgaaa cgacggcata tgcgccaagt agcccctatt ctgcgtcaaa agcatccagc    4620
gatcatttag tccgtgcctg gcggcgtacc tatggtctac caacgatcgt taccaattgt    4680
tctaataact atggccctta tcacttccct gaaaaactga ttccgttggt cattttgaac    4740
gcactggaag gaaagccttt gccaatttat ggcaaagggg atcagattcg cgattggcta    4800
tatgtagaag atcatgctcg cgcgcttcat atggtagtga ctgaaggcaa ggcaggggag    4860
acttataaca ttggtggaca caatgagaag aaaaatctcg atgtggtatt taccatctgt    4920
gatctgctgg atgagattgt acccaaagcg acttcttatc gtgaacaaat cacttatgtc    4980
gcggatcgtc cgggccatga tcgtcgttat gccattgatg caggtaaaat tagccgcgaa    5040
ttaggctgga accgctgga gacctttgaa agcggtattc gtaaacagt ggaatggtac      5100 cttgcaaata ctcaatgggt aaacaatgtt aaaagtgggg cgtatcagag ttggatagaa    5160
cagaactatg aaggacgcca gtaatgaata tcttactttt tggtaagaca gggcaagtag    5220
gctgggagtt gcaacgttct ctggcaccgg tagggaatct gattgccctg gatgtccatt    5280
```

```
caaaagagtt ttgcggtgat tttagtaatc cgaaaggcgt tgccgaaacc gttcgtaagc    5340
ttcgtcccga tgtgattgtt aacgcagcag cccatactgc agtagataaa gcagagtctg    5400
aaccagaact ggcgcagtta cttaacgcca ccagtgtgga agccatcgct aaagcagcca    5460
acgaaactgg cgcatgggta gtgcattatt caaccgatta tgtatttcct ggtaccggcg    5520
atatcccatg gcaggaaacg gacgctacgt cgccgctgaa tgtctatggc aaaaccaaac    5580
tggcgggaga aaaggccctg caggataact gccctaaaca ccttatcttc cgcaccagtt    5640
gggtttatgc aggtaagggc aataatttcg caaagacaat gcttcgtctg gcgaaagagc    5700
gtcagacact ttcagtcatt aacgatcagt acggtgcgcc aaccggtgcg gaattactgg    5760
ctgactgtac ggcgcatgcg atccgtgtgg cgttaaataa accagaagtc gcaggtcttt    5820
accatctggt tgccggggga accacaacct ggcatgacta cgcggcctta gtctttgacg    5880
aggcgcgcaa agcagggata acgcttgcgc tgactgagct taatgctgtg ccgaccagcg    5940 cctaccgac gccggcgagc agaccaggca attcgcgtct caatactgaa aagtttcagc    6000
gtaattttga ccttattctg cctcaatggg aattaggagt taagcgtatg ctgactgaaa    6060
tgtttacgac gacaaccatc taataaattt aaatgcccat cagggcattt tctatgaatg    6120
agaaatggaa atgaaaacgc gtaagggcat tattttagcg gggggctccg gcacccgtct    6180
ttatccggtg accatggcgg taagtaagca attgctacca atttatgata aaccgatgat    6240
ttactatccc ctttccacgc ttatgctggc aggcattcgg gatatcctga tcatcagtac    6300
gccacaggac acgccgcgtt ttcaacaact gctgggagac ggcagccagt gggggctgaa    6360
tcttcaatat aaagtacagc caagcccgga tggcttagca caggcgttta ttattggtga    6420
agagttcatt ggtcatgatg attgtgcatt agtgctgggt gacaatatct tctatggtca    6480
tgatttacca aagttaatgg aagctgccgt taataaagaa agtggtgcta ccgtcttcgc    6540
ttatcatgta aacgatccgg agcgctacgg tgtggttgag tttgaccaaa agggcacagc    6600
cgttagtctg gaagaaaaac cattacaacc gaagagtaat tacgcggtaa cggggctgta    6660
tttttatgat aatagcgtgg tggagatggc gaaaaatctt aagccttccg ctcgcggtga    6720
gttagaaatc acggatatta accgtatcta tatggagcag ggaagattgt ctgtcgctat    6780 gatgggcgc ggttatgcct ggctggatac agggacgcat cagagtttga tagaggccag    6840
taattttatt gcaaccatcg aagaacgcca ggggctaaaa gtgtcctgcc cggaagagat    6900
cgcatttcgt aaaaatttta taaatgcaca acaggttata gaactggccg ggccattatc    6960
aaaaaatgat tatggcaaat atttgctgaa gatggtgaaa ggtttataag tgatgattgt    7020
gattaaaaca gcaataccag atgtcttgat cttagagcct aaagtttttg gcgatgagag    7080
gggattcttt tttgaaagtt ataaccagca gacctttgaa gagttgattg gacgtaaagt    7140
tacatttgtt caagataatc attcaaaatc caaaaagaac gtactcagag ggctacattt    7200
tcagagagga gaaaatgcac aggggaagtt agttcgttgt gctgtcggtg aggttttga    7260 tgttgcggtc gatatccgaa aagaatcgcc tactttggt caatggggttg gtgtaaatct    7320 gtctgctgag aataagcgac agctttggat tccagaaggt tttgctcatg gttttgttac    7380
tcttagtgag tatgcagagt ttctgtacaa agcaactaat tattactcac cttcatcgga    7440
aggtagcatt ctatggaatg atgaggcaat aggtattgaa tggcctttt ctcagctgcc    7500 tgagctttca gcaaaagatg ctgcagcacc tttactggat caagccttgt taacagagta    7560
agcatcgtgt ctcatattat taagattttt ccatcaaata ttgaatttc cggtagagag    7620 gatgaatcaa tcctcgatgc tgcgctatcg gctggtatcc atcttgaaca tagctgcaaa    7680
```

-continued

```
gcgggtgatt gtggtatctg tgagtccgat ttgttggcgg gagaagttgt tgactccaaa    7740
ggtaatattt ttggacaggg tgataaaata ctaacctgct gctgtaaacc taaaaccgcc    7800
cttgagctaa atgcgcattt ttttcctgaa ctagctggac agacaaaaaa aattgtccca    7860
tgcaaggtaa atagtgctgt actggtttca ggcgatgtta tgactttgaa gttacgcaca    7920
ccaccaacag caaaaattgg cttccttcca ggcagtata tcaatttaca ttataaaggt     7980
gtaactcgca gttattctat cgctaatagt gatgagtcga atggtattga gttgcatgta    8040
aggaatgttc ccaatggtca gatgagttcg ctcattttg gggagttaca agaaaatact     8100
cttatgcgca ttgaagggcc ttgcggaaca ttttttattc gtgaaagtga cagacctata    8160
atcttccttg caggcggtac tggattcgct ccagttaaat caatggttga gcatctcatt    8220
cagggaaaat gtcgtcgtga gatctacatt tactgggaa tgcaatatag taaagatttt     8280
tactctgcat taccgcagca gtggagtgaa cagcacgaca cgttcatta tatccctgtt     8340
gtttctggtg atgacgccga atggggggga agaaagggat ttgtccatca tgccgtgatg    8400
gatgattttg attctctaga gttcttcgat atatatgcat gtggttcacc tgtgatgatc    8460
gatgccagta aaaggactt tatgatgaaa aatctctctg tagaacattt ctattctgat     8520
gcatttaccg catctaataa tattgaggat aatttatgaa agcggtcatc ctggctggtg    8580
gacttggtac cagactaagt gaagaaacaa ttgtaaaacc aaaaccgatg gtagaaattg    8640
gtggcaagcc tattctttgg cacattatga aaatgtattc tgtgcatggt atcaaggatt    8700
ttattatctg ctgtggttat aaaggatatg tgattaaaga atattttgcg aactacttcc    8760
ttcacatgtc agatgtaaca ttccatatgg ctgaaaaccg tatggaagtt caccataaac    8820
gtgttgaacc atggaatgtc acattggttg atacgggtga ttcttcaatg actggtggtc    8880
gtctgaaacg tgttgctgaa tacgtaaaag atgacgaggc tttcctgttt acttatggtg    8940
atggcgttgc cgaccttgat atcaaagcga ctatcgattt ccataaggct cacggtaaga    9000
aagcgacttt aacagctact tttccaccag gacgctttgg cgcattagat atccgagctg    9060
gtcaggtccg gtcattccag gaaaaaccga aaggcgatgg ggcaatgatc aatggtggtt    9120
tctttgtgtt gaatccatcg gttatcgatc tcatcgataa cgatgcaaca acctgggaac    9180
aagagccatt aatgacattg gcacaacagg gggagttaat ggcttttgaa cacccaggtt    9240
tctggcagcc gatggatacc ctacgtgata agtttacct cgaagggctg tgggaaaaag    9300
gtaaagctcc gtgaaaaacc tgggagtaac tagatgattg ataaaaattt ttggcaaggt    9360
aaacgtgtat tcgttaccgg ccatactggc tttaaaggaa gctggctttc gctatggctg    9420
actgaaatgg gtgcaattgt aaaaggctat gcacttgatg cgccaactgt tccaagttta    9480
tttgagatag tgcgtcttaa tgatcttatg gaatctcata ttggcgacat tcgtgatttt    9540
gaaaagctgc gcaattctat tgcagaattt aagccagaaa ttgttttcca tatggcagcc    9600
cagcctttag tgcgcctatc ttatgaacag ccaatcgaaa catactcaac aaatgttatg    9660
ggtactgtcc atttgcttga aacagttaag caagtaggta acataaaggc agtcgtaaat    9720
atcaccagtg ataagtgcta cgacaatcgt gagtgggtgt ggggctatcg tgagaacgaa    9780
cccatgggag gtacgatcc atactctaat agtaaaggtt gtgcagaatt agtcgcgtct    9840
gcattccgga actcattctt caatcctgca aattatgagc aacatggcgt tggtttggcg    9900
tctgtgaggg ctggtaatgt cataggcgga ggcgattggg ctaaagaccg tttaattccc    9960
gatattctgc gctcatttga aaataaccag caggttatta ttcgaaaccc atattctatc   10020
```

```
cgtccctggc agcatgtact ggagcctctt tctggttaca ttgtggtggc gcaacgctta    10080
tatacagaag gtgctaagtt ttctgaagga tggaatttcg gcccgcgtga tgaagatgcg    10140
aagacggtcg aatttattgt tgacaagatg gtcacgcttt ggggtgatga tgcaagctgg    10200
ttactggatg gtgagaatca tcctcatgag gcacattacc tgaaactgga ttgctctaaa    10260
gcaaatatgc aattaggatg gcatccgcgt tggggattga ctgaaacact tggtcgcatc    10320
gtaaaatggc ataaagcatg gattcgcggc gaagatatgt tgatttgttc aaagcgtgaa    10380
atcagcgact atatgtctgc aactactcgt taagaaaata agtttaagga atcaaagtaa    10440
tgacagcaaa taacctgcgt gagcaaatct ctcagcttgt cgctcagtat gcgaatgagg    10500
cattgagccc gaaacctttt gttgcaggta caagcgttgt gcctccttcc gggaaggtta    10560
ttggtgccaa agagttacaa ttgatggttg aggcgtctct tgatgatgg ctaactactg     10620 gtcgtttcaa tgatgccttt gaaaaaaaac ttggggaatt tattggggtt cctcatgttt    10680
taacgacaac atctggctct tcggcaaact tgctggcact gactgcgctg acttccccaa    10740
aattaggcga gcgagctctc aaacctggtg atgaggttat tactgtcgct gctggcttcc    10800
cgactacagt taacccggcg atccagaatg gtttaatacc ggtattcgtg gatgttgata    10860
tcccgacata taatatcgat gcctctctca ttgaagctgc agttactgag aaatcaaaag    10920
cgataatgat cgctcataca ctcggtaatg catttaacct gagtgaagtt cgtcggattg    10980
ccgataaata taacttatgg ttgattgaag actgctgtga tgcccttggg acgacttatg    11040
aaggccagat ggtaggtacc tttggtgaca tcggaaccgt tagtttttat ccggctcacc    11100
atatcacaat gggtgaaggc ggtgctgtat tcaccaagtc aggtgaactg aagaaaatta    11160
ttgagtcgtt ccgtgactgg ggccgggatt gttattgtgc gccaggatgc gataacacct    11220
gcggtaaacg ttttggtcag caattgggat cacttcctca aggctatgat cacaaatata    11280
cttattccca cctcggatat aatctcaaaa tcacggacat gcaggcagca tgtggtctgg    11340
ctcagttgga gcgcgtagaa gagtttgtag agcagcgtaa agctaacttt tcctatctga    11400
aacagggctt gcaatcttgc actgaattcc tcgaattacc agaagcaaca gagaaatcag    11460
atccatcctg gtttggcttc cctatcaccc tgaaagaaac tagcggtgtt aaccgtgtcg    11520
aactggtgaa attccttgat gaagcaaaaa tcggtacacg tttactgttt gctggaaatc    11580
tgattcgcca accgtatttt gctaatgtga atatcgtgt agtgggtgag ttgacaaata     11640
ccgaccgtat aatgaatcaa acgttctgga ttggtattta tccaggcttg actacagagc    11700
atttagatta tgtagttagc aagtttgaag agttctttgg tttgaatttc taattcaatt    11760
tattctatct ggtgattgcg atgacctttt tgaaagaata tgtaattgtc agtgggctt     11820 ccggctttat tggtaagcat ttactcgaag cgctaaaaaa atcggggatt tcagttgtcg    11880
caatcactcg agatgtaata aaaaataata gtaatgcatt agctaatgtt agatggtgca    11940
gttgggataa tatcgaatta ttagtcgagg agttatcaat tgattctgca ttaattggta    12000
tcattcattt ggcaacagaa tatgggcata aacatcatc tctcataaat attgaagatg      12060
caaatgttat aaaaccatta agcttcttg atttggcaat aaaatatcgg gcggatatct      12120
ttttaaatac agatagtttt tttgccaaga agattttaa ttatcaacat atgcggcctt      12180
atataattac taaaagacac tttgatgaaa ttgggcatta ttatgctaat atgcatgaca    12240
tttcatttgt aaacatgcga ttagagcatg tatatgggcc tggggatggt gaaaataaat    12300
ttattccata cattatcgac tgcttaaata aaaaacagag ttgcgtgaaa tgtacaacag    12360
gcgaacagat aagagacttt attttttgtag atgatgtggt aaatgcttat ttaactatat    12420
```

-continued

```
tagaaaatag aaaagaagta ccttcatata ctgagtatca agttggaact ggtgctgggg    12480
taagtttgaa agattttctg gtttatttgc aaaatactat gatgccaggt tcatcgagta    12540
tatttgaatt tggtgcgata gagcaaagag ataatgaaat aatgttctct gtagcaaata    12600
ataaaatttt aaaagcaatg ggctggaaac caaatttcga ttataaaaaa ggaattgaag    12660
aactactgaa acggttatga gattttcatg atcttttaat aaataaatcg ttaacaaatt    12720
agtcgcgtta tgttgtaaaa actaagtcgt ttaattgcat agtgaaagtt caattgttaa    12780
aaattccgag tcatttaatt gttgcaggtt catcatggtt atccaaaata ataattgccg    12840
gggtgcagtt agcaagtatt tcatatctta tttctatgct aggtgaagag aaatatgcaa    12900
tctttagttt gttaactggt ttattagtat ggtgtagcgc tgttgatttt ggcataggta    12960
caggactgca aaattatata tcagaatgca gagccaaaaa caaaagttat gatgcatata    13020
ttaaatcagc attacatcta agctttatag ctattatttt ttttattgct ttatttata     13080 ttttttctgg ggtaatttcc gctaaatatc tttcttcttt tcatgaggta ttacaggaca    13140
aaaccagaat gctcttttt acctcatgtc tggttttcag ttctattgga atcggagcta     13200
ttgcttataa aatacttttt gccgaattgg tcgggtggaa agctaatcta ttaaacgcat    13260
tatcttatat gataggtatg ctcggcttgc tatatatata ctataggggg atctcagttg    13320
acataaaatt atcactaata gtcctgtatc ttccagtggg tatgatttca ttgtgctata    13380
ttgtatatag atacataaag ctttatcatg ttaaaacaac aaaatctcat tatatagcaa    13440
ttttacgtag atcttcaggg tttttctctt ttactttatt atcgatagtg gtgcttcaaa    13500
cagattatat ggtcatttct caaaggctaa ctcctgctga tattgttcaa tatacagtaa    13560
cgatgaaaat ttttggttta gtctttttta tttatactgc tattttgcaa gcattatggc    13620
ctatatgtgc tgaattgaga gtcaaacagc aatggaaaaa acttaacaaa atgataggtg    13680
tcaatatttt gcttggctca ctatatgttg ttggatgtac aatatttatt tatttattta    13740
aagaacagat attttcagta atagccaaag atattaatta tcaagtttct attttatctt    13800
ttatgttaat tggcatatat ttctgtattc gcgtttggtg tgacacttat gcaatgttat    13860
tgcaaagtat gaattatta aaaatacttt ggatattagt accactacaa gcaataattg     13920
gtggaatagc acaatggtat tttttctagta cgcttggaat cagtggagtg ctgcttggct    13980
tgattatatc ttttgctttta actgtttttt ggggggcttcc actaacttac ttaattaagg    14040
caaataaggg ataatcatat gcttatatca ttttgtattc caacttataa tagaaaacaa     14100
tatcttgaag agttgttgaa tagtataaat aatcaggaaa aatttaattt agatattgag    14160
atatgtatat cagataatgc ctctactgat ggtacagagg aaatgattga tgtttggagg    14220
aacaattata atttcccaat aatatatcgg cgtaatagcg ttaaccttgg gccagatagg    14280
aattttcttg cttcagtatc ccttgcgaat ggggattatt gttggatatt tggcagtgat    14340
gatgctcttg cgaaagactc gttagcgata ttacaaactt atctcgattc tcaagcagat    14400
atatatttat gtgacagaaa agagaccggg tgtgatttag ttgagattag aaaccctcat    14460
cgttcttggc tcagaacaga tgatgaactt tatgtgttta ataataattt agataggaa     14520 atctatctca gtagatgctt atctattggt ggtgtattta gctatctaag ttctttaata    14580 gtaaaaaag aacgatggga tgccattgat tttgatgcgt cctatattgg cacttcctat     14640
cctcatgtat ttatcatgat gagcgtattt aatacgccag ggtgcctttt gcattatata    14700
tcaaaaccac tcgtaatatg ccgaggagat aatgatagtt tcgagaagaa aggaaaggcc    14760
```

```
agacgaattt taattgattt tattgcatat ttaaaattag ctaatgattt ttacagtaaa   14820
aatatatctt taaaacgagc atttgaaaat gttttgctaa agagagacc atggttatat    14880 acaactttgg ctatggcatg ttatggcaat agtgatgaaa aaagagattt atctgaattt   14940
tatgcaaagc taggttgtaa taaaaatatg atcaacactg tacttcgatt tgggaaacta   15000
gcatatgcag tgaaaaatat taccgtgctt aagaatttta ctaaacggat aattaagtag   15060
tagtaagtta ttatattgag attaaatgta gatttaacct ttctggattc agctagattt   15120
acgttactga cttttctttt taatgaaaat catatttgat atatataaat aaatttggat   15180
agcttaacta cttagatgtt tttttctggg aatgttagta taataatata tttctttatg   15240 attgttttg tagtgtttta ctgccggtat tacattaact ctattattaa gaattacacc    15300
tagtgtaagc ttcgtaatat tatttatcct tatgattatt gctttaaaga tgcgtatgga   15360
aaaacggaga gctattcaat gatcgtaaac ctatcacgtt taggtaaaag tggtacggga   15420
atgtggcaat actcgattaa attttttaacg gcactgcgag aaatagctga tgttgacgca   15480
ataatctgta gcaaggtaca cgctgattat tttgaaaagc tcggttatgc agtagttact   15540
gttccgaata ttgttagcaa cacatcaaaa acatcgcgac ttagaccatt agtatggtat   15600
gtatatagtt actggcttgc gctgagggtt ttaattaagt ttggtaataa aaaattggtg   15660
tgtactacac atcacactat ccccttactg agaaaccaaa cgataaccgt acatgatata   15720
agaccttttt attatccaga tagttttatt cagaaagtgt attttcgctt tttattaaaa   15780
atgtccgtta agcgatgtaa gcatgttttta acggtatctt ataccgttaa agatagcatt   15840
gctaaaactt ataatgtaga tagtgagaaa atatcagtaa tttataatag tgttaataaa   15900
tctgatttta tacaaaaaaa agaaaaagag aattacttt tagctgttgg tgcaagttgg    15960
ccacataaaa atattcattc attcataaaa aataaaaaag tttggtctga ctcttataat   16020
ttaattattg tatgtggtcg tactgactat gcaatgtctc tccaacaaat ggtcgttgat   16080
ctggaactaa aagataaagt gactttttta catgaagtct catttaatga attaaagatt   16140
ttatattcta aagcctacgc gcttgtttat ccatctattg atgagggttt tggtatacct   16200
cctattgaag cgatggcatc aaatactcca gttatagtgt ccgatatacc agtatttcat   16260
gaagtgttaa ccaatggtgc attatatgtg aatccggatg atgaaaaaag ctggcagagt   16320
gcaattaaaa atatagagca gttgcctgat gcaatttccc gatttaacaa ctatgtcgca   16380
cggtatgact ttgataatat gaagcagatg gttggcaatt ggttggcgga atcaaaataa   16440
atgaaaataa cattaattat tcccacatat aatgcagggt cgctttggcc taatgttctg   16500
gatgcgatta agcagcaaac tatatatccg gataaattga ttgttataga ctcaggttct   16560
aaagatgaaa cggttccgtt agcctcagac ctgaaaaata tatcaatatt taatattgac   16620
tctaaagatt ttaatcatgg aggaaccaga aatttagcag ttgcaaaaac tctggacgct   16680
gatgttataa tttttctaac gcaagatgca attctcgcgg attcggatgc aattaaaaat   16740
ttggtttatt attttcaga tccattgata gcagcggttt gtggtagaca acttcctcat    16800
aaagatgcta atcccttgc agtgcatgcc agaaatttta attatagttc aaaatctatt    16860
gttaaaagta aggcagatat agaaaaattg ggtattaaaa ctgtatttat gtccaattct   16920
tttgctgcct atcgccgttc cgttttgaa gagttaagtg ggtttcctga acatacaatt    16980
cttgccgagg atatgtttat ggcggctaag atgattcagg cgggttataa ggtcgcctac   17040
tgcgctgaag cggtggtaag acactcccat aattataccc cgcgagaaga gtttcaacga   17100
tattttgata ctggtgtatt tcatgcttgt tctccgtgga ttcagcgtga ctttggcgga   17160
```

```
gccggtggtg agggtttccg cttcgtaaaa tcagagattc aattcctgct taaaaatgca   17220
ccgttctgga ttccaagagc tttattaaca acctttgcta aattcttggg ttacaaatta   17280
ggcaagcatt ggcaatcttt accgttgtct acatgtcgct attttagcat gtacaagagt   17340
tattggaata atatccaata ttcttcgtca aaagagataa aataaatgtc ttttcttccc   17400
gtaattatgg ctggcggcac aggtagccgt ttatggccgc tttacgcgca atatcatccg   17460
aagcagtttc taagcgttga aggtaaacta tcaatgctgc aaaatactat aaagcgatta   17520
gcttcacttt ctacagaaga acccgttgtc atttgcaatg acagacaccg tttcttagtc   17580
gctgaacaac tccgtgaaat tgacaagtta gcaaataata ttattctcga accggtaggc   17640
cgtaatactg caccagcgat cgctcttgcc gcgttttgtg cgctccagaa tgctgataat   17700
gctgatcctc ttttgttggt tcttgctgca gatcatgtga ttcaggatga aatagctttt   17760
acgaaagctg tcagacatgc tgaagaatac gctgcaaatg gtaagcttgt aacttttggt   17820
attgttccaa cgcatgctga acgggttat ggatatattc gtcgtggtga gttgatagga   17880
aatgacgctt atgcagtggc tgaatttgtg gagaaaccgg atatcgatac cgccggtgac   17940
tatttcaaat cagggaaata ttactggaat agcggtatgt ttttatttcg tgcaagctct   18000
tatttaaacg aattaaagta tttatcacct gaaatttata aagcttgtga aaaggcggta   18060
ggacatataa atcccgatct tgattttatt cgtattgata agaagagtt tatgtcatgc   18120
ccgagtgatt ctatcgatta tgcagttatg gagcacacac agcatgcggt ggtgatacca   18180
atgagcgctg gctggtcgga tgtgggttcc tggtcctcac tttgggatat atcgaataaa   18240
gatcatcaga gaaatgtttt aaaggagat attttcgcac atgcttgtaa tgataattac   18300
atttattccg aagatatgtt tataagtgcg attggtgtaa gcaatcttgt cattgttcaa   18360
acaacagacg ctttactggt ggctaataaa gatacagtac aagatgttaa aaaaattgtc   18420
gattatttaa aacggaatga taggaacgaa tataaacaac atcaagaagt tttccgcccc   18480
tggggaaaat ataatgtgat tgatagcggc aaaaattacc tcgttcgatg tatcactgtt   18540
aagccgggtg agaaatttgt ggcgcagatg catcaccacc gggctgagca ttggatagta   18600
ttatccggga ctgctcgtgt tacaaaggga gagcagactt atatggtttc tgaaaatgaa   18660
tcaacattta ttcctccgaa tactattcac gcgctggaaa tcctggaat gaccccctg    18720
aagttaattg agattcaatc aggtacctat cttggtgagg atgatattat tcgtttagaa   18780
caacgttctg gattttcgaa ggagtggact aatgaacgta gttaataata gccgtgatgt   18840
tatttattca tcaggtattg tgtttggaac gagtggggct cgcggtcttg taaaagattt   18900
tacacctcag gtatgtgctg cttttacggt ttcatttgtt gccgttatgc aggaacattt   18960
ttcctttgat accgtagcat tggcaataga taatcgtcca agtagttatg ggatggctca   19020
ggcgtgtgct gctgcattgg cggataaagg cgttaactgt atttttttatg gagtggtacc   19080
aaccccagct ttggcctttc agtctatgtc tgacaatatg cctgcgataa tggttacggg   19140
aagtcatatt ccattcgagc ggaacggcct caagttttat cgtcctgatg gtgaaatcac   19200
gaaacatgat gaggctgcga tccttagtgt tgaagatacg tgcagccatt tagagcttaa   19260
agaactcata gtttcagaaa tggctgctgt taattatata tctcgttata catctttatt   19320
ttctactcca ttcctgaaaa ataagcgtat tggtatttac gaacattcaa gcgctgggcg   19380
tgatctttat aagcctttat ttattgcatt gggggctgaa gtcgttagct tgggtagaag   19440
cgataatttt gtacctatag atacagaggc tgtaagcaaa gaggatcggg aaaaagctcg   19500
```

```
ctcatgggct aaagagttcg atttagatgc catattctcg acagatgggg atggtgatcg    19560
ccctcttatt gctgatgagg ccggtgagtg gctaagaggc gatatactag gtctattatg    19620
ttcacttgca ttggatgcag aagccgtcgc tattcctgtt agttgtaaca gcataatttc    19680
ttctggccgc ttttttaaac atgttaagct tacaaaaatt ggctcgcctt atgttatcga    19740
agcttttaat gaattatcgc ggagttatag tcgtattgtc ggttttgaag ccaatggcgg    19800
tttttttatta ggaagcgaca tctgtattaa cgagcagaat cttcatgcct taccaactcg    19860
tgatgctgta ttaccagcaa taatgctgct ttacaaaagt aggaatacca gcattagcgc    19920
tttagtcaat gaactcccaa ctcgttacac ccattctgac agattacagg ggattacaac    19980
tgataaaagt caatccttaa ttagtatggg cagagaaaat ctgagcaacc tcttaagcta    20040
tattggtttg gagaatgaag gtgcaatttc tacagatatg acagatggta tgcgaattac    20100
tttacgtgat ggatgtattg tgcatttgcg cgcttctggt aatgcacctg agttacgctg    20160
ctatgcagaa gctaatttat taaataggc tcaggatctt gtaaatacaa cgcttgctaa     20220
tattaaaaaa cgatgcttgc tgtaaaaaaa ttgaatgtta tttacttaat atgcctattt    20280
tatttacatt atgcacggtc agagggtgag gattaaatgg ataatattga taataagtat    20340
aatccacagc tatgtaaaat ttttttggct atatcggatt tgatttttt taatttagcc     20400
ttatggtttt cattaggatg tgtctattt attttgatc aagtacagcg atttattcct      20460
caagaccaat tagatacaag agttattacg catttatttt tgtcagtagt atgtgtcggt    20520
tggttttgga ttcgtttgcg acattatact atccgcaagc catttggta tgagttaaaa     20580
gaaattttc gtacgatcgt tatttttgct atatttgatt tggctctgat agcgtttaca    20640
aaatggcagt tttcacgcta tgtctgggtg ttttgttgga cttttgccct aatcctggtg    20700
ccttttttc gcgcacttac aaagcattta ttgaacaagc taggtatctg gaagaaaaaa     20760
actatcatcc tggggagcgg acagaatgct cgtggtgcat attctgcgct gcaaagtgag    20820
gagatgatgg ggtttgatgt tatcgctttt tttgatacgg atgcgtcaga tgctgaaata    20880
aatatgttgc cggtgataaa ggatactgag attatttggg atttaaatcg tacaggtgat    20940
gtccattata tccttgctta tgaatacacc gagttggaga aaacacattt ttggctacgt    21000
gaactttcaa aacatcattg tcgttctgtt actgtagtcc cctcgtttag aggattgcca    21060
ttatataata ctgatatgtc ttttatcttt agccatgaag ttatgttatt aaggatacaa    21120
aataacttgg ctaaaaggtc gtcccgtttt ctcaaacgga catttgatat tgtttgttca    21180
ataatgattc ttataattgc atcaccactt atgatttatc tgtggtataa agttactcga    21240
gatggtggtc cggctatta tggtcaccag cgagtaggtc ggcatggaaa acttttccca    21300
tgctacaaat ttcgttctat ggttatgaat tctcaagagg tactaaaaga acttttggct    21360
aacgatccta ttgccagggc tgaatgggag aaagatttta aactgaaaaa tgatcctcga    21420
atcacagctg taggtcgatt tatacgtaaa actagccttg atgagttgcc acaacttttt    21480
aatgtactaa aaggtgatat gagcctggtt ggaccacgac ctatcgtttc ggatgaactg    21540
gagcgttatt gtgatgatgt tgattattat ttgatggcaa agccgggcat gacaggtcta    21600
tggcaagtga gtgggcgtaa tgatgttgat tatgacactc gtgttatttt tgattcctgg    21660
tatgttaaaa actggacgct ttggaatgat attgccattc tgtttaaaac agcgaaagtt    21720
gttttgcggc gagatggtgc gtattaagct taccgagaag tactgaataa taattgtata    21780
aattagcctg cgtaaaatct gaacgcatca atcgctacct taatatcata cctttgagtt    21840
aacatactat tcacctttaa cctgccatga ccgtttgtgg cagggtttcc acacctgaca    21900
```

```
ggagtatgta atgtccaagc aacagatcgg cgtcgtcggt atggcagtga tggggcgcaa    21960
cctcgcgctc aacatcgaaa gccgtggtta taccgtctcc gttttcaacc gctcccgtga    22020
aaagaccgaa gaagtgattg ccgagaatcc cggcaaaaag ctggtgcctt attacacggt    22080
```